US008426676B2

(12) United States Patent
Oswald et al.

(10) Patent No.: US 8,426,676 B2

(45) Date of Patent: Apr. 23, 2013

(54) SEED ENHANCEMENT BY COMBINATIONS OF PYRUVATE KINASES

(75) Inventors: Oliver Oswald, Lautertal (DE); Heiko A. Härtel, Eisfeld (DE); Christoph Benning, East Lansing, MI (US); Carl Andre, Patchogue, NY (US)

(73) Assignee: BASF Plant Science GmbH (DE)

( * ) Notice: Subject to any disclaimer, the term of this patent is extended or adjusted under 35 U.S.C. 154(b) by 426 days.

(21) Appl. No.: 12/598,611

(22) PCT Filed: Apr. 29, 2008

(86) PCT No.: PCT/EP2008/055266

§ 371 (c)(1), (2), (4) Date: Nov. 3, 2009

(87) PCT Pub. No.: WO2008/135467

PCT Pub. Date: Nov. 13, 2008

(65) Prior Publication Data

US 2010/0088782 A1 Apr. 8, 2010

Related U.S. Application Data

(60) Provisional application No. 60/916,118, filed on May 4, 2007.

(30) Foreign Application Priority Data

May 4, 2007 (EP) .................................... 07107563

(51) Int. Cl.

| | |
|---|---|
| ***A01H 1/00*** | (2006.01) |
| ***A01H 5/00*** | (2006.01) |
| ***A01H 5/10*** | (2006.01) |
| ***C12N 15/82*** | (2006.01) |
| ***C07H 21/04*** | (2006.01) |

(52) U.S. Cl.

USPC ........... 800/278; 800/281; 800/298; 435/410; 435/419; 435/468; 435/320.1

(58) Field of Classification Search ........................ None

See application file for complete search history.

(56) References Cited

U.S. PATENT DOCUMENTS

| | | | | |
|---|---|---|---|---|
| 5,914,449 | A * | 6/1999 | Murase et al. | 800/281 |
| 5,955,650 | A | 9/1999 | Hitz | |
| 6,084,164 | A | 7/2000 | Bidney et al. | |
| 2004/0019931 | A1 | 1/2004 | Tarczynski et al. | |
| 2006/0288451 | A1 * | 12/2006 | Val et al. | 800/281 |

FOREIGN PATENT DOCUMENTS

| | | | |
|---|---|---|---|
| EP | 0787801 | A2 | 8/1997 |
| WO | WO-2004/013304 | A2 | 2/2004 |
| WO | WO-2006/034228 | A2 | 3/2006 |
| WO | WO-2006/127991 | A2 | 11/2006 |

OTHER PUBLICATIONS

BLAST results—Accession No. NP 001065454, Oct. 2, 2006.*

Ambasht et al, Biologia Plantarum, vol. 45, No. 1, pp. 1-10, 2002.*

Sangwan et al, Planta, 1992, vol. 187, pp. 198-202.*

Topfer, R., et al., "Modification of Plant Lipid Synthesis", Science, vol. 268, (1995), pp. 681-686.

Cahoon, E.B., et al., "Expression of a Coriander Desaturase Results in Petroselinic Acid Production in Transgenic Tobacco", Proc. Natl. Acad. Sci. USA, vol. 89, (1992), pp. 11184-11188.

Millar, A.A., et al., "All Fatty Acids are not Equal: Discrimination in Plant Membrane Lipids", Trends in Plant Science, vol. 5, No. 3, (2000), pp. 95-101.

Browse, J., et al., "Fluxes Through the Prokaryotic and Eukaryotic Pathways of Lipid Synthesis in the '16:3' Plant *Arabidopsis thaliana*", Biochemical J., vol. 235, (1986), pp. 25-31.

Ohlrogge, J., et al., "Lipid Biosynthesis", The Plant Cell, vol. 7, (1995), pp. 957-970.

Shanklin, J., et al., "Desaturation and Related Modifications of Fatty Acids", Annu. Rev. Plant Physiol. Mol. Biol., vol. 49, (1998), pp. 611-641.

Frentzen, M., "Acyltransferases from Basic Science to Modified Seed Oils", Fett/Lipid, vol. 100, (1998), pp. 161-166.

Millar. A.A., et al., "Very-long-chain Fatty Acid Biosynthesis is Controlled Through the Expression and Specificity of the Condensing Enzyme", The Plant Journal, vol. 12, No. 1, (1997), pp. 121-131.

Plaxton, W. C., "The Organization and Regulation of Plant Glycolysis", Annu. Rev. Plant Physiol. Plant Mol. Biol., vol. 47, (1996), pp. 185-214.

Kang, F., et al., "Starch and Fatty Acid Synthesis in Plastids from Developing Embryos of Oilseed Rape (*Brassica napus* L.)", The Plant Journal, vol. 6, No. 6, (1994), pp. 795-805.

Van De Loo, F.J., et al., "An Oleate 12-hydroxylase from *Ricinus communis* L. is a Fatty Acyl Desaturase Homolog", Proc. Nat'l Acad. Sci. USA, vol. 92, (1995), pp. 6743-6747.

Brenner, R. R., "Regulatory Function of Δ6 Desaturase—Key Enzyme of Polyunsaturated Fatty Acid Synthesis", Adv. Exp. Med. Biol., vol. 83, (1976), pp. 85-101.

Turner, W. L., et al. "Cytosolic Pyruvate Kinase: Subunit Composition, Activity, and Amount in Developing Castor and Soybean Seeds, and Biochemical Characterization of the Purified Castor Seed Enzyme", Planta, vol. 222, (2005), pp. 1051-1062.

Turner, W. L., et al., "Purification and Characterization of Cytosolic Pyruvate Kinase from Banana Fruit", Biochem. J., vol. 352, (2000), pp. 875-882.

Ruuska, A, et al., "Contrapuntal Networks of Gene Expression During *Arabidopsis* Seed Filling", The Plant Cell, vol. 14, (2002), pp. 1191-1206.

(Continued)

*Primary Examiner* — Eileen B O Hara

(74) *Attorney, Agent, or Firm* — Roberte M.D. Makowski

(57) ABSTRACT

Described herein are inventions in the field of genetic engineering of plants, including combinations of nucleic acid molecules encoding pyruvate kinase subunits to improve agronomic, horticultural, and quality traits. This invention relates generally to the combination of nucleic acid sequences encoding pyruvate kinase proteins that are related to the presence of seed storage compounds in plants. More specifically, the present invention relates to the use of these combinations of these sequences, their order and direction in the combination, and the regulatory elements used to control expression and transcript termination in these combinations in transgenic plants. In particular, the invention is directed to methods for manipulating seed storage compounds in plants and seeds. The invention further relates to methods of using these novel combinations of polypeptides to stimulate plant growth and/or root growth and/or to increase yield and/or composition of seed storage compounds.

52 Claims, 4 Drawing Sheets

OTHER PUBLICATIONS

White, J. A., et al., "A New Set of *Arabidopsis* Expressed Sequence Tags from Developing Seeds. The Metabolic Pathway from Carbohydrates to Seed Oil", Plant Physiology, vol. 124, No. 4, (2000), pp. 1582-1594.

Sangwan, R. S., et al., "Pyruvate-kinase Isoenzymes from Zygotic and Microspore-derived Embryos of *Brassica napus*", Planta, vol. 187, (1992), pp. 198-202.

Ambasht, P. K., et al., "Plant Pyruvate Kinase", Biologia Plantarum, vol. 45, No. 1, (2002), pp. 1-10.

Ma, H., et al., "A Pyruvate Kinase cDNA from Soybean Somatic Embryos", Plant Physiol., vol. 102, No. 4, (1993), p. 1345.

"*Arabidopsis thaliana* At1g32440/F5D14_7, mRNA, complete cds. ", Database EMBL Accession No. AY058121, Nov. 5, 2001.

"*Arabidopsis thaliana* clone 109919 mRNA, complete sequence", Database EMBL Accession No. AY084507, Jun. 14, 2002.

"*Arabidopsis thaliana* AT3g22960/F5N5_15 mRNA, complete cds. ", Database EMBL Accession No. AY058084, Nov. 5, 2001.

Andre, C., et al., "A Heteromeric Plastidic Pyruvate Kinase Complex Involved in Seed Oil Biosynthesis in *Arabidopsis*", The Plant Cell, vol. 19, (2007), pp. 2006-2022.

Andre, C., et al., "*Arabidopsis* Seedlings Deficient in a Plastidic Pyruvate Kinase are Unable to Utilize Seed Storage Compounds for Germination and Establishment", Plant Physiology, vol. 145, (2007), pp. 1670-1680.

* cited by examiner

SEED ENHANCEMENT BY COMBINATIONS OF PYRUVATE KINASES

RELATED APPLICATIONS

This application is a national stage application (under 35 U.S.C. §371) of PCT/EP2008/055266, filed Apr. 29, 2008, which claims benefit of European application 07107563.4, filed May 4, 2007 and U.S. provisional application 60/916,118, filed May 4, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List__13156__00300US. The size of the text file is 278 KB, and the text file was created on Nov. 3, 2009.

Description

Described herein are inventions in the field of genetic engineering of plants, including combinations of nucleic acid molecules encoding pyruvate kinase subunits to improve agronomic, horticultural, and quality traits. This invention relates generally to the combination of nucleic acid sequences encoding pyruvate kinase proteins that are related to the presence of seed storage compounds in plants. More specifically, the present invention relates to the use of these combinations of these sequences, their order and direction in the combination, and the regulatory elements used to control expression and transcript termination in these combinations in transgenic plants. In particular, the invention is directed to methods for manipulating seed storage compounds in plants and seeds. The invention further relates to methods of using these novel combinations of polypeptides to stimulate plant growth and/or root growth and/or to increase yield and/or composition of seed storage compounds.

The study and genetic manipulation of plants has a long history that began even before the famed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al. 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164), and rapeseed (Töpfer et al. 1995, Science 268:681-686), and non-traditional oil seed plants such as tobacco (Cahoon et al. 1992, Proc. Natl. Acad. Sci. USA 89:11184-11188).

Plant seed oils comprise both neutral and polar lipids (see Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes, plastidial and mitochondrial membranes and the cell membrane. The neutral and polar lipids contain several common fatty acids (see Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al. 1993, Unusual Fatty Acids in Lipid Metabolism in Plants pp. 91-126, editor T S Moore Jr. CRC Press; Millar et al. 2000, Trends Plant Sci. 5:95-101). Lipids are synthesized from fatty acids and their synthesis may be divided into two parts: the prokaryotic pathway and the eukaryotic pathway (Browse et al. 1986, Biochemical J. 235:25-31; Ohlrogge & Browse 1995, Plant Cell 7:957-970). The prokaryotic pathway is located in plastids that are also the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction, in which the acyl group from acetyl-CoA is transferred to malonyl-ACP to form 3-ketobutyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first double bond into the fatty acid. In the prokaryotic pathway the saturated and monounsaturated acyl-ACPs are direct substrates for the plastidial glycerol-3-phosphate acyltransferase and the lysophosphatidic acid acyltransferase, which catalyze the esterification of glycerol-3-phosphate at the sn-1 and sn-2 position. The resulting phosphatidic acid is the precursor for plastidial lipids, in which further desaturation of the acyl-residues can occur. In the eukaryotic lipid biosynthesis pathway thio-esterases cleave the fatty acids from the ACP cofactor and free fatty acids are exported to the cytoplasm where they participate as fatty acyl-CoA esters in the eukaryotic pathway. In this pathway the fatty acids are esterified by glycerol-3-phosphate acyltransferase and lysophosphatidic acid acyl-transferase to the sn-1 and sn-2 positions of glycerol-3-phosphate, respectively, to yield phosphatidic acid (PA). The PA is the precursor for other polar and neutral lipids, the latter being formed in the Kennedy of other pathways (Voelker 1996, Genetic Engineering ed.: Setlow 18:111-113; Shanklin & Cahoon 1998, Annu. Rev. Plant Physiol. Plant Mol. Biol. 49:611-641; Frentzen 1998, Lipids 100:161-166; Millar et al. 2000, Trends Plant Sci. 5:95-101). The acyl-CoAs resulted from the export of plastidic fatty acids can also be elongated to yield very-long-chain fatty acids with more than 18 carbon atoms. Fatty acid elongases are multienzyme complexes consisting of at least four enzyme activities: beta-ketoacyl-CoA synthases, beta-ketoacyl-CoA reductase, beta-hydroxyacyl-CoA dehydratase and enoyl-CoA reductase. It is well known that the beta-ketoacyl-CoA synthase determines the activity and the substrate selectivity of the fatty acid elongase complex (Millar & Kunst 1997, Plant J. 12:121-131). The very-long-chain fatty acids can be either used for wax and sphingolipid biosynthesis or enter the pathways for seed storage lipid biosynthesis. Storage lipids in seeds are synthesized from carbohydrate-derived precursors. Plants have a complete glycolytic pathway in the cytosol (Plaxton 1996, Annu. Rev. Plant Physiol. Plant Mol. Biol. 47:185-214), and it has been shown that a complete pathway also exists in the plastids of rapeseeds (Kang & Rawsthorne 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions and the exact contribution of each reaction is still being debated (Ohlrogge & Browse 1995, Plant Cell 7:957-970). It is however accepted that a large part of the acetyl-CoA is derived from glucose-6-phosphate and pyruvate that are imported from the cytoplasm into the plastids. Sucrose is produced in the source organs (leaves, or anywhere where photosynthesis occurs) and is transported to the developing seeds that are also termed sink organs. In the developing seeds, sucrose is the precursor for all the storage compounds, i.e. starch, lipids, and partly the seed storage proteins. Generally the breakdown of lipids is considered to be performed in plants in peroxisomes in the process know as beta-oxidation. This process involves the enzymatic reactions of acyl-CoA oxidase, hydroxyacyl-CoA-dehydrogenase (both found as a multifunctional complex) and ketoacyl-CoA-thiolase, with catalase in a supporting role (Graham and Eastmond 2002). In addition to the breakdown of common fatty acids beta-oxidation also plays a role in the removal of unusual fatty acids and fatty acid oxidation products, the glyoxylate cycle and the metabolism of branched chain amino acids.

Storage compounds, such as triacylglycerols (seed oil), serve as carbon and energy reserves, which are used during germination and growth of the young seedling. Seed (vegetable) oil and other seed storage compounds, such as amino acids, are also essential components of the human diet and are valuable commodity providing feedstocks for the chemical industry. Although the seed storage compound content, and/or composition, can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (see, e.g., Töfer et al., 1995, Science 268:681-686). For example, introduction of a Δ12-hydroxylase nucleic acid sequence into transgenic tobacco resulted in the introduction of a novel fatty acid, ricinoleic acid, into the tobacco seed oil (Van de Loo et al. 1995, Proc. Natl. Acad. Sci. USA 92:6743-6747). Tobacco plants have also been engineered to produce low levels of petroselinic acid by the introduction and expression of an acyl-ACP desaturase from coriander (Cahoon et al. 1992, Proc. Natl. Acad. Sci. USA 89:11184-11188). The modification of seed storage compounds in plants has significant medical, nutritional and economic ramifications. With regard to the medical ramifications, e.g., the long chain fatty acids (C18 and longer) found in many seed oils have been linked to reductions in hypercholesterolemia and other clinical disorders related to coronary heart disease (Brenner 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils. The same reasoning applies for other seed storage compounds such as amino acids. In order to increase or alter the levels of seed storage compounds in plants, nucleic acid sequences and proteins regulating the metabolism of the said seed storage compounds must be identified.

Plant Pyruvate kinases (EC 2.7.1.40) are thought to be modulators of several metabolic pathways involved in seed storage compounds such as seed oil and/or amino acids. Pyruvate kinase (PK) catalyses the irreversible transfer of phosphate (Pi) from phosphoenol pyruvate (PEP) to ADP yielding pyruvate and ATP. In most eukaryotes PK exists as a cytosolic homotetramer composed of subunits of 55±60 kDa. Many animal and yeast PKs are regulated by allosteric effectors (with fructose 1,6-bisphosphate acting as a potent activator), as well as by reversible protein kinase-mediated phosphorylation. In vascular plants and green algae, PK exists as cytosolic (PKc) and plastidic (PKp) isoenzymes that differ markedly with respect to their physical, immunological and kinetic characteristics. In addition, plant PKc appears to occur as tissue-specific isoenzymes that demonstrate substantial differences in their kinetic and regulatory properties differences that reflect the distinctive metabolic quirements of the respective tissues. Kinetic studies of purified plant PKc indicated that the enzyme exists naturally in an activated state (similar to the non-plant enzyme activated by fructose 1,6-bisphosphate. Feedback regulation of PKc by various inhibitors serves to modulate its activity in accordance with the cell's momentary demands for tricarboxylic acid cycle and respiratory end-products, namely ATP and/or carbon skeletons that serve as biosynthetic precursors (Turner 2005, Planta 222: 1051-1062; Turner 2000, Biochem J. 352: 875-882). Plant pyruvate kinases have been cloned and nucleic acid as well as amino acid sequences thereof are described in, e.g., WO2006/034228.

Although several compounds are known that generally affect plant and seed development, there is a clear need to specifically identify factors or combinations thereof that are more specific for the developmental regulation of seed storage compound accumulation and which have the capacity to confer altered, increased or improve seed storage compound production and, in particular, production of oil compounds and/or amino acids, to its host plant and to other plant species.

The technical problem underlying the present invention, thus, could be seen as the provision of means and methods for complying with the aforementioned needs. The technical problem is solved by the embodiments characterized in the claims and disclosed hereinafter.

Accordingly, the present invention relates to a polynucleotide comprising (i) at least one first nucleic acid molecule operatively linked to a first expression control sequence and a first terminator sequence, said first nucleic acid molecule being selected from the group of nucleic acid molecules consisting of:

(a) a nucleic acid molecule having a nucleic acid sequence as shown in any one of SEQ ID NOs: 7, 15, 17, 19, 21, 23 and 27;

(b) a nucleic acid molecule encoding a polypeptide having an amino acid sequence as shown in any one of SEQ ID NOs: 8, 16, 18, 20, 22, 24 and 28;

(c) a nucleic acid molecule having a nucleic acid sequence which is at least 70% identical to the nucleic acid sequence of the nucleic acid molecule of (a) or (b), wherein said nucleic acid molecule encodes a polypeptide contemplating or having pyruvate kinase activity;

(d) a nucleic acid molecule encoding an amino acid sequence being at least 70% identical to an amino acid sequence encoded by the nucleic acid molecule of (a) or (b), wherein said nucleic acid molecule encodes a polypeptide contemplating or having pyruvate kinase activity; and (e) a nucleic acid molecule being a fragment of any one of (a) to (d), wherein said fragment encodes a polypeptide contemplating or having pyruvate kinase activity, and (ii) at least one second nucleic acid molecule operatively linked to a second expression control sequence and a second terminator sequence, said second nucleic acid molecule being selected from the group of nucleic acid molecules consisting of:

(a) a nucleic acid molecule having a nucleic acid sequence as shown in any one of SEQ ID NOs: 3, 5, 11, 13, 17, 21, 23, 25 and 27;

(b) a nucleic acid molecule encoding a polypeptide having an amino acid sequence as shown in any one of SEQ ID NOs: 2, 4, 6, 10, 12, 14, 26 and 28;

(c) a nucleic acid molecule having a nucleic acid sequence which is at least 70% identical to the nucleic acid sequence of the nucleic acid molecule of (a) or (b), wherein said nucleic acid molecule encodes a polypeptide having or contemplating pyruvate kinase activity;

(d) a nucleic acid molecule encoding an amino acid sequence being at least 70% identical to an amino acid sequence encoded by the nucleic acid molecule of (a) or (b), wherein said nucleic acid molecule encodes a polypeptide contemplating or having pyruvate kinase activity; and (e) a nucleic acid molecule being a fragment of any one of (a) to (d), wherein said fragment encodes a polypeptide having or contemplating pyruvate kinase activity.

The term "polynucleotide" as used in accordance with the present invention relates to a polynucleotide comprising a first and a second nucleic acid molecule wherein said first and said second nucleic acid molecules have different nucleic acid sequences. The first nucleic acid molecule and the second nucleic acid molecule are, preferably, covalently linked to each other thereby forming a single nucleic molecule, such as an expression construct or expression cassette specified below. The first and the second nucleic acid molecule may be included into the polynucleotide of the invention in the same orientation or in opposite orientations. The polynucleotide of the present invention, in addition to the first and the second nucleic acid molecule, may comprise additional nucleotides, such as spacer and/or flanking nucleotides between the first and the second nucleic acid molecule.

Moreover, the polynucleotide of the present invention may comprise further nucleic acid molecules. Preferably, the polynucleotide of the present invention further comprises (iii) at least one third nucleic acid molecule operatively linked to a third expression control sequence and a third terminator sequence, said second nucleic acid molecule being selected from the group of nucleic acid molecules consisting of:

(a) a nucleic acid molecule having a nucleic acid sequence as shown in any one of SEQ ID NOs: 1, 3, 5, 9, 11, 13, 17, 19, 25 and 27;

(b) a nucleic acid molecule encoding a polypeptide having an amino acid sequence as shown in any one of SEQ ID NOs: 2, 4, 6, 10, 12, 14, 18, 20, 26, and 28;

(c) a nucleic acid molecule having a nucleic acid sequence which is at least 70% identical to the nucleic acid sequence of the nucleic acid molecule of (a) or (b), wherein said nucleic acid molecule encodes a polypeptide having or contemplating pyruvate kinase activity;

(d) a nucleic acid molecule encoding an amino acid sequence being at least 70% identical to an amino acid sequence encoded by the nucleic acid molecule of (a) or (b), wherein said nucleic acid molecule encodes a polypeptide contemplating or having pyruvate kinase activity; and (e) a nucleic acid molecule being a fragment of any one of (a) to (c), wherein said fragment encodes a polypeptide having or contemplating pyruvate kinase activity.

It is to be also understood that the said third nucleic acid molecule shall have a nucleic acid sequence being different from the nucleic acid sequence of the said first and the said second nucleic acid molecule. Moreover, the third nucleic acid molecule may be included into the polynucleotide of the invention in the same orientation as either the first or the second or both other nucleic acid molecule or in the opposite orientation. The polynucleotide of the present invention is, preferably, a DNA or RNA molecule.

Preferably, the polynucleotide of the present invention, upon expression in a plant seed, is capable of significantly increasing the content of at least one seed storage compound. Preferably the content or amount of a seed storage compound is determined as dry weight as measured by near infrared spectroscopy, gas chromatography coupled to mass spectroscopy or liquid chromatography coupled to mass spectrometry. How to determine whether an increase is significant is described elsewhere in this specification. Further details are to be found in the accompanying Examples, below. More preferably, the polynucleotide of the present invention upon expression in the seed of a transgenic plant is capable of significantly increasing the amount by weight of at least one seed storage compound, more preferably, of a lipid, a fatty acid, a protein or an amino acid. More preferably, such an increase as referred to in accordance with the present invention is an increase of the amount by weight of at least 1, 2.5, 5, 7.5, 10, 12.5, 15, 17.5, 20, 22.5 or 25% as compared to a control. Whether an increase is significant can be determined by statistical tests well known in the art including, e.g., Student's t-test. The percent increase rates of a seed storage compound are, preferably, determined compared to an empty vector control. An empty vector control is a transgenic plant, which has been transformed with the same vector or construct as a transgenic plant according to the present invention except for such a vector or construct is lacking the polynucleotide of the present invention. Alternatively, an untreated plant (i.e. a plant which has not been genetically manipulated or which is a non-transgenic segregant of the transgenic plants) may be used as a control.

The polynucleotide of the present invention shall be provided, preferably, either as an isolated polynucleotide (i.e. isolated in that the first and the second or the first, second and third nucleic acid molecules are isolated from their natural context) or in genetically modified or exogenously (i.e. artificially) manipulated form. An isolated polynucleotide can, for example, comprise less than approximately 20 kb, 18 kb, 15 kb, 13 kb, 10 kb, 8 kb, 5 kb, 4 kb or 3 kb of nucleotide sequences which naturally flank the nucleic acid molecule in the genomic DNA of the cell from which the nucleic acid is derived. The polynucleotide, preferably, is double or single stranded DNA including cDNA or RNA.

The term encompasses single- as well as double-stranded polynucleotides. Moreover, comprised are also chemically modified polynucleotides including naturally occurring modified polynucleotides such as glycosylated or methylated polynucleotides or artificial modified ones such as biotinylated polynucleotides.

The term "nucleic acid molecule" refers to a nucleic acid molecule having a nucleic acid sequence encoding a polypeptide subunit of an pyruvate kinase, wherein said pyruvate kinase being capable of increasing the seed storage compound content when expressed in transgenic plants. It is to be understood that the subunits encoded by the first and second nucleic acid molecules comprised by the polynucleotide of the present invention will, preferably, upon expression form homo- or hetero-oligomeric polypeptides, preferably tetramers, i.e. the assembled pyruvate kinase polypeptide (EC 2.7.1.40). The capability of assembling a biologically active pyruvate kinase is also referred to herein as the capability of a subunit of contemplating pyruvate kinase activity. Pyruvate kinases catalyze the irreversible transfer of phosphate (Pi) from phosphoenolpyruvate (PEP) to ADP, yielding pyruvate and ATP. The pyruvate thus generated is a key metabolite for the lipid and fatty acid synthesis as well as for the amino acid synthesis. The polypeptides encoded by the aforementioned nucleic acid molecules are also sometimes referred to as "Storage Metabolism Protein (SMP)" herein below. Suitable assays for measuring the pyruvate kinase activities are well known in the art and are described, preferably, in Turner 2005, loc cit.

Nucleic acid molecules which are suitable for a polynucleotide of the present invention have been obtained from *Arabidopsis thaliana*. However, it is to be understood that those sequences may be also obtained as orthologs of the nucleic acids from other plant species as disclosed herein below or from algae or as paralogs from *Arabidopsis thaliana*. Moreover, it is to be understood that a polypeptide having the aforementioned specific amino acid sequences may be encoded due to the degenerated genetic code by other nucleic acid molecules as well.

Moreover, the term "nucleic acid molecule" as used in accordance with the present invention further encompasses variants of the aforementioned specific nucleic acid molecules. The variants, preferably, also comprise a nucleic acid sequence characterized in that the sequence can be derived from the aforementioned specific nucleic acid sequences shown in the SEQ ID NOs by at least one nucleotide substitution, addition and/or deletion whereby the variant nucleic acid sequence shall still encode a polypeptide subunit having a biological activity as specified above. Variants also encompass nucleic acid molecules comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, variants are obtainable by PCR-based techniques such as mixed oligonucleotide primer-based amplification of DNA, i.e. using degenerated primers against conserved domains of the polypeptides of the present invention. Conserved domains of the polypeptide subunits may be identified by a sequence comparison of the nucleic acid sequences of the nucleic acid molecules or the amino acid sequences of the polypeptide subunits. Oligonucleotides suitable as PCR primers as well as suitable PCR conditions are described in the accompanying Examples. As a template, DNA or cDNA from bacteria, fungi, plants or animals may be used. Further, variants include nucleic acid molecules comprising nucleic acid sequences which are at least 70%, at least 75%, at least 80%, at least 85%, at least 90%, at least 95%, at least 98% or at least 99% identical to the nucleic acid sequences shown in the aforementioned SEQ ID NOs retaining a biological activity as specified above. Moreover, also encompassed are nucleic acid molecules which comprise nucleic acid sequences encoding amino acid sequences which are at least 70%, at least 75%, at least 80%, at least 85%, at least 90%, at least 95%, at least 98% or at least 99% identical to the amino acid sequences shown in the aforementioned SEQ ID NOs wherein the polypeptide comprising the amino acid sequence retains a biological activity as specified above. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. For the purposes of the invention, the percent sequence identity between two nucleic acid or polypeptide sequences can be also determined using the Vector NTI 7.0 (PC) software package (InforMax, 7600 Wisconsin Ave., Bethesda, Md. 20814). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide sequence is equivalent to a uracil nucleotide.

A nucleic acid molecule being or comprising a fragment of any of the aforementioned nucleic acid molecules is also envisaged by the present invention. The fragment shall encode a polypeptide subunit which still has a biological activity as specified above. Accordingly, the polypeptide may comprise or consist of the domains of the polypeptide of the present invention conferring the said biological activity. A fragment as meant herein, preferably, comprises at least 20, at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant nucleic acid molecules or fragments referred to above, preferably, encode pyruvate kinase subunits contemplating or having at least 10%, at least 20%, at least 30%, at least 40%, at least 50%, at least 60%, at least 70%, at least 80% or at least 90% of the biological activity exhibited by a pyruvate kinase being assembled by the polypeptide subunits having the amino acid sequences as shown in the aforementioned SEQ ID NOs.

The nucleic acid molecules referred to in accordance with the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the nucleic acid molecules of the present invention may encode fusion proteins wherein one partner of the fusion protein is a polypeptide being encoded by a nucleic acid sequence recited above. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like. Moreover, the nucleic acid molecules may comprise nucleotide sequences encoding plastid transit peptides. Nucleotide sequences encoding suitable plastid transit peptides are well known, as disclosed, for example, in U.S. Pat. Nos. 5,717,084, 5,728,925, 6,063,601, and 6,130,366.

Variant nucleic acid molecules also include those having a nucleic acid sequence which has been adopted to the specific codon- usage of the organism, e.g., the plant species, in which the polynucleotide shall be expressed (i.e. the target organism). This is, in general, achieved by changing the codons of a nucleic acid sequence obtained from a first organism (i.e. the donor organism) encoding a given amino acid sequence into the codons normally used by the target organism whereby the amino acid sequence is retained. It is in principle acknowledged that the genetic code is redundant (i.e. degenerated). Specifically, 61codons are used to encode only 20 amino acids. Thus, a majority of the 20 amino acids will be encoded by more than one codon. The codons for the amino acids are well known in the art and are universal to all organisms. However, among the different codons which may be used to encode a given amino acid, each organism may preferably use certain codons. The presence of rarely used codons in a nucleic acid sequence will result a depletion of the respective tRNA pools and, thereby, lower the translation efficiency. Thus, it may be advantageous to provide a polynucleotide comprising a nucleic acid sequence encoding a polypeptide as referred to above wherein said nucleic acid sequence is optimized for expression in the target organism with respect to the codon usage. In order to optimize the codon usage for a target organism, a plurality of known genes from the said organism may be investigated for the most commonly used codons encoding the amino acids. In a subsequent step, the codons of a nuclei acid sequence from the donor organism will be optimized by replacing the codons in the donor sequence by the codons most commonly used by the target organism for encoding the same amino acids. It is to be understood that if the same codon is used preferably by both organisms, no replacement will be necessary. For various target organisms, tables with the preferred codon usages are already known in the art; see e.g., webpage at kazusa.or.jp/Kodon/E.html. Moreover, computer programs exist for the optimization, e.g., the Leto software, version 1.0 (Entelechon GmbH, Germany) or the GeneOptimizer (Geneart AG, Germany). For the optimization of a nucleic acid sequence, several criteria may be taken into account. For example, for a given amino acid, always the most commonly used codon may be selected for each codon to be exchanged. Alternatively, the codons used by the target organism may replace those in a donor sequence according to their naturally frequency. Accordingly, at some positions even less commonly used codons of the target organism will appear in the optimized nucleic acid sequence. The distribution of the different replacement codons of the target organism to the donor nucleic acid sequence may be randomly. Preferred target organisms in accordance with the present invention are recited elsewhere in this specification.

The term "expression control sequence" as used herein refers to a nucleic acid sequence which is capable of governing the expression of a nucleic acid molecule operatively linked thereto, e.g., the aforementioned first, second or third nucleic acid molecules. The expression control sequence, preferably, is a DNA a DNA nucleic acid molecule. An expression control sequence as referred to in accordance with the present invention, preferably, comprises sequence motifs which are recognized and bound by polypeptides, i.e. transcription factors. The said transcription factors shall upon binding recruit RNA polymerases, preferably, RNA polymerase I, II or III, more preferably, RNA polymerase II. Thereby transcription of a nucleic acid operatively linked to the expression control sequence will be initiated the. It is to be understood that dependent on the type of nucleic acid to be expressed, expression as meant herein may comprise transcription of RNA from the nucleic acid sequence (as suitable for, e.g., anti-sense approaches or RNAi approaches) or may comprises transcription of RNA followed by translation of the said RNA into polypeptides (as suitable for, e.g., gene expression and recombinant polypeptide production approaches). In order to govern expression of a nucleic acid sequence, the expression control sequence may be located immediately adjacent to the nucleic acid to be expressed, i.e. physically linked to the said nucleic acid at its 5' end. Alternatively, it may be located in physical proximity. In the latter case, however, the sequence must be located so as to allow functional interaction with the nucleic acid to be expressed. Preferred expression control sequences to be used in the polynucleotides of the present invention allow for a preferred expression of the first, second and/or third nucleic acid molecules in plants and, more preferably, in the seeds of the plants and, most preferably, in the endosperm or embryo. Preferably, such expression control sequences are constitutive promoters, more preferably, maize ubiquitin promoter and maize branching enzyme-1 promoter. The promoters include the endosperm-preferred promoters, preferably, the 10 kD zein promoter, the 19 kD zein promoter, and the 27 kD zein promoter. The promoters include the seed preferred promoters, preferably, maize branching enzyme 2b promoter and maize shrunken-2 promoter. For embryo-preferred expression promoters such as globulin-1 can be, preferably, used. A constitutive promoter to be used as expression control sequence according to the present invention can be, for example, the superpromoter (Ni et al., Plant J. 7:661-676, 1995; U.S. Pat. No. 5,955,646) or the PtxA promoter (PF 55368-2 US, Song H. et al., 2004, see Example 11). The tissue-specific promoter can be also active in vegetative tissue or reproductive tissue. The tissue-specific promoter active in reproductive tissue can be a seed-specific promoter. The seed-specific promoter can be, for example, the USP promoter (Bäumlein et al. 1991, Mol. Gen. Genetics 225:459-67) or the leguminB4 promoter (Bäumlein et al. 1992, Plant Journal 2(2): 233-238). The tissue-specific promoter active in vegetative tissue can be a root-specific, shoot-specific, meristem-specific or leaf-specific promoter. Additionally, suitable nucleic acid sequences for these expression control sequences are known in the art and are also described elsewhere in this specification. The terms "expression control sequence" and "regulatory sequence" will be used interchangeably hereinafter and shall have the same meaning for those skilled in the art. Most preferably, a first expression control sequence is shown in SEQ ID NO: 31, a second expression control sequence is shown in SEQ ID NO: 30 and a third expression control sequence to be used in accordance with the present invention is shown in SEQ ID NO: 29.

The term "terminator sequence" refers to a nucleic acid sequence being capable of terminating transcription in a eukaryotic cell, preferably in a plant cell and, more preferably in a seed of a plant. Terminator sequences will optimize expression of the gene in the seed including the plastids and/or cytosol of the endosperm and/or the embryo. Terminator sequences are well known in the art and have been described elsewhere in this specification. More preferably, the terminator sequences referred to herein (i.e. the first, second and third terminator sequences) are biologically active in seeds. A more preferred first terminator sequence is shown in SEQ ID NO: 32 or 34. A more preferred second terminator sequence is shown in SEQ ID NO: 35. A more preferred third terminator sequence is shown in SEQ ID NO: 33.

The term "operatively linked" as used herein means that the expression control sequence of the present invention and a nucleic acid molecule to be expressed, e.g., the first, second and/or third nucleic acid molecule, are linked so that the expression can be governed by the said expression control sequence, i.e. the expression control sequence shall be functionally linked to said nucleic acid molecule to be expressed. Accordingly, the expression control sequence and the nucleic acid molecule to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is functionally linked to the nucleic acid molecule to be expressed. The expression control sequence and the nucleic acid to be expressed are, preferably, separated by not more than 1,000 bp, 500 bp, 300 bp, 100 bp, 50 bp, 25 bp, 10 by or 5 bp.

More preferred combinations of first and second as well as first, second and third nucleic acid molecules for preferred polynucleotides of the present invention are listed in Table 3, below. Moreover, Table 4, below, further recites preferred first, second and third expression control sequences and terminators to be used in the said preferred polynucleotides.

Advantageously, it has been found in the studies underlying the present invention that expressing the nucleic acid molecules encoding the pyruvate kinase subunits comprised by the polynucleotide of the present invention increases the content of seed storage compounds and, in particular, of lipids, fatty acids, proteins or individual amino acids, in plants. Thus, the polynucleotide of the present invention is, in principle, useful for the synthesis of seed storage compounds. Moreover, they may be used to generate transgenic plants or seeds having a modified, preferably increased, amount of seed storage compounds. Such transgenic plants or seeds may be used for the manufacture of compositions containing the aforementioned seed storage compounds, such as seed oil or amino acid compositions to be used, e.g., as feed or food stuff.

The present invention also relates to a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous recombination or heterologous insertion as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion, see below. Vectors can be introduced into prokaryotic or eukaryotic cells via conventional transformation or transfection techniques. An "expression vector" according to the present invention is characterized in that it comprises an expression control sequence as referred to elsewhere in this specification. Preferred vectors, expression vectors and transformation or transfection techniques are specified elsewhere in this specification in detail.

Further, the present invention contemplates a host cell comprising the polynucleotide or the vector of the present invention or which comprises an assembled pyruvate kinase according to the present invention.

Host cells are primary cells or cell lines derived from multicellular organisms such as plants or animals. Furthermore, host cells encompass prokaryotic or eukaryotic single cell organisms (also referred to as microorganisms), e.g. bacteria, fungi including yeast or a unicellular algae. Primary cells or cell lines to be used as host cells in accordance with the present invention may be derived from the multicellular organisms, preferably from plants. Specifically preferred host cells, microorganisms or multicellular organism from which host cells may be obtained are disclosed below.

The polynucleotides or vectors of the present invention may be incorporated into a host cell or a cell of a transgenic non-human organism by heterologous insertion or homologous recombination. "Heterologous" as used in the context of the present invention refers to a polynucleotide which is inserted (e.g., by ligation) or is manipulated to become inserted to a nucleic acid sequence context which does not naturally encompass the said polynucleotide, e.g., an artificial nucleic acid sequence in a genome of an organism. Thus, a heterologous polynucleotide is not endogenous to the cell into which it is introduced, but has been obtained from another cell. Generally, although not necessarily, such heterologous polynucleotides encode proteins that are normally not produced by the cell expressing the said heterologous polynucleotide. An expression control sequence as used in a targeting construct or expression vector is considered to be "heterologous" in relation to another sequence (e.g., encoding a marker sequence or an agronomically relevant trait) if said two sequences are either not combined or operatively linked in a different way in their natural environment. Preferably, said sequences are not operatively linked in their natural environment (i.e. originate from different genes). Most preferably, said regulatory sequence is covalently joined (i.e. ligated) and adjacent to a nucleic acid to which it is not adjacent in its natural environment. "Homologous" as used in accordance with the present invention relates to the insertion of a polynucleotide in the sequence context in which the said polynucleotide naturally occurs. Usually, a heterologous polynucleotide is also incorporated into a cell by homologous recombination. To this end, the heterologous polynucleotide is flanked by nucleic acid sequences being homologous to a target sequence in the genome of a host cell or a non-human organism. Homologous recombination now occurs between the homologous sequences. However, as a result of the homologous recombination of the flanking sequences, the heterologous polynucleotide will be inserted, too. How to prepare suitable target constructs for homologous recombination and how to carry out the said homologous recombination is well known in the art.

A host cell comprising the assembled pyruvate kinase is also, preferably, obtainable by introducing into the host cell separate nucleic acid molecules encoding the pyruvate kinase subunits, i.e. a separate first and second nucleic acid molecule in expressible form (e.g. in the form of separate expression vectors) or a first, second and third nucleic acid molecule. Upon expression of the pyruvate kinase subunits a assembled pyruvate kinase will be generated within the said host cell.

The present invention encompasses a method for the manufacture of a pyruvate kinase polypeptide being capable of increasing the seed storage compound content when expressed in transgenic plants comprising:

(a) expressing the polynucleotide of the present invention in a host cell under conditions allowing assembly of the pyruvate kinase polypeptide; and
(b) obtaining the said assembled pyruvate kinase polypeptide from the host cell.

As set forth already elsewhere in this specification, the polynucleotide of the present invention comprises nucleic acid molecules encoding specific pyruvate kinase subunits. Upon expression in a cell or a cellular extract mimicking intracellular physiological conditions, the said subunits will form the functional pyruvate kinase consisting of the said subunits. This multimeric complex of subunits is also called assembled pyruvate kinase in the context of the present invention. The assembled pyruvate kinase polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention also relates to an assembled pyruvate kinase polypeptide comprising the polypeptides encoded by the polynucleotide of the present invention or which is obtainable by the aforementioned method of the present invention.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like. The terms "polypeptide", "peptide" or "protein" are used interchangeable throughout this specification. The polypeptide of the present invention shall exhibit pyruvate kinase activity and, more preferably, it shall be capable of increasing the amount of seed storage compounds, preferably, fatty acids, lipids, proteins or amino acids, when present in plant seeds as referred to above.

The present invention also relates to an antibody which specifically recognizes the assembled pyruvate kinase polypeptide of the present invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a human or humanized antibody or primatized, chimerized or fragment thereof. Also comprised as antibodies by the present invention are a bispecific antibody, a synthetic antibody, an antibody fragment, such as Fab, Fv or scFv fragments etc., or a chemically modified derivative of any of these. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré Meth. Enzymol. 73 (1981), 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of compounds interacting with the proteins according to the invention.

The present invention also relates to a transgenic non-human organism comprising the polynucleotide, the vector, the host cell or the assembled pyruvate kinase of the present invention.

The term "non-human transgenic organism", preferably, relates to a plant, an algae, an animal or a multicellular microorganism. The polynucleotide or vector may be present in the cytoplasm of the organism or may be incorporated into the genome either heterologous or by homologous recombination. Host cells, in particular those obtained from plants or animals, may be introduced into a developing embryo in order to obtain mosaic or chimeric organisms, i.e. non-human transgenic organisms comprising the host cells of the present invention. Preferably, the non-human transgenic organism expresses the polynucleotide of the present invention in order to produce the polypeptide in an amount resulting in a detectable biological activity as specified above. Suitable transgenic organisms are, preferably, all those organisms which are capable of synthesizing fatty acids or lipids. Preferred organisms and methods for transgenesis are disclosed in detail below. A transgenic organism or tissue may comprise one or more transgenic cells. Preferably, the organism or tissue is substantially consisting of transgenic cells (i.e., more than 80%, preferably 90%, more preferably 95%, most preferably 99% of the cells in said organism or tissue are transgenic). The term “transgene” as used herein refers to any nucleic acid sequence, which is introduced into the genome of a cell or which has been manipulated by experimental manipulations including techniques such as chimeraplasty or genoplasty. Preferably, said sequence is resulting in a genome which is significantly different from the overall genome of an organism (e.g., said sequence, if endogenous to said organism, is introduced into a location different from its natural location, or its copy number is increased or decreased). A trans-gene may comprise an endogenous polynucleotide (i.e. a polynucleotide having a nucleic acid sequence obtained from the same organism or host cell) or may be obtained from a different organism or hast cell, wherein said different organism is, preferably an organism of another species and the said different host cell is, preferably, a different microorganism, a host cell of a different origin or derived from a an organism of a different species.

Particularly preferred as a plant to be used in accordance with the present invention is an oil producing plant or algae species. Most preferably, the said plant is selected from the group consisting of canola, linseed, soybean, sunflower, maize (corn), oat, rye, barley, wheat, rice, pepper, tagetes, cotton, oil palm, coconut palm, flax, castor and peanut.

The seed storage compound content weight percentage is increased in the transgenic non-human organism as compared to an empty vector control, preferably, by at least 1, 2.5, 5, 7.5, 10, 12.5, 15, 17.5, 20, 22.5, 25, 27.5 or 30% by weight or more, preferably by 5% by weight or more, more preferably by 7.5% by weight or more and even more preferably by 10% by weight or more as compared to an empty vector control.

Also preferred as non-human transgenic organisms in accordance with the present invention are seeds of plants and, in particular, of the plants recited above and herein below, wherein said transgenic plant seeds comprise a polynucleotide of the present invention. Preferably, the polynucleotide of the present invention is expressed in the endosperm and/or embryo plastids and/or cytosol of the said plant seeds. For example, seeds may be transformed into a inbred or hybrid using particle bombardment as set forth in U.S. Pat. Nos. 4,945,050; 5,036,006; 5,100,792; 5,302,523; 5,464,765; 5,120,657; 6,084,154; and the like. More preferably, transformation may be achieved using *Agrobacterium* transformation, as described in U.S. Pat. Nos. 5,591,616; 5,731,179; 5,981,840; 6,162,965; 6,420,630, U.S. patent application publication number 2002/0104132.

A transgenic non-human organism comprising the assembled pyruvate kinase is also, preferably, obtainable by introducing into the organism separate nucleic acid molecules encoding the pyruvate kinase subunits, i.e. a separate first and second nucleic acid molecule in expressible form (e.g. in the form of separate expression vectors) or a first, second and third nucleic acid molecule. Upon expression of the pyruvate kinase subunits a assembled pyruvate kinase will be generated within the said organism.

In principle, the present invention, however, also relates to a seed comprising the assembled pyruvate kinase polypeptide of the present invention in its endosperm, embryo plastids or cytosol, wherein said seed is further characterized in that it has:

(a) an increase, preferably of at least 5%, in oil content in comparison to an isogenic seed,
(b) an increase, preferably of 1 to 5%, in embryo weight in comparison to an isogenic seed,
(c) an increase; preferably of 1 to 5%, in the amino acid content in comparison to an isogenic seed for an amino acid selected from the group consisting of: aspartic acid, threonine, glycine, cysteine, valine, methionine, isoleucine, histidine, lysine, arginine, and tryptophan, or
(d) an increase, preferably of 1 to 5%, of the protein content.

The seed is a remarkable factory, composed of pericarp, embryo, and endosperm. Most protein and oil are synthesized and stored in the embryo, while the endosperm tissue, usually, contains the starch-based energy store. Sucrose is delivered to developing seeds from the leaves and converted to hexose sugars, such as glucose, which in turn are used for respiration and synthesis of storage compounds such as starch, protein and oil. A non-human transgenic seed as used herein encompasses seeds from an inbred plant line or any seed including F1 hybrid, F2 seeds.

The term “isogenic seed” means the untransformed parental inbred seed or any seed from which the transgenic seed of the invention is derived. It also includes seeds from non-transgenic segregants of the transgenic plants carrying the combination of SMPs referred to in accordance with the present invention. Said isogenic seed does not express the polynucleotide of the present invention nor comprises the assembled pyruvate kinase.

All percentages of content or weight referred to above are, preferably, percent dry weight.

As set forth above, amino acids, which are increased in the seed of the invention, are preferably selected from the group consisting of aspartic acid, threonine, glycine, cysteine, valine, methionine, isoleucine, histidine, lysine, arginine, and tryptophan. More preferably, the seed of the invention demonstrates increases of at least 1 to 5% in amino acids selected from the group consisting of aspartic acid, threonine, glycine, cysteine, valine, methionine, isoleucine, histidine, lysine, arginine, and tryptophan. Most preferably, seed of the invention demonstrates increases of at least 1 to 5% in amino acids selected from the group consisting of threonine, cysteine, valine, methionine, lysine, arginine and tryptophan. Any combination of the most preferred amino acids may be selected in this embodiment of the invention. For example, in one preferred embodiment, tryptophan, arginine and lysine are increased by at least 1 to 5% in the transgenic corn seed of the invention. In another preferred embodiment, valine, lysine, and tryptophan are increased by at least 1 to 5% in the seed of the invention. In yet another preferred embodiment, valine, methionine, and lysine are increased by at least 1 to 5%, and so forth.

In accordance with the invention, the protein content of the seed of the invention is preferably increased by at least 1%, more preferably increased by at least 3%, and most preferably increased by at least 5%, over the protein content of isogenic seed which does not express the polynucleotide of the present invention or comprises the assembled pyruvate kinase in the endosperm and/or embryo plastids and/or cytosol.

The oil content of the seed of the invention is increased by at least 5% over the oil content of isogenic seed, more preferably increased by at least 10%, and most preferably increased by at least 15%, over the oil content of isogenic seed which does not express the polynucleotide of the present invention or comprises the assembled pyruvate kinase in the endosperm and/or embryo plastids and/or cytosol.

The non-human transgenic seed of the invention is particularly useful as animal feed, since the improved amino acid profile, protein content, and/or oil content of the invention will allow farmers to feed less grain to animals while obtaining the same or higher yield of meat from the animals. The potential for reducing costs associated with meat production using the transgenic corn seed of the invention is great. The improved amino acid profile and oil content of the transgenic corn seed of the invention will allow animal feed producers to reduce feed cost and minimize use of feed-additives in animal feed, thus minimizing possible contamination of the human food chain with infectious agents such as the bovine spongiform encephalopathy agent. Therefore, the present invention also encompasses the use of a transgenic non-human organism and, preferably a seed as specified herein above, for the manufacture of food or feed stuff.

The present invention further relates to a method for the manufacture of a seed storage compound comprising the steps of:

(a) cultivating the host cell or the transgenic non-human organism of the present invention or a host cell or a non-human transgenic organism comprising the assembled pyruvate kinase under conditions allowing synthesis of the said seed storage compound; and
(b) obtaining the said seed storage compound from the host cell or the transgenic non-human organism.

As is evident from the foregoing, the term "seed storage compound" as used herein, preferably, refers to proteins, amino acids, fatty acids, lipids or mixtures of those compounds. More preferred lipids are those listed in the accompanying Table 1. More preferred fatty acids are listed in the accompanying Table 2. However, seed storage compound include also other compounds found in seeds such as sugars or other carbohydrates.

A plant cell comprising the assembled pyruvate kinase of the present invention may be obtained by introducing and expressing a polynucleotide of the present invention into the plant (i.e. a single polynucleotide comprising two or three expression units for the said first, second and third nucleic acid molecule) or by introducing the first, second and third nucleic acid molecules separately. This may be achieved, e.g., via introduction of separate vectors, wherein each vector comprises either the first and second or first second and third nucleic acid molecule, preferably, in expressible form. Suitable measures for providing nucleic acid molecules in expressible form are discussed elsewhere in this specification. Alternatively, the said first, second and third nucleic acid molecules, respectively, may be introduced into the genome of the host cell by site specific integration techniques whereby expression of the integrated nucleic acid molecule will be governed by an endogenous expression control sequence. Moreover, it is to be understood that the first and second and first, second and third nucleic acid molecules, respectively, need to be expressed in the host cell whereby the polypeptide subunits will be produced which subsequently will assemble the assembled pyruvate kinase polypeptide of the present invention.

The present invention, furthermore, encompasses a method for the manufacture of a plant having a modified amount of an seed storage compound comprising the steps of:

(a) introducing the polynucleotide or the vector of the present invention into a plant cell; and
(b) generating a transgenic plant from the said plant cell, wherein the polypeptide encoded by the polynucleotide modifies the amount of the said seed storage compound in the transgenic plant.

It is to be understood that the polynucleotides or the vector referred to in accordance with the above method of the present invention may be introduced into the plant cell by any of the aforementioned insertion or recombination techniques.

In a preferred embodiment of the aforementioned method of the invention, the amount of said seed storage compound is significantly increased compared to a control as specified above. The increase is, more preferably, an increase in the amount by weight of at least 1, 2.5, 5, 7.5, 10, 12.5, 15, 17.5, 20, 22.5 or 25% as compared to a control. It is to be understood that the first, second and third nucleic acid molecules comprised by the polynucleotide of the present invention shall be expressed in sense orientation, i.e. in a manner allowing transcription and translation of the pyruvate kinase subunits encoded by the said nucleic acid molecules.

In an alternative, but nevertheless also preferred embodiment of the method of the present invention, the amount of said seed storage compound is significantly decreased compared to a control, preferably an empty vector control as specified above. The decrease is, more preferably, a decrease in the amount by weight of at least 1, 2.5, 5, 7.5, 10, 12.5, 15, 17.5, 20, 22.5 or 25% as compared to a control. It is to be understood that the first, second and third nucleic acid molecules comprised by the polynucleotide of the present invention shall be expressed in anti-sense orientation. The transcription of antisense-RNA of the first, second and third nucleic acid molecule shall result in an inhibition of expression of corresponding first, second and third nucleic acid molecules in sense orientation by mechanisms such as antisense inhibition or RNA interference which are describe in detail elsewhere in this specification. Due to the inhibition of expression, the pyruvate kinase activity and the content of seed storage compounds will decrease in such plants.

From the foregoing, it is to understood further that the present invention also contemplates a method for the manufacture of a plant having a modified amount of an seed storage compound comprising the steps of:

(a) obtaining a plant cell comprising the assembled pyruvate kinase polypeptide of the present invention; and
(b) generating a transgenic plant from the said plant cell, wherein the polypeptide encoded by the polynucleotide modifies the amount of the said seed storage compound in the transgenic plant.

The aforementioned methods of the present invention may be also used to manufacture a plant having an altered total seed storage compound content in its seeds or a plant having an altered total seed storage compound content and altered levels of seed storage compounds in its seeds. Such plants are suitable sources for seed oil and may be used for the large scale manufacture thereof. They may also be used for the manufacture of feed- and food stuff in general.

Further preferred embodiments of the compounds, methods and uses according to the present invention are described in the following. Moreover, the terms used above will be explained in more detail. The pyruvate kinase subunit polypeptides of the present invention are also referred to as Storage Metabolism proteins (SMP) herein below.

Before the present compounds, compositions, and methods described in more detail, it is to be understood that this invention is not limited to specific polynucleotides, specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

The term "transgenic" or "recombinant" when used in reference to a cell or an organism (e.g., with regard to a barley plant or plant cell) refers to a cell or organism which contains a transgene, or whose genome has been altered by the introduction of a transgene. A transgenic organism or tissue may comprise one or more transgenic cells. Preferably, the organism or tissue is substantially consisting of transgenic cells (i.e., more than 80%, preferably 90%, more preferably 95%, most preferably 99% of the cells in said organism or tissue are transgenic). The term "transgene" as used herein refers to any nucleic acid sequence, which is introduced into the genome of a cell or which has been manipulated by experimental manipulations by man. Preferably, said sequence is resulting in a genome which is different from a naturally occurring organism (e.g., said sequence, if endogenous to said organism, is introduced into a location different from its natural location, or its copy number is increased or decreased). A transgene may be an "endogenous DNA sequence", "an "exogenous DNA sequence" (e.g., a foreign gene), or a "heterologous DNA sequence". The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

The term "wild-type", "natural" or of "natural origin" means with respect to an organism, polypeptide, or nucleic acid sequence, that said organism is naturally occurring or available in at least one naturally occurring organism which is not changed, mutated, or otherwise manipulated by man.

The terms "heterologous nucleic acid sequence" or "heterologous DNA" are used interchangeably to refer to a nucleotide sequence, which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. A promoter, transcription regulating sequence or other genetic element is considered to be "heterologous" in relation to another sequence (e.g., encoding a marker sequence or am agronomically relevant trait) if said two sequences are not combined or differently operably linked their natural environment. Preferably, said sequences are not operably linked in their natural environment (i.e. come from different genes). Most preferably, said regulatory sequence is covalently joined and adjacent to a nucleic acid to which it is not adjacent in its natural environment.

As set forth above already, the present invention pertains to combinations of isolated nucleic acid molecules that encode SMP polypeptides (i.e. pyruvate kinase subunits) or biologically active portions thereof, as well as nucleic acid fragments sufficient for use as hybridization probes or primers for the identification or amplification of an SMP-encoding nucleic acid (e.g., SMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one, which is substantially separated from other nucleic acid molecules, which are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism, from which the nucleic acid is derived. For example, in various embodiments, the isolated SMP nucleic acid molecule can contain less than about 5 kb, 4 kb, 3 kb, 2 kb, 1 kb, 0.5 kb or 0.1 kb of nucleotide sequences, which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or chemical precursors or other chemicals when chemically synthesized.

A polynucleotide of the present invention, e.g., a nucleic acid molecule consisting of a combination of isolated nucleotide sequences as referred to above, or a portion thereof, can be constructed using standard molecular biology techniques and the sequence information provided herein. For example, an *Arabidopsis thaliana* or *Physcomitrella patens, Brassica napus, Glycine max* or *Linum usitatissimum* SMP cDNA can be isolated from an *Arabidopsis thaliana* or *Physcomitrella patens, Brassica napus, Glycine max* or *Linum usitatissimum* library using all or portion of one of the sequences disclosed herein as a hybridization probe and standard hybridization techniques (e.g., as described in Sambrook et al. 1989, Molecular Cloning: A Laboratory Manual. 2nd, ed., Cold Spring Harbor Laboratory, Cold Spring Harbor Laboratory Press, Cold Spring Harbor, N.Y.). Moreover, a nucleic acid molecule encompassing all or a portion of one of the sequences disclosed herein can be isolated by the polymerase chain reaction using oligonucleotide primers designed based upon this sequence (e.g., a nucleic acid molecule encompassing all or a portion of one of the sequences disclosed herein can be isolated by the polymerase chain reaction using oligonucleotide primers designed based upon this same sequence disclosed herein). For example, mRNA can be isolated from plant cells (e.g., by the guanidinium-thiocyanate extraction procedure of Chirgwin et al. 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences disclosed herein and may contain restriction enzyme sites or sites for ligase independent cloning to construct the combinations described by this invention. A nucleic acid of the invention can be amplified using cDNA or, alternatively, genomic DNA, as a template and appropriate oligonucleotide primers according to standard PCR amplification techniques. The nucleic acids so amplified can be cloned into an appropriate vector in the combinations described by the present invention or variations thereof and characterized by DNA sequence analysis. Furthermore, oligonucleotides corresponding to an SMP nucleotide sequence can be prepared by standard synthetic techniques, e.g., using an automated DNA synthesizer.

In another preferred embodiment, an isolated nucleic acid molecule included in a combination of the invention comprises a nucleic acid molecule, which is a complement of one of the nucleotide sequences disclosed herein, or a portion thereof. A nucleic acid molecule, which is complementary to one or more of the nucleotide sequences disclosed herein, is one which is sufficiently complementary to one or more of the nucleotide sequences disclosed herein, such that it can hybridize to one or more of the nucleotide sequences disclosed herein, thereby forming a stable duplex.

In still another preferred embodiment, an isolated nucleic acid molecule in the combinations of the invention comprises a nucleotide sequence, which is at least about 50-60%, preferably at least about 60-70%, more preferably at least about 70-80%, 80-90%, or 90-95%, and even more preferably at least about 95%, 96%, 97%, 98%, 99% or more homologous to one or more nucleotide sequence disclosed herein, or a portion thereof. In an additional preferred embodiment, an isolated nucleic acid molecule in the combinations of the invention comprises a nucleotide sequence which hybridizes, e.g., hybridizes under stringent conditions, to one or more of the nucleotide sequences disclosed herein, or a portion thereof. For the purposes of the invention hybridization means preferably hybridization under conditions equivalent to hybridization in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C. to a nucleic acid comprising 50 to 200 or more consecutive nucleotides. A further preferred, non-limiting example of stringent hybridization conditions includes washing with a solution having a salt concentration of about 0.02 molar at pH 7 at about 60° C.

Moreover, the nucleic acid molecule in the combinations of the invention can comprise only a portion of the coding region of one of the sequences disclosed herein, for example a fragment, which can be used as a probe or primer or a fragment encoding a biologically active portion of an SMP. The nucleotide sequences determined from the cloning of the SMP *Arabidopsis thaliana* allows for the generation of probes and primers designed for use in identifying and/or cloning SMP homologues in other cell types and organisms, as well as SMP homologues from other plants or related species. Therefore this invention also provides compounds comprising the combinations of nucleic acids disclosed herein, or fragments thereof. These compounds include the nucleic acid combinations attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth herein, an anti-sense sequence of one of the sequences set forth herein, or naturally occurring mutants thereof. Primers based on a nucleotide sequence disclosed herein can be used in PCR reactions to clone SMP homologues for the combinations described by this inventions or variations thereof. Probes based on the SMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an SMP, such as by measuring a level of an SMP-encoding nucleic acid in a sample of cells, e.g., detecting SMP mRNA levels, or determining whether a genomic SMP gene has been mutated or deleted.

In one embodiment, the polynucleotide of the invention encodes a combination of proteins or portions thereof, which include amino acid sequences, which are sufficiently homologous to an amino acid encoded by a sequence disclosed herein, such that the protein or portion thereof maintains the same or a similar function as the wild-type protein. As used herein, the language "sufficiently homologous" refers to proteins or portions thereof, which have amino acid sequences, which include a minimum number of identical or equivalent (e.g., an amino acid residue, which has a similar side chain as an amino acid residue in one of the ORFs) amino acid residues to an amino acid sequence, such that the protein or portion thereof is able to participate in the metabolism of compounds necessary for the production of seed storage compounds in plants, construction of cellular membranes in microorganisms or plants, or in the transport of molecules across these membranes. Examples of SMP-encoding nucleic acid sequences are set forth herein.

As altered or increased sugar, amino acid, protein and/or fatty acid production is a general trait wished to be inherited into a wide variety of plants like maize, wheat, rye, oat, triticale, rice, barley, soybean, peanut, cotton, canola, manihot, pepper, sunflower, sugar beet, and tagetes, solanaceous plants like potato, tobacco, eggplant, and tomato, *Vicia* species, pea, alfalfa, bushy plants (coffee, cacao, tea), *Salix* species, trees (oil palm, coconut) and perennial grasses and forage crops, these crop plants are also preferred target plants for genetic engineering as one further embodiment of the present invention.

Portions of proteins encoded by the SMP nucleic acid molecules of the invention are preferably biologically active portions of one of the SMPs. As used herein, the term "biologically active portion of an SMP" is intended to include a portion, e.g., a domain/motif, of an SMP that participates in the metabolism of compounds necessary for the biosynthesis of seed storage compounds or its regulation. To determine whether an SMP or a biologically active portion thereof can participate in the metabolism of compounds necessary for the production of seed storage compounds and cellular membranes, an assay of enzymatic activity may be performed. Such assay methods are well known to those skilled in the art, and as described in the accompanying Examples. Preferably, the biological activity can be measured as pyruvate kinase activity. Biologically active portions of an SMP include peptides comprising amino acid sequences derived from the amino acid sequence of an SMP (e.g., an amino acid sequence encoded by a nucleic acid disclosed herein or the amino acid sequence of a protein homologous to an SMP, which include fewer amino acids than a full length SMP or the full length protein which is homologous to an SMP) and exhibit at least one activity of an SMP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of an SMP. Moreover, other biologically active portions, in which other regions of the protein are deleted, can be prepared by recombinant techniques and evaluated for one or more of the activities described herein. Preferably, the biologically active portions of an SMP include one or more selected domains/motifs or portions thereof having biological activity. Additional nucleic acid fragments encoding biologically active portions of an SMP can be prepared by isolating a portion of one of the sequences, expressing the encoded portion of the SMP or peptide (e.g., by recombinant expression in vitro) and assessing the activity of the encoded portion of the SMP or peptide.

The invention further encompasses combinations of nucleic acid molecules that differ from one of the nucleotide sequences disclosed herein (and portions thereof) due to degeneracy of the genetic code and thus encode the same SMP as that encoded by the nucleotide sequences disclosed herein. In a further embodiment, the combinations of nucleic acid molecule of the invention encode one or more full-length proteins, which are substantially homologous to an amino acid sequence of a polypeptide encoded by an open reading frame disclosed herein.

In one embodiment, the full-length nucleic acid or protein, or fragment of the nucleic acid or protein, is from *Arabidopsis thaliana*. In addition to the *Arabidopsis thaliana* SMP nucleotide sequences disclosed herein, it will be appreciated by those skilled in the art that DNA sequence polymorphisms that lead to changes in the amino acid sequences of SMPs may exist within a population *Arabidopsis thaliana*). Such genetic polymorphism in the SMP gene may exist among individuals within a population due to natural variation. As used herein, the terms "gene" and "recombinant gene" refer to nucleic acid molecules comprising an open reading frame encoding an SMP, preferably an *Arabidopsis thaliana* SMP. Such natural variations can typically result in 1-40% variance in the nucleotide sequence of the SMP gene. Any and all such nucleotide variations and resulting amino acid polymorphisms in SMP that are the result of natural variation and that do not alter the functional activity of SMPs are intended to be within the scope of the invention.

The invention further encompasses combinations of nucleic acid molecules corresponding to natural variants and non-*Arabidopsis thaliana* orthologs of the *Arabidopsis thaliana* SMP nucleic acid sequence disclosed herein. Nucleic acid molecules corresponding to natural variants and non-*Arabidopsis thaliana* orthologs of the *Arabidopsis thaliana* SMP cDNA described herein can be isolated based on their homology to *Arabidopsis thaliana* SMP nucleic acid disclosed herein using the *Arabidopsis thaliana* cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule is at least 15 nucleotides in length and hybridizes under stringent conditions to the nucleic acid molecule comprising a nucleotide sequence disclosed herein. In other embodiments, the nucleic acid is at least 30, 50, 100, 250, or more nucleotides in length. As used herein, the term "hybridizes under stringent conditions" is intended to describe conditions for hybridization and washing, under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y., 1989: 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule that hybridizes under stringent conditions to a sequence disclosed herein corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In addition to naturally-occurring variants of the SMP sequence that may exist in the population, the skilled artisan will further appreciate that changes can be introduced by mutation into a nucleotide sequence disclosed herein, thereby leading to changes in the amino acid sequence of the encoded SMP, without altering the functional ability of the SMP. For example, nucleotide substitutions leading to amino acid substitutions at "non-essential" amino acid residues can be made in a sequence disclosed herein. A "non-essential" amino acid residue is a residue that can be altered from the wild-type sequence of one of the SMPs without altering the activity of said SMP, whereas an "essential" amino acid residue is required for SMP activity. Other amino acid residues, however, (e.g., those that are not conserved or only semi-conserved in the domain having SMP activity) may not be essential for activity and thus are likely to be amenable to alteration without altering SMP activity. Accordingly, another aspect of the invention pertains to nucleic acid molecules encoding SMPs that contain changes in amino acid residues that are not essential for SMP activity. Such SMPs differ in amino acid sequence from a sequence yet retain at least one of the SMP activities described herein. In one embodiment, the isolated nucleic acid molecule comprises a nucleotide sequence encoding a protein, wherein the protein comprises an amino acid sequence at least about 50% homologous to an amino acid sequence encoded by a nucleic acid disclosed herein and is capable of participation in the metabolism of compounds necessary for the production of seed storage compounds in plants. Preferably, the protein encoded by the nucleic acid molecule is at least about 50-60% homologous to one of the sequences encoded by a nucleic acid disclosed herein, more preferably at least about 60-70% homologous to one of the sequences encoded by a nucleic acid disclosed herein, even more preferably at least about 70-80%, 80-90%, 90-95% homologous to one of the sequences encoded by a nucleic acid disclosed herein, and most preferably at least about 96%, 97%, 98%, or 99% homologous to one of the sequences encoded by a nucleic acid disclosed herein. To determine the percent homology of two amino acid sequences (e.g., one of the sequences encoded by a nucleic acid disclosed herein and a mutant form thereof), or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences encoded by a nucleic acid disclosed herein) is occupied by the same amino acid residue or nucleotide as the corresponding position in the other sequence (e.g., a mutant form of the sequence selected from the polypeptide encoded by a nucleic acid disclosed herein), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). The sequence identity can be generally based on any one of the full length sequences disclosed herein as 100%. For the purposes of the invention, the percent sequence identity between two nucleic acid or polypeptide sequences is determined using the Vector NTI 7.0 (PC) software package (InforMax, 7600 Wisconsin Ave., Bethesda, Md. 20814). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide sequence is equivalent to an uracil nucleotide.

An isolated nucleic acid molecule encoding an SMP homologous to a protein sequence encoded by a nucleic acid disclosed herein can be created by introducing one or more nucleotide substitutions, additions or deletions into a nucleotide sequence disclosed herein such that one or more amino acid substitutions, additions or deletions are introduced into the encoded protein. Mutations can be introduced into one of the sequences disclosed herein by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an SMP is preferably replaced with another amino acid residue from the same side chain family. Alternatively, in another embodiment, mutations can be introduced randomly along all or part of an SMP coding sequence, such as by saturation mutagenesis, and the resultant mutants can be screened for an SMP activity described herein to identify mutants that retain SMP activity. Following mutagenesis of one of the sequences disclosed herein, the encoded protein can be expressed recombinantly, and the activity of the protein can be determined using, for example, assays described herein (see accompanying Examples).

Combinations of SMPs are preferably produced by recombinant DNA techniques. For example, one or more nucleic acid molecule encoding the protein is cloned into an expression vector (as described above), the expression vector is introduced into a host cell (as described herein), and the SMPs are expressed in the host cell. The SMPs can then be isolated from the cells by an appropriate purification scheme using standard protein purification techniques. Alternative to recombinant expression, one or more SMP or peptide thereof can be synthesized chemically using standard peptide synthesis techniques. Moreover, native SMPs can be isolated from cells, for example using an anti-SMP antibody, which can be produced by standard techniques utilizing an SMP or fragment thereof of this invention.

The invention also provides combinations of SMP chimeric or fusion proteins. As used herein, an SMP "chimeric protein" or "fusion protein" comprises an SMP polypeptide operatively linked to a non-SMP polypeptide. An "SMP polypeptide" refers to a polypeptide having an amino acid sequence corresponding to an SMP, whereas a "non-SMP polypeptide" refers to a polypeptide having an amino acid sequence corresponding to a protein which is not substantially homologous to the SMP, e.g., a protein which is different from the SMP, and which is derived from the same or a different organism. Within the fusion protein, the term "operatively linked" is intended to indicate that the SMP polypeptide and the non-SMP polypeptide are fused to each other so that both sequences fulfill the proposed function attributed to the sequence used. The non-SMP polypeptide can be fused to the N-terminus or C-terminus of the SMP polypeptide. For example, in one embodiment, the fusion protein is a GST-SMP (glutathione S-transferase) fusion protein in which the SMP sequences are fused to the C-terminus of the GST sequences. Such fusion proteins can facilitate the purification of recombinant SMPs. In another embodiment, the fusion protein is an SMP containing a heterologous signal sequence at its N-terminus. In certain host cells (e.g., mammalian host cells), expression and/or secretion of an SMP can be increased through use of a heterologous signal sequence.

Preferably, a combination of SMP chimeric or fusion proteins of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). An SMP-encoding nucleic acid can be cloned into such an expression vector such that the fusion moiety is linked in-frame to the SMP.

In addition to the nucleic acid molecules encoding SMPs described above, another aspect of the invention pertains to combinations of isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire SMP coding strand, or to only a portion thereof. In one embodiment, an antisense nucleic acid molecule is antisense to a "coding region" of the coding strand of a nucleotide sequence encoding an SMP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding SMP. The term "noncoding region" refers to 5' and 3' sequences that flank the coding region that are not translated into amino acids (i.e., also referred to as 5' and 3' untranslated regions).

Given the coding strand sequences encoding SMP disclosed herein (e.g., the sequences set forth herein), combinations of antisense nucleic acids of the invention can be designed according to the rules of Watson and Crick base pairing. The antisense nucleic acid molecule can be complementary to the entire coding region of SMP mRNA, but more preferably is an oligonucleotide that is antisense to only a portion of the coding or noncoding region of SMP mRNA. For example, the antisense oligonucleotide can be complementary to the region surrounding the translation start site of SMP mRNA. An antisense oligonucleotide can be, for example, about 5, 10, 15, 20, 25, 30, 35, 40, 45, or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydro-uracil, beta-D-galactosylqueosine, inosine, N-6-isopentenyladenine, 1-methyl-guanine, 1-methylinosine, 2,2-dimethylguanine, 2-methyladenine, 2-methylguanine, 3-methylcytosine, 5-methyl-cytosine, N-6-adenine, 7-methylguanine, 5-methyl-aminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector, into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand, interfering, RNA construct can be used to cause a down-regulation of the SMP mRNA level and SMP activity in transgenic plants. This requires transforming the plants with a chimeric construct containing a portion of the SMP sequence in the sense orientation fused to the antisense sequence of the same portion of the SMP sequence. A DNA linker region of variable length can be used to separate the sense and antisense fragments of SMP sequences in the construct.

RNA interference (RNAi) approaches can be applied to modulate and, preferably down-regulate, the activity of the polypeptide encoded by the polynucleotide of the present invention. Thereby, an organism may be depleted of seed storage compounds including amino acids, proteins, fatty acids and/or lipids. As used herein, the term "RNA interference (RNAi)" refers to selective intracellular degradation of RNA used to silence expression of a selected target gene, i.e. the polynucleotide of the present invention. RNAi is a process of sequence-specific, post-transcriptional gene silencing in organisms initiated by double-stranded RNA (dsRNA) that is homologous in sequence to the gene to be silenced. The RNAi technique involves small interfering RNAs (siRNAs) that are complementary to target RNAs (encoding a gene of interest) and specifically destroy the known mRNA, thereby diminishing or abolishing gene expression. RNAi is generally used to silence expression of a gene of interest by targeting mRNA, however, any type of RNA is encompassed by the RNAi methods of the invention. Briefly, the process of RNAi in the cell is initiated by long double stranded RNAs (dsRNAs) being cleaved by a ribonuclease, thus producing siRNA duplexes. The siRNA binds to another intracellular enzyme complex which is thereby activated to target whatever mRNA molecules are homologous (or complementary) to the siRNA sequence. The function of the complex is to target the homologous mRNA molecule through base pairing interactions between one of the siRNA strands and the target mRNA. The mRNA is then cleaved approximately 12 nucleotides from the 3' terminus of the siRNA and degraded. In this manner, specific mRNAs can be targeted and degraded, thereby resulting in a loss of protein expression from the targeted mRNA. A complementary nucleotide sequence as used herein refers to the region on the RNA strand that is complementary to an RNA transcript of a portion of the target gene. The term "dsRNA" refers to RNA having a duplex structure comprising two complementary and anti-parallel nucleic acid strands. Not all nucleotides of a dsRNA necessarily exhibit complete Watson-Crick base pairs; the two RNA strands may be substantially complementary. The RNA strands forming the dsRNA may have the same or a different number of nucleotides, with the maximum number of base pairs being the number of nucleotides in the shortest strand of the dsRNA. Preferably, the dsRNA is no more than 49, more preferably less than 25, and most preferably between 19 and 23, nucleotides in length. dsRNAs of this length are particularly efficient in inhibiting the expression of the target gene using RNAi techniques. dsRNAs are subsequently degraded by a ribonuclease enzyme into short interfering RNAs (siRNAs). RNAi is mediated by small interfering RNAs (siRNAs). The term "small interfering RNA" or "siRNA" refers to a nucleic acid molecule which is a double stranded RNA agent that is complementary to i.e., able to base-pair with, a portion of a target RNA (generally mRNA), i.e. the polynucleotide of the present invention being RNA. siRNA acts to specifically guide enzymes in the host cell to cleave the target RNA. By virtue of the specificity of the siRNA sequence and its homology to the RNA target, siRNA is able to cause cleavage of the target RNA strand, thereby inactivating the target RNA molecule. Preferably, the siRNA which is sufficient to mediate RNAi comprises a nucleic acid sequence comprising an inverted repeat fragment of the target gene and the coding region of the gene of interest (or portion thereof). Also preferably, a nucleic acid sequence encoding a siRNA comprising a sequence sufficiently complementary to a target gene is operatively linked to a expression control sequence. Thus, the mediation of RNAi to inhibit expression of the target gene can be modulated by said expression control sequence. Preferred expression control sequences are those which can be regulated by a exogenous stimulus, such as the tet operator whose activity can be regulated by tetracycline or heat inducible promoters. Alternatively, an expression control sequence may be used which allows tissue-specific or preferred expression of the siRNA. The complementary regions of the siRNA allow sufficient hybridization of the siRNA to the target RNA and thus mediate RNAi. In mammalian cells, siRNAs are approximately 21-25 nucleotides in length (see Tuschl et al. 1999 and Elbashir et al. 2001). The siRNA sequence needs to be of sufficient length to bring the siRNA and target RNA together through complementary base-pairing interactions. The siRNA used with the Tet expression system of the invention may be of varying lengths. The length of the siRNA is preferably greater than or equal to ten nucleotides and of sufficient length to stably interact with the target RNA; specifically 15-30 nucleotides; more specifically any integer between 15 and 30 nucleotides, most preferably 15, 16, 17, 18, 19, 20, 21, 22, 23, 24, 25, 26, 27, 28, 29, and 30. By "sufficient length" is meant an oligonucleotide of greater than or equal to 15 nucleotides that is of a length great enough to provide the intended function under the expected condition. By "stably interact" is meant interaction of the small interfering RNA with target nucleic acid (e.g., by forming hydrogen bonds with complementary nucleotides in the target under physiological conditions). Generally, such complementarity is 100% between the siRNA and the RNA target, but can be less if desired, preferably 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences. Methods relating to the use of RNAi to silence genes in organisms are well known in the art (see, for example, Fire et al., Nature (1998) 391:806-811; Fire, Trends Genet. 15, 358-363 (1999); Sharp, RNA interference 2001. Genes Dev. 15, 485-490 (2001); Hammond et al. Nature Rev. Genet. 2, 1110-1119 (2001); Tuschl, Chem. Biochem. 2, 239-245 (2001); Hamilton et al., Science 286, 950-952 (1999); Hammond et al., Nature 404, 293-296 (2000); Zamore et al., Cell 101, 25-33 (2000); Bernstein et al., Nature 409, 363-366 (2001); Elbashir et al., Genes Dev. 15, 188-200 (2001); WO 0129058; WO 09932619; and Elbashir et al., 2001 Nature 411: 494-498).

A similar approach for modulating the activity of the polypeptide encoded by the polynucleotide of the invention is the application of microRNA (miRNA). miRNAs have been identified as regulators of gene expression in animals and plants. miRNAs are single-stranded RNAs of 20 to 24 nucleotides in length which are obtained by processing of larger RNA precursors. RNA precursors are known and can be modified by those skilled in the art as to recognize other targets (mRNA) without further ado (see Niu 2006, Nature Biotechnology, 24: 1420-1428; Schwab 2006, Plant Cell 18: 1121-113; Alvarez 2006, Plant Cell 18: 1134-1151). miRNAs which specifically recognize mRNAs encoding to pyruvate kinase subunits will inhibit the expression of the said mRNAs and will, thereby, modulate (i.e. down-regulate) the seed storage compound production.

Combinations of the antisense nucleic acid molecules of the invention are typically administered to a cell or generated in situ, such that they hybridize with or bind to cellular mRNA and/or genomic DNA encoding an SMP to thereby inhibit expression of the protein, e.g., by inhibiting transcription and/or translation. The hybridization can be by conventional nucleotide complementarity to form a stable duplex, or, for example, in the case of an antisense nucleic acid molecule, which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody, which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic, including plant promoters are preferred. In yet another embodiment, the combinations of antisense nucleic acid molecules of the invention are -anomeric nucleic acid molecules. An anomeric nucleic acid molecule forms specific double-stranded hybrids with complementary RNA, in which, contrary to the usual units, the strands run parallel to each other (Gaultier et al. 1987, Nucleic Acids Res. 15:6625-6641). The antisense nucleic acid molecule can also comprise a 2'-o-methyl-ribonucleotide (Inoue et al. 1987, Nucleic Acids Res. 15:6131-6148) or a chimeric RNA-DNA analogue (Inoue et al. 1987, FEBS Lett. 215:327-330).

In still another embodiment, a combination containing an antisense nucleic acid of the invention contains a ribozyme. Ribozymes are catalytic RNA molecules with ribonuclease activity, which are capable of cleaving a single-stranded nucleic acid, such as an mRNA, to which they have a complementary region. Thus, ribozymes (e.g., hammerhead ribozymes (described in Haselhoff & Gerlach 1988, Nature 334:585-591)) can be used to catalytically cleave SMP mRNA transcripts to thereby inhibit translation of SMP mRNA. A ribozyme having specificity for an SMP-encoding nucleic acid can be designed based upon the nucleotide sequence of an SMP cDNA disclosed herein (i.e., Bn01 in This specification) or on the basis of a heterologous sequence to be isolated according to methods taught in this invention. For example, a derivative of a *Tetrahymena* L-19 IVS RNA can be constructed, in which the nucleotide sequence of the active site is complementary to the nucleotide sequence to be cleaved in an SMP-encoding mRNA (see, e.g., Cech et al., U.S. Pat. No. 4,987,071 and Cech et al., U.S. Pat. No. 5,116,742). Alternatively, SMP mRNA can be used to select a catalytic RNA having a specific ribonuclease activity from a pool of RNA molecules (see, e.g., Bartel, D. & Szostak J. W. 1993, Science 261:1411-1418).

Alternatively, SMP gene expression of one or more genes of the combinations of this invention can be inhibited by targeting nucleotide sequences complementary to the regulatory region of an SMP nucleotide sequence (e.g., an SMP promoter and/or enhancers) to form triple helical structures that prevent transcription of an SMP gene in target cells (See generally, Helene C. 1991, Anticancer Drug Des. 6:569-84; Helene C. et al. 1992, Ann. N.Y. Acad. Sci. 660:27-36; and Maher, L. J. 1992, Bioassays 14:807-15).

Another aspect of the invention pertains to vectors, preferably expression vectors, containing a combination of nucleic acids encoding SMPs (or a portion thereof), i.e. the polynucleotide of the present invention. As used herein, the term "vector" refers to a nucleic acid molecule capable of transporting another nucleic acid, to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell, into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes, to which they are operatively linked. Such vectors are referred to herein as "expression vectors". In general, expression vectors of utility in recombinant DNA techniques are often in the form of plasmids. In the present specification, "plasmid", and "vector" can be used inter-changeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a combination of nucleic acids of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick & Thompson, Chapter 7, 89-108 including the references therein. Regulatory sequences include those that direct constitutive expression of a nucleotide sequence in many types of host cell and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., SMPs, mutant forms of SMPs, fusion proteins, etc.). The recombinant expression vectors of the invention can be designed for expression of combinations of SMPs in prokaryotic or eukaryotic cells. For example, SMP genes can be expressed in bacterial cells, insect cells (using baculovirus expression vectors), yeast and other fungal cells (see Romanos M. A. et al. 1992, Foreign gene expression in yeast: a review, Yeast 8:423-488; van den Hondel, C. A. M. J. J. et al. 1991, Heterologous gene expression in filamentous fungi, in: More Gene Manipulations in Fungi, Bennet & Lasure, eds., p. 396-428:Academic Press: an Diego; and van den Hondel & Punt 1991, Gene transfer systems and vector development for filamentous fungi, in: Applied Molecular Genetics of Fungi, Peberdy et al., eds., p. 1-28, Cambridge University Press: Cambridge), algae (Falciatore et al. 1999, Marine Biotechnology 1:239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in WO 98/01572 and multicellular plant cells (see Schmidt & Willmitzer 1988, High efficiency *Agrobacterium tumefaciens*-mediated transformation of *Arabidopsis thaliana* leaf and cotyledon plants, Plant Cell Rep.: 583-586); Plant Molecular Biology and Biotechnology, C Press, Boca Raton, Fla., chapter 6/7, S. 71-119 (1993); White, Jenes et al., Techniques for Gene Transfer, in: Transgenic Plants, Vol. 1, Engineering and Utilization, eds.: Kung and Wu, Academic Press 1993, 128-43; Potrykus 1991, Annu. Rev. Plant Physiol. Plant Mol. Biol. 42:205-225 (and references cited therein) or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

Typical fusion expression vectors include pGEX (Pharmacia Biotech Inc; Smith & Johnson 1988, Gene 67:31-40), pMAL (New England Biolabs, Beverly, Mass.) and pRIT5 (Pharmacia, Piscataway, N.J.), which fuse glutathione S-transferase (GST), maltose E binding protein, or protein A, respectively, to the target recombinant protein. In one embodiment, the coding sequence of the SMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant SMP unfused to GST can be recovered by cleavage of the fusion protein with thrombin.

Examples of suitable inducible non-fusion *E. coli* expression vectors include pTrc (Amann et al. 1988, Gene 69:301-315) and pET 11d (Studier et al. 1990, Gene Expression Technology: Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S. 1990, Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al. 1992, Nucleic Acids Res. 20:2111-2118). Such alteration of nucleic acid sequences of the invention can be carried out by standard DNA synthesis techniques.

In another embodiment, the SMP combination expression vector is a yeast expression vector. Examples of vectors for expression in yeast *S. cerevisiae* include pYepSec1 (Baldari et al. 1987, Embo J. 6:229-234), pMFa (Kurjan & Herskowitz 1982, Cell 30:933-943), pJRY88 (Schultz et al. 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt 1991, "Gene transfer systems and vector development for filamentous fungi", in: Applied Molecular Genetics of Fungi, Peberdy et al., eds., p. 1-28, Cambridge University Press: Cambridge.

Alternatively, the combinations of SMPs of the invention can be expressed in insect cells using baculovirus expression vectors. Baculovirus vectors available for expression of proteins in cultured insect cells (e.g., Sf 9 cells) include the pAc series (Smith et al. 1983, Mol. Cell. Biol. 3:2156-2165) and the pVL series (Lucklow & Summers 1989, Virology 170:31-39).

In yet another embodiment, a combination of nucleic acids of the invention is expressed in mammalian cells using a mammalian expression vector. Examples of mammalian expression vectors include pCDM8 (Seed 1987, Nature 329: 840) and pMT2PC (Kaufman et al. 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells see chapters 16 and 17 of Sambrook, Fritsh and Maniatis, Molecular Cloning: A Laboratory Manual. 2nd, ed., Cold Spring Harbor Laboratory, Cold Spring Harbor Laboratory Press, Cold Spring Harbor, N.Y., 1989.

In another embodiment, a combination of the SMPs of the invention may be expressed in unicellular plant cells (such as algae, see Falciatore et al. (1999, Marine Biotechnology 1:239-251 and references therein) and plant cells from higher plants (e.g., the spermatophytes, such as crop plants). Examples of plant expression vectors include those detailed in: Becker, Kemper, Schell and Masterson (1992, "New plant binary vectors with selectable markers located proximal to the left border", Plant Mol. Biol. 20:1195-1197) and Bevan (1984, "Binary *Agrobacterium* vectors for plant transformation", Nucleic Acids Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38).

A plant expression cassette preferably contains regulatory sequences capable to drive gene expression in plant cells, and which are operably linked so that each sequence can fulfill its function such as termination of transcription, including polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3:835) or functional equivalents thereof. but also all other terminators functionally active in plants are suitable. As plant gene expression is very often not limited on transcriptional levels a plant expression cassette preferably contains other operably-linked sequences, like translational enhancers such as the overdrive-sequence containing the 5"-untranslated leader sequence from tobacco mosaic virus enhancing the protein per RNA ratio (Gallie et al. 1987, Nucleic Acids Res. 15:8693-8711). Plant gene expression has to be operably linked to an appropriate promoter conferring gene expression in a timely, cell or tissue specific manner. Preferred are promoters driving constitutive expression (Benfey et al. 1989, EMBO J. 8:2195-2202) like those derived from plant viruses like the 35S CAMV (Franck et al. 1980, Cell 21:285-294), the 19S CaMV (see also U.S. Pat. No. 5,352,605 and WO 84/02913) or the ptxA promoter (Bown, D. P. PhD thesis (1992) Department of Biological Sciences, University of Durham, Durham, U.K) or plant promoters like those from Rubisco small subunit described in U.S. Pat. No. 4,962,028. Even more preferred are seed-specific promoters driving expression of SMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al. 1991, Mol. Gen. Genetics 225:459-67) SEQ ID No. 10, the oleosin-promoter from *Arabidopsis* (WO 98/45461), the phaseolin-promoter from *Phaseolus vulgaris* (U.S. Pat. No. 5,504,200), the Bce4-promoter from *Brassica* (WO9113980) or the legumin B4 promoter (LeB4; Baeumlein et al. 1992, Plant J. 2:233-239), as well as promoters conferring seed specific expression in monocot plants like maize, barley, wheat, rye, rice etc. Suitable promoters to note are the Ipt2 or Ipt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum* kasirin-gene, and the rye secalin gene). Plant gene expression can also be facilitated via an inducible promoter (for a review see Gatz 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404) and an ethanol inducible promoter (WO 93/21334). Promoters responding to biotic or abiotic stress conditions are also suitable promoters such as the pathogen inducible PRP1-gene promoter (Ward et al., 1993, Plant Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375 091). Other preferred sequences for use in plant gene expression cassettes are targeting-sequences necessary to direct the gene-product in its appropriate cell compartment (for review see Kermode 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes, and other compartments of plant cells. Also especially suited are promoters that confer plastid-specific gene expression, as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a combination of DNA molecules (i.e. the first, second and third nucleic acid molecules) of the invention cloned into the expression vector in an antisense orientation. That is, the DNA molecule is operatively linked to a regulatory sequence in a manner that allows for expression (by transcription of the DNA molecule) of an RNA molecule that is antisense to SMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus, in which antisense nucleic acids are produced under the control of a high efficiency regulatory region, the activity of which can be determined by the cell type, into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a combination of SMPs can be expressed in bacterial cells, insect cells, fungal cells, mammalian cells (such as Chinese hamster ovary cells (CHO) or COS cells), algae, ciliates, or plant cells. Other suitable host cells are known to those skilled in the art. Vector DNA can be introduced into prokaryotic or eukaryotic cells via conventional transformation or transfection techniques. As used herein, the terms "transformation" and "transfection", "conjugation", and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, Molecular Cloning: A Laboratory Manual. 2nd, ed., Cold Spring Harbor Laboratory, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J. For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin, kanamycin, and methotrexate or in plants that confer resistance towards an herbicide, such as glyphosate or glufosinate. A nucleic acid encoding a selectable marker can be introduced into a host cell on the same vector as that encoding a combination of SMPs or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared that contains a combination of at least a portion of an SMP gene, into which a deletion, addition or substitution has been introduced to thereby alter, e.g., functionally disrupt, the SMP gene. Preferably, this SMP gene is an *Arabidopsis thaliana* or *Physcomitrella patens* SMP gene, but it can be a homologue from a related plant or even from a mammalian, yeast, or insect source. In a preferred embodiment, the vector is designed such that, upon homologous recombination, the endogenous SMP gene is functionally disrupted (i.e., no longer encodes a functional protein; also referred to as a knock-out vector). Alternatively, the vector can be designed such that, upon homologous recombination, the endogenous SMP gene is mutated or otherwise altered but still encodes functional protein (e.g., the upstream regulatory region can be altered to thereby alter the expression of the endogenous SMP). To create a point mutation via homologous recombination, DNA-RNA hybrids can be used in a technique known as chimeraplasty (Cole-Strauss et al. 1999, Nucleic Acids Res. 27:1323-1330 and Kmiec 1999, American Scientist 87:240-247). Homologous recombination procedures in *Arabidopsis thaliana* or other crops are also well known in the art and are contemplated for use herein. In a homologous recombination vector, within the combination of genes coding for SMPs shown in As disclosed herein the altered portion of the SMP gene is flanked at its 5' and 3' ends by additional nucleic acid of the SMP gene to allow for homologous recombination to occur between the exogenous SMP gene carried by the vector and an endogenous SMP gene in a microorganism or plant. The additional flanking SMP nucleic acid is of sufficient length for successful homologous recombination with the endogenous gene. Typically, several hundreds of base pairs up to kilobases of flanking DNA (both at the 5' and 3' ends) are included in the vector (see e.g., Thomas & Capecchi 1987, Cell 51:503, for a description of homologous recombination vectors). The vector is introduced into a microorganism or plant cell (e.g., via polyethyleneglycol mediated DNA). Cells in which the introduced SMP gene has homologously recombined with the endogenous SMP gene are selected using art-known techniques. In another embodiment, recombinant microorganisms can be produced which contain selected systems, which allow for regulated expression of the introduced combinations of genes. For example, inclusion of a combination of one two or more SMP genes on a vector placing it under control of the lac operon permits expression of the SMP gene only in the presence of IPTG. Such regulatory systems are well known in the art.

A host cell of the invention, such as a prokaryotic or eukaryotic host cell in culture can be used to produce (i.e., express) a combination of SMPs. Accordingly, the invention further provides methods for producing SMPs using the host cells of the invention. In one embodiment, the method comprises culturing a host cell of the invention (into which a recombinant expression vector encoding a combination of SMPs has been introduced, or which contains a wild-type or altered SMP gene in it's genome) in a suitable medium until the combination of SMPs is produced.

An isolated SMP or a portion thereof of the invention can participate in the metabolism of compounds necessary for the production of seed storage compounds in plants. In preferred embodiments, the protein or portion thereof comprises an amino acid sequence which is sufficiently homologous to an amino acid sequence encoded by a nucleic acid disclosed herein such that the protein or portion thereof maintains the ability to participate in the metabolism of compounds necessary for the biosynthesis of the seed storage compounds. The portion of the protein is preferably a biologically active portion as described herein. In another preferred embodiment, an SMP of the invention has an amino acid sequence encoded by a nucleic acid disclosed herein. In yet another preferred embodiment, the SMP has an amino acid sequence which is encoded by a nucleotide sequence which hybridizes, e.g., hybridizes under stringent conditions, to a nucleotide sequence disclosed herein. In still another preferred embodiment, the SMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99%, or more homologous to one of the amino acid sequences encoded by a nucleic acid disclosed herein. The preferred SMPs of the present invention also preferably possess at least one of the SMP activities described herein. For example, a preferred SMP of the present invention includes an amino acid sequence encoded by a nucleotide sequence which hybridizes, e.g., hybridizes under stringent conditions, to a nucleotide sequence disclosed herein, and which can participate in the metabolism of seed storage compounds.

In other embodiments, the combination of SMPs is substantially homologous to a combination of amino acid sequences encoded by nucleic acids specifically disclosed herein and retain the functional activity of the protein of one of the sequences encoded by a nucleic acid disclosed herein yet differs in amino acid sequence due to natural variation or mutagenesis, as described in detail above. Accordingly the SMP is a protein which comprises an amino acid sequence which is at least about 50-60%, preferably at least about 60-70%, and more preferably at least about 70-80, 80-90, 90-95%, and most preferably at least about 96%, 97%, 98%, 99%, or more homologous to an entire amino acid sequence and which has at least one of the SMP activities described herein.

Dominant negative mutations or trans-dominant suppression can be used to reduce the activity of an SMP in transgenics seeds in order to change the levels of seed storage compounds. To achieve this goal, a mutation that abolishes the activity of the SMP is created and the inactive non-functional SMP gene is overexpressed as part of the combination of this invention in the transgenic plant. The inactive trans-dominant SMP protein competes with the active endogenous SMP protein for substrate or interactions with other proteins and dilutes out the activity of the active SMP. In this way the biological activity of the SMP is reduced without actually modifying the expression of the endogenous SMP gene. This strategy was used by Pontier et al to modulate the activity of plant transcription factors (Pontier D, Miao Z H, Lam E, Plant J 2001 Sep. 27(6): 529-38, Trans-dominant suppression of plant TGA factors reveals their negative and positive roles in plant defense responses).

Homologues of the SMP can be generated for combinations by mutagenesis, e.g., discrete point mutation or truncation of the SMP. As used herein, the term "homologue" refers to a variant form of the SMP that acts as an agonist or antagonist of the activity of the SMP. An agonist of the SMP can retain substantially the same, or a subset, of the biological activities of the SMP. An antagonist of the SMP can inhibit one or more of the activities of the naturally-occurring form of the SMP, by, for example, competitively binding to a downstream or upstream member of the cell membrane component metabolic cascade, which includes the SMP, or by binding to an SMP, which mediates transport of compounds across such membranes, thereby preventing translocation from taking place. In addition, libraries of fragments of the SMP coding sequences can be used to generate a variegated population of SMP fragments for screening and subsequent selection of homologues of an SMP to be included in combinations as described in table 3. In one embodiment, a library of coding sequence fragments can be generated by treating a double stranded PCR fragment of an SMP coding sequence with a nuclease under conditions, wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived, which encodes N-terminal, C-terminal and internal fragments of various sizes of the SMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SMP homologues. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify SMP homologues (Arkin & Yourvan 1992, Proc. Natl. Acad. Sci. USA 89:7811-7815; Delgrave et al. 1993, Protein Engineering 6:327-331).

In another embodiment, cell based assays can be exploited to analyze a variegated SMP library, using methods well known in the art.

The nucleic acid molecules, proteins, protein homologues and fusion proteins for the combinations described herein, and vectors, and host cells described herein can be used in one or more of the following methods: identification of *Arabidopsis thaliana* and related organisms; mapping of genomes of organisms related to *Arabidopsis thaliana*; identification and localization of *Arabidopsis thaliana* sequences of interest; evolutionary studies; determination of SMP regions required for function; modulation of an SMP activity; modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as *Brassica napus, Glycine max* or *Linum usitatissimum* which require light to drive photosynthesis and growth. Plants like *Arabidopsis thaliana, Brassica napus, Glycine max* or *Linum usitatissimum* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species, isolation of the corresponding genes and use of the later in combinations described for the sequences listed herein.

There are a number of mechanisms by which the alteration of a combination of SMPs of the invention may directly affect the accumulation and/or composition of seed storage compounds. In the case of plants expressing a combination of SMPs, increased transport can lead to altered accumulation of compounds, which ultimately could be used to affect the accumulation of one or more seed storage compounds during seed development. Expression of single genes affecting seed storage compound accumulation and/or solute partitioning within the plant tissue and organs is well known. An example is provided by Mitsukawa et al. (1997, Proc. Natl. Acad. Sci. USA 94:7098-7102), where overexpression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al. 2000, Plant J. 24:383-396) and the lipid composition in leaves and roots (Härtel et al. 2000, Proc. Natl. Acad. Sci. USA 97:10649-10654). The ABI1 and ABI2 genes encode two protein serine/threonine phosphatases 2C, which are regulators in abscisic acid signaling pathway, and thereby in early and late seed development (e.g. Merlot et al. 2001, Plant J. 25:295-303). For more examples see also the section "Background of the Invention."

The present invention also contemplates a nucleic acid molecule comprising a nucleic acid sequence selected from the group consisting of:

a. a nucleic acid sequence as shown in any one of SEQ ID NOs: 36, 38, 40, 42, 44, 46, 48, 50, 52, 54, 56, or 58;
b. a nucleic acid encoding a polypeptide having an amino acid sequence as shown in any one of SEQ ID NOs: 37, 39, 41, 43, 45, 47, 49, 51, 53, 55, 57, or 59;
c. a nucleic acid sequence which is at least 70% identical to the nucleic acid sequence of a., wherein said nucleic acid encodes a polypeptide having or contemplating pyruvate kinase activity; and
d. a nucleic acid molecule encoding a polypeptide having an amino acid sequence which is at least 70% identical to the amino acid sequence encoded by a nucleic acid of b., wherein said nucleic acid encodes a polypeptide having or contemplating pyruvate kinase activity.

The definitions and explanations made for the polynucleotides of the present invention apply mutatis mutandis for the aforementioned nucleic acid molecule of the present invention.

Moreover, the aforementioned nucleic acid molecule of the present invention is, preferably, applied for increasing the content of seed storage compounds and, in particular, of lipids, fatty acids, proteins or individual amino acids, in plants. Thus, the aforementioned nucleic acid molecule of the present invention is, in principle, useful for the synthesis of seed storage compounds. Moreover, it can be applied to generate transgenic plants or seeds having a modified, preferably increased, amount of seed storage compounds. Such transgenic plants or seeds may be used for the manufacture of compositions containing the aforementioned seed storage compounds, such as seed oil or amino acid compositions to be used, e.g., as feed or food stuff.

It is to be understood that like the polynucleotides of the present invention, the aforementioned nucleic acid molecule of the present invention can be comprised by a vector, preferably, an expression vector, can be comprised by a host cell, transgenic organism or transgenic plant as recited above or can be applied in the methods referred to before. Moreover, the nucleic acid molecule can be included into the polynucleotide of the present invention as first or second nucleic acid molecules, respectively. Specifically preferred combinations of nucleic acid molecules encompass polynucleotides comprising a first nucleic acid as recited above and a nucleic acid as shown in SEQ ID NO 36 and 40, respectively, or nucleic acids encoding an amino acid sequence as shown in SEQ ID NO: 37 and 41, respectively. Further preferred combinations of nucleic acid molecules encompass polynucleotides comprising a second nucleic acid as recited above and a nucleic acid as shown in SEQ ID NO 38 or nucleic acids encoding an amino acid sequence as shown in SEQ ID NO: 39. Also preferred are polynucleotides comprising a first nucleic acid as shown in SEQ ID NO: 38 or encoding an amino acid sequence as shown in SEQ ID NO: 39 and a second nucleic acid as shown in SEQ ID NO: 36 or 40 or encoding an amino acid sequence as shown in SEQ ID NO: 37 or 41.

Throughout this application, various publications are referenced. The disclosures of all of these publications and those references cited within those publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

FIGURES

FIG. 1 shows a schematic representation of polynucleotide no. 1 in an binary expression vector. b-RB=right border of T-DNA; c-aadA=aminoglycoside 3'-adenylyl-transferase codons; o-ColE1 replication origin of the plasmid pBR322, consisting of the two components o-REP-ColE1 and o-BOM-ColE1; VS1-rep=replication origin and repA of plasmid pVS1 VS1-sta=sta gene from plasmid pVS1; b-LB=left border of T-DNA; T-DNA cassette marks the region where the different T-DNA cassette for the different constructs are located; b-LB=left border of T-DNA, b-RB=right border of T-DNA.

EXAMPLES

Example 1

Figure 1:
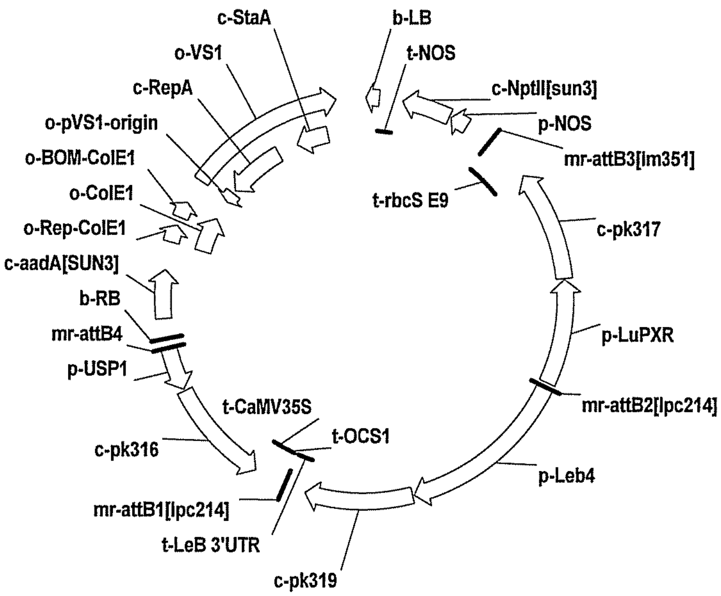

General Processes a) General Cloning Processes. Cloning processes such as, for example, restriction cleavages, agarose gel electrophoresis, purification of DNA fragments, transfer of nucleic acids to nitrocellulose and nylon membranes, linkage of DNA fragments, trans-formation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics", Cold Spring Harbor Laboratory Press: ISBN 0-87969-451-3).

b) Chemicals. The chemicals used were obtained, if not mentioned otherwise in the text, in p.a. quality from the companies Fluka (Neu-Ulm), Merck (Darmstadt), Roth (Karlsruhe), Serva (Heidelberg) and Sigma (Deisenhofen). Solutions were prepared using purified, pyrogen-free water, designated as H2O in the following text, from a Milli-Q water system water purification plant (Millipore, Eschborn). Restriction endonucleases, DNA-modifying enzymes and molecular biology kits were obtained from the companies AGS (Heidelberg), Amersham (Braunschweig), Biometra (Gottingen), Roche (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Plant Material and Growth: *Arabidopsis* plants. For this study, root material, leaves, siliques and seeds of wild-type and transgenic plants of *Arabidopsis thaliana* expressing combinations of SMPs as described within this invention were used. Wild type and transgenic *Arabidopsis* seeds were preincubated for three days in the dark at 4° C. before placing them into an incubator (AR-75, Percival Scientific, Boone, Iowa) at a photon flux density of 60-80 µmol m-2 s-1 and a light period of 16 hours (22° C.), and a dark period of 8 hours (18° C.). All plants were started on half-strength MS medium (Murashige & Skoog, 1962, Physiol. Plant. 15, 473-497), pH 6.2, 2% sucrose and 1.2% agar. Seeds were sterilized for 20 minutes in 20% bleach 0.5% triton X100 and rinsed 6 times with excess sterile water.

Example 2

Total DNA Isolation from Plants

The details for the isolation of total DNA relate to the working up of 1 gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for 1 hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g and RT for 15 min in each case. The DNA was then precipitated at −70° C. for 30 min using ice-cold isopropanol. The precipitated DNA was sedimented at 4° C. and 10,000 g for 30 min and resuspended in 180 µl of TE buffer (Sambrook et al. 1989, Cold Spring Harbor Laboratory Press: ISBN 0-87969-309-6). For further purification, the DNA was treated with NaCl (1.2 M final concentration) and precipitated again at −70° C. for 30 min using twice the volume of absolute ethanol. After a washing step with 70% ethanol, the DNA was dried and subsequently taken up in 50 µl of H2O+RNAse (50 mg/ml final concentration). The DNA was dissolved overnight at 4° C. and the RNAse digestion was subsequently carried out at 37° C. for 1 h. Storage of the DNA took place at 4° C.

Example 3

Isolation of Total RNA and Poly-(A)+ RNA from Plants—*Arabidopsis thaliana*

For the investigation of transcripts, both total RNA and poly-(A)+ RNA were isolated. RNA is isolated from siliques of *Arabidopsis* plants according to the following procedure: RNA Preparation from *Arabidopsis* Seeds—"hot" Extraction:

1. Buffers, enzymes and solution

2M KCl

Proteinase K

Phenol (for RNA)

Chloroform:Isoamylalcohol (Phenol:choloroform 1:1; pH adjusted for RNA)

4 M LiCl, DEPC-treated

DEPC-treated water

3M NaOAc, pH 5, DEPC-treated

Isopropanol

70% ethanol (made up with DEPC-treated water)

Resuspension buffer: 0.5% SDS, 10 mM Tris pH 7.5, 1 mM EDTA made up with DEPC-treated water as this solution cannot be DEPC-treated Extraction Buffer:

0.2M Na Borate 30 mM EDTA 30 mM EGTA

1% SDS (250 µl of 10% SDS-solution for 2.5 ml buffer)

1% Deoxycholate (25 mg for 2.5 ml buffer)

2% PVPP (insoluble −50 mg for 2.5 ml buffer)

2% PVP 40K (50 mg for 2.5 ml buffer)

10 mM DTT 100 mM 3-Mercaptoethanol (fresh, handle under fume hood—use 35 µl of 14.3M solution for 5 ml buffer)

2. Extraction. Heat extraction buffer up to 80° C. Grind tissue in liquid nitrogen-cooled mortar, transfer tissue powder to 1.5 ml tube. Tissue should be kept frozen until buffer is added so transfer the sample with pre-cooled spatula and keep the tube in liquid nitrogen all time. Add 350 µl preheated extraction buffer (here for 100 mg tissue, buffer volume can be as much as 500 µl for bigger samples) to tube, vortex and heat tube to 80° C. for ±1 min. Keep then on ice. Vortex sample, grind additionally with electric mortar.

3. Digestion. Add Proteinase K (0.15 mg/100 mg tissue), vortex and keep at 37° C. for one hour.

First Purification. Add 27 µl 2M KCl. Chill on ice for 10 min. Centrifuge at 12.000 rpm for 10 minutes at room temperature. Transfer supernatant to fresh, RNAase-free tube and do one phenol extraction, followed by a chloroform:isoamylalcohol extraction. Add 1 vol. isopropanol to supernatant and chill on ice for 10 min. Pellet RNA by centrifugation (7000 rpm for 10 min at RT). Resolve pellet in 1 ml 4M LiCl by 10 to 15 min vortexing. Pellet RNA by 5 min centrifugation.

Second Purification. Resuspend pellet in 500 µl Resuspension buffer. Add 500 µl phenol and vortex. Add 250 µl chloroform:isoamylalcohol and vortex. Spin for 5 min. and transfer supernatant to fresh tube. Repeat chloroform: isoamylalcohol extraction until interface is clear. Transfer supernatant to fresh tube and add 1/10 vol 3M NaOAc, pH 5 and 600 µl isopropanol. Keep at −20 for 20 min or longer. Pellet RNA by 10 min centrifugation. Wash pellet once with 70% ethanol. Remove all remaining alcohol before resolving pellet with 15 to 20 µl DEPC-water. Determine quantity and quality by measuring the absorbance of a 1:200 dilution at 260 and 280 nm. 40 µg RNA/ml=1OD260 RNA from wild-type and the transgenic *Arabidopsis*-plants is isolated as described (Hosein, 2001, Plant Mol. Biol. Rep., 19, 65a-65e; Ruuska, S. A., Girke, T., Benning, C., & Ohlrogge, J. B., 2002, Plant Cell, 14, 1191-1206).

The mRNA is prepared from total RNA, using the Amersham Pharmacia Biotech mRNA purification kit, which utilizes oligo(dT)-cellulose columns.

Isolation of Poly-(A)+ RNA was isolated using Dyna BeadsR (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

Example 4 cDNA Library Construction

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 h), 16° C. (1 h) and 22° C. (1 h). The reaction was stopped by incubation at 65° C. (10 min) and subsequently transferred to ice. Double stranded DNA molecules were blunted by T4-DNA-polymerase (Roche, Mannheim) at 37° C. (30 min). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 min). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 5

Northern-Hybridization

For RNA hybridization, 20 µg of total RNA or 1 µg of poly-(A)+ RNA is separated by gel electrophoresis in 1.25% agarose gels using formaldehyde as described in Amasino (1986, Anal. Biochem. 152:304), transferred by capillary attraction using 10×SSC to positively charged nylon membranes (Hybond N+, Amersham, Braunschweig), immobilized by UV light and pre-hybridized for 3 hours at 68° C. using hybridization buffer (10% dextran sulfate w/v, 1 M NaCl, 1% SDS, 100 µg/ml of herring sperm DNA). The labeling of the DNA probe with the Highprime DNA labeling kit (Roche, Mannheim, Germany) is carried out during the pre-hybridization using alpha-32P dCTP (Amersham, Braunschweig, Germany). Hybridization is carried out after addition of the labeled DNA probe in the same buffer at 68° C. overnight. The washing steps are carried out twice for 15 min using 2×SSC and twice for 30 min using 1×SSC, 1% SDS at 68° C. The exposure of the sealed filters is carried out at −70° C. for a period of 1 day to 14 days.

Example 6

Plasmids for Plant Transformation

For plant transformation binary vectors such as pBinAR can be used (Höfgen & Willmitzer 1990, Plant Sci. 66:221-230). Construction of the binary vectors can be performed by ligation of the cDNA in sense or antisense orientation into the T-DNA. 5' to the cDNA a plant promoter activates transcription of the cDNA. A polyadenylation sequence is located 3' to the cDNA. Tissue-specific expression can be achieved by using a tissue specific promoter. For example, seed-specific expression can be achieved by cloning the napin or LeB4 or USP promoter 5' to the cDNA. Also any other seed specific promoter element can be used. For constitutive expression within the whole plant the CaMV 35S promoter can be used. The expressed protein can be targeted to a cellular compartment using a signal peptide, for example for plastids, mitochondria, or endoplasmic reticulum (Kermode 1996, Crit. Rev. Plant Sci. 15:285-423). The signal peptide is cloned 5' in frame to the cDNA to achieve subcellular localization of the fusion protein.

Further examples for plant binary vectors is the pSUN2-GW vector, into which the combination of SMP genes are cloned. This binary vector contains an antibiotic resistance gene driven under the control of the NOS promoter and combinations (see Table 3) containing promoters as listed in Table 4, partial or full-length SMP cDNA are cloned into the multiple cloning site of the pEntry vector in sense or antisense orientation behind a seed-specific promoters or constitutive promoter in the combinations shown in Table 4 using standard cloning procedures using restriction enzymes such as ASCI, PACI, NotP and StuI. Two or more pEntry vectors containing different SMPs are then combined with a pSUN destination vector to form a binary vector containing the polynucleotides as listed in Tables 3 and 4 by the use of the GATEWAY technology (Invitrogen, webpage at invitrogen.com) following the manufacturer's instructions. The recombinant vector containing the polynucleotides of interest is transformed into Top 10 cells (Invitrogen) using standard conditions. Transformed cells are selected for on LB agar containing 50 µg/ml kanamycin grown overnight at 37° C. Plasmid DNA is extracted using the QIAprep Spin Miniprep Kit (Qiagen) following manufacturer's instructions. Analysis of subsequent clones and restriction mapping is performed according to standard molecular biology techniques (Sambrook et al. 1989, Molecular Cloning, A Laboratory Manual. 2nd Edition. Cold Spring Harbor Laboratory Press. Cold Spring Harbor, N.Y.).

Different plant promoters such as, for example, the USP, the LegB4-, the DC3 promoter or the ubiquitin promoter from parsley or other herein mentioned promoter and different terminators may advantageously be used in the polynucleotides and plasmids comprising them described herein.

Usable promoters are constitutive promoters (Benfey et al., EMBO J. 8 (1989) 2195-2202), such as those which originate from plant viruses, such as 35S CAMV (Franck et al., Cell 21 (1980) 285-294), 19S CaMV (see also U.S. Pat. No. 5,352,605 and WO 84/02913), 34S FMV (Sanger et al., Plant. Mol. Biol., 14, 1990: 433-443), the parsley ubiquitin promoter, or plant promoters such as the Rubisco small subunit promoter described in U.S. Pat. No. 4,962,028 or the plant promoters PRP1 [Ward et al., Plant. Mol. Biol. 22 (1993)], SSU, PGEL1, OCS [Leisner (1988) Proc Natl Acad Sci USA 85(5):2553-2557], lib4, usp, mas [Comai (1990) Plant Mol Biol 15 (3): 373-381], STLS1, ScBV (Schenk (1999) Plant Mol Biol 39(6):1221-1230), B33, SAD1 or SAD2 (flax promoters, Jain et al., Crop Science, 39 (6), 1999: 1696-1701) or nos [Shaw et al. (1984) Nucleic Acids Res. 12(20):7831-7846]. Stable, constitutive expression of the proteins according to the invention a plant can be advantageous.

The expression of plant genes can also be facilitated as described above via a chemical inducible promoter (for a review, see Gatz 1997, Annu. Rev. Plant Physiol. Plant Mol. Biol., 48:89-108). Chemically inducible promoters are particularly suitable when it is desired to express the gene in a time-specific manner. Examples of such promoters are a salicylic acid inducible promoter (WO 95/19443), and abscisic acid-inducible promoter (EP 335 528), a tetracyclin-inducible promoter (Gatz et al. (1992) Plant J. 2, 397-404), a cyclohexanol- or ethanol-inducible promoter (WO 93/21334) or others as described herein.

Other suitable promoters are those which react to biotic or abiotic stress conditions, for example the pathogen-induced PRP1 gene promoter (Ward et al., Plant. Mol. Biol. 22 (1993) 361-366), the tomato heat-inducible hsp80 promoter (U.S. Pat. No. 5,187,267), the potato chill-inducible alpha-amylase promoter (WO 96/12814) or the wound-inducible pinII promoter (EP-A-0 375 091) or others as described herein. Preferred promoters are in particular those which bring about gene expression in tissues and organs in which the biosynthesis of amino acids takes place, in seed cells, such as endosperm cells and cells of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), the bean arcs promoter, the carrot DcG3 promoter, or the Legumin B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Advantageous seed-specific promoters are the sucrose binding protein promoter (WO 00/26388), the phaseolin promoter and the napin promoter. Suitable promoters which must be considered are the barley Ipt2 or Ipt1 gene promoter (WO 95/15389 and WO 95/23230), and the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene and the rye secalin gene). Further suitable promoters are Amy32b, Amy 6-6 and Aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or α-amylase (barley) [EP 781 849]. Other promoters which are available for the expression of genes in plants are leaf-specific promoters such as those described in DE-A 19644478 or light-regulated promoters such as, for example, the pea petE promoter. Further suitable plant promoters are the cytosolic FBPase promoter or the potato ST-LSI promoter (Stockhaus et al., EMBO J. 8, 1989, 2445), the *Glycine max* phosphoribosylpyrophosphate amidotransferase promoter (GenBank Accession No. U87999) or the node-specific promoter described in EPA-0 249 676. Other promoters, which are particularly suitable, are those which bring about plastid-specific expression. Suitable promoters such as the viral RNA polymerase promoter are described in WO 95/16783 and WO 97/06250, and the *Arabidopsis* clpP promoter, which is described in WO 99/46394. Other promoters, which are used for the strong expression of heterologous sequences in as many tissues as possible, in particular also in leaves, are, in addition to several of the above-mentioned viral and bacterial promoters, preferably, plant promoters of actin or ubiquitin genes such as, for example, the rice actin1 promoter. Further examples of constitutive plant promoters are the sugarbeet V-ATPase promoters (WO 01/14572). Examples of synthetic constitutive promoters are the Super promoter (WO 95/14098) and promoters derived from G-boxes (WO 94/12015). If appropriate, chemical inducible promoters may furthermore also be used, compare EP-A 388186, EP-A 335528, WO 97/06268.

Preferred recipient plants are, as described above, in particular those plants, which can be transformed in a suitable manner. These include monocotyledonous and dicotyledonous plants. Plants which must be mentioned in particular are agriculturally useful plants such as cereals and grasses, for example *Triticum* spp., *Zea mays, Hordeum vulgare*, oats, *Secale cereale, Oryza sativa, Pennisetum glaucum, Sorghum bicolor, Triticale, Agrostis* spp., *Cenchrus ciliaris, Dactylis glomerata, Festuca arundinacea, Lolium* spp., *Medicago* spp. and *Saccharum* spp., legumes and oil crops, for example *Brassica juncea, Brassica napus, Glycine max, Arachis hypogaea, Gossypium hirsutum, Cicer arietinum, Helianthus annuus, Lens culinaris, Linum usitatissimum, Sinapis alba, Trifolium repens* and *Vicia narbonensis*, vegetables and fruits, for example bananas, grapes, *Lycopersicon esculentum*, asparagus, cabbage, watermelons, kiwi fruit, *Solanum tuberosum, Beta vulgaris*, cassava and chicory, trees, for example *Coffea* species, *Citrus* spp., *Eucalyptus* spp., *Picea* spp., *Pinus* spp. and *Populus* spp., medicinal plants and trees, and flowers.

Likewise, a terminator, which may be used for this purpose is, for example, the OCS1 terminator, the nos3 terminator or the 35S terminator. As is the case with the promoters, different terminator sequences should be used for each gene. Terminators, which are useful in microorganism are for example the fimA terminator, txn terminator or trp terminator. Such terminators can be rho-dependent or rho-independent. Examples for transcriptional termination are polyadenylation signals. Preferred polyadenylation signals are those which originate from *Agrobacterium tumefaciens* T-DNA, such as the gene 3 of the Ti plasmid pTiACH5, which is known as octopine synthase (Gielen et al., EMBO J. 3 (1984) 835 et seq.) or functional equivalents thereof, but all the other terminators which are functionally active in plants are also suitable.

The polynucleotides suitable for plant expression preferably also comprises other operably linked regulatory elements such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711).

As already mentioned herein, further regulatory sequences, which may be expedient, if appropriate, also include sequences, which target the transport and/or the localization of the expression products. Sequences, which must be mentioned in this context are, in particular, the signal-peptide- or transit-peptide-encoding sequences which are known per se. For example, plastid-transit-peptide-encoding sequences enable the targeting of the expression product into the plastids of a plant cell.

Other preferred sequences for use in operable linkage in gene expression constructs (i.e. the polynucleotides described herein) are targeting sequences, which are required for targeting the gene product into specific cell compartments (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, elaioplasts, peroxisomes, glycosomes, and other compartments of cells or extracellular. Sequences, which must be mentioned in this context are, in particular, the signal-peptide- or transit-peptide-encoding sequences which are known per se. For example, plastid-transit-peptide-encoding sequences enable the targeting of the expression product into the plastids of a plant cell Targeting sequences are also known for eukaryotic and to a lower extent for prokaryotic organisms and can advantageously be operable linked with the nucleic acid molecule of the present invention to achieve an expression in one of said compartments or extracellular.

Example 7

*Agrobacterium* Mediated Plant Transformation

*Agrobacterium* mediated plant transformation with the combination of SMP nucleic acids described herein can be performed using standard transformation and regeneration techniques (Gelvin, Stanton B. & Schilperoort R. A, Plant Molecular Biology Manual, 2nd ed. Kluwer Academic Publ., Dordrecht 1995 in Sect., Ringbuc Zentrale Signatur:BT11-P; Glick, Bernard R. and Thompson, John E. Methods in Plant Molecular Biology and Biotechnology, S. 360, CRC Press, Boca Raton 1993). For example, Agrobacterium mediated transformation can be performed using the GV3 (pMP90) (Koncz & Schell, 1986, Mol. Gen. Genet. 204:383-396) or LBA4404 (Clontech) *Agrobacterium tumefaciens* strain.

*Arabidopsis thaliana* can be grown and transformed according to standard conditions (Bechtold 1993, Acad. Sci. Paris. 316:1194-1199; Bent et al. 1994, Science 265:1856-1860). Additionally, rapeseed can be transformed with the combination of SMP nucleic acids of the present invention via cotyledon or hypocotyl transformation (Moloney et al. 1989, Plant Cell Report 8:238-242; De Block et al. 1989, Plant Physiol. 91:694-701). Use of antibiotic for *Agrobacterium* and plant selection depends on the binary vector and the *Agrobacterium* strain used for transformation. Rapeseed selection is normally performed using a selectable plant marker. Additionally, *Agrobacterium* mediated gene transfer to flax can be performed using, for example, a technique described by Mlynarova et al. (1994, Plant Cell Report 13:282-285).

The SMPs in the combinations described in this invention can be expressed either under the seed specific USP (unknown seed protein) promoter SEQ ID NO: 31 (Baeumlein et al. 1991, Mol. Gen. Genetics 225:459-67) or other seed-specific promoters like the legumin B4 promoter SEQ ID NO: 29 (LeB4; Baeumlein et al. 1992, Plant J. 2:233-239), the Peroxiredoxin promoter from linseed SEQ ID NO: 30, as well as promoters conferring seed-specific expression in monocot plants like maize, barley, wheat, rye, rice, etc. were used.

The nptII gene was used as a selectable marker in these constructs. FIG. 1 exemplifies the setup of the binary vectors containing the combinations of SMPs.

Transformation of soybean can be performed using, for example, a technique described in EP 0424 047, U.S. Pat. No. 5,322,783 (Pioneer Hi-Bred International) or in EP 0397 687, U.S. Pat. No. 5,376,543 or U.S. Pat. No. 5,169,770 (University Toledo), or by any of a number of other transformation procedures known in the art. Soybean seeds are surface sterilized with 70% ethanol for 4 minutes at room temperature with continuous shaking, followed by 20% (v/v) CLOROX supplemented with 0.05% (v/v) TWEEN for 20 minutes with continuous shaking. Then the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

The method of plant transformation is also applicable to *Brassica napus* and other crops. In particular, seeds of canola are surface sterilized with 70% ethanol for 4 minutes at room temperature with continuous shaking, followed by 20% (v/v) CLOROX supplemented with 0.05% (v/v) TWEEN for 20 minutes, at room temperature with continuous shaking. Then, the seeds are rinsed four times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige & Skoog 1962, Physiol. Plant. 15:473-497) medium supplemented with 100 mM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The imbibition of dry embryos with a culture of *Agrobacterium* is also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 μmol m-2s-1 and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process.

Then the plants are transferred to a growth room where they are incubated at 25° C., under 440 μmol m-2s-1 light intensity and 12-hour photoperiod for about 80 days.

The SMP encoding polynucleotide may be also transformed into a corn inbred or hybrid using particle bombardment as set forth in U.S. Pat. Nos. 4,945,050; 5,036,006; 5,100,792; 5,302,523; 5,464,765; 5,120,657; 6,084,154; and the like. More preferably, the transgenic corn seed of the invention may be made using *Agrobacterium* transformation, as described in U.S. Pat. Nos. 5,591,616; 5,731,179; 5,981,840; 6,162,965; 6,420,630, U.S. patent application publication No. 200210104132, and the like. Since the SMP transgene is dominant, any corn inbred or hybrid may express the SMP protein after being crossed to the transgenic corn. Alternatively, the transgenic corn seed of the invention may be produced using plastid transformation methods suitable for use in corn. Plastid transformation of tobacco is described, for example, in U.S. Pat. No. 6,541,682; Zoubenko, et al. (1994) *Nucleic Acids Res.* 22, 3819-3824; Ruf, et al. (2001) *Nature Biotechnol.* 19, 870-875; Kuroda et al. (2001) *Plant Physiol.* 125, 430-436; Kuroda et al. (2001) *Nucleic Acids Res.* 29, 970-975; Hajdukiewica et al. (2001) *Plant J.* 27, 161-170; and Corneille, et al. (2001) *Plant* J. 72, 171-178. Additional plastid transformation methods employing the phiC31 phage integrase are disclosed in Lutz, et al. (2004) *The Plant* J. 37, 906.

Samples of the primary transgenic plants (T0) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR as recommended by the manufacturer.

Example 8

In vivo Mutagenesis

In vivo mutagenesis of microorganisms can be performed by incorporation and passage of the plasmid (or other vector) DNA through *E. coli* or other microorganisms (e.g. *Bacillus* spp. or yeasts such as *Sacchromyces*) that are impaired in their capabilities to maintain the integrity of their genetic information. Typical mutator strains have mutations in the genes for the DNA repair system (e.g., mutHLS, mutD, mutT, etc.; for reference, see Rupp W. D. 1996, DNA repair mechanisms, in: *Escherichia coli* and Salmonella, p. 2277-2294, ASM: Washington). Such strains are well known to those skilled in the art. The use of such strains is illustrated, for example, in Greener and Callahan 1994, Strategies 7:32-34. Transfer of mutated DNA molecules into plants is preferably done after selection and testing in microorganisms. Transgenic plants are generated according to various examples within the exemplification of this document.

Example 9

Assessment of the mRNA Expression and Activity of a Recombinant Gene Product in the Transformed Organism The activity of a recombinant gene product in the transformed host organism can be measured on the transcriptional or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (see, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label, which may be readily detected. The presence and quantity of label observed indicates the presence and quantity of the desired mutant protein present in the cell.

The activity of SMPs that bind to DNA can be measured by several well-established methods, such as DNA band-shift assays (also called gel retardation assays). The effect of such SMP on the expression of other molecules can be measured using reporter gene assays (such as that described in Kolmar H. et al. 1995, EMBO J. 14:3895-3904 and references cited therein). Reporter gene test systems are well known and established for applications in both prokaryotic and eukaryotic cells, using enzymes, such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 10

In vitro Analysis of the Activity of SMPS Expressed in Combinations in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications, and examples for the determination of many enzyme activities may be found, for example, in the following references: Dixon, M. & Webb, E. C. 1979, Enzymes. Longmans: London; Fersht, (1985) Enzyme Structure and Mechanism. Freeman: New York; Walsh (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3rd ed. Academic Press: New York; Bisswanger, H., (1994) Enzymkinetik, 2nd ed. VCH: Weinheim (ISBN 3527300325); Bergmeyer, H. U., Bergmeyer, J., GrafβI, M., eds. (1983-1986) Methods of Enzymatic Analysis, 3rd ed., vol. I-XII, Verlag Chemie: Weinheim; and Ullmann's Encyclopedia of Industrial Chemistry (1987) vol. A9, Enzymes. VCH: Weinheim, p. 352-363.

Example 11

Analysis of the Impact of Combinations of Recombinant Proteins on the Production of a Desired Seed Storage Compound Seeds from *Brassica napus* plants were analyzed by gas chromatography (GC) and near infrared spectroscopy (NIRS) for total oil, protein and starch content and fatty acid profile.

The results suggest that overexpression of the combination of SMPs as described in Table 3 allows the manipulation of total seed storage content. As an example, the results of the seed storage analysis of polynucleotide number 1 (Table 4) revealed an overall increase of 3.2% compared to a control in seed storage compounds. Control plants were non-transgenic segregants grown together with the transgenic plants carrying polynucleotide number 1.

The effect of the genetic modification in plants on a desired seed storage compound (such as a sugar, an amino acid or mixture thereof, a protein, a lipid or a fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon, A. et al. 1987, Applications of HPLC in Biochemistry in: Laboratory Techniques in Biochemistry and Molecular Biology, vol. 17; Rehm et al., 1993 Product recovery and purification, Biotechnology, vol. 3, Chapter III, pp. 469-714, VCH: Weinheim; Better, P. A. et al., 1988 Bioseparations: downstream processing for biotechnology, John Wiley & Sons; Kennedy J. F. & Cabral J. M. S. 1992, Recovery processes for biological materials, John Wiley and Sons; Shaeiwitz J. A. & Henry J. D. 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland:Oily Press, 1989 Repr. 1992.—IX, 307 S.—(Oily Press Lipid Library; and "Progress in Lipid Research", Oxford: Pergamon Press, 1 (1952)-16 (1977) Progress in the Chemistry of Fats and Other Lipids CODEN.

Unequivocal proof of the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240), and for seeds by Focks & Benning (1998, Plant Physiol. 118:91-101).

Positional analysis of the fatty acid composition at the sn-1, sn-2 or sn-3 positions of the glycerol backbone is determined by lipase digestion (see, e.g., Siebertz & Heinz 1977, Z. Naturforsch. 32c:193-205, and Christie 1987, Lipid Analysis 2nd Edition, Pergamon Press, Exeter, ISBN 0-08-023791-6).

Total seed oil levels can be measured by any appropriate method. Quantitation of seed oil contents is often performed with conventional methods, such as near infrared analysis (NIR) or nuclear magnetic resonance imaging (NMR). NIR spectroscopy has become a standard method for screening seed samples whenever the samples of interest have been amenable to this technique. Samples studied include canola, soybean, maize, wheat, rice, and others. NIR analysis of single seeds can be used (see e.g. Velasco et al., Estimation of seed weight, oil content and fatty acid composition in intact single seeds of rapeseed (*Brassica napus* L.) by near-infrared reflectance spectroscopy, Euphytica, Vol. 106, 1999, pp. 79-85). NMR has also been used to analyze oil content in seeds (see e.g. Robertson & Morrison, "Analysis of oil content of sunflower seed by wide-line NMR", Journal of the American Oil Chemists Society, 1979, Vol. 56, 1979, pp. 961-964, which is herein incorporated by reference in its entirety).

A typical way to gather information regarding the influence of increased or decreased protein activities on lipid and sugar biosynthetic pathways is for example via analyzing the carbon fluxes by labeling studies with leaves or seeds using 14C-acetate or 14C-pyruvate (see, e.g. Focks & Benning 1998, Plant Physiol. 118:91-101; Eccleston & Ohlrogge 1998, Plant Cell 10:613-621). The distribution of carbon-14 into lipids and aqueous soluble components can be determined by liquid scintillation counting after the respective separation (for example on TLC plates) including standards like 14C-sucrose and 14C-malate (Eccleston & Ohlrogge 1998, Plant Cell 10:613-621).

Material to be analyzed can be disintegrated via sonification, glass milling, liquid nitrogen, and grinding, or via other applicable methods. The material has to be centrifuged after disintegration. The sediment is re-suspended in distilled water, heated for 10 minutes at 100° C., cooled on ice and centrifuged again followed by extraction in 0.5 M sulfuric acid in methanol containing 2% dimethoxypropane for 1 hour at 90° C. leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 min. at 240° C. The identity of resulting fatty acid methylesters is defined by the use of standards available form commercial sources (i.e., Sigma).

In case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves" Methods Enzymol. 174:518-552; for other methods see also Hartel et al. 1998, Plant Physiol. Biochem. 36:407-417 and Focks & Benning 1998, Plant Physiol. 118:91-101).

For the extraction of soluble sugars and starch, 50 seeds are homogenized in 500 μl of 80% (v/v) ethanol in a 1.5-ml polypropylene test tube and incubated at 70° C. for 90 min. Following centrifugation at 16,000 g for 5 min, the supernatant is transferred to a new test tube. The pellet is extracted twice with 500 μl of 80% ethanol. The solvent of the combined supernatants is evaporated at room temperature under a vacuum. The residue is dissolved in 50 μl of water, representing the soluble carbohydrate fraction. The pellet left from the ethanol extraction, which contains the insoluble carbohydrates including starch, is homogenized in 200 μl of 0.2 N KOH, and the suspension is incubated at 95° C. for 1 h to dissolve the starch. Following the addition of 35 μl of 1 N acetic acid and centrifugation for 5 min at 16,000, the supernatant is used for starch quantification. To quantify soluble sugars, 10 μl of the sugar extract is added to 990 μl of reaction buffer containing 100 mM imidazole, pH 6.9, 5 mM MgCl2, 2 mM NADP, 1 mM ATP, and 2 units 2 ml-1 of Glucose-6-P-dehydrogenase. For enzymatic determination of glucose, fructose, and sucrose, 4.5 units of hexokinase, 1 unit of phosphoglucoisomerase, and 2 μl of a saturated fructosidase solution are added in succession. The production of NADPH is photometrically monitored at a wavelength of 340 nm. Similarly, starch is assayed in 30 μl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding", Anal. Biochem. 72:248-254). For quantification of total seed protein, 15-20 seeds are homogenized in 250 μl of acetone in a 1.5-ml polypropylene test tube. Following centrifugation at 16,000 g, the supernatant is discarded and the vacuum-dried pellet is resuspended in 250 μl of extraction buffer containing 50 mM Tris-HCl, pH 8.0, 250 mM NaCl, 1 mM EDTA, and 1% (w/v) SDS. Following incubation for 2 h at 25° C., the homogenate is centrifuged at 16,000 g for 5 min and 200 ml of the supernatant will be used for protein measurements. In the assay, y-globulin is used for calibration. For protein measurements, Lowry DC protein assay (Bio-Rad) or Bradford-assay (Bio-Rad) is used.

Enzymatic assays of hexokinase and fructokinase are performed spectrophotometrically according to Renz et al. (1993, Planta 190:156-165), of phosphoglucoisomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase, and pyruvate kinase are performed according to Burrell et al. (1994, Planta 194:95-101) and of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Hartel et al. (1998, Plant Physiol. Biochem. 36:407-417) and metabolites are measured as described in Jelitto et al. (1992, Planta 188:238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al. 2000, Nature Biotech. 18:1447-1161).

For example, yeast expression vectors comprising the nucleic acids disclosed herein, or fragments thereof, can be constructed and transformed into using standard protocols. The resulting transgenic cells can then be assayed for alterations in sugar, oil, lipid, or fatty acid contents.

Similarly, plant expression vectors comprising the nucleic acids disclosed herein, or fragments thereof, can be constructed and transformed into an appropriate plant cell such as *Arabidopsis*, soybean, rapeseed, rice, maize, wheat, *Medicago truncatula*, etc., using standard protocols. The resulting transgenic cells and/or plants derived there from can then be assayed for alterations in sugar, oil, amino acid, protein, lipid or fatty acid contents.

Additionally, the combinations of sequences disclosed herein, or fragments thereof, can be used to generate knockout mutations in the genomes of various organisms, such as bacteria, mammalian cells, yeast cells, and plant cells (Girke at al. 1998, Plant J. 15:39-48). The resultant knockout cells can then be evaluated for their composition and content in seed storage compounds, and the effect on the phenotype and/or genotype of the mutation. For other methods of gene inactivation include U.S. Pat. No. 6,004,804 "Non-Chimeric Mutational Vectors" and Puttaraju et al. (1999, "Spliceosome-mediated RNA trans-splicing as a tool for gene therapy", Nature Biotech. 17:246-252).

Example 11

Purification of the Desired Products from Transformed Organisms

SMPs can be recovered from plant material by various methods well known in the art. Organs of plants can be separated mechanically from other tissue or organs prior to isolation of the seed storage compound from the plant organ. Following homogenization of the tissue, cellular debris is removed by centrifugation and the supernatant fraction containing the soluble proteins is retained for further purification of the desired compound. If the product is secreted from cells grown in culture, then the cells are removed from the culture by low-speed centrifugation and the supernate fraction is retained for further purification.

The supernatant fraction from either purification method is subjected to chromatography with a suitable resin, in which the desired molecule is either retained on a chromatography resin, while many of the impurities in the sample are not, or where the impurities are retained by the resin, while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey J. E. & Ollis D. F. 1986, Biochemical Engineering Fundamentals, McGraw-Hill: New York).

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzymatic assay, or microbiologically. Such analysis methods are reviewed in: Patek et al. (1994, Appl. Environ. Microbiol. 60:133-140), Malakhova et al. (1996, Biotekhnologiya 11:27-32) and Schmidt et al. (1998, Bioprocess Engineer 19:67-70), Ulmann's Encyclopedia of Industrial Chemistry (1996, Vol. A27, VCH: Weinheim, p. 89-90, p. 521-540, p. 540-547, p. 559-566, 575-581 and p. 581-587) and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

Those skilled in the art will recognize, or will be able to ascertain using no more than routine experimentation, many equivalents to the specific embodiments of the invention described herein. Such equivalents are intended to be encompassed by the claims to the invention disclosed and claimed herein.

TABLE 1

| Plant Lipid Classes | |
|---|---|
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

| Common Plant Fatty Acids | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid * |
| 20:0 | Arachidic acid |
| 20:1 | Eicosenoic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

* These fatty acids do not normally occur in plant seed oils, but their production in transgenic plant seed oil is of importance in plant biotechnology.

TABLE 3

Polynucleotides (combinations of pyruvate kinase subunits) capable of increasing the seed storage compounds

| Polynucleotide number (combination of pyruvate kinase subunits) | First subunit (SEQ ID NO:) | Second subunit (SEQ ID NO:) | Third subunit (SEQ ID NO:) |
|---|---|---|---|
| 1 | 23 | 27 | 25 |
| 2 | 27 | 25 | none |
| 3 | 7 | 25 | none |
| 4_1 | 7 | 23 | 27 |
| 4_2 | 7 | 25 | 27 |
| 5_1 | 15 | 17 | 3 |

TABLE 3-continued

Polynucleotides (combinations of pyruvate kinase subunits) capable of increasing the seed storage compounds

| Polynucleotide number (combination of pyruvate kinase subunits) | First subunit (SEQ ID NO:) | Second subunit (SEQ ID NO:) | Third subunit (SEQ ID NO:) |
|---|---|---|---|
| 5_2 | 19 | 17 | 3 |
| 5_3 | 15 | 21 | 3 |
| 5_4 | 19 | 21 | 3 |
| 5_5 | 15 | 17 | 5 |
| 5_6 | 19 | 17 | 5 |
| 5_7 | 15 | 21 | 5 |
| 5_8 | 19 | 21 | 5 |
| 5_9 | 15 | 17 | 11 |
| 5_10 | 19 | 17 | 11 |
| 5_11 | 15 | 21 | 11 |
| 5_12 | 19 | 21 | 11 |
| 5_13 | 15 | 17 | 13 |
| 5_14 | 19 | 17 | 13 |
| 5_15 | 15 | 21 | 13 |
| 5_16 | 19 | 21 | 13 |
| 6_1 | 17 | 3 | 1 |
| 6_2 | 17 | 3 | 9 |
| 6_3 | 21 | 3 | 1 |
| 6_4 | 21 | 3 | 9 |
| 6_5 | 17 | 5 | 1 |
| 6_6 | 17 | 5 | 9 |
| 6_7 | 21 | 5 | 1 |
| 6_8 | 21 | 5 | 9 |
| 6_9 | 17 | 11 | 1 |
| 6_10 | 17 | 11 | 9 |
| 6_11 | 21 | 11 | 1 |
| 6_12 | 21 | 11 | 9 |
| 6_13 | 17 | 13 | 1 |
| 6_14 | 17 | 13 | 9 |
| 6_15 | 21 | 13 | 1 |
| 6_16 | 21 | 13 | 9 |
| 7_1 | 15 | 3 | 1 |
| 7_2 | 15 | 3 | 9 |
| 7_3 | 19 | 3 | 1 |
| 7_4 | 19 | 3 | 9 |
| 7_5 | 15 | 5 | 1 |
| 7_6 | 15 | 5 | 9 |
| 7_7 | 19 | 5 | 1 |
| 7_8 | 19 | 5 | 9 |
| 7_9 | 15 | 11 | 1 |
| 7_10 | 15 | 11 | 9 |
| 7_11 | 19 | 11 | 1 |
| 7_12 | 19 | 11 | 9 |
| 7_13 | 15 | 13 | 1 |
| 7_14 | 15 | 13 | 9 |
| 7_15 | 19 | 13 | 1 |
| 7_16 | 19 | 13 | 9 |
| 8_1 | 15 | 17 | 1 |
| 8_2 | 15 | 17 | 9 |
| 8_3 | 19 | 17 | 1 |
| 8_4 | 19 | 17 | 9 |
| 8_5 | 15 | 21 | 1 |
| 8_6 | 15 | 21 | 9 |
| 8_7 | 19 | 21 | 1 |
| 8_8 | 19 | 21 | 9 |
| 9_1 | 25 | 27 | 1 |
| 9_2 | 25 | 27 | 13 |
| 9_3 | 25 | 27 | 17 |
| 9_4 | 25 | 27 | 19 |

TABLE 4

Preferred expression control sequences/terminator sequences to be used in the polypeptides shown in table 4

| poly-nucleotide | first expression control sequence (SEQ ID NO:) | first nucleic acid molecule (SEQ ID NO:) | first terminator (SEQ ID NO:) | second expression control sequence (SEQ ID NO:) | second nucleic acid molecule (SEQ ID NO:) | second terminator (SEQ ID NO:) | third expression control sequence (SEQ ID NO:) | third nucleic acid molecule (SEQ ID NO:) | third terminator (SEQ ID NO:) |
|---|---|---|---|---|---|---|---|---|---|
| 1 | 31 | 23 | 32 and/or 34 | 30 | 27 | 35 | 29 | 25 | 33 |
| 2 | 31 | 27 | 34 | 30 | 25 | 35 | | none | |
| 3 | 31 | 7 | 34 | 30 | 25 | 35 | | none | |
| 4_1 and 4_2 | 31 | 7 | 34 | 30 | 23 or 25 | 35 | 29 | 27 | 33 |
| 5_1 to 5_16 | 31 | 15 or 19 | 34 | 30 | 17 or 21 | 35 | 29 | 3, 5, 11 or 13 | 33 |
| 6_1 to 6_16 | 31 | 17 or 21 | 34 | 30 | 3, 5, 11 or 13 | 35 | 29 | 1 or 9 | 33 |
| 7_1 to 7_16 | 31 | 15 or 19 | 34 | 30 | 3, 5, 11 or 13 | 35 | 29 | 1 or 9 | 33 |
| 8_1 to 8_8 | 31 | 15 or 19 | 34 | 30 | 17 or 21 | 35 | 29 | 1 or 9 | 33 |
| 9_1 to 9_4 | 31 | 25 | 34 | 30 | 27 | 35 | 29 | 1, 13, 17 or 19 | 33 |

TABLE 5

Allocation of nucleic acid and protein sequences

| *Arabidopsis* Gencode | Sequence name | Source | Nucleotide SEQ ID NO: | Amino acid SEQ ID NO: |
|---|---|---|---|---|
| At2g36580 | AY069894 | *Arabidopsis* | 1 | 2 |
| At3g04050 | DQ446633 | *thaliana* | 3 | 4 |
| AT3G25960 | AT3G25960 | | 5 | 6 |
| At3g49160 | AY072177 | | 7 | 8 |
| AT3g52990 | AF367255 | | 9 | 10 |
| AT3G55650 | AT3G55650 | | 11 | 12 |
| AT3G55810 | AT3G55810 | | 13 | 14 |
| At4g26390 | At4g26390 | | 15 | 16 |
| At5g08570 | AK229614 | | 17 | 18 |
| At5g56350 | AY054551 | | 19 | 20 |
| At5g63680 | AK229638 | | 21 | 22 |
| At1g32440 | pk316 | | 23 | 24 |
| AT3g22960 | pk317 | | 25 | 26 |
| AT5g52920 | pk319 | | 27 | 28 |
| — | p_Leb4 | *Vicia faba* | 29 | none |
| — | p_LuPXR | *Linum usitatissimum* | 30 | |
| — | p_USP | *Vicia faba* | 31 | |
| — | t_CaMV_35S | Cauliflower mosaic virus | 32 | |
| — | t_Leb3 | *Vicia faba* | 33 | |
| — | t_OCS | *Agrobacterium tumefaciens* | 34 | |
| — | t_rbcSE9 | *Pisum sativum* | 35 | |
| BN06LC13357 | | *Brassica napus* | 36 | 37 |
| BN06LC14749 | | | 38 | 39 |
| BN06MC3558 | | | 40 | 41 |
| GM04MC20844 | | soybean | 42 | 43 |
| GM06MC00404 | | | 44 | 45 |
| GM06MC00441 | | | 46 | 47 |
| OS02LC26272 | | rice | 48 | 49 |
| TA02LC7955 | | wheat | 50 | 51 |
| ZM06LC30904 | | maize | 52 | 53 |
| ZM07MC06344 | | | 54 | 55 |
| ZM07MC31996 | | | 56 | 57 |
| ZM07MC33397 | | | 58 | 59 |

Example 12

Seed Oil Content in Transgenic *Brassica napus*

*Brassica napus* cultivar Westar and Stratos representing medium- and high oil varieties, respectively, have been transformed with a construct for the seed specific overexpression of SEQ ID NO:23, SEQ ID NO:25 and SEQ ID NO: 27 all encoding subunits of the plastidial pyruvate kinase from *Arabidopsis thaliana*. The sequences have been first cloned behind promoters driving their seed-specific expression. The expression cassettes have then been combined using the GATEWAY® technology (Invitrogen).

Transgenic T0 plants have been selected and the copy number of all three expression cassettes confirmed by PCR. Single copy events have been re-grown. Zygosity of the T1 plants have been determined by qPCR and eight homozygous T1 plants as well as eight corresponding null-segregants were grown until they produced sufficient T2 seeds for determination of the seed oil content by near-infrared spectrometry (NIRS).

Figure 2:
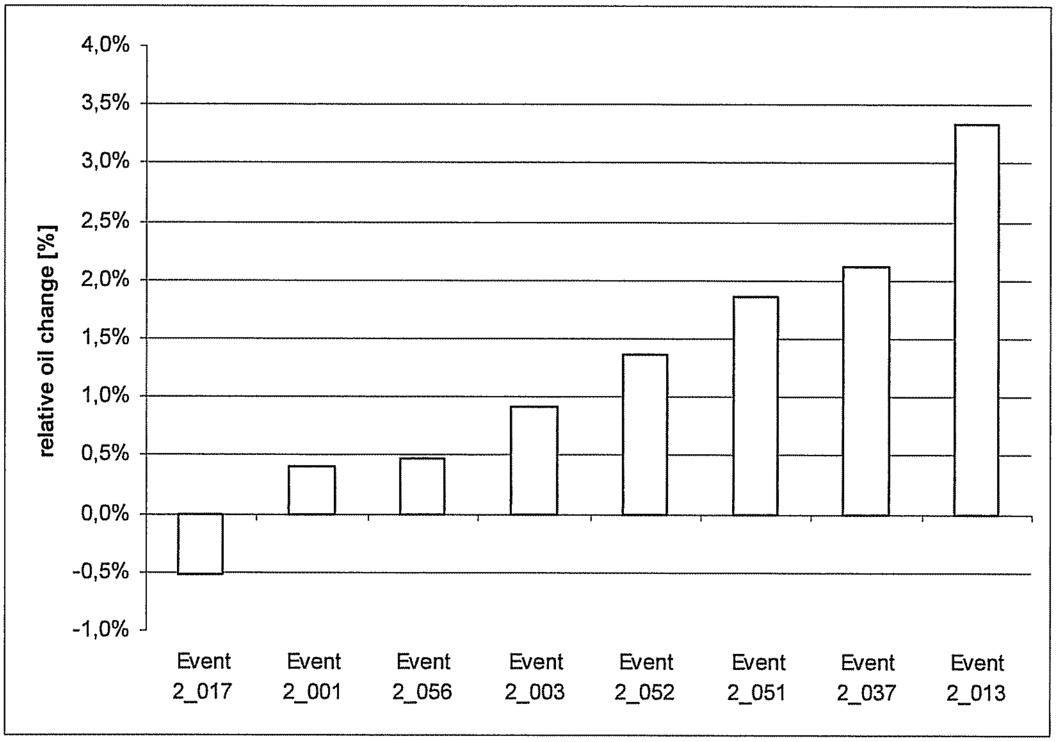
FIG. 2 shows the relative change in the seed oil content of T2 seeds of 8 transgenic homozygous *Brassica napus* cultivar Westar—all representing progenies of the trans-formation event 2—compared to the average oil content of 8 corresponding null segregants derived from the same transformation event.
Figure 3:
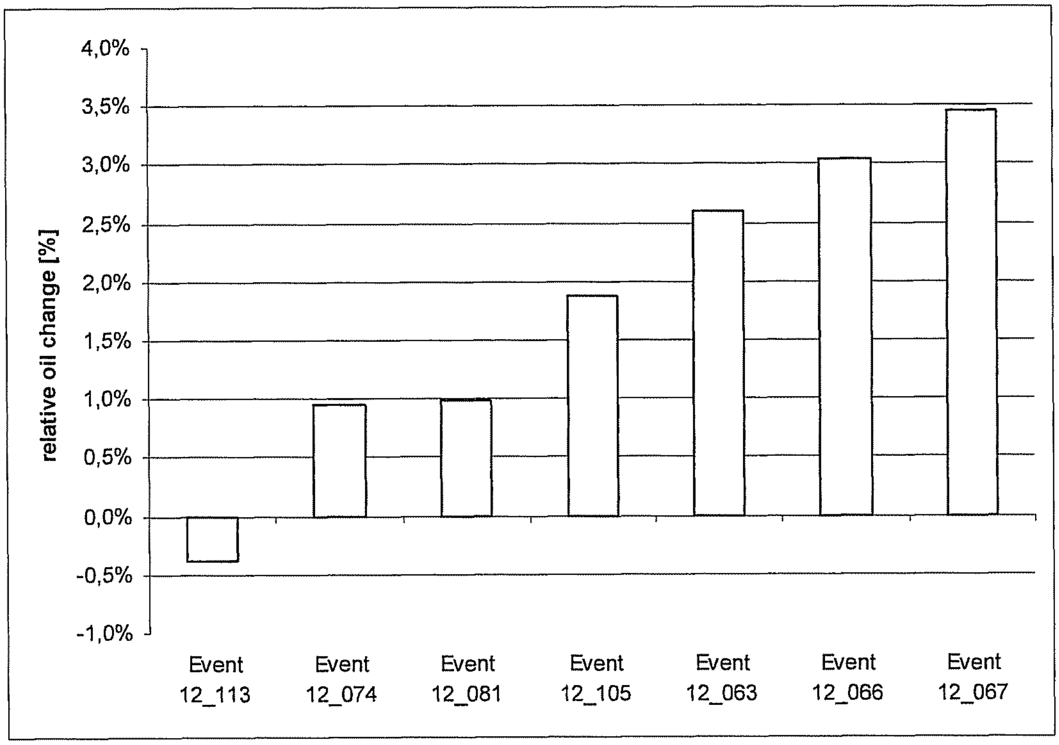
FIG. 3 shows the relative change in the seed oil content of T2 seeds of 8 transgenic homozygous *Brassica napus* cultivar Westar—all representing progenies of the trans-formation event 12—compared to the average oil content of 8 corresponding null segregants derived from the same transformation event.
Figure 4:
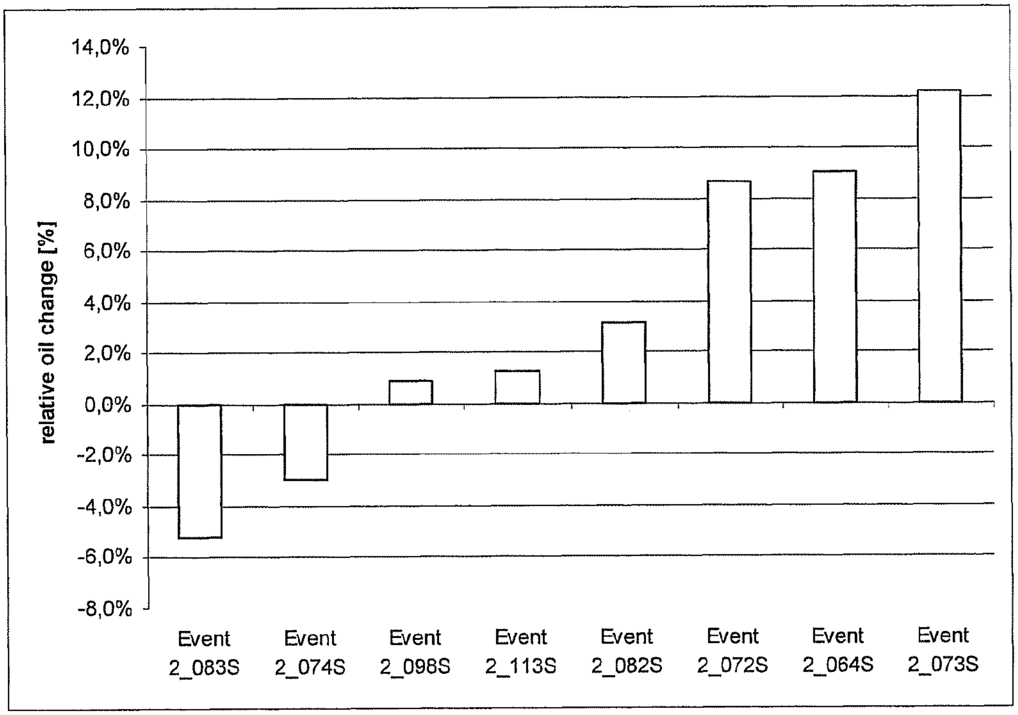
FIG. 4 shows the relative change in the seed oil content of T2 seeds of 8 transgenic homozygous *Brassica napus* cultivar Stratos—all representing progenies of the trans-formation event 2—compared to the average oil content of 8 corresponding null segregants derived from the same transformation event.

The tables 6 to 8 and FIGS. 2 to 4 below show the results of the oil content determination of two transgenic events of the *B. napus* cultivar Westar and one event of the cultivar Stratos. The tables show that absolute oil content in the T2 seeds of homozygous plants and of the corresponding null-segregants. The relative oil change in the seeds of the homozygous plants compared to the average oil content in all corresponding null-segregants is also shown. The relative oil changes are also shown in the Figures.

For all three events the majority of plants had an increased oil content compared to the average oil content of the corresponding null-segregants. The two Westar events had an increase in the seed oil content of up to 3.5%. The transgenic event of the high-oil variety Stratos had an increase in the seed oil content of almost 10% in two plants and of 12% in one plants.

TABLE 6

Oil content of null-seggregants and transgenic homozygous *Brassica napus* cultivar Westar harbouring the construct to overexpress all three subunits of the plastidial pyruvate kinase from *Arabidopsis thaliana* and the relative change in the seed oil content in the transgenic lines compared to the average oil content of corresponding null-seggregants.

| Oil content [% of seed weight] | | | | relative |
|---|---|---|---|---|
| Null-Seggregants | | Homozygous | | oil change |
| Event 2_006 | 43.7 ± 0.0 | Event 2_017 | 43.2 ± 0.0 | −0.5% |
| Event 2_010 | 43.9 ± 0.0 | Event 2_001 | 43.6 ± 0.1 | 0.4% |

TABLE 6-continued

Oil content of null-seggregants and transgenic homozygous *Brassica napus* cultivar Westar harbouring the construct to overexpress all three subunits of the plastidial pyruvate kinase from *Arabidopsis thaliana* and the relative change in the seed oil content in the transgenic lines compared to the average oil content of corresponding null-seggregants.

| Oil content [% of seed weight] | | | | relative |
|---|---|---|---|---|
| Null-Seggregants | | Homozygous | | oil change |
| Event 2_019 | 41.6 ± 0.1 | Event 2_056 | 43.7 ± 0.0 | 0.5% |
| Event 2_023 | 44.1 ± 0.0 | Event 2_003 | 43.8 ± 0.1 | 0.9% |
| Event 2_024 | 43.8 ± 0.0 | Event 2_052 | 44.0 ± 0.1 | 1.4% |
| Event 2_025 | 44.1 ± 0.0 | Event 2_051 | 44.3 ± 0.0 | 1.9% |
| Event 2_033 | 42.8 ± 0.1 | Event 2_037 | 44.4 ± 0.1 | 2.1% |
| Event 2_034 | 42.8 ± 0.1 | Event 2_013 | 44.9 ± 0.0 | 3.3% |
| Event 2_064 | 44.1 ± 0.0 | | | |
| | 43.4 ± 0.9 | | 44.0 ± 0.5 | 1.2% |

TABLE 7

Oil content of null-seggregants and transgenic homozygous *Brassica napus* cultivar Westar harbouring the construct to overexpress all three subunits of the plastidial pyruvate kinase from *Arabidopsis thaliana* and the relative change in the seed oil content in the transgenic lines compared to the average oil content of corresponding null-seggregants.

| Oil content [% of seed weight] | | | | relative |
|---|---|---|---|---|
| Null-Seggregants | | Homozygous | | oil change |
| Event 12_065 | 41.1 ± 0.0 | Event 12_113 | 42.6 ± 0.0 | −0.4% |
| Event 12_071 | 43.3 ± 0.0 | Event 12_074 | 43.2 ± 0.0 | 0.9% |
| Event 12_073 | 43.4 ± 0.1 | Event 12_081 | 43.2 ± 0.0 | 1.0% |
| Event 12_075 | 40.5 ± 0.1 | Event 12_105 | 43.6 ± 0.0 | 1.9% |
| Event 12_080 | 43.1 ± 0.0 | Event 12_063 | 43.9 ± 0.1 | 2.6% |
| Event 12_084 | 44.1 ± 0.1 | Event 12_066 | 44.1 ± 0.2 | 3.0% |
| Event 12_087 | 43.9 ± 0.1 | Event 12_067 | 44.3 ± 0.1 | 3.5% |
| | 42.8 ± 1.4 | | 43.5 ± 0.6 | 1.8% |

TABLE 8

Oil content of null-seggregants and transgenic homozygous *Brassica napus* cultivar Westar harbouring the construct to overexpress all three subunits of the plastidial pyruvate kinase from *Arabidopsis thaliana* and the relative change in the seed oil content in the transgenic lines compared to the average oil content of corresponding null-seggregants.

| Oil content [% of seed weight] | | | | relative |
|---|---|---|---|---|
| Null-Seggregants | | Homozygous | | oil change |
| Event 2_116S | 51.1 ± 0.4 | Event 2_083S | 46.3 ± 0.3 | −5.2% |
| Event 2_117S | 49.4 ± 0.0 | Event 2_074S | 47.4 ± 0.1 | −3.0% |
| Event 2_062S | 52.5 ± 0.3 | Event 2_098S | 49.3 ± 0.2 | 0.9% |
| Event 2_063S | 38.5 ± 0.3 | Event 2_113S | 49.4 ± 0.0 | 1.3% |
| Event 2_065S | 51.7 ± 0.2 | Event 2_082S | 50.3 ± 0.0 | 3.1% |
| Event 2_066S | 47.0 ± 0.2 | Event 2_072S | 53.0 ± 0.5 | 8.7% |
| Event 2_068S | 47.8 ± 0.4 | Event 2_064S | 53.2 ± 0.6 | 9.0% |
| Event 2_070S | 52.4 ± 0.3 | Event 2_073S | 54.8 ± 0.0 | 12.2% |
| | 48.8 ± 4.7 | | 50.5 ± 3.0 | 3.4% |

The invention claimed is:

1. A polynucleotide comprising (i) at least one first nucleic acid molecule operatively linked to a first expression control sequence and a first terminator sequence, said first nucleic acid molecule being selected from the group of nucleic acid molecules consisting of:

(a) a nucleic acid molecule comprising a nucleic acid sequence as shown in any one of SEQ ID NOs: 23, 25, and 27;

(b) a nucleic acid molecule encoding a polypeptide comprising an amino acid sequence as shown in any one of SEQ ID NOs: 24, 26, and 28;

(c) a nucleic acid molecule comprising a nucleic acid sequence which is at least 70% identical to the nucleic acid sequence of the nucleic acid molecule of (a) or (b), wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity;

(d) a nucleic acid molecule encoding a polypeptide comprising an amino acid sequence being at least 70% identical to an amino acid sequence encoded by the nucleic acid molecule of (a) or (b), wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity; and (e) a nucleic acid molecule being a fragment of any one of (a) to (d), wherein said fragment encodes a polypeptide having pyruvate kinase activity, having pyruvate kinase activity upon assembly of the first and second nucleic acid molecule, or upon assembly into a complex, the complex has pyruvate kinase activity, and (ii) at least one second nucleic acid molecule operatively linked to a second expression control sequence and a second terminator sequence, said second nucleic acid molecule being selected from the group of nucleic acid molecules consisting of:

(a) a nucleic acid molecule comprising a nucleic acid sequence as shown in any one of SEQ ID NOs: 23, 25, and 27;

(b) a nucleic acid molecule encoding a polypeptide comprising an amino acid sequence as shown in any one of SEQ ID NOs: 24, 26 and 28;

(c) a nucleic acid molecule comprising a nucleic acid sequence which is at least 70% identical to the nucleic acid sequence of the nucleic acid molecule of (a) or (b), wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity;

(d) a nucleic acid molecule encoding a polypeptide comprising an amino acid sequence being at least 70% identical to an amino acid sequence encoded by the nucleic acid molecule of (a) or (b), wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity; and (e) a nucleic acid molecule being a fragment of any one of (a) to (d), wherein said fragment encodes a polypeptide having pyruvate kinase activity, having pyruvate kinase activity upon assembly of the first and second nucleic acid molecule, or upon assembly into a complex, the complex has pyruvate kinase activity.

2. The polynucleotide of claim 1, wherein said first and/or second expression control sequence(s) allow for a seed specific expression of the said at least one first or at least one second nucleic acid.

3. The polynucleotide of claim 1, wherein said first and/or second terminator sequence(s) are biologically active in seeds.

4. The polynucleotide of claim 1, wherein said first expression control sequence comprises a nucleic acid sequence as shown in SEQ ID NO: 31.

5. The polynucleotide of claim 1, wherein said second expression control sequence comprises a nucleic acid sequence as shown in SEQ ID NO: 30.

6. The polynucleotide of claim 1, wherein said first terminator sequence comprises a nucleic acid sequence as shown in SEQ ID NO: 32 or 34.

7. The polynucleotide of claim 1, wherein said second terminator sequence comprises a nucleic acid sequence as shown in SEQ ID NO: 35.

8. The polynucleotide of claim 1, wherein said polynucleotide further comprises (iii) at least one third nucleic acid molecule operatively linked to a third expression control sequence and a third terminator sequence, said third nucleic acid molecule being selected from the group of nucleic acid molecules consisting of:

(a) a nucleic acid molecule comprising a nucleic acid sequence as shown in any one of SEQ ID NOs: 23, 25, and 27;

(b) a nucleic acid molecule encoding a polypeptide comprising an amino acid sequence as shown in any one of SEQ ID NOs: 24, 26, and 28;

(c) a nucleic acid molecule comprising a nucleic acid sequence which is at least 70% identical to the nucleic acid sequence of the nucleic acid molecule of (a) or (b), wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity;

(d) a nucleic acid molecule encoding a polypeptide comprising an amino acid sequence being at least 70% identical to an amino acid sequence encoded by the nucleic acid molecule of (a) or (b), wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity; and (e) a nucleic acid molecule being a fragment of any one of (a) to (d), wherein said fragment encodes a polypeptide having pyruvate kinase activity, having pyruvate kinase activity upon assembly of the first and second nucleic acid molecule, or upon assembly into a complex, the complex has pyruvate kinase activity.

9. The polynucleotide of claim 8, wherein said third expression control sequence allows for a seed specific expression of the said third nucleic acid.

10. The polynucleotide of claim 8, wherein said third terminator sequence is biologically active in seeds.

11. The polynucleotide of claim 8, wherein the first expression control sequence comprises a nucleic acid sequence as shown in SEQ ID NO: 31.

12. The polynucleotide of claim 8, wherein the second expression control sequence comprises a nucleic acid sequence as shown in SEQ ID NO: 30.

13. The polynucleotide of claim 8, wherein said third expression control sequence comprises a nucleic acid sequence as shown in SEQ ID NO: 29.

14. The polynucleotide of claim 8, wherein the first terminator sequence comprises a nucleic acid sequence as shown in SEQ ID NO: 32 or 34.

15. The polynucleotide of claim 8, wherein the second terminator sequence comprises a nucleic acid sequence as shown in SEQ ID NO: 35.

16. The polynucleotide of claim 8, wherein said third terminator sequence comprises a nucleic acid sequence as shown in SEQ ID NO: 33.

17. A vector comprising the polynucleotide of claim 1.

18. A method for the manufacture of a pyruvate kinase polypeptide being capable of increasing the seed storage compound content when expressed in transgenic plants comprising:
(a) expressing the polynucleotide of claim 1 in a host cell under conditions allowing assembly of the pyruvate kinase polypeptide; and
(b) obtaining the said assembled pyruvate kinase polypeptide from the host cell.

19. A host cell comprising the polynucleotide of claim 1.

20. A transgenic non-human organism comprising the polynucleotide of claim 1.

21. The transgenic non-human organism of claim 20, wherein said non-human transgenic organism is a plant or seed.

22. A seed comprising an assembled pyruvate kinase polypeptide comprising a polypeptide encoded by the polynucleotide of claim 1 in its endosperm, embryo plastids, or cytosol, wherein said seed comprises:
(a) an increase in oil content in comparison to an isogenic seed,
(b) an increase in embryo weight in comparison to an isogenic seed,
(c) an increase in the amino acid content of one or more amino acid in comparison to an isogenic seed for an amino acid selected from the group consisting of: aspartic acid, threonine, glycine, cysteine, valine, methionine, isoleucine, histidine, lysine, arginine, and tryptophan, and/or
(d) an increase in protein content.

23. A method for the manufacture of a seed storage compound comprising:
(a) cultivating the host cell of claim 19 under conditions allowing synthesis of a seed storage compound; and
(b) obtaining the seed storage compound from the host cell or from a transgenic non-human organism which comprises the host cell.

24. A method for the manufacture of a seed storage compound comprising:
(a) cultivating the transgenic non-human organism of claim 20 allowing synthesis of a seed storage compound; and
(b) obtaining the seed storage compound from the transgenic non-human organism or transgenic cell thereof.

25. A method for the manufacture of a plant having a modified amount of a seed storage compound comprising:
(a) introducing the polynucleotide of claim 1 into a plant cell; and
(b) generating a transgenic plant from said plant cell, wherein the polypeptide encoded by the polynucleotide modifies the amount of a seed storage compound in the transgenic plant compared to a non-transgenic control plant.

26. The method of claim 25, wherein the amount of said seed storage compound is increased compared to a non-transgenic control plant.

27. The method of claim 25, wherein said seed storage compound comprises a lipid, a fatty acid, an amino acid, a protein, or a mixture of said compounds.

28. A method for the manufacture of a plant having a modified amount of a seed storage compound comprising:
(a) obtaining a plant cell comprising an assembled pyruvate kinase polypeptide comprising a polypeptide encoded by the polynucleotide of claim 25; and
(b) generating a transgenic plant from the plant cell, wherein the polypeptide encoded by the polynucleotide modifies the amount of a seed storage compound in the transgenic plant compared to a non-transgenic control plant.

29. The method of claim 28, wherein the amount of said seed storage compound is increased compared to a non-transgenic control plant.

30. The method of claim 28, wherein said seed storage compound comprises a lipid, a fatty acid, an amino acid, a protein, or a mixture of said compounds.

31. The polynucleotide of claim 1, wherein the at least one first and second nucleic acid molecule comprises a nucleic acid molecule encoding a polypeptide comprising an amino acid sequence having at least 80% sequence identity to the amino acid sequence of SEQ ID NO: 24, 26, or 28, wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity.

32. The polynucleotide of claim 1, wherein the at least one first and second nucleic acid molecule comprises a nucleic acid molecule encoding a polypeptide comprising an amino acid sequence having at least 90% sequence identity to the amino acid sequence of SEQ ID NO: 24, 26, or 28, wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity.

33. The polynucleotide of claim 1, wherein the at least one first and second nucleic acid molecule comprises a nucleic acid molecule encoding a polypeptide comprising an amino acid sequence having at least 95% sequence identity to the amino acid sequence of SEQ ID NO: 24, 26, or 28, wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity.

34. The polynucleotide of claim 1, wherein the at least one first and second nucleic acid molecule comprises a nucleic acid molecule encoding a polypeptide comprising the amino acid sequence of SEQ ID NO: 24, 26, or 28.

35. The method of claim 28, further comprising obtaining seed and/or further progeny of the transgenic plant, wherein the seed or further progeny comprise the polynucleotide.

36. A plant cell, plant, plant part, seed, or progeny thereof comprising the polynucleotide of claim 29.

37. A plant cell, plant, plant part, seed, or progeny thereof comprising the polynucleotide of claim 30.

38. A plant cell, plant, plant part, seed, or progeny thereof comprising the polynucleotide of claim 31.

39. A plant cell, plant, plant part, seed, or progeny thereof comprising the polynucleotide of claim 32.

40. The polynucleotide of claim 8, wherein the at least one first, second, and third nucleic acid molecule comprises a nucleic acid molecule encoding a polypeptide comprising an amino acid sequence having at least 80% sequence identity to the amino acid sequence of SEQ ID NO: 24, 26, or 28, wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity.

41. The polynucleotide of claim 8, wherein the at least one first, second, and third nucleic acid molecule comprises a nucleic acid molecule encoding a polypeptide comprising an amino acid sequence having at least 90% sequence identity to the amino acid sequence of SEQ ID NO: 24, 26, or 28, wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity.

42. The polynucleotide of claim 8, wherein the at least one first, second, and third nucleic acid molecule comprises a nucleic acid molecule encoding a polypeptide comprising an amino acid sequence having at least 95% sequence identity to the amino acid sequence of SEQ ID NO: 24, 26, or 28, wherein said nucleic acid molecule encodes a polypeptide having pyruvate kinase activity, having pyruvate kinase activity upon assembly of the first and second nucleic acid molecule, or upon assembly into a complex, the complex has pyruvate kinase activity.

43. The polynucleotide of claim 8, wherein the at least one first, second, and third nucleic acid molecule comprises a nucleic acid molecule encoding a polypeptide comprising the amino acid sequence of SEQ ID NO: 24, 26, or 28.

44. A plant cell, plant, plant part, seed, or progeny thereof comprising the polynucleotide of claim 40.

45. A plant cell, plant, plant part, seed, or progeny thereof comprising the polynucleotide of claim 41.

46. A plant cell, plant, plant part, seed, or progeny thereof comprising the polynucleotide of claim 42.

47. A plant cell, plant, plant part, seed, or progeny thereof comprising the polynucleotide of claim 43.

48. An expression construct comprising the polynucleotide of claim 1.

49. An expression construct comprising the polynucleotide of claim 31.

50. An expression construct comprising the polynucleotide of claim 32.

51. An expression construct comprising the polynucleotide of claim 33.

52. An expression construct comprising the polynucleotide of claim 34.

* * * * *

SEQUENCE LISTING

```
<160> NUMBER OF SEQ ID NOS: 59

<210> SEQ ID NO 1
<211> LENGTH: 1963
<212> TYPE: DNA
<213> ORGANISM: Arabidopsis thaliana
<220> FEATURE:
<221> NAME/KEY: CDS
<222> LOCATION: (132)..(1715)
<223> OTHER INFORMATION: Pyruvate Kinase

<400> SEQUENCE: 1

gccggtcaag cgtatcaaat acccaatcac gcgaactttt ctccgcctct tctccactcc      60

aaaattcttc tccgtctttc tcccgtcacc gtcgaataaa gcctgagatc tccgaattct     120

gatcagcaac t atg cat tca agt cat ctc ctt ctc gag gaa ccg atc agg      170
             Met His Ser Ser His Leu Leu Leu Glu Glu Pro Ile Arg
             1               5                   10

atg act tca atc ctc gaa cct tct aaa tca agt ttc ttc ccg gct ttg       218
Met Thr Ser Ile Leu Glu Pro Ser Lys Ser Ser Phe Phe Pro Ala Leu
    15                  20                  25

act aag att gtt ggg act cta ggt ccg aaa tct cga tcc gtc gag gtg       266
Thr Lys Ile Val Gly Thr Leu Gly Pro Lys Ser Arg Ser Val Glu Val
30                  35                  40                  45

att gct ggt tgt ctc aaa gct gga atg tcc gtg gct cga ttc gat ttc       314
Ile Ala Gly Cys Leu Lys Ala Gly Met Ser Val Ala Arg Phe Asp Phe
                50                  55                  60
```

-continued

```
tct tgg tgc gat gct gat tat cac cag gag acg ctg gag aat ctg aag       362
Ser Trp Cys Asp Ala Asp Tyr His Gln Glu Thr Leu Glu Asn Leu Lys
            65                  70                  75

ata gct gtg aag agc act aag aag ctt tgt gct gtt atg cta gac act       410
Ile Ala Val Lys Ser Thr Lys Lys Leu Cys Ala Val Met Leu Asp Thr
        80                  85                  90

gta gga cct gag ttg caa gtt att aac aag act gag aaa gct att tct       458
Val Gly Pro Glu Leu Gln Val Ile Asn Lys Thr Glu Lys Ala Ile Ser
    95                  100                 105

ctt aaa gct gat ggc ctt gta act ttg act ccg agt caa gat caa gaa       506
Leu Lys Ala Asp Gly Leu Val Thr Leu Thr Pro Ser Gln Asp Gln Glu
110                 115                 120                 125

gcc tcc tct gaa gtc ctt ccc att aat ttt gat ggg tta gcg aag gcg       554
Ala Ser Ser Glu Val Leu Pro Ile Asn Phe Asp Gly Leu Ala Lys Ala
                130                 135                 140

gtt aag aaa gga gac act atc ttt gtt gga caa tac ctc ttc act ggt       602
Val Lys Lys Gly Asp Thr Ile Phe Val Gly Gln Tyr Leu Phe Thr Gly
            145                 150                 155

agt gaa aca act tca gtt tgg ctt gag gtt gaa gaa gtt aaa gga gat       650
Ser Glu Thr Thr Ser Val Trp Leu Glu Val Glu Glu Val Lys Gly Asp
        160                 165                 170

gat gtc att tgt att tca agg aat gct gct act ctg ggt ggt ccg tta       698
Asp Val Ile Cys Ile Ser Arg Asn Ala Ala Thr Leu Gly Gly Pro Leu
    175                 180                 185

ttc aca ttg cac gtc tct caa gtt cac att gat atg cca acc cta act       746
Phe Thr Leu His Val Ser Gln Val His Ile Asp Met Pro Thr Leu Thr
190                 195                 200                 205

gag aag gat aag gag gtt ata agt aca tgg gga gtt cag aat aag atc       794
Glu Lys Asp Lys Glu Val Ile Ser Thr Trp Gly Val Gln Asn Lys Ile
                210                 215                 220

gac ttt ctc tca tta tct tat tgt cga cat gca gaa gat gtt cgc cag       842
Asp Phe Leu Ser Leu Ser Tyr Cys Arg His Ala Glu Asp Val Arg Gln
            225                 230                 235

gcc cgt gag ttg ctt aac agt tgt ggt gac ctc tct caa aca caa ata       890
Ala Arg Glu Leu Leu Asn Ser Cys Gly Asp Leu Ser Gln Thr Gln Ile
        240                 245                 250

ttt gcg aag att gag aat gaa gag gga cta acc cac ttt gac gaa att       938
Phe Ala Lys Ile Glu Asn Glu Glu Gly Leu Thr His Phe Asp Glu Ile
    255                 260                 265

cta caa gaa gca gat ggc att att ctt tct cgt ggg aat ttg ggt atc       986
Leu Gln Glu Ala Asp Gly Ile Ile Leu Ser Arg Gly Asn Leu Gly Ile
270                 275                 280                 285

gat cta cct ccg gaa aag gtg ttt ttg ttc caa aag gct gct ctt tac      1034
Asp Leu Pro Pro Glu Lys Val Phe Leu Phe Gln Lys Ala Ala Leu Tyr
                290                 295                 300

aag tgt aac atg gct gga aag cct gcc gtt ctt act cgt gtt gta gac      1082
Lys Cys Asn Met Ala Gly Lys Pro Ala Val Leu Thr Arg Val Val Asp
            305                 310                 315

agt atg aca gac aat ctg cgg cca act cgt gca gag gca act gat gtt      1130
Ser Met Thr Asp Asn Leu Arg Pro Thr Arg Ala Glu Ala Thr Asp Val
        320                 325                 330

gct aat gct gtt tta gat gga agt gat gca att ctt ctt ggt gct gag      1178
Ala Asn Ala Val Leu Asp Gly Ser Asp Ala Ile Leu Leu Gly Ala Glu
    335                 340                 345

act ctt cgt gga ttg tac cct gtt gaa acc ata tca act gtt ggt aga      1226
Thr Leu Arg Gly Leu Tyr Pro Val Glu Thr Ile Ser Thr Val Gly Arg
350                 355                 360                 365

atc tgt tgt gag gca gag aaa gtt ttc aac caa gat ttg ttc ttt aag      1274
Ile Cys Cys Glu Ala Glu Lys Val Phe Asn Gln Asp Leu Phe Phe Lys
                370                 375                 380
```

```
aag act gtc aag tat gtt gga gaa cca atg act cac ttg gaa tct att     1322
Lys Thr Val Lys Tyr Val Gly Glu Pro Met Thr His Leu Glu Ser Ile
            385                 390                 395

gct tct tct gct gta cgg gca gca atc aag gtt aag gca tcc gta att     1370
Ala Ser Ser Ala Val Arg Ala Ala Ile Lys Val Lys Ala Ser Val Ile
        400                 405                 410

ata tgc ttc acc tcg tct ggc aga gca gca agg ttg att gcc aaa tac     1418
Ile Cys Phe Thr Ser Ser Gly Arg Ala Ala Arg Leu Ile Ala Lys Tyr
    415                 420                 425

cgt cca act atg ccc gtt ctc tct gtt gtc att ccc cga ctt acg aca     1466
Arg Pro Thr Met Pro Val Leu Ser Val Val Ile Pro Arg Leu Thr Thr
430                 435                 440                 445

aat cag ctg aag tgg agc ttt agc gga gcc ttt gag gca agg cag tca     1514
Asn Gln Leu Lys Trp Ser Phe Ser Gly Ala Phe Glu Ala Arg Gln Ser
                450                 455                 460

ctt att gtc aga ggt ctt ttc ccc atg ctt gct gat cct cgt cac cct     1562
Leu Ile Val Arg Gly Leu Phe Pro Met Leu Ala Asp Pro Arg His Pro
            465                 470                 475

gcg gaa tca aca agt gca aca aat gag tcg gtt ctt aaa gtg gct cta     1610
Ala Glu Ser Thr Ser Ala Thr Asn Glu Ser Val Leu Lys Val Ala Leu
        480                 485                 490

gac cat ggg aag caa gcc gga gtg atc aag tca cat gac aga gtt gtg     1658
Asp His Gly Lys Gln Ala Gly Val Ile Lys Ser His Asp Arg Val Val
    495                 500                 505

gtc tgt cag aaa gtg gga gat gcg tcc gtg gtc aaa atc atc gag cta     1706
Val Cys Gln Lys Val Gly Asp Ala Ser Val Val Lys Ile Ile Glu Leu
510                 515                 520                 525

gag gat tag aagaagcaga gtgagtcgtt gtctcggtct tttttgttct             1755
Glu Asp

gttactaatc aattttattt ccttcactaa aactcttggt gccgtccaag aaaaatcctt   1815

gcaatcattg tttctcgccg gctatatgct agataccgga gtgaaaatat atctcctggg   1875

cttttgtttt cgtatttagg agattgatgt ttccaagtta tgatataaac cactttccac   1935

tttatgcata atatctccat cccctagt                                      1963


<210> SEQ ID NO 2
<211> LENGTH: 527
<212> TYPE: PRT
<213> ORGANISM: Arabidopsis thaliana

<400> SEQUENCE: 2

Met His Ser Ser His Leu Leu Leu Glu Glu Pro Ile Arg Met Thr Ser
1               5                   10                  15

Ile Leu Glu Pro Ser Lys Ser Ser Phe Phe Pro Ala Leu Thr Lys Ile
            20                  25                  30

Val Gly Thr Leu Gly Pro Lys Ser Arg Ser Val Glu Val Ile Ala Gly
        35                  40                  45

Cys Leu Lys Ala Gly Met Ser Val Ala Arg Phe Asp Phe Ser Trp Cys
    50                  55                  60

Asp Ala Asp Tyr His Gln Glu Thr Leu Glu Asn Leu Lys Ile Ala Val
65                  70                  75                  80

Lys Ser Thr Lys Lys Leu Cys Ala Val Met Leu Asp Thr Val Gly Pro
                85                  90                  95

Glu Leu Gln Val Ile Asn Lys Thr Glu Lys Ala Ile Ser Leu Lys Ala
            100                 105                 110

Asp Gly Leu Val Thr Leu Thr Pro Ser Gln Asp Gln Glu Ala Ser Ser
        115                 120                 125
```

```
Glu Val Leu Pro Ile Asn Phe Asp Gly Leu Ala Lys Ala Val Lys Lys
    130                 135                 140

Gly Asp Thr Ile Phe Val Gly Gln Tyr Leu Phe Thr Gly Ser Glu Thr
145                 150                 155                 160

Thr Ser Val Trp Leu Glu Val Glu Glu Val Lys Gly Asp Asp Val Ile
                165                 170                 175

Cys Ile Ser Arg Asn Ala Ala Thr Leu Gly Gly Pro Leu Phe Thr Leu
            180                 185                 190

His Val Ser Gln Val His Ile Asp Met Pro Thr Leu Thr Glu Lys Asp
        195                 200                 205

Lys Glu Val Ile Ser Thr Trp Gly Val Gln Asn Lys Ile Asp Phe Leu
    210                 215                 220

Ser Leu Ser Tyr Cys Arg His Ala Glu Asp Val Arg Gln Ala Arg Glu
225                 230                 235                 240

Leu Leu Asn Ser Cys Gly Asp Leu Ser Gln Thr Gln Ile Phe Ala Lys
                245                 250                 255

Ile Glu Asn Glu Glu Gly Leu Thr His Phe Asp Glu Ile Leu Gln Glu
            260                 265                 270

Ala Asp Gly Ile Ile Leu Ser Arg Gly Asn Leu Gly Ile Asp Leu Pro
        275                 280                 285

Pro Glu Lys Val Phe Leu Phe Gln Lys Ala Ala Leu Tyr Lys Cys Asn
    290                 295                 300

Met Ala Gly Lys Pro Ala Val Leu Thr Arg Val Val Asp Ser Met Thr
305                 310                 315                 320

Asp Asn Leu Arg Pro Thr Arg Ala Glu Ala Thr Asp Val Ala Asn Ala
                325                 330                 335

Val Leu Asp Gly Ser Asp Ala Ile Leu Leu Gly Ala Glu Thr Leu Arg
            340                 345                 350

Gly Leu Tyr Pro Val Glu Thr Ile Ser Thr Val Gly Arg Ile Cys Cys
        355                 360                 365

Glu Ala Glu Lys Val Phe Asn Gln Asp Leu Phe Phe Lys Lys Thr Val
    370                 375                 380

Lys Tyr Val Gly Glu Pro Met Thr His Leu Glu Ser Ile Ala Ser Ser
385                 390                 395                 400

Ala Val Arg Ala Ala Ile Lys Val Lys Ala Ser Val Ile Ile Cys Phe
                405                 410                 415

Thr Ser Ser Gly Arg Ala Ala Arg Leu Ile Ala Lys Tyr Arg Pro Thr
            420                 425                 430

Met Pro Val Leu Ser Val Val Ile Pro Arg Leu Thr Thr Asn Gln Leu
        435                 440                 445

Lys Trp Ser Phe Ser Gly Ala Phe Glu Ala Arg Gln Ser Leu Ile Val
    450                 455                 460

Arg Gly Leu Phe Pro Met Leu Ala Asp Pro Arg His Pro Ala Glu Ser
465                 470                 475                 480

Thr Ser Ala Thr Asn Glu Ser Val Leu Lys Val Ala Leu Asp His Gly
                485                 490                 495

Lys Gln Ala Gly Val Ile Lys Ser His Asp Arg Val Val Val Cys Gln
            500                 505                 510

Lys Val Gly Asp Ala Ser Val Val Lys Ile Ile Glu Leu Glu Asp
        515                 520                 525
```

<210> SEQ ID NO 3
<211> LENGTH: 1533
<212> TYPE: DNA
<213> ORGANISM: Arabidopsis thaliana
<220> FEATURE:
<221> NAME/KEY: CDS
<222> LOCATION: (1)..(1533)
<223> OTHER INFORMATION: Pyruvate Kinase

<400> SEQUENCE: 3

```
atg gag aag tta ctt gct gga caa aca aac aat gga tcc ctc aag tca       48
Met Glu Lys Leu Leu Ala Gly Gln Thr Asn Asn Gly Ser Leu Lys Ser
1               5                   10                  15

aag acg aag atc gtc tgt act ctc gga ccg gct tcg aga tcg gtt gag       96
Lys Thr Lys Ile Val Cys Thr Leu Gly Pro Ala Ser Arg Ser Val Glu
            20                  25                  30

atg gtt gag aag ctt ctc aaa gcc ggt atg aac gta gcc cgg ttc aac      144
Met Val Glu Lys Leu Leu Lys Ala Gly Met Asn Val Ala Arg Phe Asn
        35                  40                  45

ttc tcc cat ggt tct cac tca tac cat caa gaa act ctt gac aat ctc      192
Phe Ser His Gly Ser His Ser Tyr His Gln Glu Thr Leu Asp Asn Leu
    50                  55                  60

aga acc gcc atg gag aac act tgt att ccc tgt gcc gtc atg ctc gac      240
Arg Thr Ala Met Glu Asn Thr Cys Ile Pro Cys Ala Val Met Leu Asp
65                  70                  75                  80

acc aag ggt cct gag atc cga acc ggg ttt ctc aaa gaa ggc aaa ccg      288
Thr Lys Gly Pro Glu Ile Arg Thr Gly Phe Leu Lys Glu Gly Lys Pro
                85                  90                  95

gtt gag cta att caa ggt caa gag att aca atc tca act gat tac acc      336
Val Glu Leu Ile Gln Gly Gln Glu Ile Thr Ile Ser Thr Asp Tyr Thr
            100                 105                 110

atg gaa gga gat tca aac aca atc tca atg agt tac aag aaa ctt gct      384
Met Glu Gly Asp Ser Asn Thr Ile Ser Met Ser Tyr Lys Lys Leu Ala
        115                 120                 125

gaa gat ctc aag tcc ggt gac gtg att ctc tgt tcc gac ggt aca atc      432
Glu Asp Leu Lys Ser Gly Asp Val Ile Leu Cys Ser Asp Gly Thr Ile
    130                 135                 140

tct ctt acc gtc ttg tct tgt gac aag aat ctc ggt ctt gtt cgt gcc      480
Ser Leu Thr Val Leu Ser Cys Asp Lys Asn Leu Gly Leu Val Arg Ala
145                 150                 155                 160

cgt tgc gag aac tct gca gtt ctt gga gaa aga aag aac gtg aac ctc      528
Arg Cys Glu Asn Ser Ala Val Leu Gly Glu Arg Lys Asn Val Asn Leu
                165                 170                 175

cct gga atc gta gtt gat ctt cca aca ctc aca gag aag gat caa gag      576
Pro Gly Ile Val Val Asp Leu Pro Thr Leu Thr Glu Lys Asp Gln Glu
            180                 185                 190

gat att ctc caa tgg gga gtt ccg aat aag atc gat atc atc gct ctt      624
Asp Ile Leu Gln Trp Gly Val Pro Asn Lys Ile Asp Ile Ile Ala Leu
        195                 200                 205

tcc ttt gtt cgt aaa gga tct gat ctg gtc gag gtc agg aag ttg ctt      672
Ser Phe Val Arg Lys Gly Ser Asp Leu Val Glu Val Arg Lys Leu Leu
    210                 215                 220

gga gag aac gca aag agt atc atg ctc atg tca aag gtg gag aat caa      720
Gly Glu Asn Ala Lys Ser Ile Met Leu Met Ser Lys Val Glu Asn Gln
225                 230                 235                 240

gaa gga gtg atg aat ttt gac aag att ctg gaa tat tct gat gca ttc      768
Glu Gly Val Met Asn Phe Asp Lys Ile Leu Glu Tyr Ser Asp Ala Phe
                245                 250                 255

atg gtg gct aga ggt gat tta gga atg gag att ccg att gaa aag atg      816
Met Val Ala Arg Gly Asp Leu Gly Met Glu Ile Pro Ile Glu Lys Met
            260                 265                 270

ttt ctt gct cag aag atg atg att cag aag gct aat gct ctt ggg aag      864
Phe Leu Ala Gln Lys Met Met Ile Gln Lys Ala Asn Ala Leu Gly Lys
        275                 280                 285

cca atc gtc aca gcc aca cag atg ctt gag tca atg acc aaa tct cct      912
```

```
Pro Ile Val Thr Ala Thr Gln Met Leu Glu Ser Met Thr Lys Ser Pro
    290                 295                 300

cgt cca act aga gca gaa gcc acc gat gta gct aac gct gtc ctt gac      960
Arg Pro Thr Arg Ala Glu Ala Thr Asp Val Ala Asn Ala Val Leu Asp
305                 310                 315                 320

ggc act gat tgc gtc atg ctc agt gga gaa acc gcc gcc gga gct cac     1008
Gly Thr Asp Cys Val Met Leu Ser Gly Glu Thr Ala Ala Gly Ala His
                325                 330                 335

cct gaa acc gcc gtg cta aca atg tca aga atc tgt aag gaa gca gag     1056
Pro Glu Thr Ala Val Leu Thr Met Ser Arg Ile Cys Lys Glu Ala Glu
            340                 345                 350

gat ttc atc gat tac gac aca atg cac aag aag att caa gat atc gtt     1104
Asp Phe Ile Asp Tyr Asp Thr Met His Lys Lys Ile Gln Asp Ile Val
        355                 360                 365

tcg ttg cct tta tct cct att gag agc ttg gcc gct tca gcc gtt tcg     1152
Ser Leu Pro Leu Ser Pro Ile Glu Ser Leu Ala Ala Ser Ala Val Ser
    370                 375                 380

acg gcg agg agt ctt tgt gcg gct gcg att gtc gtt cta acc aag gga     1200
Thr Ala Arg Ser Leu Cys Ala Ala Ala Ile Val Val Leu Thr Lys Gly
385                 390                 395                 400

ggt tac acg gtg gag ctt gtg gcc aag tac agg cct agt gtt ccg att     1248
Gly Tyr Thr Val Glu Leu Val Ala Lys Tyr Arg Pro Ser Val Pro Ile
                405                 410                 415

ctg tcc gta att gtg ccg gag att act cgt acg gat gat ttc gag tgg     1296
Leu Ser Val Ile Val Pro Glu Ile Thr Arg Thr Asp Asp Phe Glu Trp
            420                 425                 430

tcg tgc tct gaa tct gcg gct cat gtg gca aga cgt ggt ttg atc tac     1344
Ser Cys Ser Glu Ser Ala Ala His Val Ala Arg Arg Gly Leu Ile Tyr
        435                 440                 445

cgt gga att gtt cct gtg atg gcg acg gga gca tcc gct agg tct tcg     1392
Arg Gly Ile Val Pro Val Met Ala Thr Gly Ala Ser Ala Arg Ser Ser
    450                 455                 460

aac aag gac tcg acg gag gag acg att caa ttc gcc att gaa ttc gcg     1440
Asn Lys Asp Ser Thr Glu Glu Thr Ile Gln Phe Ala Ile Glu Phe Ala
465                 470                 475                 480

aag aag aag gga ata tgt aag aca gga gac tcg att gtg gcg ttg cac     1488
Lys Lys Lys Gly Ile Cys Lys Thr Gly Asp Ser Ile Val Ala Leu His
                485                 490                 495

aag atc gat ggc tcc tct gtt gtc aag att ttg aac gtg gag tag         1533
Lys Ile Asp Gly Ser Ser Val Val Lys Ile Leu Asn Val Glu
            500                 505                 510


<210> SEQ ID NO 4
<211> LENGTH: 510
<212> TYPE: PRT
<213> ORGANISM: Arabidopsis thaliana

<400> SEQUENCE: 4

Met Glu Lys Leu Leu Ala Gly Gln Thr Asn Asn Gly Ser Leu Lys Ser
1               5                   10                  15

Lys Thr Lys Ile Val Cys Thr Leu Gly Pro Ala Ser Arg Ser Val Glu
            20                  25                  30

Met Val Glu Lys Leu Leu Lys Ala Gly Met Asn Val Ala Arg Phe Asn
        35                  40                  45

Phe Ser His Gly Ser His Ser Tyr His Gln Glu Thr Leu Asp Asn Leu
    50                  55                  60

Arg Thr Ala Met Glu Asn Thr Cys Ile Pro Cys Ala Val Met Leu Asp
65                  70                  75                  80

Thr Lys Gly Pro Glu Ile Arg Thr Gly Phe Leu Lys Glu Gly Lys Pro
                85                  90                  95
```

```
Val Glu Leu Ile Gln Gly Gln Glu Ile Thr Ile Ser Thr Asp Tyr Thr
            100                 105                 110

Met Glu Gly Asp Ser Asn Thr Ile Ser Met Ser Tyr Lys Lys Leu Ala
        115                 120                 125

Glu Asp Leu Lys Ser Gly Asp Val Ile Leu Cys Ser Asp Gly Thr Ile
    130                 135                 140

Ser Leu Thr Val Leu Ser Cys Asp Lys Asn Leu Gly Leu Val Arg Ala
145                 150                 155                 160

Arg Cys Glu Asn Ser Ala Val Leu Gly Glu Arg Lys Asn Val Asn Leu
                165                 170                 175

Pro Gly Ile Val Val Asp Leu Pro Thr Leu Thr Glu Lys Asp Gln Glu
            180                 185                 190

Asp Ile Leu Gln Trp Gly Val Pro Asn Lys Ile Asp Ile Ile Ala Leu
        195                 200                 205

Ser Phe Val Arg Lys Gly Ser Asp Leu Val Glu Val Arg Lys Leu Leu
    210                 215                 220

Gly Glu Asn Ala Lys Ser Ile Met Leu Met Ser Lys Val Glu Asn Gln
225                 230                 235                 240

Glu Gly Val Met Asn Phe Asp Lys Ile Leu Glu Tyr Ser Asp Ala Phe
                245                 250                 255

Met Val Ala Arg Gly Asp Leu Gly Met Glu Ile Pro Ile Glu Lys Met
            260                 265                 270

Phe Leu Ala Gln Lys Met Met Ile Gln Lys Ala Asn Ala Leu Gly Lys
        275                 280                 285

Pro Ile Val Thr Ala Thr Gln Met Leu Glu Ser Met Thr Lys Ser Pro
    290                 295                 300

Arg Pro Thr Arg Ala Glu Ala Thr Asp Val Ala Asn Ala Val Leu Asp
305                 310                 315                 320

Gly Thr Asp Cys Val Met Leu Ser Gly Glu Thr Ala Ala Gly Ala His
                325                 330                 335

Pro Glu Thr Ala Val Leu Thr Met Ser Arg Ile Cys Lys Glu Ala Glu
            340                 345                 350

Asp Phe Ile Asp Tyr Asp Thr Met His Lys Lys Ile Gln Asp Ile Val
        355                 360                 365

Ser Leu Pro Leu Ser Pro Ile Glu Ser Leu Ala Ala Ser Ala Val Ser
    370                 375                 380

Thr Ala Arg Ser Leu Cys Ala Ala Ala Ile Val Val Leu Thr Lys Gly
385                 390                 395                 400

Gly Tyr Thr Val Glu Leu Val Ala Lys Tyr Arg Pro Ser Val Pro Ile
                405                 410                 415

Leu Ser Val Ile Val Pro Glu Ile Thr Arg Thr Asp Asp Phe Glu Trp
            420                 425                 430

Ser Cys Ser Glu Ser Ala Ala His Val Ala Arg Arg Gly Leu Ile Tyr
        435                 440                 445

Arg Gly Ile Val Pro Val Met Ala Thr Gly Ala Ser Ala Arg Ser Ser
    450                 455                 460

Asn Lys Asp Ser Thr Glu Glu Thr Ile Gln Phe Ala Ile Glu Phe Ala
465                 470                 475                 480

Lys Lys Lys Gly Ile Cys Lys Thr Gly Asp Ser Ile Val Ala Leu His
                485                 490                 495

Lys Ile Asp Gly Ser Ser Val Val Lys Ile Leu Asn Val Glu
            500                 505                 510
```

<210> SEQ ID NO 5
<211> LENGTH: 1494
<212> TYPE: DNA
<213> ORGANISM: Arabidopsis thaliana
<220> FEATURE:
<221> NAME/KEY: CDS
<222> LOCATION: (1)..(1494)
<223> OTHER INFORMATION: Pyruvate Kinase

<400> SEQUENCE: 5

```
atg gag atg tta ctt ggt gga caa gca acc aat gga gct ctt cgt tca       48
Met Glu Met Leu Leu Gly Gly Gln Ala Thr Asn Gly Ala Leu Arg Ser
1               5                   10                  15

aag acg aag ata gtt tgt act ctt gga cca gct tca aga tcg gtg gag       96
Lys Thr Lys Ile Val Cys Thr Leu Gly Pro Ala Ser Arg Ser Val Glu
            20                  25                  30

atg att gag aag ctt ctc aag gct ggt atg aac gta gcc cgg ttc aat      144
Met Ile Glu Lys Leu Leu Lys Ala Gly Met Asn Val Ala Arg Phe Asn
        35                  40                  45

ttc tcc cat ggt tct cac tct tac cat caa gaa act ctc gat aat ctc      192
Phe Ser His Gly Ser His Ser Tyr His Gln Glu Thr Leu Asp Asn Leu
    50                  55                  60

aga acc gcc atg gac aac act ggt atc ctc tgc gcc gtc atg ctc gac      240
Arg Thr Ala Met Asp Asn Thr Gly Ile Leu Cys Ala Val Met Leu Asp
65                  70                  75                  80

aca aag agt cct gtg ata cga acc ggg ttt ctc aaa gaa ggc aaa ccg      288
Thr Lys Ser Pro Val Ile Arg Thr Gly Phe Leu Lys Glu Gly Lys Pro
                85                  90                  95

ata cag cta aag caa ggt caa gag atc acc atc tca att gat tac aag      336
Ile Gln Leu Lys Gln Gly Gln Glu Ile Thr Ile Ser Ile Asp Tyr Lys
            100                 105                 110

ata caa gga gat tcc aac act atc tcc atg agc tac aag aaa ctt gca      384
Ile Gln Gly Asp Ser Asn Thr Ile Ser Met Ser Tyr Lys Lys Leu Ala
        115                 120                 125

gag gat ctc aaa cct ggt gac gtg atc ctt tgt tca gac gga aca atc      432
Glu Asp Leu Lys Pro Gly Asp Val Ile Leu Cys Ser Asp Gly Thr Ile
    130                 135                 140

tct cta aat gtc ttg tcc tgt gac aag tat ctc ggt ctt gtt cgt tgc      480
Ser Leu Asn Val Leu Ser Cys Asp Lys Tyr Leu Gly Leu Val Arg Cys
145                 150                 155                 160

cga tgc gag aac tct gct ctt ctt gga gaa aga aaa aac gtt aat ctt      528
Arg Cys Glu Asn Ser Ala Leu Leu Gly Glu Arg Lys Asn Val Asn Leu
                165                 170                 175

cct gga att gta gtt gat ctc cca aca ctc act gag aaa gat aaa gaa      576
Pro Gly Ile Val Val Asp Leu Pro Thr Leu Thr Glu Lys Asp Lys Glu
            180                 185                 190

gat att atg caa tgg gga gtt ccg aac aaa atc gac att atc gct ctc      624
Asp Ile Met Gln Trp Gly Val Pro Asn Lys Ile Asp Ile Ile Ala Leu
        195                 200                 205

tct ttt gtt cgt aaa gga tct gac cta atc caa gta agg aaa tta ctt      672
Ser Phe Val Arg Lys Gly Ser Asp Leu Ile Gln Val Arg Lys Leu Leu
    210                 215                 220

gga gag cac tca aag agc atc atg ctt atg tca aag gtg gag aat caa      720
Gly Glu His Ser Lys Ser Ile Met Leu Met Ser Lys Val Glu Asn Gln
225                 230                 235                 240

gaa gga gta atg aat ttc gat aag atc ctg gag aat tct gat gct ttc      768
Glu Gly Val Met Asn Phe Asp Lys Ile Leu Glu Asn Ser Asp Ala Phe
                245                 250                 255

atg gtg gct aga gga gat ctt ggg atg gag ata cca atc gaa aag atg      816
Met Val Ala Arg Gly Asp Leu Gly Met Glu Ile Pro Ile Glu Lys Met
            260                 265                 270

ttt ctt gct cag aaa aca atg atc aac aag gct aat gct cat ggg aaa      864
```

```
Phe Leu Ala Gln Lys Thr Met Ile Asn Lys Ala Asn Ala His Gly Lys
        275                 280                 285

cca gtg gtc aca gcc aca cag atg ctt gaa tcc atg aca gtc tct cct      912
Pro Val Val Thr Ala Thr Gln Met Leu Glu Ser Met Thr Val Ser Pro
    290                 295                 300

cgc ccg act aga gct gaa gct acc gac gta gca aac gcg gtt ctt gac      960
Arg Pro Thr Arg Ala Glu Ala Thr Asp Val Ala Asn Ala Val Leu Asp
305                 310                 315                 320

ggg aca gat tgc gtt atg ctt agc gga gaa act gct gct gga gct cac     1008
Gly Thr Asp Cys Val Met Leu Ser Gly Glu Thr Ala Ala Gly Ala His
                325                 330                 335

cct gag act gcc gtg tta aca atg tca agg atc tgc aaa gaa gca gag     1056
Pro Glu Thr Ala Val Leu Thr Met Ser Arg Ile Cys Lys Glu Ala Glu
            340                 345                 350

gat ttc ata gat tac gac att ctc cac aag aaa acc cta gga atg gtt     1104
Asp Phe Ile Asp Tyr Asp Ile Leu His Lys Lys Thr Leu Gly Met Val
        355                 360                 365

tcg tta ccg tta tct cca atc gag agc tta gct gct tca gct gtt tcg     1152
Ser Leu Pro Leu Ser Pro Ile Glu Ser Leu Ala Ala Ser Ala Val Ser
    370                 375                 380

act gcg cgg agt gtt ttc gcg tcc gcg atc gtt gtt ctc act aga ggc     1200
Thr Ala Arg Ser Val Phe Ala Ser Ala Ile Val Val Leu Thr Arg Gly
385                 390                 395                 400

ggt tac acg gcg gag ctt gtg gct aaa tac agg cca agc gtt ccg att     1248
Gly Tyr Thr Ala Glu Leu Val Ala Lys Tyr Arg Pro Ser Val Pro Ile
                405                 410                 415

ctg tcg gtg att atg cca gag att gct gaa tgc tcg gac tcg gta gct     1296
Leu Ser Val Ile Met Pro Glu Ile Ala Glu Cys Ser Asp Ser Val Ala
            420                 425                 430

cat gtg gcg aga cgt ggt ttg att tac cgt ggg att att ccg gtg gtg     1344
His Val Ala Arg Arg Gly Leu Ile Tyr Arg Gly Ile Ile Pro Val Val
        435                 440                 445

gga tgt tca gct aga gat tca acg gag gag atg att aga tta gct ata     1392
Gly Cys Ser Ala Arg Asp Ser Thr Glu Glu Met Ile Arg Leu Ala Ile
    450                 455                 460

gga ttt gcc aag acg aag gga att tgt aag act gga gat tcc att gtg     1440
Gly Phe Ala Lys Thr Lys Gly Ile Cys Lys Thr Gly Asp Ser Ile Val
465                 470                 475                 480

gct ttg cac aag att gat ggt tca tct att gtc agg ata gtg agc gtc     1488
Ala Leu His Lys Ile Asp Gly Ser Ser Ile Val Arg Ile Val Ser Val
                485                 490                 495

gag taa                                                              1494
Glu

<210> SEQ ID NO 6
<211> LENGTH: 497
<212> TYPE: PRT
<213> ORGANISM: Arabidopsis thaliana

<400> SEQUENCE: 6

Met Glu Met Leu Leu Gly Gly Gln Ala Thr Asn Gly Ala Leu Arg Ser
1               5                   10                  15

Lys Thr Lys Ile Val Cys Thr Leu Gly Pro Ala Ser Arg Ser Val Glu
            20                  25                  30

Met Ile Glu Lys Leu Leu Lys Ala Gly Met Asn Val Ala Arg Phe Asn
        35                  40                  45

Phe Ser His Gly Ser His Ser Tyr His Gln Glu Thr Leu Asp Asn Leu
    50                  55                  60

Arg Thr Ala Met Asp Asn Thr Gly Ile Leu Cys Ala Val Met Leu Asp
65                  70                  75                  80
```

-continued

```
Thr Lys Ser Pro Val Ile Arg Thr Gly Phe Leu Lys Glu Gly Lys Pro
                85                  90                  95

Ile Gln Leu Lys Gln Gly Gln Glu Ile Thr Ile Ser Ile Asp Tyr Lys
            100                 105                 110

Ile Gln Gly Asp Ser Asn Thr Ile Ser Met Ser Tyr Lys Lys Leu Ala
        115                 120                 125

Glu Asp Leu Lys Pro Gly Asp Val Ile Leu Cys Ser Asp Gly Thr Ile
    130                 135                 140

Ser Leu Asn Val Leu Ser Cys Asp Lys Tyr Leu Gly Leu Val Arg Cys
145                 150                 155                 160

Arg Cys Glu Asn Ser Ala Leu Leu Gly Glu Arg Lys Asn Val Asn Leu
                165                 170                 175

Pro Gly Ile Val Val Asp Leu Pro Thr Leu Thr Glu Lys Asp Lys Glu
            180                 185                 190

Asp Ile Met Gln Trp Gly Val Pro Asn Lys Ile Asp Ile Ile Ala Leu
        195                 200                 205

Ser Phe Val Arg Lys Gly Ser Asp Leu Ile Gln Val Arg Lys Leu Leu
    210                 215                 220

Gly Glu His Ser Lys Ser Ile Met Leu Met Ser Lys Val Glu Asn Gln
225                 230                 235                 240

Glu Gly Val Met Asn Phe Asp Lys Ile Leu Glu Asn Ser Asp Ala Phe
                245                 250                 255

Met Val Ala Arg Gly Asp Leu Gly Met Glu Ile Pro Ile Glu Lys Met
            260                 265                 270

Phe Leu Ala Gln Lys Thr Met Ile Asn Lys Ala Asn Ala His Gly Lys
        275                 280                 285

Pro Val Val Thr Ala Thr Gln Met Leu Glu Ser Met Thr Val Ser Pro
    290                 295                 300

Arg Pro Thr Arg Ala Glu Ala Thr Asp Val Ala Asn Ala Val Leu Asp
305                 310                 315                 320

Gly Thr Asp Cys Val Met Leu Ser Gly Glu Thr Ala Ala Gly Ala His
                325                 330                 335

Pro Glu Thr Ala Val Leu Thr Met Ser Arg Ile Cys Lys Glu Ala Glu
            340                 345                 350

Asp Phe Ile Asp Tyr Asp Ile Leu His Lys Lys Thr Leu Gly Met Val
        355                 360                 365

Ser Leu Pro Leu Ser Pro Ile Glu Ser Leu Ala Ala Ser Ala Val Ser
    370                 375                 380

Thr Ala Arg Ser Val Phe Ala Ser Ala Ile Val Val Leu Thr Arg Gly
385                 390                 395                 400

Gly Tyr Thr Ala Glu Leu Val Ala Lys Tyr Arg Pro Ser Val Pro Ile
                405                 410                 415

Leu Ser Val Ile Met Pro Glu Ile Ala Glu Cys Ser Asp Ser Val Ala
            420                 425                 430

His Val Ala Arg Arg Gly Leu Ile Tyr Arg Gly Ile Ile Pro Val Val
        435                 440                 445

Gly Cys Ser Ala Arg Asp Ser Thr Glu Glu Met Ile Arg Leu Ala Ile
    450                 455                 460

Gly Phe Ala Lys Thr Lys Gly Ile Cys Lys Thr Gly Asp Ser Ile Val
465                 470                 475                 480

Ala Leu His Lys Ile Asp Gly Ser Ser Ile Val Arg Ile Val Ser Val
                485                 490                 495

Glu
```

```
<210> SEQ ID NO 7
<211> LENGTH: 2463
<212> TYPE: DNA
<213> ORGANISM: Arabidopsis thaliana
<220> FEATURE:
<221> NAME/KEY: CDS
<222> LOCATION: (175)..(2307)
<223> OTHER INFORMATION: Pyruvate Kinase

<400> SEQUENCE: 7

attaagaaaa ttcttcatca ttctttcttc tgcttcttct tcttcttctt cgttgaaaaa     60

tctgtcttct cttcttcttc ttcttcttct tcttcttctt ctcctcaaga cgagagcgaa    120

gacattatct gaacaaagcg cttctccata acaaaggtga ttcaattagt cgat atg      177
                                                            Met
                                                            1

gta gga ctt gat tca agc cac ttg ttg aga gac aag atc ctt tgc ttc      225
Val Gly Leu Asp Ser Ser His Leu Leu Arg Asp Lys Ile Leu Cys Phe
            5                   10                  15

tcc agc agg tct cac ata aac aac caa cat aag aag aca agt tat gca      273
Ser Ser Arg Ser His Ile Asn Asn Gln His Lys Lys Thr Ser Tyr Ala
        20                  25                  30

tta tca ctt aat cac atg aaa ctt cct att cag aga acc tta gct ttt      321
Leu Ser Leu Asn His Met Lys Leu Pro Ile Gln Arg Thr Leu Ala Phe
    35                  40                  45

gcc tta gct cgc ggg aaa ggc gaa gct gaa agt ttc agc aga ttg gaa      369
Ala Leu Ala Arg Gly Lys Gly Glu Ala Glu Ser Phe Ser Arg Leu Glu
50                  55                  60                  65

gcc acc ttt ggt gat aat acc tcc aca gaa tgt acc tgg agt ttt gac      417
Ala Thr Phe Gly Asp Asn Thr Ser Thr Glu Cys Thr Trp Ser Phe Asp
                70                  75                  80

ttt cca gat tct aaa gat gct atg tct cat ctc aag tca gaa gca gac      465
Phe Pro Asp Ser Lys Asp Ala Met Ser His Leu Lys Ser Glu Ala Asp
            85                  90                  95

ctc tct gga agc aat ggg gcc aat aat gtg gct agt gtt atc gaa aaa      513
Leu Ser Gly Ser Asn Gly Ala Asn Asn Val Ala Ser Val Ile Glu Lys
        100                 105                 110

ctg aat gct ctt cgg tca cat ctc tta gca gca gag aaa tgg aat gct      561
Leu Asn Ala Leu Arg Ser His Leu Leu Ala Ala Glu Lys Trp Asn Ala
    115                 120                 125

tct caa cta cac tta tgt gac agt aag tat ctg gaa tgt gca aca aac      609
Ser Gln Leu His Leu Cys Asp Ser Lys Tyr Leu Glu Cys Ala Thr Asn
130                 135                 140                 145

tta gtt cat tat atg gct ttg aga tct ctg gac att gag cag ctc aac      657
Leu Val His Tyr Met Ala Leu Arg Ser Leu Asp Ile Glu Gln Leu Asn
                150                 155                 160

agt cat cta gct tct ctt ggt ctg tca agt tta gac aac aac aat ctg      705
Ser His Leu Ala Ser Leu Gly Leu Ser Ser Leu Asp Asn Asn Asn Leu
            165                 170                 175

gat gtt ctc gcc cac ctt aac gcc tct att aat ctt ttg atg aac gat      753
Asp Val Leu Ala His Leu Asn Ala Ser Ile Asn Leu Leu Met Asn Asp
        180                 185                 190

caa aac gct gtg acg gag tct tgg act aat gta tat ccc aag gga aaa      801
Gln Asn Ala Val Thr Glu Ser Trp Thr Asn Val Tyr Pro Lys Gly Lys
    195                 200                 205

agt act aag aag aat gat aaa ggg agg gta tta tca tac aaa gag tca      849
Ser Thr Lys Lys Asn Asp Lys Gly Arg Val Leu Ser Tyr Lys Glu Ser
210                 215                 220                 225

tta ctt ggt aaa ctt cgt gag gga aga agt act cat atc atg gta act      897
Leu Leu Gly Lys Leu Arg Glu Gly Arg Ser Thr His Ile Met Val Thr
                230                 235                 240
```

-continued

```
att ggt gaa gaa gca act ttg agt gaa aca ttt ata act gat att ctt      945
Ile Gly Glu Glu Ala Thr Leu Ser Glu Thr Phe Ile Thr Asp Ile Leu
            245                 250                 255

aaa gct gga aca tct gtt atc cgt ata aac tgt gca cat gga gat cca      993
Lys Ala Gly Thr Ser Val Ile Arg Ile Asn Cys Ala His Gly Asp Pro
        260                 265                 270

agt att tgg ggt gag atc atc aaa aga gta aga aga act tct cag atg     1041
Ser Ile Trp Gly Glu Ile Ile Lys Arg Val Arg Arg Thr Ser Gln Met
    275                 280                 285

tta gag atg cca tgt cgc gtt cat atg gat tta gca gga cca aaa ctc     1089
Leu Glu Met Pro Cys Arg Val His Met Asp Leu Ala Gly Pro Lys Leu
290                 295                 300                 305

aga act ggt acc tta aaa cct ggt ccg tgt gtg atg aaa att tca cca     1137
Arg Thr Gly Thr Leu Lys Pro Gly Pro Cys Val Met Lys Ile Ser Pro
                310                 315                 320

aag aaa gat gct tat gga aat gtt gtt tct cct gct ttg gta tgg ctc     1185
Lys Lys Asp Ala Tyr Gly Asn Val Val Ser Pro Ala Leu Val Trp Leu
            325                 330                 335

tgc ctc aca gga aca gaa cct cct gct cat gtt tcc cct gat gct act     1233
Cys Leu Thr Gly Thr Glu Pro Pro Ala His Val Ser Pro Asp Ala Thr
        340                 345                 350

ata tcg gtc caa ggc caa gat ttt ctt gct ggt ctc caa att ggt gat     1281
Ile Ser Val Gln Gly Gln Asp Phe Leu Ala Gly Leu Gln Ile Gly Asp
    355                 360                 365

tct ata aga cta tgt gac gct aga ggg aga aag agg aga ctt aaa atc     1329
Ser Ile Arg Leu Cys Asp Ala Arg Gly Arg Lys Arg Arg Leu Lys Ile
370                 375                 380                 385

tca aaa gag ttt cat gtt ttc aac agt acc ggg ttt gtg gct gaa tgt     1377
Ser Lys Glu Phe His Val Phe Asn Ser Thr Gly Phe Val Ala Glu Cys
                390                 395                 400

ttc gac act gct tac ata gaa agt gga act gag tta agt gtt aag gga     1425
Phe Asp Thr Ala Tyr Ile Glu Ser Gly Thr Glu Leu Ser Val Lys Gly
            405                 410                 415

aag aaa ggg aga cgt tta gtt gga cga gta gta gat gtt cct ccc aaa     1473
Lys Lys Gly Arg Arg Leu Val Gly Arg Val Val Asp Val Pro Pro Lys
        420                 425                 430

gaa tct ttt gta agg cta aaa gtt gga gat tta cta gtc ata acc cga     1521
Glu Ser Phe Val Arg Leu Lys Val Gly Asp Leu Leu Val Ile Thr Arg
    435                 440                 445

gaa gga tcg ctc gat gaa cca tct gta act gtt cca gga gct cat agg     1569
Glu Gly Ser Leu Asp Glu Pro Ser Val Thr Val Pro Gly Ala His Arg
450                 455                 460                 465

tta act tgt cct tcc ggt tat ttg ttt gat tca gtc aag cct ggt gaa     1617
Leu Thr Cys Pro Ser Gly Tyr Leu Phe Asp Ser Val Lys Pro Gly Glu
                470                 475                 480

acc att ggt ttt gat gat gga aaa ata tgg gga gtc ata aaa gga aca     1665
Thr Ile Gly Phe Asp Asp Gly Lys Ile Trp Gly Val Ile Lys Gly Thr
            485                 490                 495

agt cct tca gag gta att gtc tcc ata act cat gca cgt cca aaa ggt     1713
Ser Pro Ser Glu Val Ile Val Ser Ile Thr His Ala Arg Pro Lys Gly
        500                 505                 510

aca aaa cta gga tca gag aag tcc att aac ata ccg cag agc gat atc     1761
Thr Lys Leu Gly Ser Glu Lys Ser Ile Asn Ile Pro Gln Ser Asp Ile
    515                 520                 525

cat ttc aaa ggc tta aca tca aaa gat att aaa gat ctt gat tat gta     1809
His Phe Lys Gly Leu Thr Ser Lys Asp Ile Lys Asp Leu Asp Tyr Val
530                 535                 540                 545

gct tca cat gct gat atg gtt ggt att tct ttc ata cgt gat gtc cat     1857
Ala Ser His Ala Asp Met Val Gly Ile Ser Phe Ile Arg Asp Val His
                550                 555                 560
```

```
gat ata acc gtt ctt cga caa gag ttg aag aaa aga aaa cta gat gat     1905
Asp Ile Thr Val Leu Arg Gln Glu Leu Lys Lys Arg Lys Leu Asp Asp
            565                 570                 575

ctt ggt att gtt tta aag att gaa acg aaa agt gga ttc aag aat ttg     1953
Leu Gly Ile Val Leu Lys Ile Glu Thr Lys Ser Gly Phe Lys Asn Leu
        580                 585                 590

tct ttg att ctt tta gaa gca atg aag tgt tcg aat cct tta gga att     2001
Ser Leu Ile Leu Leu Glu Ala Met Lys Cys Ser Asn Pro Leu Gly Ile
    595                 600                 605

atg ata gct aga ggt gat ctt gca gtg gaa tgt gga tgg gag aga ttg     2049
Met Ile Ala Arg Gly Asp Leu Ala Val Glu Cys Gly Trp Glu Arg Leu
610                 615                 620                 625

gct aat atg cag gag gag att ata gct att tgt aaa gct gct cgt gta     2097
Ala Asn Met Gln Glu Glu Ile Ile Ala Ile Cys Lys Ala Ala Arg Val
                630                 635                 640

ccg gtg att atg gca act cag gtt ctt gaa tca ctt gtg aaa tcc gga     2145
Pro Val Ile Met Ala Thr Gln Val Leu Glu Ser Leu Val Lys Ser Gly
            645                 650                 655

gtt cca act aga gct gag att act gat gct gca aat gca aaa agg gcg     2193
Val Pro Thr Arg Ala Glu Ile Thr Asp Ala Ala Asn Ala Lys Arg Ala
        660                 665                 670

agc tgt gtg atg tta aac aaa ggc aag aat atc gtt gaa gct gtt tca     2241
Ser Cys Val Met Leu Asn Lys Gly Lys Asn Ile Val Glu Ala Val Ser
    675                 680                 685

atg ttg gat act att ctt cat acc aag ctt atc tac aag aaa tcg gac     2289
Met Leu Asp Thr Ile Leu His Thr Lys Leu Ile Tyr Lys Lys Ser Asp
690                 695                 700                 705

tct gaa aat ctc cat tga tctgcttgta gtttgcttgg ccatttatat            2337
Ser Glu Asn Leu His
                710

tcgtattgtt gttttataag aaagagattt taggggaaat gtacaatgta tttaggatat   2397

gatgaatgaa tagagatcat aacatggaag gattaagctt gttgattcca aaaaaaaaaa   2457

aaaaaa                                                              2463


<210> SEQ ID NO 8
<211> LENGTH: 710
<212> TYPE: PRT
<213> ORGANISM: Arabidopsis thaliana

<400> SEQUENCE: 8

Met Val Gly Leu Asp Ser Ser His Leu Leu Arg Asp Lys Ile Leu Cys
1               5                   10                  15

Phe Ser Ser Arg Ser His Ile Asn Asn Gln His Lys Lys Thr Ser Tyr
            20                  25                  30

Ala Leu Ser Leu Asn His Met Lys Leu Pro Ile Gln Arg Thr Leu Ala
        35                  40                  45

Phe Ala Leu Ala Arg Gly Lys Gly Glu Ala Glu Ser Phe Ser Arg Leu
    50                  55                  60

Glu Ala Thr Phe Gly Asp Asn Thr Ser Thr Glu Cys Thr Trp Ser Phe
65                  70                  75                  80

Asp Phe Pro Asp Ser Lys Asp Ala Met Ser His Leu Lys Ser Glu Ala
                85                  90                  95

Asp Leu Ser Gly Ser Asn Gly Ala Asn Asn Val Ala Ser Val Ile Glu
            100                 105                 110

Lys Leu Asn Ala Leu Arg Ser His Leu Leu Ala Ala Glu Lys Trp Asn
        115                 120                 125

Ala Ser Gln Leu His Leu Cys Asp Ser Lys Tyr Leu Glu Cys Ala Thr
```

```
    130                 135                 140

Asn Leu Val His Tyr Met Ala Leu Arg Ser Leu Asp Ile Glu Gln Leu
145                 150                 155                 160

Asn Ser His Leu Ala Ser Leu Gly Leu Ser Ser Leu Asp Asn Asn Asn
                165                 170                 175

Leu Asp Val Leu Ala His Leu Asn Ala Ser Ile Asn Leu Leu Met Asn
            180                 185                 190

Asp Gln Asn Ala Val Thr Glu Ser Trp Thr Asn Val Tyr Pro Lys Gly
        195                 200                 205

Lys Ser Thr Lys Lys Asn Asp Lys Gly Arg Val Leu Ser Tyr Lys Glu
    210                 215                 220

Ser Leu Leu Gly Lys Leu Arg Glu Gly Arg Ser Thr His Ile Met Val
225                 230                 235                 240

Thr Ile Gly Glu Glu Ala Thr Leu Ser Glu Thr Phe Ile Thr Asp Ile
                245                 250                 255

Leu Lys Ala Gly Thr Ser Val Ile Arg Ile Asn Cys Ala His Gly Asp
            260                 265                 270

Pro Ser Ile Trp Gly Glu Ile Ile Lys Arg Val Arg Arg Thr Ser Gln
        275                 280                 285

Met Leu Glu Met Pro Cys Arg Val His Met Asp Leu Ala Gly Pro Lys
    290                 295                 300

Leu Arg Thr Gly Thr Leu Lys Pro Gly Pro Cys Val Met Lys Ile Ser
305                 310                 315                 320

Pro Lys Lys Asp Ala Tyr Gly Asn Val Val Ser Pro Ala Leu Val Trp
                325                 330                 335

Leu Cys Leu Thr Gly Thr Glu Pro Pro Ala His Val Ser Pro Asp Ala
            340                 345                 350

Thr Ile Ser Val Gln Gly Gln Asp Phe Leu Ala Gly Leu Gln Ile Gly
        355                 360                 365

Asp Ser Ile Arg Leu Cys Asp Ala Arg Gly Arg Lys Arg Arg Leu Lys
    370                 375                 380

Ile Ser Lys Glu Phe His Val Phe Asn Ser Thr Gly Phe Val Ala Glu
385                 390                 395                 400

Cys Phe Asp Thr Ala Tyr Ile Glu Ser Gly Thr Glu Leu Ser Val Lys
                405                 410                 415

Gly Lys Lys Gly Arg Arg Leu Val Gly Arg Val Val Asp Val Pro Pro
            420                 425                 430

Lys Glu Ser Phe Val Arg Leu Lys Val Gly Asp Leu Leu Val Ile Thr
        435                 440                 445

Arg Glu Gly Ser Leu Asp Glu Pro Ser Val Thr Val Pro Gly Ala His
    450                 455                 460

Arg Leu Thr Cys Pro Ser Gly Tyr Leu Phe Asp Ser Val Lys Pro Gly
465                 470                 475                 480

Glu Thr Ile Gly Phe Asp Asp Gly Lys Ile Trp Gly Val Ile Lys Gly
                485                 490                 495

Thr Ser Pro Ser Glu Val Ile Val Ser Ile Thr His Ala Arg Pro Lys
            500                 505                 510

Gly Thr Lys Leu Gly Ser Glu Lys Ser Ile Asn Ile Pro Gln Ser Asp
        515                 520                 525

Ile His Phe Lys Gly Leu Thr Ser Lys Asp Ile Lys Asp Leu Asp Tyr
    530                 535                 540

Val Ala Ser His Ala Asp Met Val Gly Ile Ser Phe Ile Arg Asp Val
545                 550                 555                 560
```

```
His Asp Ile Thr Val Leu Arg Gln Glu Leu Lys Lys Arg Lys Leu Asp
            565                 570                 575

Asp Leu Gly Ile Val Leu Lys Ile Glu Thr Lys Ser Gly Phe Lys Asn
        580                 585                 590

Leu Ser Leu Ile Leu Leu Glu Ala Met Lys Cys Ser Asn Pro Leu Gly
    595                 600                 605

Ile Met Ile Ala Arg Gly Asp Leu Ala Val Glu Cys Gly Trp Glu Arg
    610                 615                 620

Leu Ala Asn Met Gln Glu Glu Ile Ile Ala Ile Cys Lys Ala Ala Arg
625                 630                 635                 640

Val Pro Val Ile Met Ala Thr Gln Val Leu Glu Ser Leu Val Lys Ser
            645                 650                 655

Gly Val Pro Thr Arg Ala Glu Ile Thr Asp Ala Ala Asn Ala Lys Arg
        660                 665                 670

Ala Ser Cys Val Met Leu Asn Lys Gly Lys Asn Ile Val Glu Ala Val
    675                 680                 685

Ser Met Leu Asp Thr Ile Leu His Thr Lys Leu Ile Tyr Lys Lys Ser
    690                 695                 700

Asp Ser Glu Asn Leu His
705                 710


<210> SEQ ID NO 9
<211> LENGTH: 1984
<212> TYPE: DNA
<213> ORGANISM: Arabidopsis thaliana
<220> FEATURE:
<221> NAME/KEY: CDS
<222> LOCATION: (167)..(1750)
<223> OTHER INFORMATION: Pyruvate Kinase

<400> SEQUENCE: 9

gtcttccgtt gcgtgagata ttattgaacg gtgtttgtta ttcggagaag aagaagaaga      60

agaactgaag aagcatattc gacggtcacc accaaacctc ttccgtcgga ttttcactct     120

ccgtttatcg aacatctgag atctctctcc acttccgtca ccgaag atg cat tcc        175
                                                   Met His Ser
                                                   1

agt cat ctt ctt ctc gag gag ccg atc agg atg gct tca atc ctc gag       223
Ser His Leu Leu Leu Glu Glu Pro Ile Arg Met Ala Ser Ile Leu Glu
    5                   10                  15

cct tcc aaa tct agt ttc ttc ccg gca ttg act aag atc gtc gga act       271
Pro Ser Lys Ser Ser Phe Phe Pro Ala Leu Thr Lys Ile Val Gly Thr
20                  25                  30                  35

cta ggt cct aaa tcc cga tcc gtc gag gct ctc tcc ggc tgt ctc aaa       319
Leu Gly Pro Lys Ser Arg Ser Val Glu Ala Leu Ser Gly Cys Leu Lys
            40                  45                  50

gcc ggc atg tct gtg gct cga ttt gat ttc tcg tgg gga gat gct gat       367
Ala Gly Met Ser Val Ala Arg Phe Asp Phe Ser Trp Gly Asp Ala Asp
        55                  60                  65

tat cac cag gag aca ctt gat aat ttg aaa gtt gct gtg agg agc act       415
Tyr His Gln Glu Thr Leu Asp Asn Leu Lys Val Ala Val Arg Ser Thr
        70                  75                  80

aag aag ctt tgt gct gtt atg ctt gat act gtt gga cct gag cta caa       463
Lys Lys Leu Cys Ala Val Met Leu Asp Thr Val Gly Pro Glu Leu Gln
    85                  90                  95

gtt att aac aaa tct gag aaa gct att act ttg aaa gct gat ggc ctt       511
Val Ile Asn Lys Ser Glu Lys Ala Ile Thr Leu Lys Ala Asp Gly Leu
100                 105                 110                 115

gta act ttg aca ccg aat caa gat caa gaa gct tct tct gaa gtt ctt       559
Val Thr Leu Thr Pro Asn Gln Asp Gln Glu Ala Ser Ser Glu Val Leu
```

-continued

```
                120                 125                 130

ccc att aat ttc aat gga ctt gcc aag gca gtg aag aaa gga gac acc      607
Pro Ile Asn Phe Asn Gly Leu Ala Lys Ala Val Lys Lys Gly Asp Thr
            135                 140                 145

atc ttc gtt ggg caa tac cta ttc act ggt agt gaa aca act tca gtt      655
Ile Phe Val Gly Gln Tyr Leu Phe Thr Gly Ser Glu Thr Thr Ser Val
        150                 155                 160

tgg ctc gag gtt gat gaa gtt aaa gga gat gat gtc att tgc ctt tca      703
Trp Leu Glu Val Asp Glu Val Lys Gly Asp Asp Val Ile Cys Leu Ser
    165                 170                 175

agg aat gct gct act ctg gct ggt tct ttg ttc act tta cac tcc tct      751
Arg Asn Ala Ala Thr Leu Ala Gly Ser Leu Phe Thr Leu His Ser Ser
180                 185                 190                 195

caa gtt cac att gat ctc cca acg ctt aca gag aag gat aag gag gtt      799
Gln Val His Ile Asp Leu Pro Thr Leu Thr Glu Lys Asp Lys Glu Val
                200                 205                 210

ata agc aca tgg gga gtt caa aat aaa atc gat ttt ctc tca ttg tct      847
Ile Ser Thr Trp Gly Val Gln Asn Lys Ile Asp Phe Leu Ser Leu Ser
            215                 220                 225

tat tgt cgt cat gct gag gat gtt cgc cag acc cgt gaa atg ctt aaa      895
Tyr Cys Arg His Ala Glu Asp Val Arg Gln Thr Arg Glu Met Leu Lys
        230                 235                 240

aag ttg ggc gac ctc tct caa aca caa ata ttt gct aag att gag aac      943
Lys Leu Gly Asp Leu Ser Gln Thr Gln Ile Phe Ala Lys Ile Glu Asn
    245                 250                 255

gta gag gga cta acc cac ttc gat gag att cta caa gaa gct gat ggc      991
Val Glu Gly Leu Thr His Phe Asp Glu Ile Leu Gln Glu Ala Asp Gly
260                 265                 270                 275

att att ctt tct cgt ggg aat ttg ggt ata gat tta ccc ccg gaa aag     1039
Ile Ile Leu Ser Arg Gly Asn Leu Gly Ile Asp Leu Pro Pro Glu Lys
                280                 285                 290

gtg ttt ttg ttt caa aag gct gct ctt tac aag tgc aac atg gct gga     1087
Val Phe Leu Phe Gln Lys Ala Ala Leu Tyr Lys Cys Asn Met Ala Gly
            295                 300                 305

aag cca gct gtt ctt acc cgt gtt gtt gac agt atg act gac aac ttg     1135
Lys Pro Ala Val Leu Thr Arg Val Val Asp Ser Met Thr Asp Asn Leu
        310                 315                 320

cga cca act cgt gct gag gcc acg gat gtt gct aat gct gtt tta gat     1183
Arg Pro Thr Arg Ala Glu Ala Thr Asp Val Ala Asn Ala Val Leu Asp
    325                 330                 335

gga agt gat gca att ctt ctt ggt gct gag acc ctt cgt gga ttg tac     1231
Gly Ser Asp Ala Ile Leu Leu Gly Ala Glu Thr Leu Arg Gly Leu Tyr
340                 345                 350                 355

cct gtt gag aca ata tca act gtt ggt agg atc tgt gct gag gca gaa     1279
Pro Val Glu Thr Ile Ser Thr Val Gly Arg Ile Cys Ala Glu Ala Glu
                360                 365                 370

aag gtt ttc aat caa gat ttg tac ttt aag aag act gtc aag tat gtt     1327
Lys Val Phe Asn Gln Asp Leu Tyr Phe Lys Lys Thr Val Lys Tyr Val
            375                 380                 385

gga gaa cca atg act cac ttg gaa tcg att gct tct tca gct gta cgg     1375
Gly Glu Pro Met Thr His Leu Glu Ser Ile Ala Ser Ser Ala Val Arg
        390                 395                 400

gca gcc att aag gtt aag gca tcc gta att ata tgc ttc acc tct tct     1423
Ala Ala Ile Lys Val Lys Ala Ser Val Ile Ile Cys Phe Thr Ser Ser
    405                 410                 415

gga aga gca gcc aga ttg att gcc aaa tac agg cca acg atg ccg gtt     1471
Gly Arg Ala Ala Arg Leu Ile Ala Lys Tyr Arg Pro Thr Met Pro Val
420                 425                 430                 435

att tct gtt gtc att ccc cgg gtt aag aca aat caa ctg aaa tgg agc     1519
Ile Ser Val Val Ile Pro Arg Val Lys Thr Asn Gln Leu Lys Trp Ser
```

```
                440                 445                 450

ttt agt gga gct ttt gag gcg agg cag tca ctt att gtc aga ggc ctc      1567
Phe Ser Gly Ala Phe Glu Ala Arg Gln Ser Leu Ile Val Arg Gly Leu
            455                 460                 465

ttc cct atg ctt gct gac cct cgt cac cct gcg gaa tct aca agt gcg      1615
Phe Pro Met Leu Ala Asp Pro Arg His Pro Ala Glu Ser Thr Ser Ala
        470                 475                 480

aca aac gag tca gtc ctg aag gtt gct cta gac cat ggg aag cat gct      1663
Thr Asn Glu Ser Val Leu Lys Val Ala Leu Asp His Gly Lys His Ala
    485                 490                 495

gga gta atc aag tcg cat gac aga gta gtg gtg tgt cag aaa gtt ggt      1711
Gly Val Ile Lys Ser His Asp Arg Val Val Cys Gln Lys Val Gly
500                 505                 510                 515

gat gca tct gtg gtt aag atc att gag ctt gag gat taa cttttgcctc       1760
Asp Ala Ser Val Val Lys Ile Ile Glu Leu Glu Asp
                520                 525

gcaaaaacat tatataattg gctgcatttt gggttgcctt gaattgatga taactcccaa    1820

tgccggagtg aaaatattat ctccgggact tctggtttct ttttgtatac ttaggagatt    1880

tgatgtctct aaggtttcag ctatatttga ttaccttcaa atgtacgcat atgataaaag    1940

tatacaatgc ctagcaattt tataataagc tgttacattc cctt                     1984


<210> SEQ ID NO 10
<211> LENGTH: 527
<212> TYPE: PRT
<213> ORGANISM: Arabidopsis thaliana

<400> SEQUENCE: 10

Met His Ser Ser His Leu Leu Leu Glu Glu Pro Ile Arg Met Ala Ser
1               5                   10                  15

Ile Leu Glu Pro Ser Lys Ser Ser Phe Phe Pro Ala Leu Thr Lys Ile
            20                  25                  30

Val Gly Thr Leu Gly Pro Lys Ser Arg Ser Val Glu Ala Leu Ser Gly
        35                  40                  45

Cys Leu Lys Ala Gly Met Ser Val Ala Arg Phe Asp Phe Ser Trp Gly
    50                  55                  60

Asp Ala Asp Tyr His Gln Glu Thr Leu Asp Asn Leu Lys Val Ala Val
65                  70                  75                  80

Arg Ser Thr Lys Lys Leu Cys Ala Val Met Leu Asp Thr Val Gly Pro
                85                  90                  95

Glu Leu Gln Val Ile Asn Lys Ser Glu Lys Ala Ile Thr Leu Lys Ala
            100                 105                 110

Asp Gly Leu Val Thr Leu Thr Pro Asn Gln Asp Gln Glu Ala Ser Ser
        115                 120                 125

Glu Val Leu Pro Ile Asn Phe Asn Gly Leu Ala Lys Ala Val Lys Lys
    130                 135                 140

Gly Asp Thr Ile Phe Val Gly Gln Tyr Leu Phe Thr Gly Ser Glu Thr
145                 150                 155                 160

Thr Ser Val Trp Leu Glu Val Asp Glu Val Lys Gly Asp Asp Val Ile
                165                 170                 175

Cys Leu Ser Arg Asn Ala Ala Thr Leu Ala Gly Ser Leu Phe Thr Leu
            180                 185                 190

His Ser Ser Gln Val His Ile Asp Leu Pro Thr Leu Thr Glu Lys Asp
        195                 200                 205

Lys Glu Val Ile Ser Thr Trp Gly Val Gln Asn Lys Ile Asp Phe Leu
    210                 215                 220
```

-continued

```
Ser Leu Ser Tyr Cys Arg His Ala Glu Asp Val Arg Gln Thr Arg Glu
225                 230                 235                 240

Met Leu Lys Lys Leu Gly Asp Leu Ser Gln Thr Gln Ile Phe Ala Lys
                245                 250                 255

Ile Glu Asn Val Glu Gly Leu Thr His Phe Asp Glu Ile Leu Gln Glu
            260                 265                 270

Ala Asp Gly Ile Ile Leu Ser Arg Gly Asn Leu Gly Ile Asp Leu Pro
        275                 280                 285

Pro Glu Lys Val Phe Leu Phe Gln Lys Ala Ala Leu Tyr Lys Cys Asn
    290                 295                 300

Met Ala Gly Lys Pro Ala Val Leu Thr Arg Val Val Asp Ser Met Thr
305                 310                 315                 320

Asp Asn Leu Arg Pro Thr Arg Ala Glu Ala Thr Asp Val Ala Asn Ala
                325                 330                 335

Val Leu Asp Gly Ser Asp Ala Ile Leu Leu Gly Ala Glu Thr Leu Arg
            340                 345                 350

Gly Leu Tyr Pro Val Glu Thr Ile Ser Thr Val Gly Arg Ile Cys Ala
        355                 360                 365

Glu Ala Glu Lys Val Phe Asn Gln Asp Leu Tyr Phe Lys Lys Thr Val
    370                 375                 380

Lys Tyr Val Gly Glu Pro Met Thr His Leu Glu Ser Ile Ala Ser Ser
385                 390                 395                 400

Ala Val Arg Ala Ala Ile Lys Val Lys Ala Ser Val Ile Ile Cys Phe
                405                 410                 415

Thr Ser Ser Gly Arg Ala Ala Arg Leu Ile Ala Lys Tyr Arg Pro Thr
            420                 425                 430

Met Pro Val Ile Ser Val Val Ile Pro Arg Val Lys Thr Asn Gln Leu
        435                 440                 445

Lys Trp Ser Phe Ser Gly Ala Phe Glu Ala Arg Gln Ser Leu Ile Val
    450                 455                 460

Arg Gly Leu Phe Pro Met Leu Ala Asp Pro Arg His Pro Ala Glu Ser
465                 470                 475                 480

Thr Ser Ala Thr Asn Glu Ser Val Leu Lys Val Ala Leu Asp His Gly
                485                 490                 495

Lys His Ala Gly Val Ile Lys Ser His Asp Arg Val Val Val Cys Gln
            500                 505                 510

Lys Val Gly Asp Ala Ser Val Val Lys Ile Ile Glu Leu Glu Asp
        515                 520                 525


<210> SEQ ID NO 11
<211> LENGTH: 1533
<212> TYPE: DNA
<213> ORGANISM: Arabidopsis thaliana
<220> FEATURE:
<221> NAME/KEY: CDS
<222> LOCATION: (1)..(1533)
<223> OTHER INFORMATION: Pyruvate Kinase

<400> SEQUENCE: 11

atg gag atg tta ctt ggt gga caa gca acc aat gga gct ctt cgt tca       48
Met Glu Met Leu Leu Gly Gly Gln Ala Thr Asn Gly Ala Leu Arg Ser
1               5                   10                  15

aag acg aag ata att tgt act ctt gga ccg gtt tca aga tcg gtg gag       96
Lys Thr Lys Ile Ile Cys Thr Leu Gly Pro Val Ser Arg Ser Val Glu
            20                  25                  30

atg att gag aag ctt ctc aag gct ggt atg aac gta gcc cgg ttc aat      144
Met Ile Glu Lys Leu Leu Lys Ala Gly Met Asn Val Ala Arg Phe Asn
        35                  40                  45
```

```
ttc tct cat ggt tct cac tct tac cat caa gaa act ctc gat aat ctc      192
Phe Ser His Gly Ser His Ser Tyr His Gln Glu Thr Leu Asp Asn Leu
    50                  55                  60

cga acc gcc atg gac aac act ggt att ctc tcc gcc gtc atg ctc gac      240
Arg Thr Ala Met Asp Asn Thr Gly Ile Leu Ser Ala Val Met Leu Asp
65                  70                  75                  80

aca aag ggt cct gag ata cga acc ggg ttt ctc aaa gaa ggc aaa ccg      288
Thr Lys Gly Pro Glu Ile Arg Thr Gly Phe Leu Lys Glu Gly Lys Pro
                85                  90                  95

ata cag cta aac caa ggt caa gag atc acc atc tca att gat tac atg      336
Ile Gln Leu Asn Gln Gly Gln Glu Ile Thr Ile Ser Ile Asp Tyr Met
            100                 105                 110

ata gaa gga gat tca aac gtt atc tcc atg agc tac aag aaa ctt gca      384
Ile Glu Gly Asp Ser Asn Val Ile Ser Met Ser Tyr Lys Lys Leu Ala
        115                 120                 125

gaa gac gtc aaa cct ggt gat gtg att ctc tgt tca gac ggc aca atc      432
Glu Asp Val Lys Pro Gly Asp Val Ile Leu Cys Ser Asp Gly Thr Ile
    130                 135                 140

tct tta act gtc ttg tcc tgt gac aag tct ttc ggt ctt gtt cgt tgc      480
Ser Leu Thr Val Leu Ser Cys Asp Lys Ser Phe Gly Leu Val Arg Cys
145                 150                 155                 160

cgt tgc gag aac tct gca att cta gga gaa aga aaa aac gtt aat ctt      528
Arg Cys Glu Asn Ser Ala Ile Leu Gly Glu Arg Lys Asn Val Asn Leu
                165                 170                 175

cct gga att gta gtt gat ctc cca aca ctt act gag aaa gat aaa gaa      576
Pro Gly Ile Val Val Asp Leu Pro Thr Leu Thr Glu Lys Asp Lys Glu
            180                 185                 190

gat atc atc caa tgg gga gtt ccg aac aaa atc gac atc atc gct ctt      624
Asp Ile Ile Gln Trp Gly Val Pro Asn Lys Ile Asp Ile Ile Ala Leu
        195                 200                 205

tct ttt gtt cgt aaa gga tct gac cta act gaa gtt agg agg tta ctt      672
Ser Phe Val Arg Lys Gly Ser Asp Leu Thr Glu Val Arg Arg Leu Leu
    210                 215                 220

gga gaa cac tca aag aac atc atg ctc atg tca aag gtg gag aat caa      720
Gly Glu His Ser Lys Asn Ile Met Leu Met Ser Lys Val Glu Asn Gln
225                 230                 235                 240

gaa ggg gtc atg aat tgt gaa aag att ctg gag aat tct gat gct ttc      768
Glu Gly Val Met Asn Cys Glu Lys Ile Leu Glu Asn Ser Asp Ala Phe
                245                 250                 255

atg gtg gct aga gga gat ctt gga atg gag att ccg atc gaa aag atg      816
Met Val Ala Arg Gly Asp Leu Gly Met Glu Ile Pro Ile Glu Lys Met
            260                 265                 270

ttc ctt gct cag aaa aca atg atc aag atg gct aat gct ctt ggg aaa      864
Phe Leu Ala Gln Lys Thr Met Ile Lys Met Ala Asn Ala Leu Gly Lys
        275                 280                 285

cca gtt gtc aca gcc aca cag atg ctt gaa tcc atg aca gta tct cct      912
Pro Val Val Thr Ala Thr Gln Met Leu Glu Ser Met Thr Val Ser Pro
    290                 295                 300

cgt ccg act aga gct gaa gcc act gac gtt gca aac gct gtt ctt gac      960
Arg Pro Thr Arg Ala Glu Ala Thr Asp Val Ala Asn Ala Val Leu Asp
305                 310                 315                 320

ggg aca gac tgc gtt atg ctt agt gga gaa acc gct gct gga gct cac     1008
Gly Thr Asp Cys Val Met Leu Ser Gly Glu Thr Ala Ala Gly Ala His
                325                 330                 335

cct gag gct gcc gtg cta aca atg tca agg atc tgt aaa gaa gca gag     1056
Pro Glu Ala Ala Val Leu Thr Met Ser Arg Ile Cys Lys Glu Ala Glu
            340                 345                 350

gat ttc atc gat tac gac att ctc cac aag aaa acc cta gga atg gtt     1104
Asp Phe Ile Asp Tyr Asp Ile Leu His Lys Lys Thr Leu Gly Met Val
        355                 360                 365
```

```
tcg tta ccg tta tct ccg atc gag agc tta gct gct tca gtt gtt tcg      1152
Ser Leu Pro Leu Ser Pro Ile Glu Ser Leu Ala Ala Ser Val Val Ser
    370                 375                 380

acg gca cag agt gtt ttt gcg tcg gcg atc gtt gtt ctc acc aaa ggc      1200
Thr Ala Gln Ser Val Phe Ala Ser Ala Ile Val Val Leu Thr Lys Gly
385                 390                 395                 400

ggt tac acg gcg gag ctt gtg gct aaa tac agg ccg agc gtt ccg att      1248
Gly Tyr Thr Ala Glu Leu Val Ala Lys Tyr Arg Pro Ser Val Pro Ile
                405                 410                 415

ttg tca gtg att gtg cca gag att gct caa ggg aat gat atg gag atg      1296
Leu Ser Val Ile Val Pro Glu Ile Ala Gln Gly Asn Asp Met Glu Met
            420                 425                 430

tcg tgc tca gac tcg gtg gct cat gcg gcg aga cgt ggt ttg att tac      1344
Ser Cys Ser Asp Ser Val Ala His Ala Ala Arg Arg Gly Leu Ile Tyr
        435                 440                 445

cgt agg att att ccg gtg gtg gcg acg gga tct tcg gct agg gat tca      1392
Arg Arg Ile Ile Pro Val Val Ala Thr Gly Ser Ser Ala Arg Asp Ser
    450                 455                 460

aac aaa gat gca acg gag gag atg att aat ttg gct atc gga ttc gcg      1440
Asn Lys Asp Ala Thr Glu Glu Met Ile Asn Leu Ala Ile Gly Phe Ala
465                 470                 475                 480

aag acg aag gga att tgc aag aat gga gat tcg att gtg gcg ttg cac      1488
Lys Thr Lys Gly Ile Cys Lys Asn Gly Asp Ser Ile Val Ala Leu His
                485                 490                 495

aag att gat ggt tcc tct gtt gtt aag ata gtg acc gtg gag taa          1533
Lys Ile Asp Gly Ser Ser Val Val Lys Ile Val Thr Val Glu
            500                 505                 510


<210> SEQ ID NO 12
<211> LENGTH: 510
<212> TYPE: PRT
<213> ORGANISM: Arabidopsis thaliana

<400> SEQUENCE: 12

Met Glu Met Leu Leu Gly Gly Gln Ala Thr Asn Gly Ala Leu Arg Ser
1               5                   10                  15

Lys Thr Lys Ile Ile Cys Thr Leu Gly Pro Val Ser Arg Ser Val Glu
            20                  25                  30

Met Ile Glu Lys Leu Leu Lys Ala Gly Met Asn Val Ala Arg Phe Asn
        35                  40                  45

Phe Ser His Gly Ser His Ser Tyr His Gln Glu Thr Leu Asp Asn Leu
    50                  55                  60

Arg Thr Ala Met Asp Asn Thr Gly Ile Leu Ser Ala Val Met Leu Asp
65                  70                  75                  80

Thr Lys Gly Pro Glu Ile Arg Thr Gly Phe Leu Lys Glu Gly Lys Pro
                85                  90                  95

Ile Gln Leu Asn Gln Gly Gln Glu Ile Thr Ile Ser Ile Asp Tyr Met
            100                 105                 110

Ile Glu Gly Asp Ser Asn Val Ile Ser Met Ser Tyr Lys Lys Leu Ala
        115                 120                 125

Glu Asp Val Lys Pro Gly Asp Val Ile Leu Cys Ser Asp Gly Thr Ile
    130                 135                 140

Ser Leu Thr Val Leu Ser Cys Asp Lys Ser Phe Gly Leu Val Arg Cys
145                 150                 155                 160

Arg Cys Glu Asn Ser Ala Ile Leu Gly Glu Arg Lys Asn Val Asn Leu
                165                 170                 175

Pro Gly Ile Val Val Asp Leu Pro Thr Leu Thr Glu Lys Asp Lys Glu
            180                 185                 190
```

Asp Ile Ile Gln Trp Gly Val Pro Asn Lys Ile Asp Ile Ile Ala Leu
195 200 205

Ser Phe Val Arg Lys Gly Ser Asp Leu Thr Glu Val Arg Arg Leu Leu
210 215 220

Gly Glu His Ser Lys Asn Ile Met Leu Met Ser Lys Val Glu Asn Gln
225 230 235 240

Glu Gly Val Met Asn Cys Glu Lys Ile Leu Glu Asn Ser Asp Ala Phe
245 250 255

Met Val Ala Arg Gly Asp Leu Gly Met Glu Ile Pro Ile Glu Lys Met
260 265 270

Phe Leu Ala Gln Lys Thr Met Ile Lys Met Ala Asn Ala Leu Gly Lys
275 280 285

Pro Val Val Thr Ala Thr Gln Met Leu Glu Ser Met Thr Val Ser Pro
290 295 300

Arg Pro Thr Arg Ala Glu Ala Thr Asp Val Ala Asn Ala Val Leu Asp
305 310 315 320

Gly Thr Asp Cys Val Met Leu Ser Gly Glu Thr Ala Ala Gly Ala His
325 330 335

Pro Glu Ala Ala Val Leu Thr Met Ser Arg Ile Cys Lys Glu Ala Glu
340 345 350

Asp Phe Ile Asp Tyr Asp Ile Leu His Lys Lys Thr Leu Gly Met Val
355 360 365

Ser Leu Pro Leu Ser Pro Ile Glu Ser Leu Ala Ala Ser Val Val Ser
370 375 380

Thr Ala Gln Ser Val Phe Ala Ser Ala Ile Val Val Leu Thr Lys Gly
385 390 395 400

Gly Tyr Thr Ala Glu Leu Val Ala Lys Tyr Arg Pro Ser Val Pro Ile
405 410 415

Leu Ser Val Ile Val Pro Glu Ile Ala Gln Gly Asn Asp Met Glu Met
420 425 430

Ser Cys Ser Asp Ser Val Ala His Ala Ala Arg Arg Gly Leu Ile Tyr
435 440 445

Arg Arg Ile Ile Pro Val Val Ala Thr Gly Ser Ser Ala Arg Asp Ser
450 455 460

Asn Lys Asp Ala Thr Glu Glu Met Ile Asn Leu Ala Ile Gly Phe Ala
465 470 475 480

Lys Thr Lys Gly Ile Cys Lys Asn Gly Asp Ser Ile Val Ala Leu His
485 490 495

Lys Ile Asp Gly Ser Ser Val Val Lys Ile Val Thr Val Glu
500 505 510

<210> SEQ ID NO 13
<211> LENGTH: 1479
<212> TYPE: DNA
<213> ORGANISM: Arabidopsis thaliana
<220> FEATURE:
<221> NAME/KEY: CDS
<222> LOCATION: (1)..(1479)
<223> OTHER INFORMATION: Pyruvate Kinase

<400> SEQUENCE: 13 atg gag atg tta ctt ggt ggc cga gca acc aat gga gct ctc cgt tca 48
Met Glu Met Leu Leu Gly Gly Arg Ala Thr Asn Gly Ala Leu Arg Ser
1 5 10 15 aag acg aag ata gtt tgt act ctt gga ccg gtt tca aga tcg gtg gag 96
Lys Thr Lys Ile Val Cys Thr Leu Gly Pro Val Ser Arg Ser Val Glu
20 25 30

-continued

```
atg att gag aag ctt ctc aag gct gaa act ctc gat aat ctc cga act      144
Met Ile Glu Lys Leu Leu Lys Ala Glu Thr Leu Asp Asn Leu Arg Thr
        35                  40                  45

gcc atg aac aac act ggt atc ctc tgc gcc gtc atg ctc gat aca aag      192
Ala Met Asn Asn Thr Gly Ile Leu Cys Ala Val Met Leu Asp Thr Lys
    50                  55                  60

ggt cct gag ata cga acc ggt ttt ctc aaa gaa ggc aaa ccg ata cag      240
Gly Pro Glu Ile Arg Thr Gly Phe Leu Lys Glu Gly Lys Pro Ile Gln
65                  70                  75                  80

cta aac caa ggt caa gag atc acc atc tca att gat tac aag ata gaa      288
Leu Asn Gln Gly Gln Glu Ile Thr Ile Ser Ile Asp Tyr Lys Ile Glu
                85                  90                  95

gga gat tca aac att atc tcc atg agc tac aag aaa ctt gca gag gac      336
Gly Asp Ser Asn Ile Ile Ser Met Ser Tyr Lys Lys Leu Ala Glu Asp
            100                 105                 110

gtc aaa cct ggt gat gtg att ctc tgt tca gac ggc aca atc tct tta      384
Val Lys Pro Gly Asp Val Ile Leu Cys Ser Asp Gly Thr Ile Ser Leu
        115                 120                 125

act gtc ttg tcc tgt gac aag tct ttc ggt ctt gtt cgt tgc cgt tgc      432
Thr Val Leu Ser Cys Asp Lys Ser Phe Gly Leu Val Arg Cys Arg Cys
    130                 135                 140

gag aac tct aca att cta gga gaa aga aaa aac gtt aat ctt cct gga      480
Glu Asn Ser Thr Ile Leu Gly Glu Arg Lys Asn Val Asn Leu Pro Gly
145                 150                 155                 160

att gta gtt gat ctc cca aca ctt act gag aaa gat aaa gaa gat atc      528
Ile Val Val Asp Leu Pro Thr Leu Thr Glu Lys Asp Lys Glu Asp Ile
                165                 170                 175

atc caa tgg gga gtt ccg aac aaa atc gac atc atc gct ctt tct ttt      576
Ile Gln Trp Gly Val Pro Asn Lys Ile Asp Ile Ile Ala Leu Ser Phe
            180                 185                 190

gtt cgt aaa gga tct gac cta act gaa gtt agg aag tta ctt gga gaa      624
Val Arg Lys Gly Ser Asp Leu Thr Glu Val Arg Lys Leu Leu Gly Glu
        195                 200                 205

cac tca aag aac atc atg ctc atg tca aag gtg gag aat caa gaa ggg      672
His Ser Lys Asn Ile Met Leu Met Ser Lys Val Glu Asn Gln Glu Gly
    210                 215                 220

gtc atg aat tgt gaa aag att ctg gag aat tct gat gct ttc atg gtg      720
Val Met Asn Cys Glu Lys Ile Leu Glu Asn Ser Asp Ala Phe Met Val
225                 230                 235                 240

gct aga gga gat ctt gga atg gag att cag atc gaa aag atg ttc ctt      768
Ala Arg Gly Asp Leu Gly Met Glu Ile Gln Ile Glu Lys Met Phe Leu
                245                 250                 255

gct cag aaa aca atg atc aag atg gct aat gct ctt ggg aaa cca gtt      816
Ala Gln Lys Thr Met Ile Lys Met Ala Asn Ala Leu Gly Lys Pro Val
            260                 265                 270

gtc aca gcc aca cag atg ctt gaa tcc atg aca gta tct cct cgt ccg      864
Val Thr Ala Thr Gln Met Leu Glu Ser Met Thr Val Ser Pro Arg Pro
        275                 280                 285

act aga gct gaa gcc act gac gtt gca aac gct gtt ctt gac ggg aca      912
Thr Arg Ala Glu Ala Thr Asp Val Ala Asn Ala Val Leu Asp Gly Thr
    290                 295                 300

gat tgc gtt atg ctt agt gga gaa acc gct gca gga gct cac cct gag      960
Asp Cys Val Met Leu Ser Gly Glu Thr Ala Ala Gly Ala His Pro Glu
305                 310                 315                 320

gct gcc gtg cta aca atg tca agg atc tgt aaa gaa gca gag gat ttc     1008
Ala Ala Val Leu Thr Met Ser Arg Ile Cys Lys Glu Ala Glu Asp Phe
                325                 330                 335

atc gat tac gac att ctc cac aag aaa acc cta gga atg ctt tcg tta     1056
Ile Asp Tyr Asp Ile Leu His Lys Lys Thr Leu Gly Met Leu Ser Leu
            340                 345                 350
```

```
ccg tta tct ccg atc gag agc tta gct gct tca gtt gtt tcg acg gca      1104
Pro Leu Ser Pro Ile Glu Ser Leu Ala Ala Ser Val Val Ser Thr Ala
        355                 360                 365

cag agt gtt ttt gcg tcg gct atc gtc gtt ctc acc aaa ggc ggt tac      1152
Gln Ser Val Phe Ala Ser Ala Ile Val Val Leu Thr Lys Gly Gly Tyr
    370                 375                 380

acg gcg gag ctt gtg gct aaa tac agg ccg agc gtt ccg att ttg tcg      1200
Thr Ala Glu Leu Val Ala Lys Tyr Arg Pro Ser Val Pro Ile Leu Ser
385                 390                 395                 400

gtg att gtg cct gag att gct caa ggg aat gat ata gag atg tcg tgc      1248
Val Ile Val Pro Glu Ile Ala Gln Gly Asn Asp Ile Glu Met Ser Cys
                405                 410                 415

tcg gac tcg gtg gct cat gtg gcg aga cgt ggt ttg att tac cgt ggg      1296
Ser Asp Ser Val Ala His Val Ala Arg Arg Gly Leu Ile Tyr Arg Gly
            420                 425                 430

att att ccg gtg gtg gcg acg gga tca tcg gct agg gat tca aac aaa      1344
Ile Ile Pro Val Val Ala Thr Gly Ser Ser Ala Arg Asp Ser Asn Lys
        435                 440                 445

gat gca acg gag gag atg att aat ttg gct atc gga ttc gcg aag acg      1392
Asp Ala Thr Glu Glu Met Ile Asn Leu Ala Ile Gly Phe Ala Lys Thr
    450                 455                 460

aag gga att tgc aag aat gga gat tcg att gtg gcg ttg cac aag att      1440
Lys Gly Ile Cys Lys Asn Gly Asp Ser Ile Val Ala Leu His Lys Ile
465                 470                 475                 480

gat ggt tcc tct gtt gtg aag ata gtg agc gtt gag taa                  1479
Asp Gly Ser Ser Val Val Lys Ile Val Ser Val Glu
                485                 490


<210> SEQ ID NO 14
<211> LENGTH: 492
<212> TYPE: PRT
<213> ORGANISM: Arabidopsis thaliana

<400> SEQUENCE: 14

Met Glu Met Leu Leu Gly Gly Arg Ala Thr Asn Gly Ala Leu Arg Ser
1               5                   10                  15

Lys Thr Lys Ile Val Cys Thr Leu Gly Pro Val Ser Arg Ser Val Glu
            20                  25                  30

Met Ile Glu Lys Leu Leu Lys Ala Glu Thr Leu Asp Asn Leu Arg Thr
        35                  40                  45

Ala Met Asn Asn Thr Gly Ile Leu Cys Ala Val Met Leu Asp Thr Lys
    50                  55                  60

Gly Pro Glu Ile Arg Thr Gly Phe Leu Lys Glu Gly Lys Pro Ile Gln
65                  70                  75                  80

Leu Asn Gln Gly Gln Glu Ile Thr Ile Ser Ile Asp Tyr Lys Ile Glu
                85                  90                  95

Gly Asp Ser Asn Ile Ile Ser Met Ser Tyr Lys Lys Leu Ala Glu Asp
            100                 105                 110

Val Lys Pro Gly Asp Val Ile Leu Cys Ser Asp Gly Thr Ile Ser Leu
        115                 120                 125

Thr Val Leu Ser Cys Asp Lys Ser Phe Gly Leu Val Arg Cys Arg Cys
    130                 135                 140

Glu Asn Ser Thr Ile Leu Gly Glu Arg Lys Asn Val Asn Leu Pro Gly
145                 150                 155                 160

Ile Val Val Asp Leu Pro Thr Leu Thr Glu Lys Asp Lys Glu Asp Ile
                165                 170                 175

Ile Gln Trp Gly Val Pro Asn Lys Ile Asp Ile Ile Ala Leu Ser Phe
            180                 185                 190
```

```
Val Arg Lys Gly Ser Asp Leu Thr Glu Val Arg Lys Leu Leu Gly Glu
        195                 200                 205

His Ser Lys Asn Ile Met Leu Met Ser Lys Val Glu Asn Gln Glu Gly
    210                 215                 220

Val Met Asn Cys Glu Lys Ile Leu Glu Asn Ser Asp Ala Phe Met Val
225                 230                 235                 240

Ala Arg Gly Asp Leu Gly Met Glu Ile Gln Ile Glu Lys Met Phe Leu
                245                 250                 255

Ala Gln Lys Thr Met Ile Lys Met Ala Asn Ala Leu Gly Lys Pro Val
            260                 265                 270

Val Thr Ala Thr Gln Met Leu Glu Ser Met Thr Val Ser Pro Arg Pro
        275                 280                 285

Thr Arg Ala Glu Ala Thr Asp Val Ala Asn Ala Val Leu Asp Gly Thr
    290                 295                 300

Asp Cys Val Met Leu Ser Gly Glu Thr Ala Ala Gly Ala His Pro Glu
305                 310                 315                 320

Ala Ala Val Leu Thr Met Ser Arg Ile Cys Lys Glu Ala Glu Asp Phe
                325                 330                 335

Ile Asp Tyr Asp Ile Leu His Lys Lys Thr Leu Gly Met Leu Ser Leu
            340                 345                 350

Pro Leu Ser Pro Ile Glu Ser Leu Ala Ala Ser Val Val Ser Thr Ala
        355                 360                 365

Gln Ser Val Phe Ala Ser Ala Ile Val Val Leu Thr Lys Gly Gly Tyr
    370                 375                 380

Thr Ala Glu Leu Val Ala Lys Tyr Arg Pro Ser Val Pro Ile Leu Ser
385                 390                 395                 400

Val Ile Val Pro Glu Ile Ala Gln Gly Asn Asp Ile Glu Met Ser Cys
                405                 410                 415

Ser Asp Ser Val Ala His Val Ala Arg Arg Gly Leu Ile Tyr Arg Gly
            420                 425                 430

Ile Ile Pro Val Val Ala Thr Gly Ser Ser Ala Arg Asp Ser Asn Lys
        435                 440                 445

Asp Ala Thr Glu Glu Met Ile Asn Leu Ala Ile Gly Phe Ala Lys Thr
    450                 455                 460

Lys Gly Ile Cys Lys Asn Gly Asp Ser Ile Val Ala Leu His Lys Ile
465                 470                 475                 480

Asp Gly Ser Ser Val Val Lys Ile Val Ser Val Glu
                485                 490


<210> SEQ ID NO 15
<211> LENGTH: 1498
<212> TYPE: DNA
<213> ORGANISM: Arabidopsis thaliana
<220> FEATURE:
<221> NAME/KEY: CDS
<222> LOCATION: (5)..(1498)
<223> OTHER INFORMATION: Pyruvate Kinase

<400> SEQUENCE: 15

tgcg atg gct atg gaa cag agg cct aag acg aag atc gtg tgc aca ctc      49
     Met Ala Met Glu Gln Arg Pro Lys Thr Lys Ile Val Cys Thr Leu
     1               5                   10                  15

ggg ccg gcg tcc aga tct gtc cca atg gtc gag aag ctt ctt atg gcg       97
Gly Pro Ala Ser Arg Ser Val Pro Met Val Glu Lys Leu Leu Met Ala
                20                  25                  30

ggg atg agc gtg gct cgc ttc aac ttt tct cat gga tct tac gaa tat      145
Gly Met Ser Val Ala Arg Phe Asn Phe Ser His Gly Ser Tyr Glu Tyr
```

-continued

```
            35                  40                  45

cac cag gag act ctc gac aat ctt cgt cag gcc atg ctt aac act ggc       193
His Gln Glu Thr Leu Asp Asn Leu Arg Gln Ala Met Leu Asn Thr Gly
        50                  55                  60

atg cta tgt gct gtc atg ctc gac acc aag gga cca gag att cga acc       241
Met Leu Cys Ala Val Met Leu Asp Thr Lys Gly Pro Glu Ile Arg Thr
    65                  70                  75

ggg ttc tta aag gat ggg aaa cct atc cag ctc aaa caa ggc caa gaa       289
Gly Phe Leu Lys Asp Gly Lys Pro Ile Gln Leu Lys Gln Gly Gln Glu
80                  85                  90                  95

atc acc att tca act gac tat gac ttg aag ggt gat gag aaa act att       337
Ile Thr Ile Ser Thr Asp Tyr Asp Leu Lys Gly Asp Glu Lys Thr Ile
                100                 105                 110

tgc atg agc tac aag aag ttg gcg caa gat gtg aat cca ggc atg gtc       385
Cys Met Ser Tyr Lys Lys Leu Ala Gln Asp Val Asn Pro Gly Met Val
            115                 120                 125

ata ctc tgt gcc gat ggt acc atc tcg tta aag gtc ctt tct tgt gac       433
Ile Leu Cys Ala Asp Gly Thr Ile Ser Leu Lys Val Leu Ser Cys Asp
        130                 135                 140

aaa gaa aag ggc act gtc cgt tgt cgt tgt gag aac act tca atg ctt       481
Lys Glu Lys Gly Thr Val Arg Cys Arg Cys Glu Asn Thr Ser Met Leu
    145                 150                 155

ggt gaa aga aag aac gtt aat ctc cct ggt gtt gtg gtt gat ctc cca       529
Gly Glu Arg Lys Asn Val Asn Leu Pro Gly Val Val Val Asp Leu Pro
160                 165                 170                 175

act cta act gaa aaa gac aag caa gac att ctt gaa tgg gga gtt ccc       577
Thr Leu Thr Glu Lys Asp Lys Gln Asp Ile Leu Glu Trp Gly Val Pro
                180                 185                 190

aat caa atc gac atg att gct ctg tct ttt gtc aga aaa ggt tcg gac       625
Asn Gln Ile Asp Met Ile Ala Leu Ser Phe Val Arg Lys Gly Ser Asp
            195                 200                 205

ttg gta caa gtt agg aag cta ctt gga aaa cat gct aaa acc ata ctt       673
Leu Val Gln Val Arg Lys Leu Leu Gly Lys His Ala Lys Thr Ile Leu
        210                 215                 220

ctc atg tca aag gtt gaa aac caa gaa ggt gta gcg aat ttt gat gat       721
Leu Met Ser Lys Val Glu Asn Gln Glu Gly Val Ala Asn Phe Asp Asp
    225                 230                 235

atc ttg ata aac tcg gat gcg ttt atg atc gca aga ggt gac ctt gga       769
Ile Leu Ile Asn Ser Asp Ala Phe Met Ile Ala Arg Gly Asp Leu Gly
240                 245                 250                 255

atg gag att cca att gag aag ata ttc tta gct cag aaa gtg atg atc       817
Met Glu Ile Pro Ile Glu Lys Ile Phe Leu Ala Gln Lys Val Met Ile
                260                 265                 270

tac aag tgc aat ttc atg ggg aag cca gtg gtt aca gcg act cag atg       865
Tyr Lys Cys Asn Phe Met Gly Lys Pro Val Val Thr Ala Thr Gln Met
            275                 280                 285

ctt gag tct atg atc aaa tcc cca cga cca aca aga gca gaa gct act       913
Leu Glu Ser Met Ile Lys Ser Pro Arg Pro Thr Arg Ala Glu Ala Thr
        290                 295                 300

gat gtt gca aat gct gtc ctc gat ggc aca gac tgt gtc atg ctt agt       961
Asp Val Ala Asn Ala Val Leu Asp Gly Thr Asp Cys Val Met Leu Ser
    305                 310                 315

ggt gaa acc gca gct gga gca tac cca gag ctt gct gtt cgt aca atg      1009
Gly Glu Thr Ala Ala Gly Ala Tyr Pro Glu Leu Ala Val Arg Thr Met
320                 325                 330                 335

gcc aag ata tgt gtg gaa gca gag agc aca ctt gac tat gga gac atc      1057
Ala Lys Ile Cys Val Glu Ala Glu Ser Thr Leu Asp Tyr Gly Asp Ile
                340                 345                 350

ttc aag agg ata atg ctt cac gct gcg gtc cct atg agc ccg atg gag      1105
Phe Lys Arg Ile Met Leu His Ala Ala Val Pro Met Ser Pro Met Glu
```

```
            355                 360                 365

tca ctt gct tca tct gcg gtc aga acc gct act tcc tca aga gcc act      1153
Ser Leu Ala Ser Ser Ala Val Arg Thr Ala Thr Ser Ser Arg Ala Thr
        370                 375                 380

ctt atg atg gtc ttg acc aga gga ggc agc acg gcg agg ctg gtg gct      1201
Leu Met Met Val Leu Thr Arg Gly Gly Ser Thr Ala Arg Leu Val Ala
    385                 390                 395

aag tat aga cca ggg ata ccc att ttg tcc gtg gtg gtt cct gaa atc      1249
Lys Tyr Arg Pro Gly Ile Pro Ile Leu Ser Val Val Val Pro Glu Ile
400                 405                 410                 415

acg tct gac tct ttt gat tgg gcg tgt agc aac gag gca ccg gca aga      1297
Thr Ser Asp Ser Phe Asp Trp Ala Cys Ser Asn Glu Ala Pro Ala Arg
                420                 425                 430

cac agt ctc atc tac cgt ggt tta gtc ccg gtg ctg tat gct gga tcg      1345
His Ser Leu Ile Tyr Arg Gly Leu Val Pro Val Leu Tyr Ala Gly Ser
            435                 440                 445

gct aga gcc tcg atc gac gag tca aca gaa gaa act ctc gag ttc gcg      1393
Ala Arg Ala Ser Ile Asp Glu Ser Thr Glu Glu Thr Leu Glu Phe Ala
        450                 455                 460

tca gag tat ggt aaa aag aag caa ctc tgc aag acc gga gac tct gtt      1441
Ser Glu Tyr Gly Lys Lys Lys Gln Leu Cys Lys Thr Gly Asp Ser Val
    465                 470                 475

gtg gct ctc ttc cgt aca ggt aac gct att gtt atc aag atc ttg acc      1489
Val Ala Leu Phe Arg Thr Gly Asn Ala Ile Val Ile Lys Ile Leu Thr
480                 485                 490                 495

gtc aag tga                                                          1498
Val Lys


<210> SEQ ID NO 16
<211> LENGTH: 497
<212> TYPE: PRT
<213> ORGANISM: Arabidopsis thaliana

<400> SEQUENCE: 16

Met Ala Met Glu Gln Arg Pro Lys Thr Lys Ile Val Cys Thr Leu Gly
1               5                   10                  15

Pro Ala Ser Arg Ser Val Pro Met Val Glu Lys Leu Leu Met Ala Gly
            20                  25                  30

Met Ser Val Ala Arg Phe Asn Phe Ser His Gly Ser Tyr Glu Tyr His
        35                  40                  45

Gln Glu Thr Leu Asp Asn Leu Arg Gln Ala Met Leu Asn Thr Gly Met
    50                  55                  60

Leu Cys Ala Val Met Leu Asp Thr Lys Gly Pro Glu Ile Arg Thr Gly
65                  70                  75                  80

Phe Leu Lys Asp Gly Lys Pro Ile Gln Leu Lys Gln Gly Gln Glu Ile
                85                  90                  95

Thr Ile Ser Thr Asp Tyr Asp Leu Lys Gly Asp Glu Lys Thr Ile Cys
            100                 105                 110

Met Ser Tyr Lys Lys Leu Ala Gln Asp Val Asn Pro Gly Met Val Ile
        115                 120                 125

Leu Cys Ala Asp Gly Thr Ile Ser Leu Lys Val Leu Ser Cys Asp Lys
    130                 135                 140

Glu Lys Gly Thr Val Arg Cys Arg Cys Glu Asn Thr Ser Met Leu Gly
145                 150                 155                 160

Glu Arg Lys Asn Val Asn Leu Pro Gly Val Val Val Asp Leu Pro Thr
                165                 170                 175

Leu Thr Glu Lys Asp Lys Gln Asp Ile Leu Glu Trp Gly Val Pro Asn
            180                 185                 190
```

```
Gln Ile Asp Met Ile Ala Leu Ser Phe Val Arg Lys Gly Ser Asp Leu
        195                 200                 205

Val Gln Val Arg Lys Leu Leu Gly Lys His Ala Lys Thr Ile Leu Leu
    210                 215                 220

Met Ser Lys Val Glu Asn Gln Glu Gly Val Ala Asn Phe Asp Asp Ile
225                 230                 235                 240

Leu Ile Asn Ser Asp Ala Phe Met Ile Ala Arg Gly Asp Leu Gly Met
                245                 250                 255

Glu Ile Pro Ile Glu Lys Ile Phe Leu Ala Gln Lys Val Met Ile Tyr
            260                 265                 270

Lys Cys Asn Phe Met Gly Lys Pro Val Val Thr Ala Thr Gln Met Leu
        275                 280                 285

Glu Ser Met Ile Lys Ser Pro Arg Pro Thr Arg Ala Glu Ala Thr Asp
    290                 295                 300

Val Ala Asn Ala Val Leu Asp Gly Thr Asp Cys Val Met Leu Ser Gly
305                 310                 315                 320

Glu Thr Ala Ala Gly Ala Tyr Pro Glu Leu Ala Val Arg Thr Met Ala
                325                 330                 335

Lys Ile Cys Val Glu Ala Glu Ser Thr Leu Asp Tyr Gly Asp Ile Phe
            340                 345                 350

Lys Arg Ile Met Leu His Ala Ala Val Pro Met Ser Pro Met Glu Ser
        355                 360                 365

Leu Ala Ser Ser Ala Val Arg Thr Ala Thr Ser Ser Arg Ala Thr Leu
    370                 375                 380

Met Met Val Leu Thr Arg Gly Gly Ser Thr Ala Arg Leu Val Ala Lys
385                 390                 395                 400

Tyr Arg Pro Gly Ile Pro Ile Leu Ser Val Val Val Pro Glu Ile Thr
                405                 410                 415

Ser Asp Ser Phe Asp Trp Ala Cys Ser Asn Glu Ala Pro Ala Arg His
            420                 425                 430

Ser Leu Ile Tyr Arg Gly Leu Val Pro Val Leu Tyr Ala Gly Ser Ala
        435                 440                 445

Arg Ala Ser Ile Asp Glu Ser Thr Glu Glu Thr Leu Glu Phe Ala Ser
    450                 455                 460

Glu Tyr Gly Lys Lys Lys Gln Leu Cys Lys Thr Gly Asp Ser Val Val
465                 470                 475                 480

Ala Leu Phe Arg Thr Gly Asn Ala Ile Val Ile Lys Ile Leu Thr Val
                485                 490                 495

Lys


<210> SEQ ID NO 17
<211> LENGTH: 1772
<212> TYPE: DNA
<213> ORGANISM: Arabidopsis thaliana
<220> FEATURE:
<221> NAME/KEY: CDS
<222> LOCATION: (89)..(1621)
<223> OTHER INFORMATION: Pyruvate Kinase

<400> SEQUENCE: 17

aagtccaagc ccgaaaacaa gggttcttgc tccgacacga caacaaatcc agattttgag      60

cttagggaaa cttgagaagg agaaaaaa atg tcg aac ata gac ata gaa ggg      112
                               Met Ser Asn Ile Asp Ile Glu Gly
                               1               5

atc ttg aag gag cta cct aat gat ggg agg atc cca aag acg aag ata      160
Ile Leu Lys Glu Leu Pro Asn Asp Gly Arg Ile Pro Lys Thr Lys Ile
```

```
    10                  15                  20

gtt tgc aca tta gga cca gct tct cgc act gtt tcc atg atc gaa aag       208
Val Cys Thr Leu Gly Pro Ala Ser Arg Thr Val Ser Met Ile Glu Lys
25                  30                  35                  40

ctt ttg aaa gcc ggt atg aat gtg gct cgc ttc aac ttc tca cat gga       256
Leu Leu Lys Ala Gly Met Asn Val Ala Arg Phe Asn Phe Ser His Gly
                45                  50                  55

agc cat gaa tac cat caa gag aca ctc gac aac ctc cgc tct gct atg       304
Ser His Glu Tyr His Gln Glu Thr Leu Asp Asn Leu Arg Ser Ala Met
            60                  65                  70

cat aat acc ggc att ctc gct gct gtc atg ctt gat act aag ggg cct       352
His Asn Thr Gly Ile Leu Ala Ala Val Met Leu Asp Thr Lys Gly Pro
        75                  80                  85

gag att cgt act ggt ttc ttg aaa gat ggg aac cct ata caa ctg aag       400
Glu Ile Arg Thr Gly Phe Leu Lys Asp Gly Asn Pro Ile Gln Leu Lys
    90                  95                  100

gaa ggt caa gag att act ata acc act gat tat gac att caa gga gac       448
Glu Gly Gln Glu Ile Thr Ile Thr Thr Asp Tyr Asp Ile Gln Gly Asp
105                 110                 115                 120

gaa tca acg ata tcc atg agc tat aaa aag ctg cct ttg gat gtg aag       496
Glu Ser Thr Ile Ser Met Ser Tyr Lys Lys Leu Pro Leu Asp Val Lys
                125                 130                 135

ccc gga aac acc ata ctc tgt gca gat gga agc ata agt cta gct gtc       544
Pro Gly Asn Thr Ile Leu Cys Ala Asp Gly Ser Ile Ser Leu Ala Val
            140                 145                 150

ttg tca tgt gat cct gag tct gga act gtt agg tgc cgg tgt gaa aac       592
Leu Ser Cys Asp Pro Glu Ser Gly Thr Val Arg Cys Arg Cys Glu Asn
        155                 160                 165

tcg gcg atg ctt ggt gaa aga aag aat gtg aat ctt cct ggc gtt gtt       640
Ser Ala Met Leu Gly Glu Arg Lys Asn Val Asn Leu Pro Gly Val Val
    170                 175                 180

gtt gat ctt ccc act ttg aca gat aag gat att gaa gat att ctc ggt       688
Val Asp Leu Pro Thr Leu Thr Asp Lys Asp Ile Glu Asp Ile Leu Gly
185                 190                 195                 200

tgg ggt gtt ccg aac agc att gat atg att gct ctt tcg ttt gtc cgt       736
Trp Gly Val Pro Asn Ser Ile Asp Met Ile Ala Leu Ser Phe Val Arg
                205                 210                 215

aaa ggt tcg gat ctt gtt aat gtc cgc aag gtt ctt gga tct cat gct       784
Lys Gly Ser Asp Leu Val Asn Val Arg Lys Val Leu Gly Ser His Ala
            220                 225                 230

aaa agc ata atg ctc atg tca aag gtt gag aac cag gaa ggt gtg att       832
Lys Ser Ile Met Leu Met Ser Lys Val Glu Asn Gln Glu Gly Val Ile
        235                 240                 245

aac ttt gat gag atc ttg cgt gaa aca gat gcg ttc atg gtt gcc cgt       880
Asn Phe Asp Glu Ile Leu Arg Glu Thr Asp Ala Phe Met Val Ala Arg
    250                 255                 260

ggt gat ctc ggg atg gag att ccg ata gag aag atc ttc ttg gct caa       928
Gly Asp Leu Gly Met Glu Ile Pro Ile Glu Lys Ile Phe Leu Ala Gln
265                 270                 275                 280

aag ttg atg atc tac aag tgt aac ctt gcg ggt aaa ccg gtg gtc aca       976
Lys Leu Met Ile Tyr Lys Cys Asn Leu Ala Gly Lys Pro Val Val Thr
                285                 290                 295

gcc act cag atg ctg gag tca atg atc aaa tca cct cgg cca acc cga      1024
Ala Thr Gln Met Leu Glu Ser Met Ile Lys Ser Pro Arg Pro Thr Arg
            300                 305                 310

gct gaa gcc aca gat gtt gca aat gct gtt ctt gat ggt act gac tgt      1072
Ala Glu Ala Thr Asp Val Ala Asn Ala Val Leu Asp Gly Thr Asp Cys
        315                 320                 325

gtg atg ctt agc ggt gag agt gca gca gga gct tat ccg gaa ata gct      1120
Val Met Leu Ser Gly Glu Ser Ala Ala Gly Ala Tyr Pro Glu Ile Ala
```

```
    330                 335                 340

gtg aaa gtc atg gct aag atc tgc att gaa gcc gaa tcc tcg ctt gat      1168
Val Lys Val Met Ala Lys Ile Cys Ile Glu Ala Glu Ser Ser Leu Asp
345                 350                 355                 360

tac aac aca atc ttt aaa gag atg atc cga gca act cca ctt cca atg      1216
Tyr Asn Thr Ile Phe Lys Glu Met Ile Arg Ala Thr Pro Leu Pro Met
                365                 370                 375

agc cca ctc gag agt ctt gca tca tcc gct gta cgg act gct aac aaa      1264
Ser Pro Leu Glu Ser Leu Ala Ser Ser Ala Val Arg Thr Ala Asn Lys
            380                 385                 390

gcg agg gca aaa ctc atc att gtg ttg aca cgt gga ggt tca act gct      1312
Ala Arg Ala Lys Leu Ile Ile Val Leu Thr Arg Gly Gly Ser Thr Ala
        395                 400                 405

aat ctc gtg gct aaa tac aga ccg gct gtt ccg att ctg tca gtg gtt      1360
Asn Leu Val Ala Lys Tyr Arg Pro Ala Val Pro Ile Leu Ser Val Val
    410                 415                 420

gtc ccg gtt atg acc act gat tcc ttt gac tgg tct tgt agt gac gag      1408
Val Pro Val Met Thr Thr Asp Ser Phe Asp Trp Ser Cys Ser Asp Glu
425                 430                 435                 440

tca cct gca agg cat agt ctg ata tac aga ggt cta atc cct atg ttg      1456
Ser Pro Ala Arg His Ser Leu Ile Tyr Arg Gly Leu Ile Pro Met Leu
                445                 450                 455

gct gaa gga tct gca aag gca aca gat agt gaa gcc acc gaa gtt atc      1504
Ala Glu Gly Ser Ala Lys Ala Thr Asp Ser Glu Ala Thr Glu Val Ile
            460                 465                 470

att gaa gct gct ctg aag tcg gct act cag aga gga ctg tgc aac cgt      1552
Ile Glu Ala Ala Leu Lys Ser Ala Thr Gln Arg Gly Leu Cys Asn Arg
        475                 480                 485

ggt gat gca atc gtg gcg ctg cac cgt att gga gct gcc tca gtt att      1600
Gly Asp Ala Ile Val Ala Leu His Arg Ile Gly Ala Ala Ser Val Ile
    490                 495                 500

aag atc tgt gtg gtt aag tga gattacagac ttctttcaat acctcaaatc         1651
Lys Ile Cys Val Val Lys
505                 510

ttggattgtt ggtaatcgta actgagattt tgctttgtag catgaaataa agaaaacagg   1711

tcacaatagt tcctgaaact ctgttacttt taagatatct ctctctcttt taaaaaaaaa   1771

a                                                                    1772


<210> SEQ ID NO 18
<211> LENGTH: 510
<212> TYPE: PRT
<213> ORGANISM: Arabidopsis thaliana

<400> SEQUENCE: 18

Met Ser Asn Ile Asp Ile Glu Gly Ile Leu Lys Glu Leu Pro Asn Asp
1               5                   10                  15

Gly Arg Ile Pro Lys Thr Lys Ile Val Cys Thr Leu Gly Pro Ala Ser
            20                  25                  30

Arg Thr Val Ser Met Ile Glu Lys Leu Leu Lys Ala Gly Met Asn Val
        35                  40                  45

Ala Arg Phe Asn Phe Ser His Gly Ser His Glu Tyr His Gln Glu Thr
    50                  55                  60

Leu Asp Asn Leu Arg Ser Ala Met His Asn Thr Gly Ile Leu Ala Ala
65                  70                  75                  80

Val Met Leu Asp Thr Lys Gly Pro Glu Ile Arg Thr Gly Phe Leu Lys
                85                  90                  95

Asp Gly Asn Pro Ile Gln Leu Lys Glu Gly Gln Glu Ile Thr Ile Thr
            100                 105                 110
```

```
Thr Asp Tyr Asp Ile Gln Gly Asp Glu Ser Thr Ile Ser Met Ser Tyr
        115                 120                 125

Lys Lys Leu Pro Leu Asp Val Lys Pro Gly Asn Thr Ile Leu Cys Ala
    130                 135                 140

Asp Gly Ser Ile Ser Leu Ala Val Leu Ser Cys Asp Pro Glu Ser Gly
145                 150                 155                 160

Thr Val Arg Cys Arg Cys Glu Asn Ser Ala Met Leu Gly Glu Arg Lys
                165                 170                 175

Asn Val Asn Leu Pro Gly Val Val Val Asp Leu Pro Thr Leu Thr Asp
            180                 185                 190

Lys Asp Ile Glu Asp Ile Leu Gly Trp Gly Val Pro Asn Ser Ile Asp
        195                 200                 205

Met Ile Ala Leu Ser Phe Val Arg Lys Gly Ser Asp Leu Val Asn Val
    210                 215                 220

Arg Lys Val Leu Gly Ser His Ala Lys Ser Ile Met Leu Met Ser Lys
225                 230                 235                 240

Val Glu Asn Gln Glu Gly Val Ile Asn Phe Asp Glu Ile Leu Arg Glu
                245                 250                 255

Thr Asp Ala Phe Met Val Ala Arg Gly Asp Leu Gly Met Glu Ile Pro
            260                 265                 270

Ile Glu Lys Ile Phe Leu Ala Gln Lys Leu Met Ile Tyr Lys Cys Asn
        275                 280                 285

Leu Ala Gly Lys Pro Val Val Thr Ala Thr Gln Met Leu Glu Ser Met
    290                 295                 300

Ile Lys Ser Pro Arg Pro Thr Arg Ala Glu Ala Thr Asp Val Ala Asn
305                 310                 315                 320

Ala Val Leu Asp Gly Thr Asp Cys Val Met Leu Ser Gly Glu Ser Ala
                325                 330                 335

Ala Gly Ala Tyr Pro Glu Ile Ala Val Lys Val Met Ala Lys Ile Cys
            340                 345                 350

Ile Glu Ala Glu Ser Ser Leu Asp Tyr Asn Thr Ile Phe Lys Glu Met
        355                 360                 365

Ile Arg Ala Thr Pro Leu Pro Met Ser Pro Leu Glu Ser Leu Ala Ser
    370                 375                 380

Ser Ala Val Arg Thr Ala Asn Lys Ala Arg Ala Lys Leu Ile Ile Val
385                 390                 395                 400

Leu Thr Arg Gly Gly Ser Thr Ala Asn Leu Val Ala Lys Tyr Arg Pro
                405                 410                 415

Ala Val Pro Ile Leu Ser Val Val Val Pro Val Met Thr Thr Asp Ser
            420                 425                 430

Phe Asp Trp Ser Cys Ser Asp Glu Ser Pro Ala Arg His Ser Leu Ile
        435                 440                 445

Tyr Arg Gly Leu Ile Pro Met Leu Ala Glu Gly Ser Ala Lys Ala Thr
    450                 455                 460

Asp Ser Glu Ala Thr Glu Val Ile Ile Glu Ala Ala Leu Lys Ser Ala
465                 470                 475                 480

Thr Gln Arg Gly Leu Cys Asn Arg Gly Asp Ala Ile Val Ala Leu His
                485                 490                 495

Arg Ile Gly Ala Ala Ser Val Ile Lys Ile Cys Val Val Lys
            500                 505                 510
```

<210> SEQ ID NO 19
<211> LENGTH: 1853
<212> TYPE: DNA

-continued

<213> ORGANISM: Arabidopsis thaliana
<220> FEATURE:
<221> NAME/KEY: CDS
<222> LOCATION: (127)..(1623)
<223> OTHER INFORMATION: Pyruvate Kinase

<400> SEQUENCE: 19

```
tctctgtttt ccttgttctc caagccagat ctctctccat aaatctctct tcatctctct      60

ctttccacca aacatccgcg atcctcgatt ctcaattccg tgtctgtttt ttttcttcac     120

ttagcg atg gcg atg ata gag caa agg ccg aag acg aag atc gtt tgt        168
       Met Ala Met Ile Glu Gln Arg Pro Lys Thr Lys Ile Val Cys
       1               5                   10

act cta ggt cca gct tcc aga tct gtt ccg atg gtc gag aag ctt ctt       216
Thr Leu Gly Pro Ala Ser Arg Ser Val Pro Met Val Glu Lys Leu Leu
15                  20                  25                  30

agg gct ggt atg aac gtt gct cgt ttc aat ttc tct cat gga tct cat       264
Arg Ala Gly Met Asn Val Ala Arg Phe Asn Phe Ser His Gly Ser His
                35                  40                  45

gaa tac cat caa gag act ctc gat aat ctt cat caa gct atg ctt aac       312
Glu Tyr His Gln Glu Thr Leu Asp Asn Leu His Gln Ala Met Leu Asn
            50                  55                  60

act ggg att ctc tgt gcc gtc atg ctc gac acc aag ggt cca gaa atc       360
Thr Gly Ile Leu Cys Ala Val Met Leu Asp Thr Lys Gly Pro Glu Ile
        65                  70                  75

cga acc ggg ttc ttg aaa gat ggg aaa cca atc cag ctg aaa caa gga       408
Arg Thr Gly Phe Leu Lys Asp Gly Lys Pro Ile Gln Leu Lys Gln Gly
    80                  85                  90

caa gag atc act att tcg act gac tat gac ttg aag ggt gac gag aac       456
Gln Glu Ile Thr Ile Ser Thr Asp Tyr Asp Leu Lys Gly Asp Glu Asn
95                  100                 105                 110

acg att tgc atg agc tac aaa aag ttg gct gtt gat gtg aac cca gga       504
Thr Ile Cys Met Ser Tyr Lys Lys Leu Ala Val Asp Val Asn Pro Gly
                115                 120                 125

atg gtc att ctt tgt gct gat ggt aca atc tcc tta ctg gtt ctc tct       552
Met Val Ile Leu Cys Ala Asp Gly Thr Ile Ser Leu Leu Val Leu Ser
            130                 135                 140

tgt gac aaa gag aac ggt aca gtc cgt tgc cgg tgt gag aac tct gcg       600
Cys Asp Lys Glu Asn Gly Thr Val Arg Cys Arg Cys Glu Asn Ser Ala
        145                 150                 155

atg ctc ggt gag aga aag aac gtt aat ctc cca ggt gtt gtt gtg gat       648
Met Leu Gly Glu Arg Lys Asn Val Asn Leu Pro Gly Val Val Val Asp
    160                 165                 170

ctc cca act cta act gag aaa gac aaa gaa gac atc atg caa tgg gga       696
Leu Pro Thr Leu Thr Glu Lys Asp Lys Glu Asp Ile Met Gln Trp Gly
175                 180                 185                 190

gtc ccg aat caa atc gac atg att gct ctg tct ttt gtc agg aaa ggt       744
Val Pro Asn Gln Ile Asp Met Ile Ala Leu Ser Phe Val Arg Lys Gly
                195                 200                 205

tca gac ttg gtt caa gtc cgg aaa ctt cta gga aag cac gcc aaa aac       792
Ser Asp Leu Val Gln Val Arg Lys Leu Leu Gly Lys His Ala Lys Asn
            210                 215                 220

att ctt ctc atg tct aag gtc gag aac caa gaa ggt gtg gca aat ttt       840
Ile Leu Leu Met Ser Lys Val Glu Asn Gln Glu Gly Val Ala Asn Phe
        225                 230                 235

gat gac att ttg gtc aat tca gac gct ttc atg att gct aga gga gat       888
Asp Asp Ile Leu Val Asn Ser Asp Ala Phe Met Ile Ala Arg Gly Asp
    240                 245                 250

ctg ggc atg gaa atc ccg att gag aag atc ttc tta gct cag aag gtg       936
Leu Gly Met Glu Ile Pro Ile Glu Lys Ile Phe Leu Ala Gln Lys Val
255                 260                 265                 270
```

```
atg atc tac aaa tgc aac atc cag gga aaa cct gtg gtc aca gca act      984
Met Ile Tyr Lys Cys Asn Ile Gln Gly Lys Pro Val Val Thr Ala Thr
                275                 280                 285

cag atg ctc gag tcc atg atc aaa tct cct aga ccc aca aga gcc gaa     1032
Gln Met Leu Glu Ser Met Ile Lys Ser Pro Arg Pro Thr Arg Ala Glu
            290                 295                 300

gct acg gat gta gca aac gca gtc ctt gat ggt aca gac tgt gtc atg     1080
Ala Thr Asp Val Ala Asn Ala Val Leu Asp Gly Thr Asp Cys Val Met
        305                 310                 315

ctc agt ggt gaa act gca gct gga gca tac cct gaa cta gcc gtc cgt     1128
Leu Ser Gly Glu Thr Ala Ala Gly Ala Tyr Pro Glu Leu Ala Val Arg
    320                 325                 330

aca atg gct aag atc tgc gtg gaa gcc gag agc acc ctt gac tac ggt     1176
Thr Met Ala Lys Ile Cys Val Glu Ala Glu Ser Thr Leu Asp Tyr Gly
335                 340                 345                 350

gat gtc ttc aag agg atc atg ctg tac tct cca gtt cca atg agt cca     1224
Asp Val Phe Lys Arg Ile Met Leu Tyr Ser Pro Val Pro Met Ser Pro
                355                 360                 365

ctc gag tca ctt gca tct tca gct gtc aga act gct aac tca gct aga     1272
Leu Glu Ser Leu Ala Ser Ser Ala Val Arg Thr Ala Asn Ser Ala Arg
            370                 375                 380

gcc act ctc atc atg gtc cta acc aga gga gga agc aca gca aga ctt     1320
Ala Thr Leu Ile Met Val Leu Thr Arg Gly Gly Ser Thr Ala Arg Leu
        385                 390                 395

gtg gct aag tac aga cca gga atg cct att cta tcc gtc gtt gtt cct     1368
Val Ala Lys Tyr Arg Pro Gly Met Pro Ile Leu Ser Val Val Val Pro
    400                 405                 410

gag atc aaa acc gac ttc ttt gac tgg tct tgc agc gat gaa tcc ccc     1416
Glu Ile Lys Thr Asp Phe Phe Asp Trp Ser Cys Ser Asp Glu Ser Pro
415                 420                 425                 430

gcg aga cac agc ctt atc ttc cgt ggt ctg atc cca gtg ctc tac gct     1464
Ala Arg His Ser Leu Ile Phe Arg Gly Leu Ile Pro Val Leu Tyr Ala
                435                 440                 445

gga tcc gca aga gcc tca cac gat gaa tca aca gaa gaa gct atc gag     1512
Gly Ser Ala Arg Ala Ser His Asp Glu Ser Thr Glu Glu Ala Ile Glu
            450                 455                 460

ttt gct act cag tac ggg aaa gag aaa gag cta tgc aag act gga gat     1560
Phe Ala Thr Gln Tyr Gly Lys Glu Lys Glu Leu Cys Lys Thr Gly Asp
        465                 470                 475

tcc gtt gtt gct cta ctc cga gtc ggt aat gct tcc gtg atc aag atc     1608
Ser Val Val Ala Leu Leu Arg Val Gly Asn Ala Ser Val Ile Lys Ile
    480                 485                 490

ttg acc gtc aag tga tgattccact caaaaattca cgtttttggc gtttggggaa     1663
Leu Thr Val Lys
495

cgctacttta aacgttttat tatgaaacta ttcaagattg tgattaaaat cttgagatag   1723

aaaactcaag ttctattttt tgcttattac cacaactact gtgaccggtg aatccactta   1783

acagctcctt ttgggatatt ttggttgtat tgaaacctat tggatcattc atacacgtat   1843

caattatcat                                                          1853
```

```
<210> SEQ ID NO 20
<211> LENGTH: 498
<212> TYPE: PRT
<213> ORGANISM: Arabidopsis thaliana

<400> SEQUENCE: 20

Met Ala Met Ile Glu Gln Arg Pro Lys Thr Lys Ile Val Cys Thr Leu
1               5                   10                  15

Gly Pro Ala Ser Arg Ser Val Pro Met Val Glu Lys Leu Leu Arg Ala
```

-continued

```
            20                  25                  30

Gly Met Asn Val Ala Arg Phe Asn Phe Ser His Gly Ser His Glu Tyr
        35                  40                  45

His Gln Glu Thr Leu Asp Asn Leu His Gln Ala Met Leu Asn Thr Gly
    50                  55                  60

Ile Leu Cys Ala Val Met Leu Asp Thr Lys Gly Pro Glu Ile Arg Thr
65                  70                  75                  80

Gly Phe Leu Lys Asp Gly Lys Pro Ile Gln Leu Lys Gln Gly Gln Glu
                85                  90                  95

Ile Thr Ile Ser Thr Asp Tyr Asp Leu Lys Gly Asp Glu Asn Thr Ile
            100                 105                 110

Cys Met Ser Tyr Lys Lys Leu Ala Val Asp Val Asn Pro Gly Met Val
        115                 120                 125

Ile Leu Cys Ala Asp Gly Thr Ile Ser Leu Leu Val Leu Ser Cys Asp
    130                 135                 140

Lys Glu Asn Gly Thr Val Arg Cys Arg Cys Glu Asn Ser Ala Met Leu
145                 150                 155                 160

Gly Glu Arg Lys Asn Val Asn Leu Pro Gly Val Val Val Asp Leu Pro
                165                 170                 175

Thr Leu Thr Glu Lys Asp Lys Glu Asp Ile Met Gln Trp Gly Val Pro
            180                 185                 190

Asn Gln Ile Asp Met Ile Ala Leu Ser Phe Val Arg Lys Gly Ser Asp
        195                 200                 205

Leu Val Gln Val Arg Lys Leu Leu Gly Lys His Ala Lys Asn Ile Leu
    210                 215                 220

Leu Met Ser Lys Val Glu Asn Gln Glu Gly Val Ala Asn Phe Asp Asp
225                 230                 235                 240

Ile Leu Val Asn Ser Asp Ala Phe Met Ile Ala Arg Gly Asp Leu Gly
                245                 250                 255

Met Glu Ile Pro Ile Glu Lys Ile Phe Leu Ala Gln Lys Val Met Ile
            260                 265                 270

Tyr Lys Cys Asn Ile Gln Gly Lys Pro Val Val Thr Ala Thr Gln Met
        275                 280                 285

Leu Glu Ser Met Ile Lys Ser Pro Arg Pro Thr Arg Ala Glu Ala Thr
    290                 295                 300

Asp Val Ala Asn Ala Val Leu Asp Gly Thr Asp Cys Val Met Leu Ser
305                 310                 315                 320

Gly Glu Thr Ala Ala Gly Ala Tyr Pro Glu Leu Ala Val Arg Thr Met
                325                 330                 335

Ala Lys Ile Cys Val Glu Ala Glu Ser Thr Leu Asp Tyr Gly Asp Val
            340                 345                 350

Phe Lys Arg Ile Met Leu Tyr Ser Pro Val Pro Met Ser Pro Leu Glu
        355                 360                 365

Ser Leu Ala Ser Ser Ala Val Arg Thr Ala Asn Ser Ala Arg Ala Thr
    370                 375                 380

Leu Ile Met Val Leu Thr Arg Gly Gly Ser Thr Ala Arg Leu Val Ala
385                 390                 395                 400

Lys Tyr Arg Pro Gly Met Pro Ile Leu Ser Val Val Val Pro Glu Ile
                405                 410                 415

Lys Thr Asp Phe Phe Asp Trp Ser Cys Ser Asp Glu Ser Pro Ala Arg
            420                 425                 430

His Ser Leu Ile Phe Arg Gly Leu Ile Pro Val Leu Tyr Ala Gly Ser
        435                 440                 445
```

```
Ala Arg Ala Ser His Asp Glu Ser Thr Glu Glu Ala Ile Glu Phe Ala
    450                 455                 460

Thr Gln Tyr Gly Lys Glu Lys Glu Leu Cys Lys Thr Gly Asp Ser Val
465                 470                 475                 480

Val Ala Leu Leu Arg Val Gly Asn Ala Ser Val Ile Lys Ile Leu Thr
                485                 490                 495

Val Lys


<210> SEQ ID NO 21
<211> LENGTH: 1890
<212> TYPE: DNA
<213> ORGANISM: Arabidopsis thaliana
<220> FEATURE:
<221> NAME/KEY: CDS
<222> LOCATION: (126)..(1658)
<223> OTHER INFORMATION: Pyruvate Kinase

<400> SEQUENCE: 21

ctgttcgtcg atataaaact ttcttcgtta ccattttgag tctccggcgg ctttcacact      60

ccagaaaaaa aacacagaag ctacgttttt caggactttg attaggtttt tggagattta     120

caaaa atg tcg aac ata gac ata gaa gga ata ttg aag gag cta cct aat     170
      Met Ser Asn Ile Asp Ile Glu Gly Ile Leu Lys Glu Leu Pro Asn
      1               5                   10                  15

gat ggg agg act cct aag act aag atc gtt tgt aca tta ggt cct gcg       218
Asp Gly Arg Thr Pro Lys Thr Lys Ile Val Cys Thr Leu Gly Pro Ala
                20                  25                  30

tct agg tct gtg aca atg att gag aag ctt ctt aaa gca ggc atg aat       266
Ser Arg Ser Val Thr Met Ile Glu Lys Leu Leu Lys Ala Gly Met Asn
            35                  40                  45

gta gct cga ttc aat ttc tct cac gga agc cat gag tac cat cag gag       314
Val Ala Arg Phe Asn Phe Ser His Gly Ser His Glu Tyr His Gln Glu
        50                  55                  60

act ctt gac aat ctc cgc acc gct atg cag aat acc ggc att ctc gct       362
Thr Leu Asp Asn Leu Arg Thr Ala Met Gln Asn Thr Gly Ile Leu Ala
    65                  70                  75

gct gtt atg ctt gat aca aag ggg cct gag att cgt acc ggt ttc ttg       410
Ala Val Met Leu Asp Thr Lys Gly Pro Glu Ile Arg Thr Gly Phe Leu
80                  85                  90                  95

aaa gat ggg aac cct ata caa cta aag gaa ggc caa gag atc aca att       458
Lys Asp Gly Asn Pro Ile Gln Leu Lys Glu Gly Gln Glu Ile Thr Ile
                100                 105                 110

acc act gat tat gac atc aag ggc gat gag aaa acg att tcc atg agc       506
Thr Thr Asp Tyr Asp Ile Lys Gly Asp Glu Lys Thr Ile Ser Met Ser
            115                 120                 125

tac aaa aag ctc cca gtg gat gtg aag ccc gga aat acc ata cta tgt       554
Tyr Lys Lys Leu Pro Val Asp Val Lys Pro Gly Asn Thr Ile Leu Cys
        130                 135                 140

gca gat gga agc ata agt ctt gct gtc gtg tca tgt gat cca aac gct       602
Ala Asp Gly Ser Ile Ser Leu Ala Val Val Ser Cys Asp Pro Asn Ala
    145                 150                 155

ggg act gtt ata tgt cga tgt gaa aat aca gcc atg cta ggt gaa aga       650
Gly Thr Val Ile Cys Arg Cys Glu Asn Thr Ala Met Leu Gly Glu Arg
160                 165                 170                 175

aaa aat gtg aat ctc cca ggt gtt gtt gtt gat ctc ccc aca ttg act       698
Lys Asn Val Asn Leu Pro Gly Val Val Val Asp Leu Pro Thr Leu Thr
                180                 185                 190

gac aag gat gta gaa gat att ctt aaa tgg ggt gtt cca aac aac atc       746
Asp Lys Asp Val Glu Asp Ile Leu Lys Trp Gly Val Pro Asn Asn Ile
            195                 200                 205

gat atg att gct ctt tca ttt gtt cgc aaa ggt tca gat ctt gtt aat       794
```

-continued

```
Asp Met Ile Ala Leu Ser Phe Val Arg Lys Gly Ser Asp Leu Val Asn
        210                 215                 220

gtc cgg aaa gtc ctt gga tca cat tcc aag agt ata atg ttg atg tcg      842
Val Arg Lys Val Leu Gly Ser His Ser Lys Ser Ile Met Leu Met Ser
    225                 230                 235

aag gtt gag aac caa gaa gga gtc ctg aat ttc gat gag att ttg cgt      890
Lys Val Glu Asn Gln Glu Gly Val Leu Asn Phe Asp Glu Ile Leu Arg
240                 245                 250                 255

gaa act gat gca ttc atg gtt gct cgt ggt gat ctt ggg atg gag att      938
Glu Thr Asp Ala Phe Met Val Ala Arg Gly Asp Leu Gly Met Glu Ile
                260                 265                 270

ccg ata gag aag atc ttc ttg gct cag aag att atg atc tac aag tgt      986
Pro Ile Glu Lys Ile Phe Leu Ala Gln Lys Ile Met Ile Tyr Lys Cys
            275                 280                 285

aac ctt gca ggt aaa ccg gtg gtc aca gcc act caa atg ctc gag tcg     1034
Asn Leu Ala Gly Lys Pro Val Val Thr Ala Thr Gln Met Leu Glu Ser
        290                 295                 300

atg atc aaa tca cca cgg cca aca cga gca gaa gcc aca gat gta gca     1082
Met Ile Lys Ser Pro Arg Pro Thr Arg Ala Glu Ala Thr Asp Val Ala
    305                 310                 315

aac gca gtt ctc gat ggc act gac tgt gtg atg ctt agc gga gaa agt     1130
Asn Ala Val Leu Asp Gly Thr Asp Cys Val Met Leu Ser Gly Glu Ser
320                 325                 330                 335

gct gca gga gct tac cct gaa ata gca gtg aaa aca atg gct aaa atc     1178
Ala Ala Gly Ala Tyr Pro Glu Ile Ala Val Lys Thr Met Ala Lys Ile
                340                 345                 350

tgc atc gag gcg gaa tca tcg ctt gac tac aac aca atc ttc aag gag     1226
Cys Ile Glu Ala Glu Ser Ser Leu Asp Tyr Asn Thr Ile Phe Lys Glu
            355                 360                 365

atg att aga gca act cca ctt cca atg agc act ctt gag agt ctt gca     1274
Met Ile Arg Ala Thr Pro Leu Pro Met Ser Thr Leu Glu Ser Leu Ala
        370                 375                 380

tca tca gct gta cga acg gca aac aaa gcc aaa gcc aaa ctc atc atc     1322
Ser Ser Ala Val Arg Thr Ala Asn Lys Ala Lys Ala Lys Leu Ile Ile
    385                 390                 395

gtg ttg acc aga gga ggt aca aca gct aaa ctg gtg gcc aag tat aga     1370
Val Leu Thr Arg Gly Gly Thr Thr Ala Lys Leu Val Ala Lys Tyr Arg
400                 405                 410                 415

ccg gct gtt cca att cta tcg gtg gtt gtt ccg gtc ttc acc agc gat     1418
Pro Ala Val Pro Ile Leu Ser Val Val Val Pro Val Phe Thr Ser Asp
                420                 425                 430

acg ttt aac tgg agt tgc agc gat gag tca ccg gcg agg cat agt ttg     1466
Thr Phe Asn Trp Ser Cys Ser Asp Glu Ser Pro Ala Arg His Ser Leu
            435                 440                 445

ata tat aga ggt ctg ata ccg gtt ttg ggt gaa gga tct gca aaa gca     1514
Ile Tyr Arg Gly Leu Ile Pro Val Leu Gly Glu Gly Ser Ala Lys Ala
        450                 455                 460

act gat agt gaa tcc aca gag gag att att gaa tct gct ttg aag tca     1562
Thr Asp Ser Glu Ser Thr Glu Glu Ile Ile Glu Ser Ala Leu Lys Ser
    465                 470                 475

gcg aca gag aaa gga ctg tgt aac cat ggt gat gct gtg gtg gct ctg     1610
Ala Thr Glu Lys Gly Leu Cys Asn His Gly Asp Ala Val Val Ala Leu
480                 485                 490                 495

cac cgt att gga gct gct tcg gtt atc aag atc tgt gtg gtg aag tga     1658
His Arg Ile Gly Ala Ala Ser Val Ile Lys Ile Cys Val Val Lys
                500                 505                 510

tttttctact aaatatcttg aattttattc ttggttaatg tttcttgatg aaataatcca   1718

ataaagaacc agggaatagg ttcctgaaag tgttttgtgt ggggcatttc ttctctttct   1778

tttgctgttt tagcttataa gattatgaat gcactaatga ctcttgctca tattattata   1838
```

```
gtttaattag ccaataataa caatttttaa ggctcgtttt ctaaaaaaaa aa          1890


<210> SEQ ID NO 22
<211> LENGTH: 510
<212> TYPE: PRT
<213> ORGANISM: Arabidopsis thaliana

<400> SEQUENCE: 22

Met Ser Asn Ile Asp Ile Glu Gly Ile Leu Lys Glu Leu Pro Asn Asp
1               5                   10                  15

Gly Arg Thr Pro Lys Thr Lys Ile Val Cys Thr Leu Gly Pro Ala Ser
            20                  25                  30

Arg Ser Val Thr Met Ile Glu Lys Leu Leu Lys Ala Gly Met Asn Val
        35                  40                  45

Ala Arg Phe Asn Phe Ser His Gly Ser His Glu Tyr His Gln Glu Thr
    50                  55                  60

Leu Asp Asn Leu Arg Thr Ala Met Gln Asn Thr Gly Ile Leu Ala Ala
65                  70                  75                  80

Val Met Leu Asp Thr Lys Gly Pro Glu Ile Arg Thr Gly Phe Leu Lys
                85                  90                  95

Asp Gly Asn Pro Ile Gln Leu Lys Glu Gly Gln Glu Ile Thr Ile Thr
            100                 105                 110

Thr Asp Tyr Asp Ile Lys Gly Asp Glu Lys Thr Ile Ser Met Ser Tyr
        115                 120                 125

Lys Lys Leu Pro Val Asp Val Lys Pro Gly Asn Thr Ile Leu Cys Ala
    130                 135                 140

Asp Gly Ser Ile Ser Leu Ala Val Val Ser Cys Asp Pro Asn Ala Gly
145                 150                 155                 160

Thr Val Ile Cys Arg Cys Glu Asn Thr Ala Met Leu Gly Glu Arg Lys
                165                 170                 175

Asn Val Asn Leu Pro Gly Val Val Val Asp Leu Pro Thr Leu Thr Asp
            180                 185                 190

Lys Asp Val Glu Asp Ile Leu Lys Trp Gly Val Pro Asn Asn Ile Asp
        195                 200                 205

Met Ile Ala Leu Ser Phe Val Arg Lys Gly Ser Asp Leu Val Asn Val
    210                 215                 220

Arg Lys Val Leu Gly Ser His Ser Lys Ser Ile Met Leu Met Ser Lys
225                 230                 235                 240

Val Glu Asn Gln Glu Gly Val Leu Asn Phe Asp Glu Ile Leu Arg Glu
                245                 250                 255

Thr Asp Ala Phe Met Val Ala Arg Gly Asp Leu Gly Met Glu Ile Pro
            260                 265                 270

Ile Glu Lys Ile Phe Leu Ala Gln Lys Ile Met Ile Tyr Lys Cys Asn
        275                 280                 285

Leu Ala Gly Lys Pro Val Val Thr Ala Thr Gln Met Leu Glu Ser Met
    290                 295                 300

Ile Lys Ser Pro Arg Pro Thr Arg Ala Glu Ala Thr Asp Val Ala Asn
305                 310                 315                 320

Ala Val Leu Asp Gly Thr Asp Cys Val Met Leu Ser Gly Glu Ser Ala
                325                 330                 335

Ala Gly Ala Tyr Pro Glu Ile Ala Val Lys Thr Met Ala Lys Ile Cys
            340                 345                 350

Ile Glu Ala Glu Ser Ser Leu Asp Tyr Asn Thr Ile Phe Lys Glu Met
        355                 360                 365
```

```
Ile Arg Ala Thr Pro Leu Pro Met Ser Thr Leu Glu Ser Leu Ala Ser
    370                 375                 380

Ser Ala Val Arg Thr Ala Asn Lys Ala Lys Ala Lys Leu Ile Ile Val
385                 390                 395                 400

Leu Thr Arg Gly Gly Thr Thr Ala Lys Leu Val Ala Lys Tyr Arg Pro
                405                 410                 415

Ala Val Pro Ile Leu Ser Val Val Val Pro Val Phe Thr Ser Asp Thr
            420                 425                 430

Phe Asn Trp Ser Cys Ser Asp Glu Ser Pro Ala Arg His Ser Leu Ile
        435                 440                 445

Tyr Arg Gly Leu Ile Pro Val Leu Gly Glu Gly Ser Ala Lys Ala Thr
    450                 455                 460

Asp Ser Glu Ser Thr Glu Glu Ile Ile Glu Ser Ala Leu Lys Ser Ala
465                 470                 475                 480

Thr Glu Lys Gly Leu Cys Asn His Gly Asp Ala Val Val Ala Leu His
                485                 490                 495

Arg Ile Gly Ala Ala Ser Val Ile Lys Ile Cys Val Val Lys
            500                 505                 510


<210> SEQ ID NO 23
<211> LENGTH: 1716
<212> TYPE: DNA
<213> ORGANISM: Arabidopsis thaliana
<220> FEATURE:
<221> NAME/KEY: CDS
<222> LOCATION: (1)..(1716)
<223> OTHER INFORMATION: Pyruvate Kinase

<400> SEQUENCE: 23

atg gct gct tat ggt caa atc tcc tcg gga atg act gta gat cct cag       48
Met Ala Ala Tyr Gly Gln Ile Ser Ser Gly Met Thr Val Asp Pro Gln
1               5                   10                  15

gtt ctc tct tcc tcc aga aac att gga gtt tcc cta tca cct ctc tgg       96
Val Leu Ser Ser Ser Arg Asn Ile Gly Val Ser Leu Ser Pro Leu Trp
            20                  25                  30

aga aca cta atc ggc gcc gga gtt agg tct act agt atc tct ctc cgt      144
Arg Thr Leu Ile Gly Ala Gly Val Arg Ser Thr Ser Ile Ser Leu Arg
        35                  40                  45

caa tgt tct ctc tcc gtt aga tcg att aaa atc tcc gaa gat agc cgc      192
Gln Cys Ser Leu Ser Val Arg Ser Ile Lys Ile Ser Glu Asp Ser Arg
    50                  55                  60

aaa cct aaa gct tat gca gag aac ggt gct ttt gat gtg gga gtt ttg      240
Lys Pro Lys Ala Tyr Ala Glu Asn Gly Ala Phe Asp Val Gly Val Leu
65                  70                  75                  80

gat tct tca tca tat aga ttg gtt gat tca aga aca agt agt aat gat      288
Asp Ser Ser Ser Tyr Arg Leu Val Asp Ser Arg Thr Ser Ser Asn Asp
                85                  90                  95

tca agg agg aag act aag att gtg tgt acg att gga ccg tct tcg agt      336
Ser Arg Arg Lys Thr Lys Ile Val Cys Thr Ile Gly Pro Ser Ser Ser
            100                 105                 110

tct agg gaa atg att tgg aaa ctc gcg gaa gct gga atg aat gtg gct      384
Ser Arg Glu Met Ile Trp Lys Leu Ala Glu Ala Gly Met Asn Val Ala
        115                 120                 125

cgt ttg aat atg tct cat ggt gat cat gct tct cat cag ata act att      432
Arg Leu Asn Met Ser His Gly Asp His Ala Ser His Gln Ile Thr Ile
    130                 135                 140

gat tta gtt aag gag tat aat tct ttg ttt gtt gac aaa gct att gct      480
Asp Leu Val Lys Glu Tyr Asn Ser Leu Phe Val Asp Lys Ala Ile Ala
145                 150                 155                 160

att atg ttg gat aca aag ggt cct gag gtt cga agc ggg gat gta ccg      528
```

-continued

```
Ile Met Leu Asp Thr Lys Gly Pro Glu Val Arg Ser Gly Asp Val Pro
                165                 170                 175

cag ccg ata ttt ctt gaa gag ggt caa gag ttt aac ttt act atc aag      576
Gln Pro Ile Phe Leu Glu Glu Gly Gln Glu Phe Asn Phe Thr Ile Lys
            180                 185                 190

aga ggt gtt tcg ctt aaa gac act gtt agt gta aat tat gat gat ttt      624
Arg Gly Val Ser Leu Lys Asp Thr Val Ser Val Asn Tyr Asp Asp Phe
        195                 200                 205

gtg aac gat gtt gaa gtt ggg gat ata ctt ttg gtg gat ggt gga atg      672
Val Asn Asp Val Glu Val Gly Asp Ile Leu Leu Val Asp Gly Gly Met
    210                 215                 220

atg tcg tta gct gtt aaa tca aag acg agt gat ttg gtg aag tgt gtg      720
Met Ser Leu Ala Val Lys Ser Lys Thr Ser Asp Leu Val Lys Cys Val
225                 230                 235                 240

gtt att gat ggt gga gag ctt caa tct aga cgt cac ttg aat gtt cga      768
Val Ile Asp Gly Gly Glu Leu Gln Ser Arg Arg His Leu Asn Val Arg
                245                 250                 255

gga aag agt gcg act ctt cca tcc att aca gac aaa gat tgg gaa gac      816
Gly Lys Ser Ala Thr Leu Pro Ser Ile Thr Asp Lys Asp Trp Glu Asp
            260                 265                 270

ata aaa ttt gga gtg gac aac caa gtc gat ttc tac gcc gtc tcc ttt      864
Ile Lys Phe Gly Val Asp Asn Gln Val Asp Phe Tyr Ala Val Ser Phe
        275                 280                 285

gtt aag gat gct aaa gtt gtc cat gag ttg aag aac tat ctc aaa acc      912
Val Lys Asp Ala Lys Val Val His Glu Leu Lys Asn Tyr Leu Lys Thr
    290                 295                 300

tgc agt gca gac ata tcg gtg att gtg aaa att gaa agt gca gac tct      960
Cys Ser Ala Asp Ile Ser Val Ile Val Lys Ile Glu Ser Ala Asp Ser
305                 310                 315                 320

ata aag aat ctt cct tct atc ata tct gct tgt gat ggg gca atg gtt     1008
Ile Lys Asn Leu Pro Ser Ile Ile Ser Ala Cys Asp Gly Ala Met Val
                325                 330                 335

gct cgt gga gat ctt gga gct gaa ctt ccc att gaa gag gtc ccg ttg     1056
Ala Arg Gly Asp Leu Gly Ala Glu Leu Pro Ile Glu Glu Val Pro Leu
            340                 345                 350

tta cag gaa gaa ata atc aga agg tgt aga agc att cat aaa cca gtg     1104
Leu Gln Glu Glu Ile Ile Arg Arg Cys Arg Ser Ile His Lys Pro Val
        355                 360                 365

att gtt gcc aca aac atg cta gag agt atg att aat cat cca acg cct     1152
Ile Val Ala Thr Asn Met Leu Glu Ser Met Ile Asn His Pro Thr Pro
    370                 375                 380

aca aga gct gaa gtc tct gac att gca att gca gta cgt gaa ggc gca     1200
Thr Arg Ala Glu Val Ser Asp Ile Ala Ile Ala Val Arg Glu Gly Ala
385                 390                 395                 400

gat gct atc atg ctt tct ggt gaa acc gca cat gga aag ttt ccg ctg     1248
Asp Ala Ile Met Leu Ser Gly Glu Thr Ala His Gly Lys Phe Pro Leu
                405                 410                 415

aaa gct gtt aac gta atg cat act gtg gcg ttg aga acc gag gca agt     1296
Lys Ala Val Asn Val Met His Thr Val Ala Leu Arg Thr Glu Ala Ser
            420                 425                 430

cta cct gtc aga acc tcg gca tcc cgt acc act gct tac aag ggt cac     1344
Leu Pro Val Arg Thr Ser Ala Ser Arg Thr Thr Ala Tyr Lys Gly His
        435                 440                 445

atg ggc caa atg ttt gct ttt cat gct tct ata atg gca aat aca ctg     1392
Met Gly Gln Met Phe Ala Phe His Ala Ser Ile Met Ala Asn Thr Leu
    450                 455                 460

agc tca ccg cta att gta ttt acg aga acc gga tcc atg gca gtg ctt     1440
Ser Ser Pro Leu Ile Val Phe Thr Arg Thr Gly Ser Met Ala Val Leu
465                 470                 475                 480

cta agc cat tac cgc cca tct gca aca att ttc gcc ttc aca aac cag     1488
```

-continued

```
Leu Ser His Tyr Arg Pro Ser Ala Thr Ile Phe Ala Phe Thr Asn Gln
                485                 490                 495

aga aga ata atg caa agg ctt gct ctt tat caa ggt gtc atg cct ata      1536
Arg Arg Ile Met Gln Arg Leu Ala Leu Tyr Gln Gly Val Met Pro Ile
            500                 505                 510

tat atg gag ttc tcg gat gat gca gaa gat aca tat gcc cgg tct ctc      1584
Tyr Met Glu Phe Ser Asp Asp Ala Glu Asp Thr Tyr Ala Arg Ser Leu
        515                 520                 525

aaa ctc tta cag gac gag aat atg ctc aag gaa gga caa cat gta act      1632
Lys Leu Leu Gln Asp Glu Asn Met Leu Lys Glu Gly Gln His Val Thr
    530                 535                 540

ctt gtc caa agt ggc tcg caa ccc att tgg cgt gaa gaa tca aca cat      1680
Leu Val Gln Ser Gly Ser Gln Pro Ile Trp Arg Glu Glu Ser Thr His
545                 550                 555                 560

ctc ata caa gtc cgt aag ata aag ata ggt gga tga                      1716
Leu Ile Gln Val Arg Lys Ile Lys Ile Gly Gly
                565                 570


<210> SEQ ID NO 24
<211> LENGTH: 571
<212> TYPE: PRT
<213> ORGANISM: Arabidopsis thaliana

<400> SEQUENCE: 24

Met Ala Ala Tyr Gly Gln Ile Ser Ser Gly Met Thr Val Asp Pro Gln
1               5                   10                  15

Val Leu Ser Ser Ser Arg Asn Ile Gly Val Ser Leu Ser Pro Leu Trp
            20                  25                  30

Arg Thr Leu Ile Gly Ala Gly Val Arg Ser Thr Ser Ile Ser Leu Arg
        35                  40                  45

Gln Cys Ser Leu Ser Val Arg Ser Ile Lys Ile Ser Glu Asp Ser Arg
    50                  55                  60

Lys Pro Lys Ala Tyr Ala Glu Asn Gly Ala Phe Asp Val Gly Val Leu
65                  70                  75                  80

Asp Ser Ser Ser Tyr Arg Leu Val Asp Ser Arg Thr Ser Ser Asn Asp
                85                  90                  95

Ser Arg Arg Lys Thr Lys Ile Val Cys Thr Ile Gly Pro Ser Ser Ser
            100                 105                 110

Ser Arg Glu Met Ile Trp Lys Leu Ala Glu Ala Gly Met Asn Val Ala
        115                 120                 125

Arg Leu Asn Met Ser His Gly Asp His Ala Ser His Gln Ile Thr Ile
    130                 135                 140

Asp Leu Val Lys Glu Tyr Asn Ser Leu Phe Val Asp Lys Ala Ile Ala
145                 150                 155                 160

Ile Met Leu Asp Thr Lys Gly Pro Glu Val Arg Ser Gly Asp Val Pro
                165                 170                 175

Gln Pro Ile Phe Leu Glu Glu Gly Gln Glu Phe Asn Phe Thr Ile Lys
            180                 185                 190

Arg Gly Val Ser Leu Lys Asp Thr Val Ser Val Asn Tyr Asp Asp Phe
        195                 200                 205

Val Asn Asp Val Glu Val Gly Asp Ile Leu Leu Val Asp Gly Gly Met
    210                 215                 220

Met Ser Leu Ala Val Lys Ser Lys Thr Ser Asp Leu Val Lys Cys Val
225                 230                 235                 240

Val Ile Asp Gly Gly Glu Leu Gln Ser Arg Arg His Leu Asn Val Arg
                245                 250                 255

Gly Lys Ser Ala Thr Leu Pro Ser Ile Thr Asp Lys Asp Trp Glu Asp
```

```
        260                 265                 270

Ile Lys Phe Gly Val Asp Asn Gln Val Asp Phe Tyr Ala Val Ser Phe
        275                 280                 285

Val Lys Asp Ala Lys Val Val His Glu Leu Lys Asn Tyr Leu Lys Thr
    290                 295                 300

Cys Ser Ala Asp Ile Ser Val Ile Val Lys Ile Glu Ser Ala Asp Ser
305                 310                 315                 320

Ile Lys Asn Leu Pro Ser Ile Ile Ser Ala Cys Asp Gly Ala Met Val
                325                 330                 335

Ala Arg Gly Asp Leu Gly Ala Glu Leu Pro Ile Glu Glu Val Pro Leu
            340                 345                 350

Leu Gln Glu Glu Ile Ile Arg Arg Cys Arg Ser Ile His Lys Pro Val
        355                 360                 365

Ile Val Ala Thr Asn Met Leu Glu Ser Met Ile Asn His Pro Thr Pro
    370                 375                 380

Thr Arg Ala Glu Val Ser Asp Ile Ala Ile Ala Val Arg Glu Gly Ala
385                 390                 395                 400

Asp Ala Ile Met Leu Ser Gly Glu Thr Ala His Gly Lys Phe Pro Leu
                405                 410                 415

Lys Ala Val Asn Val Met His Thr Val Ala Leu Arg Thr Glu Ala Ser
            420                 425                 430

Leu Pro Val Arg Thr Ser Ala Ser Arg Thr Thr Ala Tyr Lys Gly His
        435                 440                 445

Met Gly Gln Met Phe Ala Phe His Ala Ser Ile Met Ala Asn Thr Leu
    450                 455                 460

Ser Ser Pro Leu Ile Val Phe Thr Arg Thr Gly Ser Met Ala Val Leu
465                 470                 475                 480

Leu Ser His Tyr Arg Pro Ser Ala Thr Ile Phe Ala Phe Thr Asn Gln
                485                 490                 495

Arg Arg Ile Met Gln Arg Leu Ala Leu Tyr Gln Gly Val Met Pro Ile
            500                 505                 510

Tyr Met Glu Phe Ser Asp Asp Ala Glu Asp Thr Tyr Ala Arg Ser Leu
        515                 520                 525

Lys Leu Leu Gln Asp Glu Asn Met Leu Lys Glu Gly Gln His Val Thr
    530                 535                 540

Leu Val Gln Ser Gly Ser Gln Pro Ile Trp Arg Glu Glu Ser Thr His
545                 550                 555                 560

Leu Ile Gln Val Arg Lys Ile Lys Ile Gly Gly
                565                 570
```

<210> SEQ ID NO 25
<211> LENGTH: 1791
<212> TYPE: DNA
<213> ORGANISM: Arabidopsis thaliana
<220> FEATURE:
<221> NAME/KEY: CDS
<222> LOCATION: (1)..(1791)
<223> OTHER INFORMATION: Pyruvate Kinase

<400> SEQUENCE: 25

```
atg tct cag tct att caa ttc tcc act cct tca cac act cct cac ctt       48
Met Ser Gln Ser Ile Gln Phe Ser Thr Pro Ser His Thr Pro His Leu
1               5                   10                  15

ctc cat ctc cct cac tca caa ttc aac cgt cct ctc tcc tct atc tcc       96
Leu His Leu Pro His Ser Gln Phe Asn Arg Pro Leu Ser Ser Ile Ser
            20                  25                  30

ttc cgt cgc ttc cct cta aca acc atc aaa tac act tcc atc aga gcc      144
```

-continued

```
Phe Arg Arg Phe Pro Leu Thr Thr Ile Lys Tyr Thr Ser Ile Arg Ala
        35                  40                  45

tcc tcg tca tca tct cct tca ccg gat ctc gat tca tcg tcc tca tca      192
Ser Ser Ser Ser Ser Pro Ser Pro Asp Leu Asp Ser Ser Ser Ser Ser
    50                  55                  60

tca tcc tcg caa gta ctt ctc tca cct aac ggt act ggt gcc gtg aag      240
Ser Ser Ser Gln Val Leu Leu Ser Pro Asn Gly Thr Gly Ala Val Lys
65                  70                  75                  80

tct gat gag aga tcc gtt gtc gct acg gcg gtt acg act gat acg tct      288
Ser Asp Glu Arg Ser Val Val Ala Thr Ala Val Thr Thr Asp Thr Ser
                85                  90                  95

ggg att gag gtt gat act gtg acg gaa gct gag ctt aag gag aat gga      336
Gly Ile Glu Val Asp Thr Val Thr Glu Ala Glu Leu Lys Glu Asn Gly
            100                 105                 110

ttt aga agt acg agg agg acg aag ctg atc tgt acg atc gga ccg gcg      384
Phe Arg Ser Thr Arg Arg Thr Lys Leu Ile Cys Thr Ile Gly Pro Ala
        115                 120                 125

act tgt gga ttt gag cag ctt gag gcg ctt gct gtg gga ggt atg aat      432
Thr Cys Gly Phe Glu Gln Leu Glu Ala Leu Ala Val Gly Gly Met Asn
    130                 135                 140

gtg gca agg ctt aat atg tgt cac ggt acg cgt gat tgg cac cgc ggt      480
Val Ala Arg Leu Asn Met Cys His Gly Thr Arg Asp Trp His Arg Gly
145                 150                 155                 160

gtg att cgt agt gtt cgg agg ctt aat gag gag aaa ggc ttt gcg gtt      528
Val Ile Arg Ser Val Arg Arg Leu Asn Glu Glu Lys Gly Phe Ala Val
                165                 170                 175

gct att atg atg gat act gaa ggt agt gag att cat atg gga gat ctt      576
Ala Ile Met Met Asp Thr Glu Gly Ser Glu Ile His Met Gly Asp Leu
            180                 185                 190

ggt ggt gaa gct tca gct aaa gca gag gat ggt gag gtt tgg act ttc      624
Gly Gly Glu Ala Ser Ala Lys Ala Glu Asp Gly Glu Val Trp Thr Phe
        195                 200                 205

act gtt aga gct ttt gat tct tct cgt cct gaa cgt acc att agt gtt      672
Thr Val Arg Ala Phe Asp Ser Ser Arg Pro Glu Arg Thr Ile Ser Val
    210                 215                 220

agc tac gat ggt ttc gct gaa gat gta aga gtt ggg gat gaa ctt ttg      720
Ser Tyr Asp Gly Phe Ala Glu Asp Val Arg Val Gly Asp Glu Leu Leu
225                 230                 235                 240

gtt gat ggt ggg atg gtg aga ttt gaa gtg att gag aag att ggt cct      768
Val Asp Gly Gly Met Val Arg Phe Glu Val Ile Glu Lys Ile Gly Pro
                245                 250                 255

gat gtt aag tgt cta tgt acc gat cct gga ttg ttg ctt cct cga gct      816
Asp Val Lys Cys Leu Cys Thr Asp Pro Gly Leu Leu Leu Pro Arg Ala
            260                 265                 270

aac ttg acg ttt tgg aga gat gga agt ctt gta cga gag cgt aat gcc      864
Asn Leu Thr Phe Trp Arg Asp Gly Ser Leu Val Arg Glu Arg Asn Ala
        275                 280                 285

atg ctt cca aca att tct tcc aag gac tgg ttg gat att gat ttt gga      912
Met Leu Pro Thr Ile Ser Ser Lys Asp Trp Leu Asp Ile Asp Phe Gly
    290                 295                 300

att gct gaa ggt gtg gat ttc att gct gta tcg ttt gtc aag tcg gct      960
Ile Ala Glu Gly Val Asp Phe Ile Ala Val Ser Phe Val Lys Ser Ala
305                 310                 315                 320

gaa gtc att aat cac ctt aaa agt tat ctt gct gct cgt tcc cgt gga     1008
Glu Val Ile Asn His Leu Lys Ser Tyr Leu Ala Ala Arg Ser Arg Gly
                325                 330                 335

ggg gaa att gga gtg att gca aag atc gag agt atc gat tca ctg acc     1056
Gly Glu Ile Gly Val Ile Ala Lys Ile Glu Ser Ile Asp Ser Leu Thr
            340                 345                 350

aat ttg gaa gaa att att cta gca tca gat ggg gcc atg gtt gca aga     1104
```

-continued

```
Asn Leu Glu Glu Ile Ile Leu Ala Ser Asp Gly Ala Met Val Ala Arg
        355                 360                 365

gga gat ctg gga gct cag ata cct ctt gag caa gtt cca gca gct caa     1152
Gly Asp Leu Gly Ala Gln Ile Pro Leu Glu Gln Val Pro Ala Ala Gln
    370                 375                 380

cag aga atc gtc caa gta tgc aga gct ctt aac aaa ccc gtc att gtc     1200
Gln Arg Ile Val Gln Val Cys Arg Ala Leu Asn Lys Pro Val Ile Val
385                 390                 395                 400

gct tca cag cta ttg gag tcc atg att gag tac cca act cca acc aga     1248
Ala Ser Gln Leu Leu Glu Ser Met Ile Glu Tyr Pro Thr Pro Thr Arg
                405                 410                 415

gca gaa gtt gcc gac gtg tct gaa gca gta aga caa aga tca gat gca     1296
Ala Glu Val Ala Asp Val Ser Glu Ala Val Arg Gln Arg Ser Asp Ala
            420                 425                 430

ttg atg ctc tct gga gaa tca gct atg gga caa ttc cca gac aag gcg     1344
Leu Met Leu Ser Gly Glu Ser Ala Met Gly Gln Phe Pro Asp Lys Ala
        435                 440                 445

ctc acg gtt cta agg act gtc agt tta aga atc gag aga tgg tgg agg     1392
Leu Thr Val Leu Arg Thr Val Ser Leu Arg Ile Glu Arg Trp Trp Arg
    450                 455                 460

gaa gag aaa cgc cat gag tct gta ccg ctt caa gcc ata ggc tct tca     1440
Glu Glu Lys Arg His Glu Ser Val Pro Leu Gln Ala Ile Gly Ser Ser
465                 470                 475                 480

ttt tca gac aaa atc tca gaa gag atc tgt aac tca gct gct aaa atg     1488
Phe Ser Asp Lys Ile Ser Glu Glu Ile Cys Asn Ser Ala Ala Lys Met
                485                 490                 495

gct aac aat ctt gga gtg gac gcg gtt ttc gtt tac aca acg agc gga     1536
Ala Asn Asn Leu Gly Val Asp Ala Val Phe Val Tyr Thr Thr Ser Gly
            500                 505                 510

cac atg gca tca ctg gtc tcc cga tgt cgc ccg gac tgc ccg atc ttt     1584
His Met Ala Ser Leu Val Ser Arg Cys Arg Pro Asp Cys Pro Ile Phe
        515                 520                 525

gct ttc aca acc aca acc tca gtg aga aga cgc tta aac cta caa tgg     1632
Ala Phe Thr Thr Thr Thr Ser Val Arg Arg Arg Leu Asn Leu Gln Trp
    530                 535                 540

gga ctt atc cca ttc cgt ctc agc ttc tca gac gac atg gaa agc aac     1680
Gly Leu Ile Pro Phe Arg Leu Ser Phe Ser Asp Asp Met Glu Ser Asn
545                 550                 555                 560

ttg aac aaa aca ttc tcg tta ctg aaa tca aga ggt atg atc aaa tct     1728
Leu Asn Lys Thr Phe Ser Leu Leu Lys Ser Arg Gly Met Ile Lys Ser
                565                 570                 575

ggt gac ctc gtg atc gca gtc tcg gac atg ctg caa tca atc cag gta     1776
Gly Asp Leu Val Ile Ala Val Ser Asp Met Leu Gln Ser Ile Gln Val
            580                 585                 590

atg aac gtc ccg taa                                                 1791
Met Asn Val Pro
        595


<210> SEQ ID NO 26
<211> LENGTH: 596
<212> TYPE: PRT
<213> ORGANISM: Arabidopsis thaliana

<400> SEQUENCE: 26

Met Ser Gln Ser Ile Gln Phe Ser Thr Pro Ser His Thr Pro His Leu
1               5                   10                  15

Leu His Leu Pro His Ser Gln Phe Asn Arg Pro Leu Ser Ser Ile Ser
            20                  25                  30

Phe Arg Arg Phe Pro Leu Thr Thr Ile Lys Tyr Thr Ser Ile Arg Ala
        35                  40                  45
```

-continued

```
Ser Ser Ser Ser Ser Pro Ser Pro Asp Leu Asp Ser Ser Ser Ser Ser
    50                  55                  60

Ser Ser Ser Gln Val Leu Leu Ser Pro Asn Gly Thr Gly Ala Val Lys
65                  70                  75                  80

Ser Asp Glu Arg Ser Val Val Ala Thr Ala Val Thr Thr Asp Thr Ser
                85                  90                  95

Gly Ile Glu Val Asp Thr Val Thr Glu Ala Glu Leu Lys Glu Asn Gly
            100                 105                 110

Phe Arg Ser Thr Arg Arg Thr Lys Leu Ile Cys Thr Ile Gly Pro Ala
        115                 120                 125

Thr Cys Gly Phe Glu Gln Leu Glu Ala Leu Ala Val Gly Gly Met Asn
    130                 135                 140

Val Ala Arg Leu Asn Met Cys His Gly Thr Arg Asp Trp His Arg Gly
145                 150                 155                 160

Val Ile Arg Ser Val Arg Arg Leu Asn Glu Glu Lys Gly Phe Ala Val
                165                 170                 175

Ala Ile Met Met Asp Thr Glu Gly Ser Glu Ile His Met Gly Asp Leu
            180                 185                 190

Gly Gly Glu Ala Ser Ala Lys Ala Glu Asp Gly Glu Val Trp Thr Phe
        195                 200                 205

Thr Val Arg Ala Phe Asp Ser Ser Arg Pro Glu Arg Thr Ile Ser Val
    210                 215                 220

Ser Tyr Asp Gly Phe Ala Glu Asp Val Arg Val Gly Asp Glu Leu Leu
225                 230                 235                 240

Val Asp Gly Gly Met Val Arg Phe Glu Val Ile Glu Lys Ile Gly Pro
                245                 250                 255

Asp Val Lys Cys Leu Cys Thr Asp Pro Gly Leu Leu Leu Pro Arg Ala
            260                 265                 270

Asn Leu Thr Phe Trp Arg Asp Gly Ser Leu Val Arg Glu Arg Asn Ala
        275                 280                 285

Met Leu Pro Thr Ile Ser Ser Lys Asp Trp Leu Asp Ile Asp Phe Gly
    290                 295                 300

Ile Ala Glu Gly Val Asp Phe Ile Ala Val Ser Phe Val Lys Ser Ala
305                 310                 315                 320

Glu Val Ile Asn His Leu Lys Ser Tyr Leu Ala Ala Arg Ser Arg Gly
                325                 330                 335

Gly Glu Ile Gly Val Ile Ala Lys Ile Glu Ser Ile Asp Ser Leu Thr
            340                 345                 350

Asn Leu Glu Glu Ile Ile Leu Ala Ser Asp Gly Ala Met Val Ala Arg
        355                 360                 365

Gly Asp Leu Gly Ala Gln Ile Pro Leu Glu Gln Val Pro Ala Ala Gln
    370                 375                 380

Gln Arg Ile Val Gln Val Cys Arg Ala Leu Asn Lys Pro Val Ile Val
385                 390                 395                 400

Ala Ser Gln Leu Leu Glu Ser Met Ile Glu Tyr Pro Thr Pro Thr Arg
                405                 410                 415

Ala Glu Val Ala Asp Val Ser Glu Ala Val Arg Gln Arg Ser Asp Ala
            420                 425                 430

Leu Met Leu Ser Gly Glu Ser Ala Met Gly Gln Phe Pro Asp Lys Ala
        435                 440                 445

Leu Thr Val Leu Arg Thr Val Ser Leu Arg Ile Glu Arg Trp Trp Arg
    450                 455                 460

Glu Glu Lys Arg His Glu Ser Val Pro Leu Gln Ala Ile Gly Ser Ser
465                 470                 475                 480
```

```
Phe Ser Asp Lys Ile Ser Glu Glu Ile Cys Asn Ser Ala Ala Lys Met
                485                 490                 495

Ala Asn Asn Leu Gly Val Asp Ala Val Phe Val Tyr Thr Thr Ser Gly
            500                 505                 510

His Met Ala Ser Leu Val Ser Arg Cys Arg Pro Asp Cys Pro Ile Phe
        515                 520                 525

Ala Phe Thr Thr Thr Thr Ser Val Arg Arg Arg Leu Asn Leu Gln Trp
    530                 535                 540

Gly Leu Ile Pro Phe Arg Leu Ser Phe Ser Asp Asp Met Glu Ser Asn
545                 550                 555                 560

Leu Asn Lys Thr Phe Ser Leu Leu Lys Ser Arg Gly Met Ile Lys Ser
                565                 570                 575

Gly Asp Leu Val Ile Ala Val Ser Asp Met Leu Gln Ser Ile Gln Val
            580                 585                 590

Met Asn Val Pro
        595


<210> SEQ ID NO 27
<211> LENGTH: 1740
<212> TYPE: DNA
<213> ORGANISM: Arabidopsis thaliana
<220> FEATURE:
<221> NAME/KEY: CDS
<222> LOCATION: (1)..(1740)
<223> OTHER INFORMATION: Pyruvate Kinase

<400> SEQUENCE: 27

atg gct caa gtg gtt gct acc agg tca att caa ggc tcg atg tta tct        48
Met Ala Gln Val Val Ala Thr Arg Ser Ile Gln Gly Ser Met Leu Ser
1               5                   10                  15

ccc aac ggt gga tct gtg tct aca aga tcc gag aag cta ttg aaa cca        96
Pro Asn Gly Gly Ser Val Ser Thr Arg Ser Glu Lys Leu Leu Lys Pro
            20                  25                  30

gcg agt ttt gca gtg aag gtt ctt ggc aac gaa gca aag aga agt gga       144
Ala Ser Phe Ala Val Lys Val Leu Gly Asn Glu Ala Lys Arg Ser Gly
        35                  40                  45

aga gtc tct gta aga agc aga aga gtg gtt gat act act gtg aga tcc       192
Arg Val Ser Val Arg Ser Arg Arg Val Val Asp Thr Thr Val Arg Ser
    50                  55                  60

gct cgt gtt gag act gaa gtc att cct gtt tct cct gaa gat gtg cct       240
Ala Arg Val Glu Thr Glu Val Ile Pro Val Ser Pro Glu Asp Val Pro
65                  70                  75                  80

aac aga gag gag cag ctt gag agg ttg ttg gaa atg cag cag ttt ggt       288
Asn Arg Glu Glu Gln Leu Glu Arg Leu Leu Glu Met Gln Gln Phe Gly
                85                  90                  95

gat aca tcg gta ggg atg tgg tcg aag ccg aca gtg agg agg aag aca       336
Asp Thr Ser Val Gly Met Trp Ser Lys Pro Thr Val Arg Arg Lys Thr
            100                 105                 110

aag att gtt tgc acc gtt ggt ccg tcg acc aac aca cga gaa atg ata       384
Lys Ile Val Cys Thr Val Gly Pro Ser Thr Asn Thr Arg Glu Met Ile
        115                 120                 125

tgg aaa ttg gct gaa gct ggg atg aat gtt gct agg atg aat atg tct       432
Trp Lys Leu Ala Glu Ala Gly Met Asn Val Ala Arg Met Asn Met Ser
    130                 135                 140

cat gga gat cat gct tca cat aag aag gtt att gat ttg gtt aaa gaa       480
His Gly Asp His Ala Ser His Lys Lys Val Ile Asp Leu Val Lys Glu
145                 150                 155                 160

tac aat gca caa act aaa gac aac act att gct atc atg ctt gac acc       528
Tyr Asn Ala Gln Thr Lys Asp Asn Thr Ile Ala Ile Met Leu Asp Thr
                165                 170                 175
```

-continued

```
aag ggt ccg gaa gtt agg agt gga gat tta cct cag cca att atg tta      576
Lys Gly Pro Glu Val Arg Ser Gly Asp Leu Pro Gln Pro Ile Met Leu
            180                 185                 190

gat cct ggt caa gag ttt acc ttt aca att gag aga gga gtc agc aca      624
Asp Pro Gly Gln Glu Phe Thr Phe Thr Ile Glu Arg Gly Val Ser Thr
        195                 200                 205

cca agt tgt gtc agt gtt aac tat gat gat ttc gtt aat gac gtg gaa      672
Pro Ser Cys Val Ser Val Asn Tyr Asp Asp Phe Val Asn Asp Val Glu
    210                 215                 220

gcg ggt gac atg ctt ctt gtt gat ggt ggt atg atg tcg ttt atg gtg      720
Ala Gly Asp Met Leu Leu Val Asp Gly Gly Met Met Ser Phe Met Val
225                 230                 235                 240

aag tca aag acc aaa gac tct gtc aaa tgt gaa gtt gtt gat ggt gga      768
Lys Ser Lys Thr Lys Asp Ser Val Lys Cys Glu Val Val Asp Gly Gly
                245                 250                 255

gaa ctt aag tca agg aga cac ctg aat gtc cga gga aag agt gca act      816
Glu Leu Lys Ser Arg Arg His Leu Asn Val Arg Gly Lys Ser Ala Thr
            260                 265                 270

tta cct tca atc act gag aag gac tgg gag gat att aaa ttt gga gtg      864
Leu Pro Ser Ile Thr Glu Lys Asp Trp Glu Asp Ile Lys Phe Gly Val
        275                 280                 285

gag aac aaa gtt gac ttt tat gca gtt tcc ttt gtc aaa gat gct caa      912
Glu Asn Lys Val Asp Phe Tyr Ala Val Ser Phe Val Lys Asp Ala Gln
    290                 295                 300

gtt gta cac gag ttg aag aaa tac ctt caa aat agt ggt gct gat ata      960
Val Val His Glu Leu Lys Lys Tyr Leu Gln Asn Ser Gly Ala Asp Ile
305                 310                 315                 320

cac gtg ata gtg aaa att gag agt gca gac tcc ata cct aac ttg cac     1008
His Val Ile Val Lys Ile Glu Ser Ala Asp Ser Ile Pro Asn Leu His
                325                 330                 335

tcc att atc aca gca tca gat ggg gca atg gtt gca aga ggt gat ctt     1056
Ser Ile Ile Thr Ala Ser Asp Gly Ala Met Val Ala Arg Gly Asp Leu
            340                 345                 350

ggt gca gag ctt cca att gaa gaa gtc ccc att ctt cag gag gag atc     1104
Gly Ala Glu Leu Pro Ile Glu Glu Val Pro Ile Leu Gln Glu Glu Ile
        355                 360                 365

att aac ctg tgc cgt agt atg gga aaa gct gtt att gtt gcg act aac     1152
Ile Asn Leu Cys Arg Ser Met Gly Lys Ala Val Ile Val Ala Thr Asn
    370                 375                 380

atg ctt gag agt atg ata gtt cat cca act cca acc cgg gca gag gtc     1200
Met Leu Glu Ser Met Ile Val His Pro Thr Pro Thr Arg Ala Glu Val
385                 390                 395                 400

tca gac att gct atc gct gtt aga gaa ggt gct gat gcg gta atg ctt     1248
Ser Asp Ile Ala Ile Ala Val Arg Glu Gly Ala Asp Ala Val Met Leu
                405                 410                 415

tca gga gaa act gct cac gga aag ttc cca ttg aaa gct gct gga gtg     1296
Ser Gly Glu Thr Ala His Gly Lys Phe Pro Leu Lys Ala Ala Gly Val
            420                 425                 430

atg cac act gtt gca ttg cga aca gaa gca acc att act agc ggt gaa     1344
Met His Thr Val Ala Leu Arg Thr Glu Ala Thr Ile Thr Ser Gly Glu
        435                 440                 445

atg cca cct aat ctt ggt caa gcc ttc aag aac cat atg agt gag atg     1392
Met Pro Pro Asn Leu Gly Gln Ala Phe Lys Asn His Met Ser Glu Met
    450                 455                 460

ttt gca tac cat gca acc atg atg tca aac aca ctt gga act tca act     1440
Phe Ala Tyr His Ala Thr Met Met Ser Asn Thr Leu Gly Thr Ser Thr
465                 470                 475                 480

gtt gtc ttc acc aga acc ggt ttc atg gcc ata ttg tta agt cac tat     1488
Val Val Phe Thr Arg Thr Gly Phe Met Ala Ile Leu Leu Ser His Tyr
                485                 490                 495
```

```
cgt cct tcc ggc aca atc tat gcc ttc aca aat gag aaa aaa ata caa      1536
Arg Pro Ser Gly Thr Ile Tyr Ala Phe Thr Asn Glu Lys Lys Ile Gln
            500                 505                 510

caa aga tta gct ttg tat caa ggt gta tgc ccc ata tat atg gag ttc      1584
Gln Arg Leu Ala Leu Tyr Gln Gly Val Cys Pro Ile Tyr Met Glu Phe
        515                 520                 525

aca gat gat gca gaa gaa act ttt gct aat gct ttg gct aca tta ctg      1632
Thr Asp Asp Ala Glu Glu Thr Phe Ala Asn Ala Leu Ala Thr Leu Leu
    530                 535                 540

aaa caa gga atg gtg aag aag gga gag gaa ata gca atc gta cag agc      1680
Lys Gln Gly Met Val Lys Lys Gly Glu Glu Ile Ala Ile Val Gln Ser
545                 550                 555                 560

ggt aca cag cca atc tgg cga tct caa tcg aca cat aac atc caa gtc      1728
Gly Thr Gln Pro Ile Trp Arg Ser Gln Ser Thr His Asn Ile Gln Val
                565                 570                 575

cgc aag gtt taa                                                      1740
Arg Lys Val


<210> SEQ ID NO 28
<211> LENGTH: 579
<212> TYPE: PRT
<213> ORGANISM: Arabidopsis thaliana

<400> SEQUENCE: 28

Met Ala Gln Val Val Ala Thr Arg Ser Ile Gln Gly Ser Met Leu Ser
1               5                   10                  15

Pro Asn Gly Gly Ser Val Ser Thr Arg Ser Glu Lys Leu Leu Lys Pro
            20                  25                  30

Ala Ser Phe Ala Val Lys Val Leu Gly Asn Glu Ala Lys Arg Ser Gly
        35                  40                  45

Arg Val Ser Val Arg Ser Arg Arg Val Val Asp Thr Thr Val Arg Ser
    50                  55                  60

Ala Arg Val Glu Thr Glu Val Ile Pro Val Ser Pro Glu Asp Val Pro
65                  70                  75                  80

Asn Arg Glu Glu Gln Leu Glu Arg Leu Leu Glu Met Gln Gln Phe Gly
                85                  90                  95

Asp Thr Ser Val Gly Met Trp Ser Lys Pro Thr Val Arg Arg Lys Thr
            100                 105                 110

Lys Ile Val Cys Thr Val Gly Pro Ser Thr Asn Thr Arg Glu Met Ile
        115                 120                 125

Trp Lys Leu Ala Glu Ala Gly Met Asn Val Ala Arg Met Asn Met Ser
    130                 135                 140

His Gly Asp His Ala Ser His Lys Lys Val Ile Asp Leu Val Lys Glu
145                 150                 155                 160

Tyr Asn Ala Gln Thr Lys Asp Asn Thr Ile Ala Ile Met Leu Asp Thr
                165                 170                 175

Lys Gly Pro Glu Val Arg Ser Gly Asp Leu Pro Gln Pro Ile Met Leu
            180                 185                 190

Asp Pro Gly Gln Glu Phe Thr Phe Thr Ile Glu Arg Gly Val Ser Thr
        195                 200                 205

Pro Ser Cys Val Ser Val Asn Tyr Asp Asp Phe Val Asn Asp Val Glu
    210                 215                 220

Ala Gly Asp Met Leu Leu Val Asp Gly Gly Met Met Ser Phe Met Val
225                 230                 235                 240

Lys Ser Lys Thr Lys Asp Ser Val Lys Cys Glu Val Val Asp Gly Gly
                245                 250                 255
```

-continued

```
Glu Leu Lys Ser Arg Arg His Leu Asn Val Arg Gly Lys Ser Ala Thr
            260                 265                 270

Leu Pro Ser Ile Thr Glu Lys Asp Trp Glu Asp Ile Lys Phe Gly Val
        275                 280                 285

Glu Asn Lys Val Asp Phe Tyr Ala Val Ser Phe Val Lys Asp Ala Gln
    290                 295                 300

Val Val His Glu Leu Lys Lys Tyr Leu Gln Asn Ser Gly Ala Asp Ile
305                 310                 315                 320

His Val Ile Val Lys Ile Glu Ser Ala Asp Ser Ile Pro Asn Leu His
                325                 330                 335

Ser Ile Ile Thr Ala Ser Asp Gly Ala Met Val Ala Arg Gly Asp Leu
            340                 345                 350

Gly Ala Glu Leu Pro Ile Glu Glu Val Pro Ile Leu Gln Glu Glu Ile
        355                 360                 365

Ile Asn Leu Cys Arg Ser Met Gly Lys Ala Val Ile Val Ala Thr Asn
    370                 375                 380

Met Leu Glu Ser Met Ile Val His Pro Thr Pro Thr Arg Ala Glu Val
385                 390                 395                 400

Ser Asp Ile Ala Ile Ala Val Arg Glu Gly Ala Asp Ala Val Met Leu
                405                 410                 415

Ser Gly Glu Thr Ala His Gly Lys Phe Pro Leu Lys Ala Ala Gly Val
            420                 425                 430

Met His Thr Val Ala Leu Arg Thr Glu Ala Thr Ile Thr Ser Gly Glu
        435                 440                 445

Met Pro Pro Asn Leu Gly Gln Ala Phe Lys Asn His Met Ser Glu Met
    450                 455                 460

Phe Ala Tyr His Ala Thr Met Met Ser Asn Thr Leu Gly Thr Ser Thr
465                 470                 475                 480

Val Val Phe Thr Arg Thr Gly Phe Met Ala Ile Leu Leu Ser His Tyr
                485                 490                 495

Arg Pro Ser Gly Thr Ile Tyr Ala Phe Thr Asn Glu Lys Lys Ile Gln
            500                 505                 510

Gln Arg Leu Ala Leu Tyr Gln Gly Val Cys Pro Ile Tyr Met Glu Phe
        515                 520                 525

Thr Asp Asp Ala Glu Glu Thr Phe Ala Asn Ala Leu Ala Thr Leu Leu
    530                 535                 540

Lys Gln Gly Met Val Lys Lys Gly Glu Glu Ile Ala Ile Val Gln Ser
545                 550                 555                 560

Gly Thr Gln Pro Ile Trp Arg Ser Gln Ser Thr His Asn Ile Gln Val
                565                 570                 575

Arg Lys Val
```

<210> SEQ ID NO 29
<211> LENGTH: 2769
<212> TYPE: DNA
<213> ORGANISM: Vicia faba

<400> SEQUENCE: 29

```
gtggaattcg agggggatct gtcgtctcaa actcattcat cagaaccttc ttgaacttag     60

ttatctcttg ttcagagctt cctgttagca atatgtcatc aacatataaa catgtcccag    120

aagccagaag atagaagttg gatgatagaa gtaaagtaat gttactggtg gagtaccaca    180

atacaagttc atacaaactt tattgtccag aaactaacaa agttgagttc agcatagatg    240

aaagacaaaa agaatatatt aaatgacggc tgcaaaataa ggagtaatga atacattgac    300
```

-continued

```
ctacctacta ctaggctatt tatacacaat attagggtat aataaaatat taaaataccc    360
tctatcagac ttagtcaata agacattcct aaaatataaa ttatttccaa caataatttg    420
tctcaaataa aatatagagg tgcaaaagtt aaactaagag tgcaaagtaa aattttgaga    480
gggctcaaaa ttgaatataa taacaatatt agtgtagttt aagaaaactc aggggatgca    540
gttgaactcc ctcaactgta cgtagctcct cccctggatg cagtgtaaag atttgaagat    600
atattttagt actttggata ttgtaggcca gagggtgttg aagataaagg ttcaggaact    660
aacacattca tccacaactt ctatgtgtcc atcgtcagtg aaatacatgc caaatagggg    720
agttaagaag agtagaaagg gtcaagatag tgatgtgcat cgtgatcctt cataatggga    780
gtgtggtgag ggctcgcatg ggagtcatac tacaaagaga tcatgcataa aaccaactag    840
aagtcaactg tcaagtatga cggctgacaa ttaaccgtcc accaaatctt ccagacatgt    900
ttacttgtcc cagttttctg atttcttata tccatacatt gatgacatta ttgatgttgg    960
tggcgatgga gattggggtt ttcatgctat tacagcttta cttggatggg gtgaagagtc   1020
atagcctttg attcagacgc agttagatac tcaagttcat caacaccctc aattgttttt   1080
taagttgttt tgtgacacga tctctacagt tagaaatgcg ttacgagtag aacacttggc   1140
tgtgcagggt atagataaat gaatgacgat ttatgatatg ggttacccta ttgcttctag   1200
atacaatgtc gtatttgtct cccttccaaa agacttaaca tcacgttttt tcctcttgcc   1260
ttatctccac ctatgtatac aagcaggcat aaaatcattg ttgttggttt tgtcaacaac   1320
aatcattgag tttaggtaaa gttgaaactt gattgtccat tacctcttgt cactgactgt   1380
tgaagacaga attgtactga ctgtatatat caacatatgc gagacgcgtt aggcagtgga   1440
aagacgtagt taggatgtca tcataatttg tttcgtattt ttatatgtag cacagttttt   1500
atatgtatat attttatcgg gtagtttttt atcgattcag ttatttgaga aaaagtaatg   1560
cagacaaaaa gtggaaaaga caatctgact gtacataaga aatttccaat ttttgaaatt   1620
tttttataat tatcagaaat tttaaaattt ccgataaaaa catacatgta tagatcgaaa   1680
atttcaaatt tctagtactt tcaaatttct tgcagtaaaa gttgtaattt tttaaaaatt   1740
tacgataatt tacagtattt aaaaaaaaat ccaatcttaa ataaagggta taagaataaa   1800
agcactcatg tggagtggca ggtttcgtca caccctaaga acatccctaa atacaccaca   1860
tatgtataag tattaagtga ttgatgttaa gtgaaacgaa aatatttata tgtgaaattt   1920
aatattcagc ttacttgatt aaactccata gtgacccaat aagtgctaac ttttactgtc   1980
tttaccttta aatgttatat tgatttattt atgcatttct ttttcctgca tctcaatagt   2040
atatagggta tcaaatagtg attatccaaa cttaaataag ttagaggaaa caccaagata   2100
tgccatatac tctcaaattt gacactatga ttcaaagttg cacttgcata aaacttatta   2160
attcaatagt aaaaccaaac ttgtgcgtga tacagttaaa atgactaaac tactaattaa   2220
ggtccctccc attagtaaat aagttatttt tttagaaaaa gaaaataata aaaagaatga   2280
cgagtctatc taaatcatat taacaagtaa tacatattga ttcattcgat ggaggaggcc   2340
aataattgta gtaaacaagc agtgccgagg ttaatatatg ctcaagacag taaataatct   2400
aaatgaatta agacagtgat ttgcaaagag tagatgcaga gaagagaact aaagatttgc   2460
tgctacacgt atataagaat agcaacagat attcattctg tctctttgtg gaatatggat   2520
atctactaat catcatctat ctgtgaagaa taaaagaagc ggccacaagc gcagcgtcgc   2580
acatatgatg tgtatcaaat taggactcca tagccatgca tgctgaagaa tgtcacacac   2640
gttctgtcac acgtgttact ctctcactgt tctcctcttc ctataaatca ccgcgccaca   2700
```

gcttctccac ttcaccactt caccacttca ctcacaatcc ttcattagtt gtttactatc 2760
acagtcaca 2769

<210> SEQ ID NO 30
<211> LENGTH: 1700
<212> TYPE: DNA
<213> ORGANISM: Linum usitatissimum

<400> SEQUENCE: 30
atagtatgct tcagacaaag agctaggaaa gaactcttga tggaggttaa gagaaaaaag 60
tgctagaggg gcatagtaat caaacttgtc aaaaccgtca tcatgatgag ggatgacata 120
atataaaaag ttgactaagg tcttggtagt actctttgat tagtattata tattggtgag 180
aacatgagtc aagaggagac aagaaaccga ggaaccatag tttagcaaca agatggaagt 240
tgcaaagttg agctagccgc tcgattagtt acatctccta agcagtacta caaggaatgg 300
tctctatact ttcatgttta gcacatggta gtgcggattg acaagttaga aacagtgctt 360
aggagacaaa gagtcagtaa aggtattgaa agagtgaagt tgatgctcga caggtcagga 420
gaagtccctc cgccagatgg tgactaccaa ggggttggta tcagctgaga cccaaataag 480
attcttcggt tgaaccagtg gttcgaccga gactcttagg gtgggatttc actgtaagat 540
ttgtgcattt tgttgaatat aaattgacaa tttttttat ttaattatag attatttaga 600
atgaattaca tatttagttt ctaacaagga tagcaatgga tgggtatggg tacaggttaa 660
acatatctat tacccaccca tctagtcgtc gggttttaca cgtacccacc cgtttacata 720
aaccagaccg gaattttaaa ccgtacccgt ccgttagcgg gtttcagatt tacccgttta 780
atcgggtaaa acctgattac taaatatata ttttttattt gataaacaaa acaaaaatgt 840
taatattttc atattggatg caattttaag aaacacatat tcataaattt ccatatttgt 900
aggaaaataa aaagaaaaat atattcaaga acacaaattt caccgacatg actttttatta 960 cagagttgga attagatcta acaattgaaa aattaaaatt aagatagaat atgttgagga 1020
acatgacata gtataatgct gggttacccg tcgggtaggt atcgaggcgg atactactaa 1080
atccatccca ctcgctatcc gataatcact ggtttcgggt atacccattc ccgtcaacag 1140
gcctttttaa ccggataatt tcaacttata gtgaatgaat tttgaataaa tagttagaat 1200
accaaaatcc tggattgcat ttgcaatcaa attttgtgaa ccgttaaatt ttgcatgtac 1260
ttgggataga tataatagaa ccgaattttc attagtttaa tttataactt actttgttca 1320
aagaaaaaaa atatctatcc aatttactta taataaaaaa taatctatcc aagttactta 1380
ttataatcaa cttgtaaaaa ggtaagaata caaatgtggt agcgtacgtg tgattatatg 1440
tgacgaaatg ttatatctaa caaaagtcca aattcccatg gtaaaaaaaa tcaaaatgca 1500
tggcaggctg tttgtaacct tggaataaga tgttggccaa ttctggagcc gccacgtacg 1560
caagactcag ggccacgttc tcttcatgca aggatagtag aacaccactc cacccacctc 1620
ctatattaga cctttgccca accctcccca actttcccat cccatccaca aagaaaccga 1680
catttttatc ataaatcact 1700

<210> SEQ ID NO 31
<211> LENGTH: 674
<212> TYPE: DNA
<213> ORGANISM: Vicia faba

<400> SEQUENCE: 31
caaatttaca cattgccact aaacgtctaa acccttgtaa tttgtttttg ttttactatg 60

```
tgtgttatgt atttgatttg cgataaattt ttatatttgg tactaaattt ataacacctt    120

ttatgctaac gtttgccaac acttagcaat ttgcaagttg attaattgat tctaaattat    180

ttttgtcttc taaatacata tactaatcaa ctggaaatgt aaatatttgc taatatttct    240

actataggag aattaaagtg agtgaatatg gtaccacaag gtttggagat ttaattgttg    300

caatgatgca tggatggcat atacaccaaa cattcaataa ttcttgagga taataatggt    360

accacacaag atttgaggtg catgaacgtc acgtggacaa aaggtttagt aatttttcaa    420

gacaacaatg ttaccacaca caagttttga ggtgcatgca tggatgccct gtggaaagtt    480

taaaaatatt ttggaaatga tttgcatgga agccatgtgt aaaaccatga catccacttg    540

gaggatgcaa taatgaagaa aactacaaat ttacatgcaa ctagttatgc atgtagtcta    600

tataatgagg attttgcaat actttcattc atacacactc actaagtttt acacgattat    660

aatttcttca tagc                                                      674


<210> SEQ ID NO 32
<211> LENGTH: 216
<212> TYPE: DNA
<213> ORGANISM: Cauliflower mosaic virus

<400> SEQUENCE: 32

tcgacaagct cgagtttctc cataataatg tgtgagtagt tcccagataa gggaattagg     60

gttcctatag ggtttcgctc atgtgttgag catataagaa acccttagta tgtatttgta    120

tttgtaaaat acttctatca ataaaatttc taattcctaa aaccaaaatc cagtactaaa    180

atccagatcc cccgaattaa ttcggcgtta attcag                              216


<210> SEQ ID NO 33
<211> LENGTH: 297
<212> TYPE: DNA
<213> ORGANISM: Vicia faba

<400> SEQUENCE: 33

atcctgcaat agaatgttga ggtgaccact ttctgtaata aaataattat aaaataaatt     60

tagaattgct gtagtcaaga acatcagttc taaaatatta ataaagttat ggccttttga    120

catatgtgtt tcgataaaaa aatcaaaata aattgagatt tattcgaaat acaatgaaag    180

tttgcagata tgagatatgt ttctacaaaa taataactta aaactcaact atatgctaat    240

gtttttcttg gtgtgtttca tagaaaattg tatccgtttc ttagaaaatg ctcgtaa       297


<210> SEQ ID NO 34
<211> LENGTH: 194
<212> TYPE: DNA
<213> ORGANISM: Agrobacterium tumefaciens

<400> SEQUENCE: 34

ctgctttaat gagatatgcg agacgcctat gatcgcatga tatttgcttt caattctgtt     60

gtgcacgttg taaaaaacct gagcatgtgt agctcagatc cttaccgccg gtttcggttc    120

attctaatga atatatcacc cgttactatc gtatttttat gaataatatt ctccgttcaa    180

tttactgatt gtcc                                                      194


<210> SEQ ID NO 35
<211> LENGTH: 670
<212> TYPE: DNA
<213> ORGANISM: Pisum sativum

<400> SEQUENCE: 35
```

```
ggatcctcta gctagagctt tcgttcgtat catcggtttc gacaacgttc gtcaagttca     60
atgcatcagt ttcattgcgc acacaccaga atcctactga gtttgagtat tatggcattg    120
ggaaaactgt ttttcttgta ccatttgttg tgcttgtaat ttactgtgtt ttttattcgg    180
ttttcgctat cgaactgtga aatggaaatg gatggagaag agttaatgaa tgatatggtc    240
cttttgttca ttctcaaatt aatattattt gttttttctc ttatttgttg tgtgttgaat    300
ttgaaattat aagagatatg caaacatttt gttttgagta aaaatgtgtc aaatcgtggc    360
ctctaatgac cgaagttaat atgaggagta aaacacttgt agttgtacca ttatgcttat    420
tcactaggca acaaatatat tttcagacct agaaaagctg caaatgttac tgaatacaag    480
tatgtcctct tgtgttttag acatttatga actttccttt atgtaatttt ccagaatcct    540
tgtcagattc taatcattgc tttataatta tagttatact catggatttg tagttgagta    600
tgaaaatatt ttttaatgca ttttatgact tgccaattga ttgacaacat gcatcaatcg    660
accgggtacc                                                           670
```

<210> SEQ ID NO 36
<211> LENGTH: 2046
<212> TYPE: DNA
<213> ORGANISM: Brassica napus

<400> SEQUENCE: 36

```
gctcccactc tcattctttc gcaacttctt ctccgcggaa accaaaatgg ctcaggtcgt     60
tgctacaagg tcgattcaag gctcgatgtt gagtcccaac ggtggatctg tttccacgag    120
atccgacaag cttctgaagc cggcgagttt cgcagtgaag gttcttggca acgaatccaa    180
gaagagcgga agagtgtccg taagaggagg aagaaaggtt gataccactg tgagatccgc    240
tcgtgtggag accgaagtca ttccagtgtc tcccgaggat gttccaaaca gagaggagca    300
actggagcgg tttttggaaa tgcagaagtt tagtgacaca tcggtaggga tgtggtcgaa    360
accgacagtg aggaggaaga ctaagattgt gtgcaccgtt ggtccttcta ccaacacacg    420
agagatgata tggaaactag ctgaagctgg gatgaatgtt gcaaggatga acatgtctca    480
tggggatcat gcttctcata agaaggttat tgatttggtc aaagagtaca atgcgcagtc    540
taaggacaac accattgcta tcatgctgga tactaagggt ccagaagtta ggagtggaga    600
tttaccccag ccgattatgt tagaccctgg tcaagagttt acttttacaa ttgagagagg    660
agtcagcaca ccaagctgtg tcagtgttaa ctatgatgat tttgtcaacg atgtggaggc    720
cggagacatg ctccttgttg atggtggtat gatgtcgttt atggtgaagt ctaagactaa    780
agagactgtc atatgtgagg ttgttgatgg tggagagctt aagtcaagga gacacttgaa    840
tgtccgaggg aaaagtgcaa cattaccgtc aatcactgag aaggattggg aggatattaa    900
gttcggagtg gagaacaaag ttgactttta tgcagtttct tttgtcaaag atgcacaagt    960
ggtacacgaa ctcaagaatt acctcaaagg ttgtggtgct gatattcacg tgatagtaaa   1020
aattgaaagc gcagactcca tacctaactt gaattccatt atcaccgcat cagatggggc   1080
aatggttgca agaggtgatc ttggtgcaga gcttcctatt gaagaagtac ccattcttca   1140
ggagaggatc attaacctat gccgtagcat gggaaaagct gttattgttg caactaacat   1200
gcttgagagt atgatagttc atccgactcc aacccgagcg gaggtttctg atattgctat   1260
agctgttaga gaaggtgctg atgcagtcat gctttcagga gaaactgctc acggaaagtt   1320
cccactgaaa gctgctggag tgatgcatac agtcgcactg cgaacagaag caaccattac   1380
tactagtact gaaatgccac ctaatcttgg tcaagccttc aagaaccata tgagtgagat   1440
```

-continued

```
gtttgcatac catgcaacca tgatgtcaaa cacgcttgga acttcaactg ttgtcttcac   1500

cagaactggt ttcatggcca tacttttaag tcactatcgc ccttctggca ccatctacgc   1560

cttcacgaat gagaaaaaaa tacagcaaag attagccttg tatcaagggg tgtgccccat   1620

atatatggag ttctcagatg atgcagagga cactttcact aaagctttgg ctacactact   1680

gaaacaagga atggtgaaga agggagagga aatagcgatt gtacagagcg ggtcacaacc   1740

aatctggcgg tctcaatcga ctcataacat ccaagtccgc aaggtgtaag gagtctcagt   1800

atctcacctg gtcaatgttt ttctttcatt tatctgtaaa accggtttcg gttaactttc   1860

cttgcacgtc cttgtgtact ctaaaaccta ctgtttactg tatcttattc agtttgtttt   1920

actttggcag acgttgttgt tagctcatta gttgtttgtg agacaaatgt taatttagat   1980

tgagtaataa atgtgtgaga atcctctaat acacagctat gttgttgtaa aaaaaaaaaa   2040

aaaaaa                                                              2046
```

<210> SEQ ID NO 37
<211> LENGTH: 580
<212> TYPE: PRT
<213> ORGANISM: Brassica napus

<400> SEQUENCE: 37

```
Met Ala Gln Val Val Ala Thr Arg Ser Ile Gln Gly Ser Met Leu Ser
1               5                   10                  15

Pro Asn Gly Gly Ser Val Ser Thr Arg Ser Asp Lys Leu Leu Lys Pro
            20                  25                  30

Ala Ser Phe Ala Val Lys Val Leu Gly Asn Glu Ser Lys Lys Ser Gly
        35                  40                  45

Arg Val Ser Val Arg Gly Gly Arg Lys Val Asp Thr Thr Val Arg Ser
    50                  55                  60

Ala Arg Val Glu Thr Glu Val Ile Pro Val Ser Pro Glu Asp Val Pro
65                  70                  75                  80

Asn Arg Glu Glu Gln Leu Glu Arg Phe Leu Glu Met Gln Lys Phe Ser
                85                  90                  95

Asp Thr Ser Val Gly Met Trp Ser Lys Pro Thr Val Arg Arg Lys Thr
            100                 105                 110

Lys Ile Val Cys Thr Val Gly Pro Ser Thr Asn Thr Arg Glu Met Ile
        115                 120                 125

Trp Lys Leu Ala Glu Ala Gly Met Asn Val Ala Arg Met Asn Met Ser
    130                 135                 140

His Gly Asp His Ala Ser His Lys Lys Val Ile Asp Leu Val Lys Glu
145                 150                 155                 160

Tyr Asn Ala Gln Ser Lys Asp Asn Thr Ile Ala Ile Met Leu Asp Thr
                165                 170                 175

Lys Gly Pro Glu Val Arg Ser Gly Asp Leu Pro Gln Pro Ile Met Leu
            180                 185                 190

Asp Pro Gly Gln Glu Phe Thr Phe Thr Ile Glu Arg Gly Val Ser Thr
        195                 200                 205

Pro Ser Cys Val Ser Val Asn Tyr Asp Asp Phe Val Asn Asp Val Glu
    210                 215                 220

Ala Gly Asp Met Leu Leu Val Asp Gly Gly Met Met Ser Phe Met Val
225                 230                 235                 240

Lys Ser Lys Thr Lys Glu Thr Val Ile Cys Glu Val Val Asp Gly Gly
                245                 250                 255

Glu Leu Lys Ser Arg Arg His Leu Asn Val Arg Gly Lys Ser Ala Thr
            260                 265                 270
```

```
Leu Pro Ser Ile Thr Glu Lys Asp Trp Glu Asp Ile Lys Phe Gly Val
        275                 280                 285

Glu Asn Lys Val Asp Phe Tyr Ala Val Ser Phe Val Lys Asp Ala Gln
    290                 295                 300

Val Val His Glu Leu Lys Asn Tyr Leu Lys Gly Cys Gly Ala Asp Ile
305                 310                 315                 320

His Val Ile Val Lys Ile Glu Ser Ala Asp Ser Ile Pro Asn Leu Asn
                325                 330                 335

Ser Ile Ile Thr Ala Ser Asp Gly Ala Met Val Ala Arg Gly Asp Leu
            340                 345                 350

Gly Ala Glu Leu Pro Ile Glu Glu Val Pro Ile Leu Gln Glu Arg Ile
        355                 360                 365

Ile Asn Leu Cys Arg Ser Met Gly Lys Ala Val Ile Val Ala Thr Asn
    370                 375                 380

Met Leu Glu Ser Met Ile Val His Pro Thr Pro Thr Arg Ala Glu Val
385                 390                 395                 400

Ser Asp Ile Ala Ile Ala Val Arg Glu Gly Ala Asp Ala Val Met Leu
                405                 410                 415

Ser Gly Glu Thr Ala His Gly Lys Phe Pro Leu Lys Ala Ala Gly Val
            420                 425                 430

Met His Thr Val Ala Leu Arg Thr Glu Ala Thr Ile Thr Thr Ser Thr
        435                 440                 445

Glu Met Pro Pro Asn Leu Gly Gln Ala Phe Lys Asn His Met Ser Glu
    450                 455                 460

Met Phe Ala Tyr His Ala Thr Met Met Ser Asn Thr Leu Gly Thr Ser
465                 470                 475                 480

Thr Val Val Phe Thr Arg Thr Gly Phe Met Ala Ile Leu Leu Ser His
                485                 490                 495

Tyr Arg Pro Ser Gly Thr Ile Tyr Ala Phe Thr Asn Glu Lys Lys Ile
            500                 505                 510

Gln Gln Arg Leu Ala Leu Tyr Gln Gly Val Cys Pro Ile Tyr Met Glu
        515                 520                 525

Phe Ser Asp Asp Ala Glu Asp Thr Phe Thr Lys Ala Leu Ala Thr Leu
    530                 535                 540

Leu Lys Gln Gly Met Val Lys Lys Gly Glu Glu Ile Ala Ile Val Gln
545                 550                 555                 560

Ser Gly Ser Gln Pro Ile Trp Arg Ser Gln Ser Thr His Asn Ile Gln
                565                 570                 575

Val Arg Lys Val
            580
```

<210> SEQ ID NO 38
<211> LENGTH: 2007
<212> TYPE: DNA
<213> ORGANISM: Brassica napus

<400> SEQUENCE: 38

```
gaagagccta tactaaatct cccggagctc tacttctccg gccgaaacta tgtctcagtc     60

tatccaattc tcaactcctt cacgcactcc tcaccttctc cacctcccta actcacgctt    120

ccaccgtcct ctcacttcct tatccttccg ccaattccct ctcaagtaca cctcaatcag    180

agcctcctcc tctccagatc tcggctcctc ctcatcctcc caggtccttc actctcctaa    240

cggcactggc gctgccaaac cggaagagcg atccgtcgta gccaccgcgg tctccacgga    300

tacggcagcg atagacgtag ataccgtgac ggaagcggag ctgaaggaga atggattcag    360
```

-continued

```
gagcacgagg aggacgaagc tgatctgcac gatcgggcct gccacgtgcg ggttcgagca    420

actggaagcg ctcgcggagg gaggcatgaa cgtggcgagg ctcaacatgt gccacggcac    480

gcgcgagtgg caccgcgatg tgatacgcag cgttaggaag cttaacgagg agaaaggatt    540

cgcggttgct atcatgatgg acactgaagg cagggagatt cacatgggag atctgggcgg    600

tggtgaatct tctgctaaat ctgaggatgg tgaggttggg acattcactg ttagagcctt    660

tgattcttct cgacctgcac gtaccatcag tgtgagctat gatggttttg cggaagatgt    720

aagagttggt gatgagcttc tggttgatgg tggaatggtg agatttgaag tgattgagaa    780

gattggtcct gatgtcaagt gtctatgcac cgaccctggg ttgttgcttc ctcgagctaa    840

cttgactttc tggagagatg ggagtcttgt tcgtgagcgt aacgctatgc ttccaacaat    900

ttcctccaag gactggttgg atattgattt tggaattgct gaaggtgtgg acttcattgc    960

tgtatccttt gtcaagtctg ctgaagtaat taatcatctt aaaagttatc ttgcagctcg   1020

tcccggtgga ggggacatag gagtgattgc aaagatcgag agtatcgatt cactgacaaa   1080

cttggaagaa atcatcctag catcagatgg agccatggtt gcaagaggag acctgggagc   1140

tcagatacct ctcgagcaag ttccagcagc tcagcaaaga atcgtcaaag tctgcagagc   1200

gctgaacaaa cccgtcatcg ttgcttcgca gctactcgag tccatgatcg agtacccaac   1260

tccaaccaga gcagaagtag ccgacgtttc cgaagcagta aggcagagat cagacgcgtt   1320

gatgctctct ggagaatcag ctatgggtca gttcccggac aaggctctca cggttctcag   1380

gagtgtcagt ctaagaatcg aaagatggtg gagggaagag aaacgctacg aggctacacc   1440

acttcaagcc ataagctctg cttcttcaga caaaatctct gaagaaatct gcaactctgc   1500

ttctaaaatg gctaacaatc ttggagtcga cgccgtcttc gtgtacacaa agaacggaca   1560

catggcgtct ctagtctccc gatgccgccc tgactgtccg atctttgctt tcacgaacac   1620

aacctcggtg agaagacgct taaacctaca atggggactg atcccgttcc gtctaagctt   1680

ctcagaggac atggagagca acttgaacaa aacattctct ttactgaaat caagaggtat   1740

gatcaagtcg ggtgacctgg tgatcgctgt ctctgacatg ctgcaatcca tccaggtcat   1800

gaacgttccg tagatttcac tctcttttaa cattgcagac attccccaca gactctttag   1860

tttcctactt ttggtttgat ttatcgtccg acagttgtaa gcttttgtgt attgtgtgta   1920

ctatgtttat ctttttgttt ttttctctgg ctttcaataa atattagtaa tctaaaacta   1980

taatattcgg aaaaaaaaaa aaaaaaa                                       2007


<210> SEQ ID NO 39
<211> LENGTH: 587
<212> TYPE: PRT
<213> ORGANISM: Brassica napus

<400> SEQUENCE: 39

Met Ser Gln Ser Ile Gln Phe Ser Thr Pro Ser Arg Thr Pro His Leu
1               5                   10                  15

Leu His Leu Pro Asn Ser Arg Phe His Arg Pro Leu Thr Ser Leu Ser
            20                  25                  30

Phe Arg Gln Phe Pro Leu Lys Tyr Thr Ser Ile Arg Ala Ser Ser Ser
        35                  40                  45

Pro Asp Leu Gly Ser Ser Ser Ser Ser Gln Val Leu His Ser Pro Asn
    50                  55                  60

Gly Thr Gly Ala Ala Lys Pro Glu Glu Arg Ser Val Val Ala Thr Ala
65                  70                  75                  80
```

-continued

```
Val Ser Thr Asp Thr Ala Ala Ile Asp Val Asp Thr Val Thr Glu Ala
                85                  90                  95

Glu Leu Lys Glu Asn Gly Phe Arg Ser Thr Arg Arg Thr Lys Leu Ile
            100                 105                 110

Cys Thr Ile Gly Pro Ala Thr Cys Gly Phe Glu Gln Leu Glu Ala Leu
        115                 120                 125

Ala Glu Gly Gly Met Asn Val Ala Arg Leu Asn Met Cys His Gly Thr
    130                 135                 140

Arg Glu Trp His Arg Asp Val Ile Arg Ser Val Arg Lys Leu Asn Glu
145                 150                 155                 160

Glu Lys Gly Phe Ala Val Ala Ile Met Met Asp Thr Glu Gly Arg Glu
                165                 170                 175

Ile His Met Gly Asp Leu Gly Gly Gly Glu Ser Ser Ala Lys Ser Glu
            180                 185                 190

Asp Gly Glu Val Gly Thr Phe Thr Val Arg Ala Phe Asp Ser Ser Arg
        195                 200                 205

Pro Ala Arg Thr Ile Ser Val Ser Tyr Asp Gly Phe Ala Glu Asp Val
    210                 215                 220

Arg Val Gly Asp Glu Leu Leu Val Asp Gly Gly Met Val Arg Phe Glu
225                 230                 235                 240

Val Ile Glu Lys Ile Gly Pro Asp Val Lys Cys Leu Cys Thr Asp Pro
                245                 250                 255

Gly Leu Leu Leu Pro Arg Ala Asn Leu Thr Phe Trp Arg Asp Gly Ser
            260                 265                 270

Leu Val Arg Glu Arg Asn Ala Met Leu Pro Thr Ile Ser Ser Lys Asp
        275                 280                 285

Trp Leu Asp Ile Asp Phe Gly Ile Ala Glu Gly Val Asp Phe Ile Ala
    290                 295                 300

Val Ser Phe Val Lys Ser Ala Glu Val Ile Asn His Leu Lys Ser Tyr
305                 310                 315                 320

Leu Ala Ala Arg Pro Gly Gly Gly Asp Ile Gly Val Ile Ala Lys Ile
                325                 330                 335

Glu Ser Ile Asp Ser Leu Thr Asn Leu Glu Glu Ile Ile Leu Ala Ser
            340                 345                 350

Asp Gly Ala Met Val Ala Arg Gly Asp Leu Gly Ala Gln Ile Pro Leu
        355                 360                 365

Glu Gln Val Pro Ala Ala Gln Gln Arg Ile Val Lys Val Cys Arg Ala
    370                 375                 380

Leu Asn Lys Pro Val Ile Val Ala Ser Gln Leu Leu Glu Ser Met Ile
385                 390                 395                 400

Glu Tyr Pro Thr Pro Thr Arg Ala Glu Val Ala Asp Val Ser Glu Ala
                405                 410                 415

Val Arg Gln Arg Ser Asp Ala Leu Met Leu Ser Gly Glu Ser Ala Met
            420                 425                 430

Gly Gln Phe Pro Asp Lys Ala Leu Thr Val Leu Arg Ser Val Ser Leu
        435                 440                 445

Arg Ile Glu Arg Trp Trp Arg Glu Glu Lys Arg Tyr Glu Ala Thr Pro
    450                 455                 460

Leu Gln Ala Ile Ser Ser Ala Ser Ser Asp Lys Ile Ser Glu Glu Ile
465                 470                 475                 480

Cys Asn Ser Ala Ser Lys Met Ala Asn Asn Leu Gly Val Asp Ala Val
                485                 490                 495

Phe Val Tyr Thr Lys Asn Gly His Met Ala Ser Leu Val Ser Arg Cys
            500                 505                 510
```

-continued

```
Arg Pro Asp Cys Pro Ile Phe Ala Phe Thr Asn Thr Thr Ser Val Arg
        515                 520                 525

Arg Arg Leu Asn Leu Gln Trp Gly Leu Ile Pro Phe Arg Leu Ser Phe
    530                 535                 540

Ser Glu Asp Met Glu Ser Asn Leu Asn Lys Thr Phe Ser Leu Leu Lys
545                 550                 555                 560

Ser Arg Gly Met Ile Lys Ser Gly Asp Leu Val Ile Ala Val Ser Asp
                565                 570                 575

Met Leu Gln Ser Ile Gln Val Met Asn Val Pro
            580                 585
```

<210> SEQ ID NO 40
<211> LENGTH: 2024
<212> TYPE: DNA
<213> ORGANISM: Brassica napus

<400> SEQUENCE: 40

```
tcgacgattc cgtatgcccc tctctctctc tctcttaaat atcagtttta acagaaaacc     60

tcattctcat tctctctcct ctgcttgacc tctgttcttc aagttgtacg acatggcggc    120

gacaggtcaa atctcgacga gaatgacggt ggatcgcact ctgtcctcct ccaggaacgc    180

tggactttcc ctttcaccat caccccagag aacgctaatc ggcgtcgccg gtaggtctgg    240

tatcgctcac cgtcaactgt ctctctccgt cagagcgatt aacaccaatg aagatagccg    300

gaaagtcaag gtttatgcag agaacggcgc tttcgatttg ggagtgatgg atccttcagt    360

ggagccatat aaatttgcgg agccaagaac aagtcataat gattcgagga ggaaaaccaa    420

gattgtgtgt accattggac cttcctctag ctctcgtgaa atgatttgga aactcgcgga    480

agcaggaatg aatgtggctc gtttgaatat gtctcatgga gatcatgctt ctcatcagat    540

tactattgat cttgttaaag aatacaactc tctctttgtt gacaaagcca ttgctatcat    600

gttggataca aagggtcctg aggttcgaag tggggatgta cctcagccga tcttccttga    660

agagggtcaa gagtttaatt ttaccatcaa gagaggtgtc tcaatgaaag acaccgtcag    720

tgtcaactat gatgattttg ttaacgatgt cgaagttgga gacatacttt tggtcgatgg    780

tggaatgatg tcactagctg ttaagtccaa gacgagcgat ttggtgaaat gtgtagttat    840

tgacggtgga gagcttcaat ctagacgtca cttgaatgtt cgaggaaaga gtgctactct    900

tccttccata acagacaaag attgggaaga catcaaattt ggagtggaca accaagttga    960

tttctatgct gtctcttttg ttaaggatgc taaagttgtc catgagttga aaaactacct   1020

caaaagctgc agtgcggata tctctgtgat tgtgaaaatt gaaagcgcag attctataaa   1080

gaatcttcct tccattatat ctgcttgtga tggggcaatg gttgctcgtg gagatcttgg   1140

agctgaactt cccattgagg aggttccctt gttacaggag gagataatca caaggtgtag   1200

gaacattcat aaaccagtga ttgtcgccac aaacatgcta gagagtatga ttaatcatcc   1260

aacacctaca agagctgaag tatctgacat tgcaattgca gtgcgcgaag gagcagatgc   1320

aatcatgctt tctggtgaaa ccgcacacgg aaagtttcct ctgaaagctg ttaacgtgat   1380

gcataccgtg gctttgagaa ctgaggctag tctacctgtt agaacctcag caatccggac   1440

cactgcttac aagggtcgca tgggccaaat gtttgctttc catgcttcta taatggcgaa   1500

tacactgaac acaccgatca ttgtgttcac aagaactgga tccatggcag tgcttctgag   1560

tcactaccgc ccgtcctcaa caattttcgc cttcacaaac cagaggagaa taatgcaaag   1620

gctggctctt taccaaggtg tcatgcctat atacatggag ttttctgatg atgcagaaga   1680
```

-continued tacatatgcc cgttccttga aactcctaca ggacgagaat atgcttaagg aaggacaaca 1740
tgtaactctt gtccaaagtg gtgcgcaacc catttggcgt gaagaatcaa cacatctcat 1800
acaagtccgt aagattaaga taggttgatg tttttcacta ctcgagcttc tatatccctg 1860
actttatttt tcttacacga tttgatccaa tattgtttta tgtcactcac agtgaaacca 1920
tatatatttg ttttaagttc ttgaaccaca tgactgtaaa aacaaaacag tcttttcgat 1980
gaaaaagact aatccgaaaa agccttttaa aaaaaaaaaa aaaa 2024

<210> SEQ ID NO 41
<211> LENGTH: 571
<212> TYPE: PRT
<213> ORGANISM: Brassica napus

<400> SEQUENCE: 41

Met Ala Ala Thr Gly Gln Ile Ser Thr Arg Met Thr Val Asp Arg Thr
1 5 10 15

Leu Ser Ser Ser Arg Asn Ala Gly Leu Ser Leu Ser Pro Ser Pro Gln
20 25 30

Arg Thr Leu Ile Gly Val Ala Gly Arg Ser Gly Ile Ala His Arg Gln
35 40 45

Leu Ser Leu Ser Val Arg Ala Ile Asn Thr Asn Glu Asp Ser Arg Lys
50 55 60

Val Lys Val Tyr Ala Glu Asn Gly Ala Phe Asp Leu Gly Val Met Asp
65 70 75 80

Pro Ser Val Glu Pro Tyr Lys Phe Ala Glu Pro Arg Thr Ser His Asn
85 90 95

Asp Ser Arg Arg Lys Thr Lys Ile Val Cys Thr Ile Gly Pro Ser Ser
100 105 110

Ser Ser Arg Glu Met Ile Trp Lys Leu Ala Glu Ala Gly Met Asn Val
115 120 125

Ala Arg Leu Asn Met Ser His Gly Asp His Ala Ser His Gln Ile Thr
130 135 140

Ile Asp Leu Val Lys Glu Tyr Asn Ser Leu Phe Val Asp Lys Ala Ile
145 150 155 160

Ala Ile Met Leu Asp Thr Lys Gly Pro Glu Val Arg Ser Gly Asp Val
165 170 175

Pro Gln Pro Ile Phe Leu Glu Glu Gly Gln Glu Phe Asn Phe Thr Ile
180 185 190

Lys Arg Gly Val Ser Met Lys Asp Thr Val Ser Val Asn Tyr Asp Asp
195 200 205

Phe Val Asn Asp Val Glu Val Gly Asp Ile Leu Leu Val Asp Gly Gly
210 215 220

Met Met Ser Leu Ala Val Lys Ser Lys Thr Ser Asp Leu Val Lys Cys
225 230 235 240

Val Val Ile Asp Gly Gly Glu Leu Gln Ser Arg Arg His Leu Asn Val
245 250 255

Arg Gly Lys Ser Ala Thr Leu Pro Ser Ile Thr Asp Lys Asp Trp Glu
260 265 270

Asp Ile Lys Phe Gly Val Asp Asn Gln Val Asp Phe Tyr Ala Val Ser
275 280 285

Phe Val Lys Asp Ala Lys Val Val His Glu Leu Lys Asn Tyr Leu Lys
290 295 300

Ser Cys Ser Ala Asp Ile Ser Val Ile Val Lys Ile Glu Ser Ala Asp
305 310 315 320

```
Ser Ile Lys Asn Leu Pro Ser Ile Ile Ser Ala Cys Asp Gly Ala Met
                325                 330                 335

Val Ala Arg Gly Asp Leu Gly Ala Glu Leu Pro Ile Glu Glu Val Pro
            340                 345                 350

Leu Leu Gln Glu Glu Ile Ile Thr Arg Cys Arg Asn Ile His Lys Pro
        355                 360                 365

Val Ile Val Ala Thr Asn Met Leu Glu Ser Met Ile Asn His Pro Thr
    370                 375                 380

Pro Thr Arg Ala Glu Val Ser Asp Ile Ala Ile Ala Val Arg Glu Gly
385                 390                 395                 400

Ala Asp Ala Ile Met Leu Ser Gly Glu Thr Ala His Gly Lys Phe Pro
                405                 410                 415

Leu Lys Ala Val Asn Val Met His Thr Val Ala Leu Arg Thr Glu Ala
            420                 425                 430

Ser Leu Pro Val Arg Thr Ser Ala Ile Arg Thr Thr Ala Tyr Lys Gly
        435                 440                 445

Arg Met Gly Gln Met Phe Ala Phe His Ala Ser Ile Met Ala Asn Thr
    450                 455                 460

Leu Asn Thr Pro Ile Ile Val Phe Thr Arg Thr Gly Ser Met Ala Val
465                 470                 475                 480

Leu Leu Ser His Tyr Arg Pro Ser Ser Thr Ile Phe Ala Phe Thr Asn
                485                 490                 495

Gln Arg Arg Ile Met Gln Arg Leu Ala Leu Tyr Gln Gly Val Met Pro
            500                 505                 510

Ile Tyr Met Glu Phe Ser Asp Asp Ala Glu Asp Thr Tyr Ala Arg Ser
        515                 520                 525

Leu Lys Leu Leu Gln Asp Glu Asn Met Leu Lys Glu Gly Gln His Val
    530                 535                 540

Thr Leu Val Gln Ser Gly Ala Gln Pro Ile Trp Arg Glu Glu Ser Thr
545                 550                 555                 560

His Leu Ile Gln Val Arg Lys Ile Lys Ile Gly
                565                 570
```

<210> SEQ ID NO 42
<211> LENGTH: 1965
<212> TYPE: DNA
<213> ORGANISM: Glycine max

<400> SEQUENCE: 42

```
ctgaccacca gaagaatggg acctggttgg ttgaaagtgg agcgaagaaa actaacggag      60

acttgtttgg aagctagtct ctggtgagag tgaaggcgca ccatcttcac cttgaagtca     120

acgatcatgg caaccattaa cctttcttcc gctactacgt ctctcttcca atccaaacac     180

cgaacgaaac gcattccacg cctccctaca atcgccagaa taacaaacca catcgaagga     240

actcatctta actcccccaa cggctctccc atccttggca acgcaaacaa ttcccttgag     300

gttccctcca ataactatat ctcgctacac tcttcagacg tgcgtaggaa aactaagatc     360

gtgtgcacga taggtccttc tacgagctca cgtgatatga tatggaacct ggctcaagct     420

ggaatgaacg tggcgcgttt gaacatgtcg catggggacc acgcctcgca cctccaaacc     480

attgatttgg tgaaagaata caattctcag tttcaagata aggttgtagc catcatgctc     540

gacaccaagg gtcctgaagt tagaagtggg gatgtagctc aacctatttt acttaaagag     600

ggacaagaat tctgtttcac cactatgaga ggggttagca cacatgacac ggttagcgtg     660

aactacgatg gctttgtgaa tgatgtggag ttcggagatg tgttgctggt tgatggagga     720
```

```
atgatgtctc ttgctgttaa gtcaaagaca aaagacttgg ttaaatgtga agttattgat    780

ggtggtgaac tgaaatctag gcgtcattta aatgtccgtg gaaaaagtgc aacacttcct    840

tccataactg acaaggactg ggaagatatc aagtttgggg tggacaatca agtagacttc    900

tttgctgtct catttgtcaa ggatgctaga gtggtgcacg agttaaaaca ctacctcaaa    960

agtcataatg ccgatataca cgtgattgta aaaattgaaa gtgcagattc cataccaaat   1020

ctccattcga tactttctgc ttcagatggg gccatggtcg ctcgtgggga tcttggagct   1080

gaacttccaa tagaggaagt tcctttattg caggaagaca tcattcgaag atgtcaaatt   1140

atgcaaaagc ctgttattgt ggcaacaaat atgcttgaaa gcatgattaa tcatcccaca   1200

ccaacaaggg cagaagtttc agacatcgca attgcagtaa gacaaggtgc tgatgctatc   1260

atgctttcag gagaaactgc acatggaaaa tttccattga aagctgttaa agttatgcac   1320

acggtggctc ttaggaatga atccagtgtt caaagtggtg tttcttatcc gagtcaactg   1380

agttcccatg aaagtcatat gggagaaatg tttgctttcc atgcgacaac aatgtctaac   1440

actcttaata ctcctattat tgttttcacc agaacaggat ccatggcaat tcttttgagc   1500

cattataggc cttactcaac aatctttgca ttcacaaatg aagcaagaat taagcagagg   1560

ttggcgcttt atcatggggt tatgtccata tacatgcaat tttcaaatga tgtagaagag   1620

accttctcta gagccctcaa gctactattg agtaagagtc atttacacga gggacaacat   1680

gtcacacttg ttcaaagtgg agcacaacca atctggcgtg aggaatccac tcaccacata   1740

caagttcgca aggttcatgg ataaaattct atgaaggatc tttgttcctc ataagtgtac   1800

agttttttc cccactatct tgtaactatt catagtaatg gctattcact atcttgtaac    1860

tattcatagt tatgactatt atgcacttga aacaccaaag ttggatagta aaggaatttt   1920

cataatgcaa atagtgattt attgataagg aaaaaaaaaa aaaaa                   1965


<210> SEQ ID NO 43
<211> LENGTH: 545
<212> TYPE: PRT
<213> ORGANISM: Glycine max

<400> SEQUENCE: 43

Met Ala Thr Ile Asn Leu Ser Ser Ala Thr Thr Ser Leu Phe Gln Ser
1               5                   10                  15

Lys His Arg Thr Lys Arg Ile Pro Arg Leu Pro Thr Ile Ala Arg Ile
            20                  25                  30

Thr Asn His Ile Glu Gly Thr His Leu Asn Ser Pro Asn Gly Ser Pro
        35                  40                  45

Ile Leu Gly Asn Ala Asn Asn Ser Leu Glu Val Pro Ser Asn Asn Tyr
    50                  55                  60

Ile Ser Leu His Ser Ser Asp Val Arg Arg Lys Thr Lys Ile Val Cys
65                  70                  75                  80

Thr Ile Gly Pro Ser Thr Ser Ser Arg Asp Met Ile Trp Asn Leu Ala
                85                  90                  95

Gln Ala Gly Met Asn Val Ala Arg Leu Asn Met Ser His Gly Asp His
            100                 105                 110

Ala Ser His Leu Gln Thr Ile Asp Leu Val Lys Glu Tyr Asn Ser Gln
        115                 120                 125

Phe Gln Asp Lys Val Val Ala Ile Met Leu Asp Thr Lys Gly Pro Glu
    130                 135                 140

Val Arg Ser Gly Asp Val Ala Gln Pro Ile Leu Leu Lys Glu Gly Gln
145                 150                 155                 160
```

```
Glu Phe Cys Phe Thr Thr Met Arg Gly Val Ser Thr His Asp Thr Val
                165                 170                 175

Ser Val Asn Tyr Asp Gly Phe Val Asn Asp Val Glu Phe Gly Asp Val
            180                 185                 190

Leu Leu Val Asp Gly Gly Met Met Ser Leu Ala Val Lys Ser Lys Thr
        195                 200                 205

Lys Asp Leu Val Lys Cys Glu Val Ile Asp Gly Gly Glu Leu Lys Ser
    210                 215                 220

Arg Arg His Leu Asn Val Arg Gly Lys Ser Ala Thr Leu Pro Ser Ile
225                 230                 235                 240

Thr Asp Lys Asp Trp Glu Asp Ile Lys Phe Gly Val Asp Asn Gln Val
                245                 250                 255

Asp Phe Phe Ala Val Ser Phe Val Lys Asp Ala Arg Val Val His Glu
            260                 265                 270

Leu Lys His Tyr Leu Lys Ser His Asn Ala Asp Ile His Val Ile Val
        275                 280                 285

Lys Ile Glu Ser Ala Asp Ser Ile Pro Asn Leu His Ser Ile Leu Ser
    290                 295                 300

Ala Ser Asp Gly Ala Met Val Ala Arg Gly Asp Leu Gly Ala Glu Leu
305                 310                 315                 320

Pro Ile Glu Glu Val Pro Leu Leu Gln Glu Asp Ile Ile Arg Arg Cys
                325                 330                 335

Gln Ile Met Gln Lys Pro Val Ile Val Ala Thr Asn Met Leu Glu Ser
            340                 345                 350

Met Ile Asn His Pro Thr Pro Thr Arg Ala Glu Val Ser Asp Ile Ala
        355                 360                 365

Ile Ala Val Arg Gln Gly Ala Asp Ala Ile Met Leu Ser Gly Glu Thr
    370                 375                 380

Ala His Gly Lys Phe Pro Leu Lys Ala Val Lys Val Met His Thr Val
385                 390                 395                 400

Ala Leu Arg Asn Glu Ser Ser Val Gln Ser Gly Val Ser Tyr Pro Ser
                405                 410                 415

Gln Leu Ser Ser His Glu Ser His Met Gly Glu Met Phe Ala Phe His
            420                 425                 430

Ala Thr Thr Met Ser Asn Thr Leu Asn Thr Pro Ile Ile Val Phe Thr
        435                 440                 445

Arg Thr Gly Ser Met Ala Ile Leu Leu Ser His Tyr Arg Pro Tyr Ser
    450                 455                 460

Thr Ile Phe Ala Phe Thr Asn Glu Ala Arg Ile Lys Gln Arg Leu Ala
465                 470                 475                 480

Leu Tyr His Gly Val Met Ser Ile Tyr Met Gln Phe Ser Asn Asp Val
                485                 490                 495

Glu Glu Thr Phe Ser Arg Ala Leu Lys Leu Leu Leu Ser Lys Ser His
            500                 505                 510

Leu His Glu Gly Gln His Val Thr Leu Val Gln Ser Gly Ala Gln Pro
        515                 520                 525

Ile Trp Arg Glu Glu Ser Thr His His Ile Gln Val Arg Lys Val His
    530                 535                 540

Gly
545
```

<210> SEQ ID NO 44
<211> LENGTH: 2300
<212> TYPE: DNA
<213> ORGANISM: Glycine max

<400> SEQUENCE: 44

```
ggccgctgcg tgtcggtctc ctctctcctt tcggtaaact ccccggtata ttccgcagcc      60
aaaatcccaa agtccaaaca ttggcggagt ttacaacaaa acccttcaaa ccccacatcc     120
aaatcgtcgt aaagtttgaa cctttgatac cacatttcga ttcagaccta tattgtttcc     180
agcaacaggc tttcattgac ttctctctgt ggcgatggtt ttgaaatcaa tggttgcttc     240
cgcgagcgat ctaagtctcg tgagtgttgc agggaaccct ccccttgatt tgaagaatcg     300
ggttttcggt agccgcgtca tcagcctcgg atttcgtttc aacaaaggta gtaaatggaa     360
ggggaatgaa aggtttaact ttaaggttcg tgcagctgtg gaagtgggtg tggagagatc     420
gaagagcaag gctttggagg gtggttttgg gttggatgtg gtttcagagg cagagttaac     480
ggtgaagggt tttgcggggt tgaggaagac caagctcgtg tgcactgttg gtcctgcttg     540
cagctctatg gaggatcttg agaacttggc tcttggaggc atgagtgttg ccaggctcaa     600
catgtgccat gggaccaggg agtggcaccg tgatgtgatt aggaagatca agaagttgaa     660
tgaggagaaa gggttctgtg tttctgtaat gattgacact gagggtagtc agattcatgt     720
tgttgatcat ggagctcctt cctccgttaa agttgaggaa ggttcaaatt gggtgtttac     780
tgctgaacat tatgagggtt ctcgtccatt cactgttcaa acgaactata gaggtttttc     840
tgaaggtacc gaagtgggtg atgaacttgt aattgatggt ggaatggcat gctttgaagt     900
cacagaaaag actggtaatg atttgcattg caaatgcata gatgctggtc ttttcctgcc     960
tggagccaaa tttagttttt ggagagatgg aaagcttgtg agggggaata acaagctccc    1020
cactctatcg acaaaggatt gggctgacat tgactttggt atagcagagg gagttgattt    1080
ttttgcctta tcctttgtca atcatgctga ttctgttaag gatctaaaga tgtacctctc    1140
tacgaagtca actaaatcca ttaaagtttt ggcaaagata gaaagcttag aatcccttca    1200
taaactggag gaaatagtgc aagcttctga tgggatcatg gtggctcggg gtgaccttgg    1260
tgtcgaaata ccacttgaac agattcctac agtccaagag gatataattt acgtatgcag    1320
acaattaaac aagccagtga ttgtagcttc tcagcttctt gagtcaatgg tcgagtatcc    1380
aacgccaaca cgtgctgagg tagcagatgt ttctgaagca gttcgacagt atgctgatgc    1440
tttgatgttg tctggagagt cagctattgg atcatatgga cgaaaagctt tggcagtctt    1500
ggatatggct agcagtagaa tggaatcatg gagtcgggag gaaaatagac aaagtcttgt    1560
tagccaccat caacttggag aatcattgcc agaatgcata actgagcaaa tatgcaattg    1620
tgccgttgaa atggccaaca accttggtgt ggatgccatc tttgtgtaca caaagtatgg    1680
acacatggca tcgcttctat cgcgcaaccg cccgaatcct cccatctttg ctttcaccaa    1740
cgatgacagt acccgcatgg ctctgacttt gcaatggggt gttgtgccca ttctggttga    1800
tttgtccgat gatgctgaat ctaacatctc aaagtctgtg caacttatga aatctagagg    1860
gttgatcagc caaggagatg ttgttctagt ggtctcagat gttgctccga cacgtgcctc    1920
tcctatggct ttccagtcta ttcaggtgaa gactattatc taaaacacaa ggttgcaaaa    1980
atattgaaga acacgtgtct gtgtattttc taggcttggg ataggatagt attgtattat    2040
tgtttttttt tcttcggtat tgtattattg gtttcttgtc ctttttttta tatattggtt    2100
tcttgtcctt attcaaaaca acaaaagttt ataaattcta aattgtagaa ctctagcaag    2160
ttttggaacc tctttcaaga gatgcttatg aattacactt tgtgaattgc ccatcgtaag    2220
tcactaatac agttgcacta atatatggca attatatttg gtttcaaaaa aaatataaaa    2280
acactaaaga aaaaaaaaaa                                                2300
```

<210> SEQ ID NO 45
<211> LENGTH: 582
<212> TYPE: PRT
<213> ORGANISM: Glycine max

<400> SEQUENCE: 45

```
Met Val Leu Lys Ser Met Val Ala Ser Ala Ser Asp Leu Ser Leu Val
1               5                   10                  15

Ser Val Ala Gly Asn Pro Pro Leu Asp Leu Lys Asn Arg Val Phe Gly
            20                  25                  30

Ser Arg Val Ile Ser Leu Gly Phe Arg Phe Asn Lys Gly Ser Lys Trp
        35                  40                  45

Lys Gly Asn Glu Arg Phe Asn Phe Lys Val Arg Ala Ala Val Glu Val
    50                  55                  60

Gly Val Glu Arg Ser Lys Ser Lys Ala Leu Glu Gly Gly Phe Gly Leu
65                  70                  75                  80

Asp Val Val Ser Glu Ala Glu Leu Thr Val Lys Gly Phe Ala Gly Leu
                85                  90                  95

Arg Lys Thr Lys Leu Val Cys Thr Val Gly Pro Ala Cys Ser Ser Met
            100                 105                 110

Glu Asp Leu Glu Asn Leu Ala Leu Gly Gly Met Ser Val Ala Arg Leu
        115                 120                 125

Asn Met Cys His Gly Thr Arg Glu Trp His Arg Asp Val Ile Arg Lys
    130                 135                 140

Ile Lys Lys Leu Asn Glu Glu Lys Gly Phe Cys Val Ser Val Met Ile
145                 150                 155                 160

Asp Thr Glu Gly Ser Gln Ile His Val Val Asp His Gly Ala Pro Ser
                165                 170                 175

Ser Val Lys Val Glu Glu Gly Ser Asn Trp Val Phe Thr Ala Glu His
            180                 185                 190

Tyr Glu Gly Ser Arg Pro Phe Thr Val Gln Thr Asn Tyr Arg Gly Phe
        195                 200                 205

Ser Glu Gly Thr Glu Val Gly Asp Glu Leu Val Ile Asp Gly Gly Met
    210                 215                 220

Ala Cys Phe Glu Val Thr Glu Lys Thr Gly Asn Asp Leu His Cys Lys
225                 230                 235                 240

Cys Ile Asp Ala Gly Leu Phe Leu Pro Gly Ala Lys Phe Ser Phe Trp
                245                 250                 255

Arg Asp Gly Lys Leu Val Arg Gly Asn Asn Lys Leu Pro Thr Leu Ser
            260                 265                 270

Thr Lys Asp Trp Ala Asp Ile Asp Phe Gly Ile Ala Glu Gly Val Asp
        275                 280                 285

Phe Phe Ala Leu Ser Phe Val Asn His Ala Asp Ser Val Lys Asp Leu
    290                 295                 300

Lys Met Tyr Leu Ser Thr Lys Ser Thr Lys Ser Ile Lys Val Leu Ala
305                 310                 315                 320

Lys Ile Glu Ser Leu Glu Ser Leu His Lys Leu Glu Glu Ile Val Gln
                325                 330                 335

Ala Ser Asp Gly Ile Met Val Ala Arg Gly Asp Leu Gly Val Glu Ile
            340                 345                 350

Pro Leu Glu Gln Ile Pro Thr Val Gln Glu Asp Ile Ile Tyr Val Cys
        355                 360                 365

Arg Gln Leu Asn Lys Pro Val Ile Val Ala Ser Gln Leu Leu Glu Ser
    370                 375                 380
```

```
Met Val Glu Tyr Pro Thr Pro Thr Arg Ala Glu Val Ala Asp Val Ser
385                 390                 395                 400

Glu Ala Val Arg Gln Tyr Ala Asp Ala Leu Met Leu Ser Gly Glu Ser
                405                 410                 415

Ala Ile Gly Ser Tyr Gly Arg Lys Ala Leu Ala Val Leu Asp Met Ala
            420                 425                 430

Ser Ser Arg Met Glu Ser Trp Ser Arg Glu Glu Asn Arg Gln Ser Leu
        435                 440                 445

Val Ser His His Gln Leu Gly Glu Ser Leu Pro Glu Cys Ile Thr Glu
    450                 455                 460

Gln Ile Cys Asn Cys Ala Val Glu Met Ala Asn Asn Leu Gly Val Asp
465                 470                 475                 480

Ala Ile Phe Val Tyr Thr Lys Tyr Gly His Met Ala Ser Leu Leu Ser
                485                 490                 495

Arg Asn Arg Pro Asn Pro Pro Ile Phe Ala Phe Thr Asn Asp Asp Ser
            500                 505                 510

Thr Arg Met Ala Leu Thr Leu Gln Trp Gly Val Val Pro Ile Leu Val
        515                 520                 525

Asp Leu Ser Asp Asp Ala Glu Ser Asn Ile Ser Lys Ser Val Gln Leu
    530                 535                 540

Met Lys Ser Arg Gly Leu Ile Ser Gln Gly Asp Val Val Leu Val Val
545                 550                 555                 560

Ser Asp Val Ala Pro Thr Arg Ala Ser Pro Met Ala Phe Gln Ser Ile
                565                 570                 575

Gln Val Lys Thr Ile Ile
            580


<210> SEQ ID NO 46
<211> LENGTH: 2232
<212> TYPE: DNA
<213> ORGANISM: Glycine max

<400> SEQUENCE: 46

cgatacaaac taataggtgt cgtgtcttgt gtccctccca ctttatgttt gcctcataac     60

ctgacctttg ccgaacataa cggcgacttc tccaaaacct tcaattccac cttcttcttc    120

gcaccctctt cttcaccctt ttattctcca cgcccaatcc ccttcaactc tacttctctc    180

tctctctctc tctctttcta acaatgtctc aggtagtggc cactcgatcc attcactcct    240

ccctcacgcg ccccacctca ggatctgcac accacagggc ccaaacgttg ttgaagcctc    300

caacttttgc ttccaaattg ttcggagcac aaaggaacaa cccctccaaa gtttgctccc    360

gaagttgcct cgtcaatgcg aggaaatctg cacccgctaa agttgttccc gtgtcacccg    420

aggatgattc aaagattgag gaagagttgc agcacttgcg tggtatgcag caacttggcg    480

acacttctgt tggaatgtgg tcaaaaccca cgtttaggag gaagacaaag gttgtttgca    540

ccattggtcc ttctaccaac accagggaaa tgatttggaa gctggctgag actgggatga    600

atgttgcccg attgaatatg tctcacggag accatgcttc tcatcagaaa attattgatt    660

tggttaaaga atataatgct caatccaagg acaacgtaat tgcaattatg cttgatacca    720

agggtcctga ggttaggagt ggggatttgc cacaaccaat caatttaaca actgggcagg    780

aattcacttt taccatccgg aggggtgttg gaactgcaga ttgtgttagt gtgaactatg    840

acgatttcgt caatgatgtg gatgtgggag acatgcttct tgttgatggt ggtatgatgt    900

ctttggtggt taagtctaag acagaggatt ctgtgaaatg tgaagttgtt gatggaggag    960
```

```
agctcaagtc aaggagacat ttgaatgtta gaggaaaaag tgcaacactg ccttccataa   1020

ctgagaagga ttgggatgac atcaaatttg gagtggataa caaagttgac ttctatgctg   1080

tttcttttgt taaggatgca caagtagttc atgaactgaa gaattatttg aaaagctgtg   1140

atgctgatat acacgtcatt gtaaaaattg aaagtgcaga ctctatacca aacttgcatt   1200

caattattac agcgtctgat ggggccatgg ttgcaagagg agatcttggt gcagaactcc   1260

ctattgaaga ggttccactt ttgcaggaag aaataatcac catatgtcgt agcatgggaa   1320

aggccgttat tgtggcaaca aatatgctgg aaagcatgat tgttcacccg acaccaacca   1380

gagccgaggt atccgatatt gcaattgctg ttcgagaagg ttctgatgca ataatgcttt   1440

ctggggaaac tgctcatgga aagttcccac taaaagccgt gaaagtaatg cacaccgtag   1500

cattacggac agaagccact atacctggtg gtcaaatgcc accaaatatt ggtcaagtat   1560

tcaagaacca catgagtgag atgtttgctt accatgcaac catgatgtct aataccccttg  1620

gaacctcaac tgttgtcttc actagatcag gcttcatggc tatccttttg agccactatc   1680

gaccttcagg caccatattt gcttttacag atcaaaagag gatacaacag aggttggctt   1740

tgtatcaagg agtctgtcct atttacatgg aattctctga agatgctgaa gagactttca   1800

caagggcctt ggatttgctg cagaagcaag gaatggtgaa atcaggagaa gaagtagcac   1860

tagtacaaag tggcacgcaa cccatatgga ggttccaatc cactcacaat atccaggtcc   1920

gaacagtgta aacaaaataa aaaggtgaag atggctatga attaagtttc agtctttcag   1980

gacactacat tttaatttag aagagcatgt tcccttttgg tgggttgatg ccaatttgat   2040

aagtccagta gcattttagt tgtttgtttg ttgcctaggt tttttttttt cttcatttat   2100

tactttcttg ttatcattat ttttttggtg attgttctat atttatcacg gacattagac   2160

atatgatagt gtcattgaaa ttttgattag aaattgcaat gaaaaatgct ttcagccaaa   2220

aaaaaaaaaa aa                                                       2232
```

<210> SEQ ID NO 47
<211> LENGTH: 575
<212> TYPE: PRT
<213> ORGANISM: Glycine max

<400> SEQUENCE: 47

```
Met Ser Gln Val Val Ala Thr Arg Ser Ile His Ser Ser Leu Thr Arg
1               5                   10                  15

Pro Thr Ser Gly Ser Ala His His Arg Ala Gln Thr Leu Leu Lys Pro
            20                  25                  30

Pro Thr Phe Ala Ser Lys Leu Phe Gly Ala Gln Arg Asn Asn Pro Ser
        35                  40                  45

Lys Val Cys Ser Arg Ser Cys Leu Val Asn Ala Arg Lys Ser Ala Pro
    50                  55                  60

Ala Lys Val Val Pro Val Ser Pro Glu Asp Asp Ser Lys Ile Glu Glu
65                  70                  75                  80

Glu Leu Gln His Leu Arg Gly Met Gln Gln Leu Gly Asp Thr Ser Val
                85                  90                  95

Gly Met Trp Ser Lys Pro Thr Phe Arg Arg Lys Thr Lys Val Val Cys
            100                 105                 110

Thr Ile Gly Pro Ser Thr Asn Thr Arg Glu Met Ile Trp Lys Leu Ala
        115                 120                 125

Glu Thr Gly Met Asn Val Ala Arg Leu Asn Met Ser His Gly Asp His
    130                 135                 140

Ala Ser His Gln Lys Ile Ile Asp Leu Val Lys Glu Tyr Asn Ala Gln
```

-continued

```
145                 150                 155                 160

Ser Lys Asp Asn Val Ile Ala Ile Met Leu Asp Thr Lys Gly Pro Glu
                165                 170                 175

Val Arg Ser Gly Asp Leu Pro Gln Pro Ile Asn Leu Thr Thr Gly Gln
            180                 185                 190

Glu Phe Thr Phe Thr Ile Arg Arg Gly Val Gly Thr Ala Asp Cys Val
        195                 200                 205

Ser Val Asn Tyr Asp Asp Phe Val Asn Asp Val Asp Val Gly Asp Met
    210                 215                 220

Leu Leu Val Asp Gly Gly Met Met Ser Leu Val Val Lys Ser Lys Thr
225                 230                 235                 240

Glu Asp Ser Val Lys Cys Glu Val Val Asp Gly Gly Glu Leu Lys Ser
                245                 250                 255

Arg Arg His Leu Asn Val Arg Gly Lys Ser Ala Thr Leu Pro Ser Ile
            260                 265                 270

Thr Glu Lys Asp Trp Asp Asp Ile Lys Phe Gly Val Asp Asn Lys Val
        275                 280                 285

Asp Phe Tyr Ala Val Ser Phe Val Lys Asp Ala Gln Val Val His Glu
    290                 295                 300

Leu Lys Asn Tyr Leu Lys Ser Cys Asp Ala Asp Ile His Val Ile Val
305                 310                 315                 320

Lys Ile Glu Ser Ala Asp Ser Ile Pro Asn Leu His Ser Ile Ile Thr
                325                 330                 335

Ala Ser Asp Gly Ala Met Val Ala Arg Gly Asp Leu Gly Ala Glu Leu
            340                 345                 350

Pro Ile Glu Glu Val Pro Leu Leu Gln Glu Glu Ile Ile Thr Ile Cys
        355                 360                 365

Arg Ser Met Gly Lys Ala Val Ile Val Ala Thr Asn Met Leu Glu Ser
    370                 375                 380

Met Ile Val His Pro Thr Pro Thr Arg Ala Glu Val Ser Asp Ile Ala
385                 390                 395                 400

Ile Ala Val Arg Glu Gly Ser Asp Ala Ile Met Leu Ser Gly Glu Thr
                405                 410                 415

Ala His Gly Lys Phe Pro Leu Lys Ala Val Lys Val Met His Thr Val
            420                 425                 430

Ala Leu Arg Thr Glu Ala Thr Ile Pro Gly Gly Gln Met Pro Pro Asn
        435                 440                 445

Ile Gly Gln Val Phe Lys Asn His Met Ser Glu Met Phe Ala Tyr His
    450                 455                 460

Ala Thr Met Met Ser Asn Thr Leu Gly Thr Ser Thr Val Val Phe Thr
465                 470                 475                 480

Arg Ser Gly Phe Met Ala Ile Leu Leu Ser His Tyr Arg Pro Ser Gly
                485                 490                 495

Thr Ile Phe Ala Phe Thr Asp Gln Lys Arg Ile Gln Gln Arg Leu Ala
            500                 505                 510

Leu Tyr Gln Gly Val Cys Pro Ile Tyr Met Glu Phe Ser Glu Asp Ala
        515                 520                 525

Glu Glu Thr Phe Thr Arg Ala Leu Asp Leu Leu Gln Lys Gln Gly Met
    530                 535                 540

Val Lys Ser Gly Glu Glu Val Ala Leu Val Gln Ser Gly Thr Gln Pro
545                 550                 555                 560

Ile Trp Arg Phe Gln Ser Thr His Asn Ile Gln Val Arg Thr Val
                565                 570                 575
```

<210> SEQ ID NO 48
<211> LENGTH: 2030
<212> TYPE: DNA
<213> ORGANISM: Oryza sativa

<400> SEQUENCE: 48
aacaccaagg gagagaagag agagaagaga agagacgaga aaccctcgcc tccacacgcg 60
ccctctccct ccaatggcgg cggcggcggc tgagatcgtg gggtccgcgg cggcgcgcat 120
ggcggcgccg gcagtgaggc cggctccgcc cgcggcggcg gcggcggcgg cgcccccgca 180
gccgaggagg gccgtggcgg cgcgctccct caggacctcc acctccgaca gggtggcggc 240
ggatctcgcg ctcgggagca acggctccct ctccgctcag aacattgctg agaataccgc 300
tgacgctact tcgcaagtgg tctctgcgaa ttcccgtagg aagacaaaga ttgtttgcac 360
cataggcccc tcaaccaaca cacgcgagat gatatggaaa cttgctgaga ctggaatgaa 420
cgtcgcacgc atgaatatgt cccatggtga ccaccagtcg caccagaagg tgattgattt 480
ggtgaaggag tacaatgcga agaatactga tggcaatgtc attgctatta tgctggatac 540
caagggtcca gaagtgagaa gtggggatgt tccagaacca atcatgctcg aggaaggtca 600
agagttcaat tttactatta aaagaggggt gagcaccaaa gacaccgtca gtgtgaatta 660
cgatgacttc ataaacgatg ttgaagttgg ggacatactg ttggtggatg gaggaatgat 720
gtcactcgct gtcaagtcta aaacagctga tacggttaag tgtgaagtag ttgatggtgg 780
ggaactgaaa tcaaggcgcc acctaaatgt ccgtggaaag agtgcgactt tgccatctat 840
tacagagaaa gattgggagg acataaagtt tggtgttgaa aatggtgttg atttctatgc 900
cgtttccttt gtgaaggatg caaaagttat tcatgaactg aaggactacc ttaaaagtgc 960
taatgcagat atacatgtca ttccaaagat tgaaagtgca gattcaatac caaacctcca 1020
gtccattatt gctgcttcag atggggcgat ggtggcaaga ggggatcttg gtgctgaact 1080
tccaattgag gaagttcctt tgctgcagga ggagattgtc agaacatgcc gaagcatgca 1140
gaaaccagtt attgttgcca cgaatatgtt agagagcatg atagaccatc ccactccaac 1200
aagagcagaa gtttctgata tagcaattgc agttcgtgaa ggttctgatg ccatcatgct 1260
gtctggtgaa actgcccatg gaaagttccc actgaaggca gtcaaggtga tgcacacagt 1320
ggcacagaga acagaatcca gcctgtataa cccaactaca tctcctagtc ttgttgcaca 1380
tcctcaggct ctgctcaacg aggaattttc gcaaagccaa ctaagcaaaa tgtttggatc 1440
tcatgctaca atgatggcca acaccctttg caccccaatt attgtgttta cacgaaccgg 1500
ctccatggca gtccttctca gccactaccg gccctcgtct acaatttttg catttacaaa 1560
tgaggaacga gtgaagcaac gtctggcact ctaccagggt gtggttccca tttacatgaa 1620
gttttctgat gatgcagagg aaactttctc tagagcaatt agtagcttgc tgaacgccca 1680
attcgtgaaa gaaggggact acgtgaccct tgttcagagt ggagtgaagt cgatctggag 1740
agaggagtct actcaccaca ttcaagtgag gaaagtccag ggctaatgag cctgaccgtc 1800
ataccgtcac agggatgtac ctgttcaaat tttgtttgtt acttgatgtg ctaaattacg 1860
agtaactttt acggggaaca agtttggatt attatatgtt atgttgattt tacttgtagg 1920
ctctggaatt gaataagata atctatatta attttcacat ggttccaatt ggactgaaca 1980
aaaaaaaaaa aaaaaaaaaa aaaaaaaaaa aaaaaaaaaa aaaaaaaaaa 2030

<210> SEQ ID NO 49
<211> LENGTH: 570
<212> TYPE: PRT

<213> ORGANISM: Oryza sativa

<400> SEQUENCE: 49

Met Ala Ala Ala Ala Ala Glu Ile Val Gly Ser Ala Ala Ala Arg Met
1 5 10 15

Ala Ala Pro Ala Val Arg Pro Ala Pro Pro Ala Ala Ala Ala Ala Ala
20 25 30

Ala Pro Pro Gln Pro Arg Arg Ala Val Ala Ala Arg Ser Leu Arg Thr
35 40 45

Ser Thr Ser Asp Arg Val Ala Ala Asp Leu Ala Leu Gly Ser Asn Gly
50 55 60

Ser Leu Ser Ala Gln Asn Ile Ala Glu Asn Thr Ala Asp Ala Thr Ser
65 70 75 80

Gln Val Val Ser Ala Asn Ser Arg Arg Lys Thr Lys Ile Val Cys Thr
85 90 95

Ile Gly Pro Ser Thr Asn Thr Arg Glu Met Ile Trp Lys Leu Ala Glu
100 105 110

Thr Gly Met Asn Val Ala Arg Met Asn Met Ser His Gly Asp His Gln
115 120 125

Ser His Gln Lys Val Ile Asp Leu Val Lys Glu Tyr Asn Ala Lys Asn
130 135 140

Thr Asp Gly Asn Val Ile Ala Ile Met Leu Asp Thr Lys Gly Pro Glu
145 150 155 160

Val Arg Ser Gly Asp Val Pro Glu Pro Ile Met Leu Glu Glu Gly Gln
165 170 175

Glu Phe Asn Phe Thr Ile Lys Arg Gly Val Ser Thr Lys Asp Thr Val
180 185 190

Ser Val Asn Tyr Asp Asp Phe Ile Asn Asp Val Glu Val Gly Asp Ile
195 200 205

Leu Leu Val Asp Gly Gly Met Met Ser Leu Ala Val Lys Ser Lys Thr
210 215 220

Ala Asp Thr Val Lys Cys Glu Val Val Asp Gly Gly Glu Leu Lys Ser
225 230 235 240

Arg Arg His Leu Asn Val Arg Gly Lys Ser Ala Thr Leu Pro Ser Ile
245 250 255

Thr Glu Lys Asp Trp Glu Asp Ile Lys Phe Gly Val Glu Asn Gly Val
260 265 270

Asp Phe Tyr Ala Val Ser Phe Val Lys Asp Ala Lys Val Ile His Glu
275 280 285

Leu Lys Asp Tyr Leu Lys Ser Ala Asn Ala Asp Ile His Val Ile Pro
290 295 300

Lys Ile Glu Ser Ala Asp Ser Ile Pro Asn Leu Gln Ser Ile Ile Ala
305 310 315 320

Ala Ser Asp Gly Ala Met Val Ala Arg Gly Asp Leu Gly Ala Glu Leu
325 330 335

Pro Ile Glu Glu Val Pro Leu Leu Gln Glu Glu Ile Val Arg Thr Cys
340 345 350

Arg Ser Met Gln Lys Pro Val Ile Val Ala Thr Asn Met Leu Glu Ser
355 360 365

Met Ile Asp His Pro Thr Pro Thr Arg Ala Glu Val Ser Asp Ile Ala
370 375 380

Ile Ala Val Arg Glu Gly Ser Asp Ala Ile Met Leu Ser Gly Glu Thr
385 390 395 400

Ala His Gly Lys Phe Pro Leu Lys Ala Val Lys Val Met His Thr Val

-continued

```
                405                 410                 415

Ala Gln Arg Thr Glu Ser Ser Leu Tyr Asn Pro Thr Thr Ser Pro Ser
            420                 425                 430

Leu Val Ala His Pro Gln Ala Leu Leu Asn Glu Glu Phe Ser Gln Ser
        435                 440                 445

Gln Leu Ser Lys Met Phe Gly Ser His Ala Thr Met Met Ala Asn Thr
    450                 455                 460

Leu Cys Thr Pro Ile Ile Val Phe Thr Arg Thr Gly Ser Met Ala Val
465                 470                 475                 480

Leu Leu Ser His Tyr Arg Pro Ser Ser Thr Ile Phe Ala Phe Thr Asn
                485                 490                 495

Glu Glu Arg Val Lys Gln Arg Leu Ala Leu Tyr Gln Gly Val Val Pro
            500                 505                 510

Ile Tyr Met Lys Phe Ser Asp Asp Ala Glu Glu Thr Phe Ser Arg Ala
        515                 520                 525

Ile Ser Ser Leu Leu Asn Ala Gln Phe Val Lys Glu Gly Asp Tyr Val
    530                 535                 540

Thr Leu Val Gln Ser Gly Val Lys Ser Ile Trp Arg Glu Glu Ser Thr
545                 550                 555                 560

His His Ile Gln Val Arg Lys Val Gln Gly
                565                 570


<210> SEQ ID NO 50
<211> LENGTH: 2201
<212> TYPE: DNA
<213> ORGANISM: Triticum aestivum
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (2179)..(2179)
<223> OTHER INFORMATION: n is a, c, g, or t
<220> FEATURE:
<221> NAME/KEY: misc_feature
<222> LOCATION: (2186)..(2186)
<223> OTHER INFORMATION: n is a, c, g, or t

<400> SEQUENCE: 50

gtcgggacgg cccgtgcgat agaggcctat ctagngtggc tagattgaac aagtttgtac      60

aaaaaagcag gctggtaccg ctccggaatt ccctgggata tcgtcgaccc acgcgtccgc     120

cgtctctagc gcgaaccgcg gggcgtcctc cgaacaatgg cggcggcggc ggcggagatg     180

gtgcgcgggt tcgccgcgac ggcgcgcgcg gccaggccgg ccgcgacggt ggcggcgccc     240

ccgcagccca ggcgggcggt cgccgcgcgg gtgctgcgga cctccgcctc cgagaaggtg     300

gcggcggatc tctccgtcgc cgggaccaac ggctccctct ccgccctgag caatactgat     360

gtcagtactg acgccacctc acaagcagtg gatgcgactc ccaggaggaa gacaaagata     420

gtctgcacca taggcccctc gaccaacact cgtgagatga tatggaagct tgcagagact     480

ggaatgaatg ttgcgcgtat gaatatgtcc catggagacc accagtcaca ccaaaaagtg     540

attgatttgg tcaaggagta caacgcacag aacactgatg gcaatactgt tgctattatg     600

ctggacacaa agggtccgga agtgcgaagt ggggatcttc ctgagccaat catgcttgcg     660

gaaggtcaag agttcaattt cacgattaaa agaggggtga gcaccgaaga cactgtcagc     720

gtgaattatg atgacttcat aagcgatgtt gaagctggtg acatactgtt ggtggatgga     780

ggaatgatgt cgcttgctgt gaagtcgaaa acagctgaca cagtcaagtg tgtagtagtc     840
```

-continued

```
gatggtgggg agttgaaatc aaggcgccac cttaatgtgc gcggaaagag cgcaactctg    900

ccatctataa cagagaagga ttgggaagat atcaagtttg gcgtcgaaaa tggtgttgat    960

ttctatgctg tttcgtttgt gaaggatgcc aaagttattc atgaactcaa ggcttacctg   1020

aaaagtgcta atgcggatat acatgttatt ccaaaaattg agagtgctga ttcaatccca   1080

aacctccagt ccattattgc tgcttcagat ggggcaatgg tggctcgtgg agatcttggt   1140

gctgaacttc caattgagga agttccttta ctacaggagg agattatcag aacatgccga   1200

agcatgcaga aaccagtaat tgttgcaaca aatatgttag aaagcatgat agatcatcca   1260

actccaacaa gggctgaagt ctctgatata gccattgctg ttcgggaggc tgctgatgcc   1320

attatgctat ctggtgaaac tgcccatggg aagtacccat tgaaggcagt gaaggtgatg   1380

cacactgtgg cacttagaac agaatccagc ctgtacgacc caactaaagc tcccagtctt   1440

gttgcacgcc caaaggcgct gctcaatgat gacttctgca aaagccaatt aagtaaaatg   1500

tttggatctc atgctacaat gatggcgaac acccttcgta caccgatcat tgtgtttaca   1560

cgtgtgggct ccatggctgt ccttctgagc cactaccgtc cctcgtccac catatatgca   1620

ttcactaatg aagtacgagt gaagcaacga ctggcactct atcagggcgt ggttcctatt   1680

ctcatggagt tctcagatga cgcggaagag actttctcaa gagcaattac cagcttgctg   1740

gatgcgaaat acatgaatga aggggactat gtcaccctcg ttcagagcgg gtcgcagtcg   1800

atctggagag aagaatctac ccaccacata caagtgagga aagtccagtg ctgatgcaga   1860

acatgctgaa gcacgccggt ctcccccctt atcacgaaag aaaagttttg atggcgcatc   1920

caagcgtgtt actattctac tgtgtcttgt tatgactaca tccgagtaat tcttttatgg   1980

agaacattgc tatgtcggag ctgtagctca tgctgaattt acttgtaaac actgaaatct   2040

ttaatgcaat attcattctt attggcctaa aaaaaaaaaa aaaagggcgg ccgctctaga   2100

gtatccctcg aggggcccaa gcttacgcgt acccagcttt cttgtacaaa gtgtccctaa   2160

tactagctcg tatggaagnt acctancgca cggcgtgttc a                       2201
```

<210> SEQ ID NO 51
<211> LENGTH: 565
<212> TYPE: PRT
<213> ORGANISM: Triticum aestivum

<400> SEQUENCE: 51

```
Met Ala Ala Ala Ala Ala Glu Met Val Arg Gly Phe Ala Ala Thr Ala
1               5                   10                  15

Arg Ala Ala Arg Pro Ala Ala Thr Val Ala Ala Pro Pro Gln Pro Arg
            20                  25                  30

Arg Ala Val Ala Ala Arg Val Leu Arg Thr Ser Ala Ser Glu Lys Val
        35                  40                  45

Ala Ala Asp Leu Ser Val Ala Gly Thr Asn Gly Ser Leu Ser Ala Leu
    50                  55                  60

Ser Asn Thr Asp Val Ser Thr Asp Ala Thr Ser Gln Ala Val Asp Ala
65                  70                  75                  80

Thr Pro Arg Arg Lys Thr Lys Ile Val Cys Thr Ile Gly Pro Ser Thr
                85                  90                  95

Asn Thr Arg Glu Met Ile Trp Lys Leu Ala Glu Thr Gly Met Asn Val
            100                 105                 110

Ala Arg Met Asn Met Ser His Gly Asp His Gln Ser His Gln Lys Val
        115                 120                 125

Ile Asp Leu Val Lys Glu Tyr Asn Ala Gln Asn Thr Asp Gly Asn Thr
    130                 135                 140
```

-continued

```
Val Ala Ile Met Leu Asp Thr Lys Gly Pro Glu Val Arg Ser Gly Asp
145                 150                 155                 160

Leu Pro Glu Pro Ile Met Leu Ala Glu Gly Gln Glu Phe Asn Phe Thr
                165                 170                 175

Ile Lys Arg Gly Val Ser Thr Glu Asp Thr Val Ser Val Asn Tyr Asp
            180                 185                 190

Asp Phe Ile Ser Asp Val Glu Ala Gly Asp Ile Leu Leu Val Asp Gly
        195                 200                 205

Gly Met Met Ser Leu Ala Val Lys Ser Lys Thr Ala Asp Thr Val Lys
    210                 215                 220

Cys Val Val Val Asp Gly Gly Glu Leu Lys Ser Arg Arg His Leu Asn
225                 230                 235                 240

Val Arg Gly Lys Ser Ala Thr Leu Pro Ser Ile Thr Glu Lys Asp Trp
                245                 250                 255

Glu Asp Ile Lys Phe Gly Val Glu Asn Gly Val Asp Phe Tyr Ala Val
            260                 265                 270

Ser Phe Val Lys Asp Ala Lys Val Ile His Glu Leu Lys Ala Tyr Leu
        275                 280                 285

Lys Ser Ala Asn Ala Asp Ile His Val Ile Pro Lys Ile Glu Ser Ala
    290                 295                 300

Asp Ser Ile Pro Asn Leu Gln Ser Ile Ile Ala Ala Ser Asp Gly Ala
305                 310                 315                 320

Met Val Ala Arg Gly Asp Leu Gly Ala Glu Leu Pro Ile Glu Glu Val
                325                 330                 335

Pro Leu Leu Gln Glu Glu Ile Ile Arg Thr Cys Arg Ser Met Gln Lys
            340                 345                 350

Pro Val Ile Val Ala Thr Asn Met Leu Glu Ser Met Ile Asp His Pro
        355                 360                 365

Thr Pro Thr Arg Ala Glu Val Ser Asp Ile Ala Ile Ala Val Arg Glu
    370                 375                 380

Ala Ala Asp Ala Ile Met Leu Ser Gly Glu Thr Ala His Gly Lys Tyr
385                 390                 395                 400

Pro Leu Lys Ala Val Lys Val Met His Thr Val Ala Leu Arg Thr Glu
                405                 410                 415

Ser Ser Leu Tyr Asp Pro Thr Lys Ala Pro Ser Leu Val Ala Arg Pro
            420                 425                 430

Lys Ala Leu Leu Asn Asp Asp Phe Cys Lys Ser Gln Leu Ser Lys Met
        435                 440                 445

Phe Gly Ser His Ala Thr Met Met Ala Asn Thr Leu Arg Thr Pro Ile
    450                 455                 460

Ile Val Phe Thr Arg Val Gly Ser Met Ala Val Leu Leu Ser His Tyr
465                 470                 475                 480

Arg Pro Ser Ser Thr Ile Tyr Ala Phe Thr Asn Glu Val Arg Val Lys
                485                 490                 495

Gln Arg Leu Ala Leu Tyr Gln Gly Val Val Pro Ile Leu Met Glu Phe
            500                 505                 510

Ser Asp Asp Ala Glu Glu Thr Phe Ser Arg Ala Ile Thr Ser Leu Leu
        515                 520                 525

Asp Ala Lys Tyr Met Asn Glu Gly Asp Tyr Val Thr Leu Val Gln Ser
    530                 535                 540

Gly Ser Gln Ser Ile Trp Arg Glu Glu Ser Thr His His Ile Gln Val
545                 550                 555                 560

Arg Lys Val Gln Cys
```

565

<210> SEQ ID NO 52
<211> LENGTH: 2177
<212> TYPE: DNA
<213> ORGANISM: Zea mays

<400> SEQUENCE: 52
cattgggtac ctcgaggccg gccgggatgt atatcctgcg agctgccgtc ctcggccgtg 60
gggcagctca actactcgca caacacaact gcacaaaagc acaagcctcc ctcccggctc 120
cccacctcgc agcgtccgcc ggcacaccac ctctgactcc tctccctccg cggcctccgt 180
ttcttccctc attctccgca aaccctaatc ccaatggctg cctccgccag gactaccagc 240
tcgttgccct acctagtcgc cgtctcctcc cccgcggctc accgccacgg ggccagccac 300
ccgatccgcg cctcggtggg ggaggcgaca atggacgtgg tgtcggaggc ggagctgcgg 360
gagaaagggt tcttggggat gcggaaaacg aaactggtgt gcacggtggg gcccgcctgc 420
gtcgaggcgc tgccggcgct ggcgcgcggc gggatgggcg tggcgcggat caacctctgc 480
cacggtggcc gggagtggca tcgtgccgcc atgcgctctg tgcggaggct caacgaggag 540
ggaggattct gcgtgacgct tatggtcgac accgagggtt cccagctcct cgtcgcggac 600
cacggaggcg ccacctcagt caaggccgag gatgggtcag agtggatatt tacaaacaaa 660
aaagctgatg aagcccatca gttcacaatg catgtgaatt ttgataagtt ttctgaaggc 720
attttggttg gtgatgagct tgtaatagat ggtggaatgg caacatttga agttactgag 780
aaaataggaa atgatttgcg ctgtaagtgc acggacccag gtttgcttct tcctcgagcc 840
aaattgtcat tctggaggaa cggaaaaata gttcaaagga actttggcct tcctacattg 900
tcaacaaagg attgggctga catcgaattt gggatagctg aaggagttga ttgcattgct 960
ctatcatttg taaatgatgc taatgatata aagcagttga aagcttacct ctctagaaga 1020
tcgttagagc acatcaaagt atttgcaaag attgagagtc tagaatctct caagaacctg 1080
aaagacatca tagaggcatc tgatggagtt atggtagcac gaggggatct tggagttcag 1140
attcctcttg aacagatccc agccattcaa gaatcaattg ttaaactatg tagacacctg 1200
aacaagcctg tgatagttgc ttctcagctt ctcgaatcaa tggttgaata cccaacacca 1260
actcgagcag aggtggccga tgtttcggaa gcagtgcggc aatatgcaga cgctgtgatg 1320
ctatcagcag agtcagctat aggtgcatat ccccaaaaag cgctatctgt acttcgtgca 1380
gccagtgaaa ggatggaatc atggagccgt gaggaaaaca tgcagaaact tcttccacgg 1440
catcagcttg caattgcatt gcctgaccgg atctcagagc agatttgcag ctgtgctgta 1500
gaaatggcaa acaaccttgc tgtggatgcc atatttgtct acacaaagca tggtcacatg 1560
gcatcacttc tatcgcgcaa ccgacccaac cctcccatat tcgcgttcac tgataatgcc 1620
aattcaagaa agagcatgaa cctctactgg ggagtgattc cacttcatct accattgtca 1680
aatagcatgg aggataactt caacaaaacc atcagcctga tgaggtcgaa gggttcagtg 1740
aaacccggag acacggtctt ggtggtatca gattctgatc taaaccaacc ttgtgctgcc 1800
acctcggtgt tccaatccat tcaggtccgg ctagtggagt aggttccatg agatgagatc 1860
ctactagccg tttggttggc taaaatgtaa cgtaaccaac tactactatg cgttaccatt 1920
gcaaaccatt cccaccgtct ataattagat cctatttcca tctccaaata aagattgaac 1980
cactgcgatt acagtggtgt ctgatttcaa aaaaaaaaaa aacgggtccc cgttcattga 2040
atcaaacccc gtctagtttc agtactgggt tgctgcaaat gtccccgttg acccaaaccc 2100
gaattaaagc cacctgtttc tatattcttt gaaagttgga ggcaaataaa attgctagga 2160
attctgttct ttttgtt 2177

<210> SEQ ID NO 53
<211> LENGTH: 542
<212> TYPE: PRT
<213> ORGANISM: Zea mays

<400> SEQUENCE: 53

Met Ala Ala Ser Ala Arg Thr Thr Ser Ser Leu Pro Tyr Leu Val Ala
1 5 10 15

Val Ser Ser Pro Ala Ala His Arg His Gly Ala Ser His Pro Ile Arg
20 25 30

Ala Ser Val Gly Glu Ala Thr Met Asp Val Val Ser Glu Ala Glu Leu
35 40 45

Arg Glu Lys Gly Phe Leu Gly Met Arg Lys Thr Lys Leu Val Cys Thr
50 55 60

Val Gly Pro Ala Cys Val Glu Ala Leu Pro Ala Leu Ala Arg Gly Gly
65 70 75 80

Met Gly Val Ala Arg Ile Asn Leu Cys His Gly Gly Arg Glu Trp His
85 90 95

Arg Ala Ala Met Arg Ser Val Arg Arg Leu Asn Glu Glu Gly Gly Phe
100 105 110

Cys Val Thr Leu Met Val Asp Thr Glu Gly Ser Gln Leu Leu Val Ala
115 120 125

Asp His Gly Gly Ala Thr Ser Val Lys Ala Glu Asp Gly Ser Glu Trp
130 135 140

Ile Phe Thr Asn Lys Lys Ala Asp Glu Ala His Gln Phe Thr Met His
145 150 155 160

Val Asn Phe Asp Lys Phe Ser Glu Gly Ile Leu Val Gly Asp Glu Leu
165 170 175

Val Ile Asp Gly Gly Met Ala Thr Phe Glu Val Thr Glu Lys Ile Gly
180 185 190

Asn Asp Leu Arg Cys Lys Cys Thr Asp Pro Gly Leu Leu Leu Pro Arg
195 200 205

Ala Lys Leu Ser Phe Trp Arg Asn Gly Lys Ile Val Gln Arg Asn Phe
210 215 220

Gly Leu Pro Thr Leu Ser Thr Lys Asp Trp Ala Asp Ile Glu Phe Gly
225 230 235 240

Ile Ala Glu Gly Val Asp Cys Ile Ala Leu Ser Phe Val Asn Asp Ala
245 250 255

Asn Asp Ile Lys Gln Leu Lys Ala Tyr Leu Ser Arg Arg Ser Leu Glu
260 265 270

His Ile Lys Val Phe Ala Lys Ile Glu Ser Leu Glu Ser Leu Lys Asn
275 280 285

Leu Lys Asp Ile Ile Glu Ala Ser Asp Gly Val Met Val Ala Arg Gly
290 295 300

Asp Leu Gly Val Gln Ile Pro Leu Glu Gln Ile Pro Ala Ile Gln Glu
305 310 315 320

Ser Ile Val Lys Leu Cys Arg His Leu Asn Lys Pro Val Ile Val Ala
325 330 335

Ser Gln Leu Leu Glu Ser Met Val Glu Tyr Pro Thr Pro Thr Arg Ala
340 345 350

Glu Val Ala Asp Val Ser Glu Ala Val Arg Gln Tyr Ala Asp Ala Val
355 360 365

```
Met Leu Ser Ala Glu Ser Ala Ile Gly Ala Tyr Pro Gln Lys Ala Leu
    370                 375                 380

Ser Val Leu Arg Ala Ala Ser Glu Arg Met Glu Ser Trp Ser Arg Glu
385                 390                 395                 400

Glu Asn Met Gln Lys Leu Leu Pro Arg His Gln Leu Ala Ile Ala Leu
                405                 410                 415

Pro Asp Arg Ile Ser Glu Gln Ile Cys Ser Cys Ala Val Glu Met Ala
            420                 425                 430

Asn Asn Leu Ala Val Asp Ala Ile Phe Val Tyr Thr Lys His Gly His
        435                 440                 445

Met Ala Ser Leu Leu Ser Arg Asn Arg Pro Asn Pro Pro Ile Phe Ala
    450                 455                 460

Phe Thr Asp Asn Ala Asn Ser Arg Lys Ser Met Asn Leu Tyr Trp Gly
465                 470                 475                 480

Val Ile Pro Leu His Leu Pro Leu Ser Asn Ser Met Glu Asp Asn Phe
                485                 490                 495

Asn Lys Thr Ile Ser Leu Met Arg Ser Lys Gly Ser Val Lys Pro Gly
            500                 505                 510

Asp Thr Val Leu Val Val Ser Asp Ser Asp Leu Asn Gln Pro Cys Ala
        515                 520                 525

Ala Thr Ser Val Phe Gln Ser Ile Gln Val Arg Leu Val Glu
    530                 535                 540


<210> SEQ ID NO 54
<211> LENGTH: 2197
<212> TYPE: DNA
<213> ORGANISM: Zea mays

<400> SEQUENCE: 54

cgaaaaccct cgcggcgagg agcgctctcc gtcccacaca cgcgcgccgc agcctccgca      60

gtccgcacct gcctccacga cttgtcgtgc tcgtgcgcta ctctcctcga gcgcggcgcg     120

gagcacgggg acatcaaatg gcggcagcgg cggagatcgg tggtttcgcg gcggcgagag     180

tggcggtggc gacgctcagg ccggctgcgc acccagcccc ggcggcggca ccgcagcagc     240

ctaggagggc ggtggcggcg cagtcgctgc ggacgaccgc caccgaggcg ctgacggcgg     300

atctcgccgg cacgaccaac ggcgctgtgc atgctcggat gaatagtaag gctacaagtg     360

aaatcacttc acaggcagtt actgcaaatt ctaggagaaa gacaaagata gtctgcacca     420

taggtccctc aaccaacact cgtgagatga tttggaagct tgcagagact ggaatgaatg     480

tagcacgcct taatatgtcc catggtgacc accagtcgca ccagaaggtt attgatttgg     540

tcaaggagta caatgcacag aacactgatg gcaatgttat tgccattatg ctggacacaa     600

agggtcctga agttagaagt ggggatgttc cagagccaat catgctcaag gaaggtcaag     660

agttcaactt cacgattaaa agaggggtga gcactgaaga cactgtcagc gtgaactatg     720

atgacttcat aaatgatgtt gaagctggcg acatactatt agtggatgga ggaatgatgt     780

cgcttgctgt gaagtctaaa acaaccgata cagtcaagtg taaagtagtt gatggtgggg     840

aattgaaatc acggcgccac ctaaatgtcc gtggaaagag tgctactttg ccatctatca     900

ctgagaagga ttgggaagac ataaaatttg gtgtcgaaaa cggtgttgat ttctatgcag     960

tttcctttgt gaaggatgcc aaagttatcc atgaattaaa agactacctt aaaagtgcta    1020

atgccgatat acatgtcatt ccaaaaattg aaagtgcaga ttcaatacca aacctgcagt    1080

ccattattgc tgcttcagat ggggcaatgg tggcgcgtgg agaccttggt gctgaacttc    1140
```

```
cgattgagga tgttcctttg ctacaggcag agattgtcca aacatgtcga agtatggaga   1200

aaccagtcat tgtcgctaca aatatgttgg aaagcatgat tgaccatcct actcccacta   1260

gggcagaagt ttctgacata gctattgcag ttcgggaagg tgctgatgcc atcatgttat   1320

ctggcgaaac tgctcatgga aagtatccac taaaggcagt caaggtgatg cacactgtgg   1380

cactcagaac agaatccagc ctttataacc caactacttc tcctagtctt gttgcatctg   1440

cacagggtct acagaatgag gacttctccc caagccagct aagtaaaatg ttcggatctc   1500

atgcaacgat gatggccaac acccttcgca caccaatcat tgtatttaca cagacaggct   1560

ccatggctgt cctcctgagc cattatcgtc cctcgtctac actatttgca tttacaaacg   1620

aggaacgagt gaagcaacgg ctagcactct accagggcgt catccctatt cacatgcagt   1680

tctctgacga cgcagaagaa actttctcca gagcaattag cagcttgctg aaagcacaat   1740

atgtgaagaa gggagactac gtcactcttg ttcagagcgg agtgacttca atctggagag   1800

aggaatccac tcaccacatc caagtgagga aagttcaggt ctgatgtgcc ggtgggaatt   1860

ggtcgtctga gaaattttga tagcgccgcc tgatgtgtta tcatcattat atgtgtaatt   1920

ttactgtttt accaggagat tgctacgtcg agttatatgt tgtgtcgaat tcacgtgtag   1980

gctctgaatc ttgactgtgt ccgttcattt tcgcttgttt cacactgaag tgttataagc   2040

tcaactttac tgcttttgtt ttcttgtgaa acttgagttt agtttcttgt tacaaaagga   2100

gctagcacta acagggtggt gagttttgta aaaacggggc gaggactgtt gagttaaaac   2160

tgttgtaata atgatatcgt tcctgcaaaa aaaaaaa                            2197
```

<210> SEQ ID NO 55
<211> LENGTH: 568
<212> TYPE: PRT
<213> ORGANISM: Zea mays

<400> SEQUENCE: 55

```
Met Ala Ala Ala Ala Glu Ile Gly Gly Phe Ala Ala Ala Arg Val Ala
1               5                   10                  15

Val Ala Thr Leu Arg Pro Ala Ala His Pro Ala Pro Ala Ala Ala Pro
            20                  25                  30

Gln Gln Pro Arg Arg Ala Val Ala Ala Gln Ser Leu Arg Thr Thr Ala
        35                  40                  45

Thr Glu Ala Leu Thr Ala Asp Leu Ala Gly Thr Thr Asn Gly Ala Val
    50                  55                  60

His Ala Arg Met Asn Ser Lys Ala Thr Ser Glu Ile Thr Ser Gln Ala
65                  70                  75                  80

Val Thr Ala Asn Ser Arg Arg Lys Thr Lys Ile Val Cys Thr Ile Gly
                85                  90                  95

Pro Ser Thr Asn Thr Arg Glu Met Ile Trp Lys Leu Ala Glu Thr Gly
            100                 105                 110

Met Asn Val Ala Arg Leu Asn Met Ser His Gly Asp His Gln Ser His
        115                 120                 125

Gln Lys Val Ile Asp Leu Val Lys Glu Tyr Asn Ala Gln Asn Thr Asp
    130                 135                 140

Gly Asn Val Ile Ala Ile Met Leu Asp Thr Lys Gly Pro Glu Val Arg
145                 150                 155                 160

Ser Gly Asp Val Pro Glu Pro Ile Met Leu Lys Glu Gly Gln Glu Phe
                165                 170                 175

Asn Phe Thr Ile Lys Arg Gly Val Ser Thr Glu Asp Thr Val Ser Val
            180                 185                 190
```

-continued

```
Asn Tyr Asp Asp Phe Ile Asn Asp Val Glu Ala Gly Asp Ile Leu Leu
        195                 200                 205

Val Asp Gly Gly Met Met Ser Leu Ala Val Lys Ser Lys Thr Thr Asp
    210                 215                 220

Thr Val Lys Cys Lys Val Val Asp Gly Gly Glu Leu Lys Ser Arg Arg
225                 230                 235                 240

His Leu Asn Val Arg Gly Lys Ser Ala Thr Leu Pro Ser Ile Thr Glu
                245                 250                 255

Lys Asp Trp Glu Asp Ile Lys Phe Gly Val Glu Asn Gly Val Asp Phe
            260                 265                 270

Tyr Ala Val Ser Phe Val Lys Asp Ala Lys Val Ile His Glu Leu Lys
        275                 280                 285

Asp Tyr Leu Lys Ser Ala Asn Ala Asp Ile His Val Ile Pro Lys Ile
    290                 295                 300

Glu Ser Ala Asp Ser Ile Pro Asn Leu Gln Ser Ile Ile Ala Ala Ser
305                 310                 315                 320

Asp Gly Ala Met Val Ala Arg Gly Asp Leu Gly Ala Glu Leu Pro Ile
                325                 330                 335

Glu Asp Val Pro Leu Leu Gln Ala Glu Ile Val Gln Thr Cys Arg Ser
            340                 345                 350

Met Glu Lys Pro Val Ile Val Ala Thr Asn Met Leu Glu Ser Met Ile
        355                 360                 365

Asp His Pro Thr Pro Thr Arg Ala Glu Val Ser Asp Ile Ala Ile Ala
    370                 375                 380

Val Arg Glu Gly Ala Asp Ala Ile Met Leu Ser Gly Glu Thr Ala His
385                 390                 395                 400

Gly Lys Tyr Pro Leu Lys Ala Val Lys Val Met His Thr Val Ala Leu
                405                 410                 415

Arg Thr Glu Ser Ser Leu Tyr Asn Pro Thr Thr Ser Pro Ser Leu Val
            420                 425                 430

Ala Ser Ala Gln Gly Leu Gln Asn Glu Asp Phe Ser Pro Ser Gln Leu
        435                 440                 445

Ser Lys Met Phe Gly Ser His Ala Thr Met Met Ala Asn Thr Leu Arg
    450                 455                 460

Thr Pro Ile Ile Val Phe Thr Gln Thr Gly Ser Met Ala Val Leu Leu
465                 470                 475                 480

Ser His Tyr Arg Pro Ser Ser Thr Leu Phe Ala Phe Thr Asn Glu Glu
                485                 490                 495

Arg Val Lys Gln Arg Leu Ala Leu Tyr Gln Gly Val Ile Pro Ile His
            500                 505                 510

Met Gln Phe Ser Asp Asp Ala Glu Glu Thr Phe Ser Arg Ala Ile Ser
        515                 520                 525

Ser Leu Leu Lys Ala Gln Tyr Val Lys Lys Gly Asp Tyr Val Thr Leu
    530                 535                 540

Val Gln Ser Gly Val Thr Ser Ile Trp Arg Glu Glu Ser Thr His His
545                 550                 555                 560

Ile Gln Val Arg Lys Val Gln Val
                565
```

<210> SEQ ID NO 56
<211> LENGTH: 2179
<212> TYPE: DNA
<213> ORGANISM: Zea mays

<400> SEQUENCE: 56

-continued

```
caaaaccaaa aagttctcac acgctgacgc caccgcaccg catctccctc ccattccact      60

ccagtccacc accgctccca ttccccagcc gccgtcgcca tggccagcgc cgcccactcc     120

cttctgcaca caccggaggc ccacagggcc gccacccgct cgcccttctc tcctcccgcg     180

cccactccct tcctccatct ccgccctcac cgcctccccc tccgcctccg ctccacctcc     240

ccgaccgcct ccgacctcac cgccttcccc ccgaacccga acgggatctt tgcgtccgac     300

cggcccatcg acgtggacgc cgccacggag gccgagctgc gggagaacgg gttccggagc     360

acgcgccgca ccaagctcgt ctgcaccgtg ggccccgcca cctcgcgccc ggaccagctc     420

gaggcgctcg ccgtcggcgg gatgaacgtg gcccggctca acatgtgcca cggcgacagg     480

gagtggcata gggccgccat ccgcgccgtc aggagcctca acgaggagaa gggcttcgcc     540

gtcgccgtca tgatggacac cgagggcagc gagatccaca tgggggacct cggcggcgca     600

tcctcggtca aggcggagga tggagaagta tggacgttca gtgttagatc atttgaattg     660

cctctcccag aacgaactat taatgtgaac tatgatggat ttgctgaaga tgtgagagtt     720

ggtgatgagc tccttgtgga tggtggaatg gctcggtttg aggtgattga gaagatagga     780

ccagatgtta agtgccgttg cacagatcct ggtttattgt tgccacgtgc caatcttaca     840

ttctggcgtg acggcagtat cgtccgtgag aggaatgcta tgcttcctac aatttcatca     900

aaggattggc ttgacataga ctttgggatt gccgaaggtg tagatttcat cgctgtttca     960

tttgtcaagt ctgcagaagt aattaggcac ttgaaaagct acatagctgc aaggagccgt    1020

ggaagtgaca tggcagtcat tgcgaaaatc gagagcatcg actctctaaa gaacctggag    1080

gagatcatcc gagcgtcaga cggcgccatg gtagccagag ggacatgggg ggcgcaggtt    1140

cccctggagc aggtcccctc gatacagcaa aagatcgttc agctctgcag gcagctgaac    1200

aagccggtca tcgtcgcctc ccagctcctc gagtcgatga tagagtaccc cacgcccacc    1260

agggccgagg tcgcggacgt ctccgaagcc gtccgccagc gcgccgacgc cctgatgctt    1320

tccggcgagt cggcaatggg gaggtacccg gacaaggccc tcagcgttct gaggagcgtc    1380

agcctgagga tcgagaagtg gtggagggag gagaagcggc acgaggcgct ggagctccgg    1440

agcgtctcgt cctccttctc cgacaagata tcggaggaga tctgcaactc agcagctaaa    1500

atggctaatg gcctgggagt ggacgccgtc tttgtgttca ccaagaccgg gcacatggcc    1560

tccctgctct cgcggtgccg ccccgactgc ccggtcttcg ccttcacgac gtcgacgtcc    1620

gtcaggaggc ggctgaacct gcagtggggc ctgatcccct tccgcctcgc cttctcggac    1680

gacatggaga gcaacctgaa ccgcaccttc tccctgctca aggccagggg catgatccag    1740

tctggggacc tcgtgatcgc cctctcggac atgctgcagt ccatccaggt gatgaacgta    1800

ccctgaggta gaagagcctt acctttacct ccatgccgca cggtcccgta tcggaaggaa    1860

cacgcgtgtt atcggcacct tggaaggacg gtttcttcct tccctgcgcc taaatcgctg    1920

ccctttgttt tcgctgtatc agatgctgct atgctatgct aggctctagt ctggcccagg    1980

gaactgtggc aataatctgt ggctttcagg ctggtgttag aactcttgta ctacttgtag    2040

gcttaggtga tttttatcgt gcaagtagtt ggtttgatgt ttttgtgtgg tataaaagcg    2100

actcaagcta tgggcctagg cctctttggt atacctttt tttctgaaga gtttttttag    2160

agaatctgga ttcgttgat                                                 2179
```

<210> SEQ ID NO 57
<211> LENGTH: 568
<212> TYPE: PRT
<213> ORGANISM: Zea mays

-continued

<400> SEQUENCE: 57

Met Ala Ser Ala Ala His Ser Leu Leu His Thr Pro Glu Ala His Arg
1 5 10 15

Ala Ala Thr Arg Ser Pro Phe Ser Pro Pro Ala Pro Thr Pro Phe Leu
20 25 30

His Leu Arg Pro His Arg Leu Pro Leu Arg Leu Arg Ser Thr Ser Pro
35 40 45

Thr Ala Ser Asp Leu Thr Ala Phe Pro Pro Asn Pro Asn Gly Ile Phe
50 55 60

Ala Ser Asp Arg Pro Ile Asp Val Asp Ala Ala Thr Glu Ala Glu Leu
65 70 75 80

Arg Glu Asn Gly Phe Arg Ser Thr Arg Arg Thr Lys Leu Val Cys Thr
85 90 95

Val Gly Pro Ala Thr Ser Arg Pro Asp Gln Leu Glu Ala Leu Ala Val
100 105 110

Gly Gly Met Asn Val Ala Arg Leu Asn Met Cys His Gly Asp Arg Glu
115 120 125

Trp His Arg Ala Ala Ile Arg Ala Val Arg Ser Leu Asn Glu Glu Lys
130 135 140

Gly Phe Ala Val Ala Val Met Met Asp Thr Glu Gly Ser Glu Ile His
145 150 155 160

Met Gly Asp Leu Gly Gly Ala Ser Ser Val Lys Ala Glu Asp Gly Glu
165 170 175

Val Trp Thr Phe Ser Val Arg Ser Phe Glu Leu Pro Leu Pro Glu Arg
180 185 190

Thr Ile Asn Val Asn Tyr Asp Gly Phe Ala Glu Asp Val Arg Val Gly
195 200 205

Asp Glu Leu Leu Val Asp Gly Gly Met Ala Arg Phe Glu Val Ile Glu
210 215 220

Lys Ile Gly Pro Asp Val Lys Cys Arg Cys Thr Asp Pro Gly Leu Leu
225 230 235 240

Leu Pro Arg Ala Asn Leu Thr Phe Trp Arg Asp Gly Ser Ile Val Arg
245 250 255

Glu Arg Asn Ala Met Leu Pro Thr Ile Ser Ser Lys Asp Trp Leu Asp
260 265 270

Ile Asp Phe Gly Ile Ala Glu Gly Val Asp Phe Ile Ala Val Ser Phe
275 280 285

Val Lys Ser Ala Glu Val Ile Arg His Leu Lys Ser Tyr Ile Ala Ala
290 295 300

Arg Ser Arg Gly Ser Asp Met Ala Val Ile Ala Lys Ile Glu Ser Ile
305 310 315 320

Asp Ser Leu Lys Asn Leu Glu Glu Ile Ile Arg Ala Ser Asp Gly Ala
325 330 335

Met Val Ala Arg Gly Asp Met Gly Ala Gln Val Pro Leu Glu Gln Val
340 345 350

Pro Ser Ile Gln Gln Lys Ile Val Gln Leu Cys Arg Gln Leu Asn Lys
355 360 365

Pro Val Ile Val Ala Ser Gln Leu Leu Glu Ser Met Ile Glu Tyr Pro
370 375 380

Thr Pro Thr Arg Ala Glu Val Ala Asp Val Ser Glu Ala Val Arg Gln
385 390 395 400

Arg Ala Asp Ala Leu Met Leu Ser Gly Glu Ser Ala Met Gly Arg Tyr
405 410 415

```
Pro Asp Lys Ala Leu Ser Val Leu Arg Ser Val Ser Leu Arg Ile Glu
            420                 425                 430

Lys Trp Trp Arg Glu Glu Lys Arg His Glu Ala Leu Glu Leu Arg Ser
        435                 440                 445

Val Ser Ser Ser Phe Ser Asp Lys Ile Ser Glu Glu Ile Cys Asn Ser
    450                 455                 460

Ala Ala Lys Met Ala Asn Gly Leu Gly Val Asp Ala Val Phe Val Phe
465                 470                 475                 480

Thr Lys Thr Gly His Met Ala Ser Leu Leu Ser Arg Cys Arg Pro Asp
                485                 490                 495

Cys Pro Val Phe Ala Phe Thr Thr Ser Thr Ser Val Arg Arg Arg Leu
            500                 505                 510

Asn Leu Gln Trp Gly Leu Ile Pro Phe Arg Leu Ala Phe Ser Asp Asp
        515                 520                 525

Met Glu Ser Asn Leu Asn Arg Thr Phe Ser Leu Leu Lys Ala Arg Gly
    530                 535                 540

Met Ile Gln Ser Gly Asp Leu Val Ile Ala Leu Ser Asp Met Leu Gln
545                 550                 555                 560

Ser Ile Gln Val Met Asn Val Pro
                565
```

<210> SEQ ID NO 58
<211> LENGTH: 2183
<212> TYPE: DNA
<213> ORGANISM: Zea mays

<400> SEQUENCE: 58

```
cggcatcggg cacgccgcac gccacgcctc accgagtcac cttcccagcc agctaccctt     60

ccccctacca attccaaatc tctcacccgg cttgaggatg gcggcgcagg tggtcgcagc    120

ggcgggcacc ccggtggcca ggccgctggg cggtggatct ggggccgacg cgctccggcc    180

cgcggcgagg atgccaaggg agagaaggac cggtgctgtg gccgcgagag gacgccgcga    240

gtctcaggtg gtatccgtca taagccgcgc cccacgcccc gatgccgggg tgctgccggt    300

gtcgcccgac gacgacgcgg ccgtaaagga agaagcaaac ttccagcacc ttaaggctat    360

ccagcaactt gcaactgcag caaatggcgt gtggtctaaa ccaaatgtaa ggcgcaagac    420

aaagattgtg tgtacaatcg gtccttcaac caacacaagg gacatgatat ggaaactcgc    480

tgagactggc atgaatgtgg ctcggcttaa tatgtcacat ggagaccatg catcacacca    540

gaaagttatt gatctggtaa aggagtacaa tgcatcacat gctgacaatg tgattgctat    600

catgcttgac acaaagggac cagaagttcg aagtggagat ttgcctcaac cgatatttct    660

ggaaagcgga caagaattta cttttacaat caaaagggga gttgggactg atacgtgtgt    720

tagcgttaac tatgacgact ttgttaatga tgttgaagtg ggcgacatgc tccttgtaga    780

tggaggaatg atgtcattct tggtcaaatc aaaaactgaa gattctgtga aatgtgaagt    840

tattgacggt ggtgaattga aatctaggcg ccatctgaat gttcgtggaa agagtgcaac    900

cttgccatca ataactgaca aggactggga cgacattaag tttggtgtgg ataatcaagt    960

tgattactat gctgtttctt ttgtgaagga tgctcaagtt gtccacgaac tcaaggatta   1020

tctaaaaagt tgcaatgctg acatacatgt tatcgtaaaa atagaaagtg cagactccat   1080

ccccaactta cattcaatca tcacagcatc tgatggggct atggttgcca ggggtgacct   1140

tggagctgag ctgcccattg aggaggtgcc gctgttgcag gaagaaatta ttagaatgtg   1200

caggagcatg ggaaggctgg ttattgttgc tacaaatatg ctcgaaagta tgattgttca   1260
```

tccaactcca acccgagcag aagtttcaga cattgctata gctgtccgag agggtgctga 1320
tgcagttatg ctttcaggag aaactgcaca tgggaaattt cccttgaaag ctgttaaggt 1380
catgcacact gttgccctga gaaccgaggc aactattcct ggtggggaaa cacctgcaga 1440
ccttggtcag gctttcaaga accacatgag cgaaatgttc gcataccatg caacaatgat 1500
gtcaaatacc cttcgaacat caatagtggt tttcactagg acgggattta tggctatact 1560
gcttagtcac taccgtccat ctggcactat ttttgccttt acagatgagg agagggttag 1620
gcaacgattg gctttgtacc aaggtgtatg tccggttcaa atggaatttt ctgatgatgc 1680
tgagaagaca tttggcaatg ctttgtctta tttgctgaaa catggtatgg ttaaggacgg 1740
tgaggaggtt gcgctcgttc aaagtggtaa acatcccatc tggagatcac aatcaacaca 1800
caacattcag gtgaggaaga tctgatgcgg aacgcacata gtattctgat tgttggagga 1860
catcgtttct tctagcaaac cgcaaggtct tgttacaatg ataccacact ggtagtaagt 1920
actggtattg gtgagatagt tggtgctgag ctagtgttgt gattcttttt cttacttgtg 1980
cactagtgct gttttccttc cgtgtaaaaa ggccaatcca attgccgctt ggttttagct 2040
gtagctttgg gaactgtagg cttgttgtaa tacagttcgt tctgtcaatg ttaaggactt 2100
ttgcctcgag agctaggcat aactcgaagc tcaccaaaca gcaatctacc tgcaaattgc 2160
aacgcatttt gcgtctttac ttc 2183

<210> SEQ ID NO 59
<211> LENGTH: 575
<212> TYPE: PRT
<213> ORGANISM: Zea mays

<400> SEQUENCE: 59

Met Ala Ala Gln Val Val Ala Ala Ala Gly Thr Pro Val Ala Arg Pro
1 5 10 15

Leu Gly Gly Gly Ser Gly Ala Asp Ala Leu Arg Pro Ala Ala Arg Met
20 25 30

Pro Arg Glu Arg Arg Thr Gly Ala Val Ala Ala Arg Gly Arg Arg Glu
35 40 45

Ser Gln Val Val Ser Val Ile Ser Arg Ala Pro Arg Pro Asp Ala Gly
50 55 60

Val Leu Pro Val Ser Pro Asp Asp Asp Ala Ala Val Lys Glu Glu Ala
65 70 75 80

Asn Phe Gln His Leu Lys Ala Ile Gln Gln Leu Ala Thr Ala Ala Asn
85 90 95

Gly Val Trp Ser Lys Pro Asn Val Arg Arg Lys Thr Lys Ile Val Cys
100 105 110

Thr Ile Gly Pro Ser Thr Asn Thr Arg Asp Met Ile Trp Lys Leu Ala
115 120 125

Glu Thr Gly Met Asn Val Ala Arg Leu Asn Met Ser His Gly Asp His
130 135 140

Ala Ser His Gln Lys Val Ile Asp Leu Val Lys Glu Tyr Asn Ala Ser
145 150 155 160

His Ala Asp Asn Val Ile Ala Ile Met Leu Asp Thr Lys Gly Pro Glu
165 170 175

Val Arg Ser Gly Asp Leu Pro Gln Pro Ile Phe Leu Glu Ser Gly Gln
180 185 190

Glu Phe Thr Phe Thr Ile Lys Arg Gly Val Gly Thr Asp Thr Cys Val
195 200 205

Ser Val Asn Tyr Asp Asp Phe Val Asn Asp Val Glu Val Gly Asp Met

-continued

```
    210                 215                 220

Leu Leu Val Asp Gly Gly Met Met Ser Phe Leu Val Lys Ser Lys Thr
225                 230                 235                 240

Glu Asp Ser Val Lys Cys Glu Val Ile Asp Gly Gly Glu Leu Lys Ser
                245                 250                 255

Arg Arg His Leu Asn Val Arg Gly Lys Ser Ala Thr Leu Pro Ser Ile
            260                 265                 270

Thr Asp Lys Asp Trp Asp Asp Ile Lys Phe Gly Val Asp Asn Gln Val
        275                 280                 285

Asp Tyr Tyr Ala Val Ser Phe Val Lys Asp Ala Gln Val Val His Glu
    290                 295                 300

Leu Lys Asp Tyr Leu Lys Ser Cys Asn Ala Asp Ile His Val Ile Val
305                 310                 315                 320

Lys Ile Glu Ser Ala Asp Ser Ile Pro Asn Leu His Ser Ile Ile Thr
                325                 330                 335

Ala Ser Asp Gly Ala Met Val Ala Arg Gly Asp Leu Gly Ala Glu Leu
            340                 345                 350

Pro Ile Glu Glu Val Pro Leu Leu Gln Glu Glu Ile Ile Arg Met Cys
        355                 360                 365

Arg Ser Met Gly Lys Ala Val Ile Val Ala Thr Asn Met Leu Glu Ser
    370                 375                 380

Met Ile Val His Pro Thr Pro Thr Arg Ala Glu Val Ser Asp Ile Ala
385                 390                 395                 400

Ile Ala Val Arg Glu Gly Ala Asp Ala Val Met Leu Ser Gly Glu Thr
                405                 410                 415

Ala His Gly Lys Phe Pro Leu Lys Ala Val Lys Val Met His Thr Val
            420                 425                 430

Ala Leu Arg Thr Glu Ala Thr Ile Pro Gly Gly Glu Thr Pro Ala Asp
        435                 440                 445

Leu Gly Gln Ala Phe Lys Asn His Met Ser Glu Met Phe Ala Tyr His
    450                 455                 460

Ala Thr Met Met Ser Asn Thr Leu Arg Thr Ser Ile Val Val Phe Thr
465                 470                 475                 480

Arg Thr Gly Phe Met Ala Ile Leu Leu Ser His Tyr Arg Pro Ser Gly
                485                 490                 495

Thr Ile Phe Ala Phe Thr Asp Glu Glu Arg Val Arg Gln Arg Leu Ala
            500                 505                 510

Leu Tyr Gln Gly Val Cys Pro Val Gln Met Glu Phe Ser Asp Asp Ala
        515                 520                 525

Glu Lys Thr Phe Gly Asn Ala Leu Ser Tyr Leu Leu Lys His Gly Met
    530                 535                 540

Val Lys Asp Gly Glu Glu Val Ala Leu Val Gln Ser Gly Lys His Pro
545                 550                 555                 560

Ile Trp Arg Ser Gln Ser Thr His Asn Ile Gln Val Arg Lys Ile
                565                 570                 575
```